US006602677B1

(12) United States Patent
Wood et al.

(10) Patent No.: US 6,602,677 B1
(45) Date of Patent: Aug. 5, 2003

(54) THERMOSTABLE LUCIFERASES AND METHODS OF PRODUCTION

(75) Inventors: Keith V. Wood, Madison, WI (US); Mary P. Hall, Madison, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 09/396,154

(22) Filed: Sep. 15, 1999

Related U.S. Application Data

(63) Continuation-in-part of application No. 09/156,946, filed on Sep. 18, 1998, now abandoned, and a continuation-in-part of application No. PCT/US98/19494, filed on Sep. 18, 1998.
(60) Provisional application No. 60/059,379, filed on Sep. 19, 1997.

(51) Int. Cl.$^7$ .............................. C12Q 1/66; C12N 9/02

(52) U.S. Cl. ........................... 435/8; 435/189; 536/23.2

(58) Field of Search ...................... 435/189, 8; 536/23.2

(56) References Cited

U.S. PATENT DOCUMENTS

| 5,219,737 A | 6/1993 | Kajiyama et al. .......... 435/69.1 |
|---|---|---|
| 5,605,793 A | 2/1997 | Stemmer ....................... 435/6 |
| 5,670,356 A | 9/1997 | Sherf et al. ................. 435/189 |
| 5,674,713 A | 10/1997 | McElroy et al. ........... 435/69.7 |
| 5,700,673 A | 12/1997 | McElroy et al. ............ 435/189 |

FOREIGN PATENT DOCUMENTS

| EP | 0337349 | 10/1989 | ............ C12N/9/02 |
|---|---|---|---|
| EP | 0524448 | 1/1993 | ............ C12N/15/53 |
| JP | 9-294600 | 11/1997 | ............ C12Q/1/68 |
| WO | 95/18853 | 7/1995 | ............ C12N/9/02 |
| WO | 95/25798 | 9/1995 | ............ C12N/15/53 |
| WO | 96/22376 | 7/1996 | ............ C12N/15/53 |
| WO | 98/46729 | 10/1998 | ............ C12N/9/00 |
| WO | 99/14336 | 3/1999 | ............ C12N/15/53 |

OTHER PUBLICATIONS

Arnold, F.H., "Directed Evolution: Creating Biocatalysts for the Future", *Chemical Engineering Science*, 51 (23), pp. 5091–5102, (1996).
Bowie, J.U., et al., "Deciphering the Message in Protein Sequences: Tolerance to Amino Acid Substitutions", *Science*, 247, pp. 1306–1310, (Mar. 1990).
Dementieva, E.I., et al., "Physicochemical Properties of Recombinant *Luciolo mingrelica* luciferase and its Mutant Forms", *Biochemistry*, 61 (1), pp. 115–119, (1996).
Fromant, M., et al., "Direct Random Mutagenesis of Gene-Sized DNA Fragments Using Polymerase Chain Reaction", *Analytical Biochemistry*, 224, pp. 347–353, (1995).
Hanahan, D., "Techniques for Transformation of *E. coli*", In: *DNA Cloning: A Practical Approach*, vol. 1, Chapter 6, Glover, D.W., (editor), IRL Press, Oxford, pp. 109–135, (1985).

Kajiyama, N., et al., "Thermostabilization of Firefly Luciferase by a Single Amino Acid Substitution at Position 217", *Biochemistry*, 32, pp. 13795–13799, (1993).
Kajiyama, N., et al., "Enhancement of Thermostability of Firefly Luciferase from *Luciola lateralis* by a Single Amino Acid Substitution", *Biosci. Biotech. Biochem.*, 58 (6), pp. 1170–1171, (1994).
Kutuzova, G.D., et al., "Bioluminescence Color Variation and Kinetic Behavior Relationships Among Beetle Luciferases", *Bioluminescence and Chemiluminescence, Molecular Reporting with Photons*, J W Hastings et al., (editors), John Wiley & Sons, Chinchester, England, pp. 248–252, (1996).
Manukhov, I.V., et al., "Cloning of the *Vibrio harveyi* luxA and luxB Genes and the Expression of Bioluminescence in *Escherichia coli* and *Bacillus subtilis*", *Russian Biotechnology*, 1, pp. 1–6, (1996).
Purdy, D., et al., "Heterologous Gene Expression in *Campylobacter coli*: The Use of Bacterial Luciferase in a Promoter Probe Vector", *FEMS Microbiology Letters*, 111, pp. 233–237, (1993).
Saiki, R.K., et al., "Primer–Directed Enzymatic Amplification of DNA with a Thermostable DNA Polymerase", *Science*, 239, pp. 487–491, (1988).
Stemmer, W.P., et al., "DNA Shuffling by Random Fragmentation and Reassembly: In vitro Recombination for Molecular Evolution", *Proc. Natl. Acad. Sci. USA*, 91, pp. 10747–10751, (1994).
Szittner, R., et al., "Nucleotide Sequence, Expression, and Properties of Luciferase Coded by lux Genes from a Terrestrial Bacterium", *The Journal of Biological Chemistry*, 265 (27), pp. 16581–16587, (1990).
White, P.J., et al., "Generation and Characterisation of a Thermostable Mutant of Luciferase from *Photinus Pyralis*", *Bioluminescence and Chemiluminescence, Fundamentals and Applied Aspects*, John Wiley & Sons, Cambridge, pp. 419–422, (Sep. 1994).
White, P.J., et al., "Improved thermostability of the North American firefly luciferase: saturation mutagenesis at position 354", *Biochemical Journal*, 319, pp. 343–350, (1996).
Wood, K.V., "The Chemical Mechanism and Evolutionary Development of Beetle Bioluminescence", *Photochemistry and Photobiology*, 62 (4), pp. 662–673, (1995).
Wood, K.V., et al., "bioluminescent click beetles revisited", *Journal of Bioluminescence and Chemiluminescence*, 4, pp. 31–39, (1989).

(List continued on next page.)

Primary Examiner—Rebecca E. Prouty
(74) Attorney, Agent, or Firm—Schwegman, Lundberg, Woessner & Kluth, P.A.

(57) ABSTRACT

Luciferase enzymes with greatly increased thermostability, e.g., at least half lives of 2 hours at 50° C., cDNAs encoding the novel luciferases, and hosts transformed to express the luciferases, are disclosed. Methods of producing the luciferases include recursive mutagenesis. The luciferases are used in conventional methods, some employing kits.

16 Claims, 70 Drawing Sheets

OTHER PUBLICATIONS

Wood, K.V., et al., "Complementary DNA Coding Click Beetle luciferases can elicit bioluminescence of different colors", *Science, 244*, pp. 700–702, (May 12, 1989).

Wood, K.V., et al., "Introduction to beetle luciferases and their applications", *Journal of Bioluminescence and Chemiluminescence, 4* (*1*), pp. 289–301, (Jul. 1989).

Wood, K.V., et al., "Photographic Detection of Luminescence in *Escherichia coli* Containing the Gene for Firefly Luciferase", *Analytical Biochemistry, 161*, pp. 501–507, (1987).

Ye, et al., "Cloning and Sequencing of a cDNA for firefly luciferase from *Photuris pennsylvanica*", *Biochemica et Biophysica Acta, 139*, pp. 39–52, (1997).

```
         1                                                                    50
Lcr    MENMENDE.N  IVVGPKPFYP  IEEGSAGTQL  RKYMERYAKL  .GAIAFTNAV
Lla    MENMENDE.N  IVYGPEPFYP  IEEGSAGAQL  RKYMDRYAKL  .GAIAFTNAL
Lmi    ME.MEKEE.N  VVYGPLPFYP  IEEGSAGIQL  HKYMHQYAKL  .GAIAFSNAL
Pmi    ...MEDDSKH  IMHGHRHSIL  WEDGTAGEQL  HKAMKRYAQV  PGTIAFTDAH
Ppy    ...MED.AKN  IKKGPAPFYP  LEDGTAGEQL  HKAMKRYALV  PGTIAFTDAH
Lno    ...MED.AKN  IMHGPAPFYP  LEDGTAGEQL  HKAMKRYAQV  PGTIAFTDAH
Ppe1   ...MSI.ENN  ILIGPPPYYP  LEEGTAGEQL  HRAISRYAAV  PGTLAYTDVH
Phg    MIKME..EEH  VMPGAMPRDL  LPEGTAGQQL  HRALYKHSYF  PE..AIVDSH
GR     ...MMKREKN  VVYGPEPLHP  LEDLTAGEML  FRALRKHSHL  PQ..ALVDVY
YG     ...MMKREKN  VIYGPEPLHP  LEDLTAGEML  FRALRKHSHL  PQ..ALVDVF
Ppe2   ...MED..KN  ILYGPEPFYP  LADGTAGEQM  FYALSRYADI  SGCIALTNAH
49-7C6         A
78-0B10        A                                  D
90-1B5         A                       E          D                P
133-1B2        A                       E          D                P
146-1H2        A                       E          D           A    P
Cons    ---M------  ---G------  -----AG---  ----------  ----A-----

51                                                                   100
Lcr    TGVDYSYAEY  LEKSCCLGKA  LQNYGLVVDG  RIALCSENCE  EFFIPVIAGL
Lla    TGVDYTYAEY  LEKSCCLGEA  LKNYGLVVDG  RIALCSENCE  EFFIPVLAGL
Lmi    TGVDISYQEY  FDITCRLAEA  MKNFGMKPEE  HIALCSENCE  EFFIPVLAGL
Pmi    AEVNITYSEY  FEMSCRLAET  MKRYGLGLQH  HIAVCSETSL  QFFMPVCGAL
Ppy    IEVNITYAEY  FEMSVRLAEA  MKRYGLNTNH  RIVVCSENSL  QFFMPVLGAL
Lno    AEVNITYSEY  FEMACRLAET  MKRYGLGLQH  HIAVCSENSL  QFFMPVCGAL
Ppe1   TELEVTYKEF  LDVTCRLAEA  MKNYGLGLQH  TISVCSENCV  QFFMPICAAL
Phg    THEIISYAKI  LDMSCRLAVS  FQKYGLTQNN  IIGICSENNL  NFFNPVIAAF
GR     GEEWISYKEF  FETTCLLAQS  LHNCGYKMSD  VVSICAENNK  RFFVPIIAAW
YG     GDESLSYKEF  FEATCLLAQS  LHNCGYKMND  VVSICAENNK  RFFIPIIAAW
Ppe2   TKENVLYEEF  LKLSCRLAES  FKKYGLKQND  TIAVCSENGL  QFFLPLIASL
49-7C6                                                          I
78-0B10                                                         V
90-1B5                                                          V
133-1B2                                                 S       V
146-1H2                                                 S       V
Cons    ------Y---  ------L---  ----G-----  ----C-E---  -FF-P-----

101                                                                  150
Lcr    FIGVGVAPTN  EIYTLRELVH  SLGISKPTIV  FSSKKGLDKV  ITVQKTVTTI
Lla    FIGVGVAPTN  EIYTLRELVH  SLGISKPTIV  FSSKKGLDKV  ITVQKTVATI
Lmi    YIGVAVAPTN  EIYTLRELNH  SLGIAQPTIV  FSSRKGLPKV  LEVQKTVTCI
Pmi    FIGVGVAPTN  DIYNERELYN  SLFISQPTIV  FCSKRALQKI  LGVQKKLPVI
Ppy    FIGVAVAPAN  DIYNERELLN  SMNISQPTVV  FVSKKGLQKI  LNVQKKLPII
Lno    FIGVGVASTN  DIYNERELYN  SLSISQPTIV  SCSKRALQKI  LGVQKKLPII
Ppe1   YVGVATAPTN  DIYNERELYN  SLSISQPTVV  FTSRNSLQKI  LGVQSRLPII
Phg    YLGITVATVN  DTYTDRELSE  TLNITKPQML  FCSKQSLPIV  MKTMKIMPYV
GR     YIGMIVAPVN  EGYIPDELCK  VMGISRPQLV  FCTKNILNKV  LEVQSRTDFI
YG     YIGMIVAPVN  ESYIPDELCK  VMGISKPQIV  FCTKNILNKV  LEVQSRTNFI
Ppe2   YLGIIAAPVS  DKYIERELIH  SLGIVKPRII  FCSKNTFQKV  LNVKSKLKYV
49-7C6
78-0B10                                                         S
90-1B5         V       N                            V           SI
133-1B2        V       N                            V           SI
146-1H2        V       N                            V           SI
Cons    --G---A---  --Y---EL--  ---I--P---  ----------  ----------
```

FIG. 19A

```
          151                                                        200
Lcr    KTIVILDSKV  DYRGYQCLDT  FIKRNTPPGF  QASSFKTVEV  .DRKEQVALI
Lla    KTIVILDSKV  DYRGYQSMDN  FIKKNTPQGF  KGSSFKTVEV  .NRKEQVALI
Lmi    KKIVILDSKV  NFGGHDCMET  PIKKHVELGF  QPSSFVPIDV  KNRKQHVALL
Pmi    QKIVILDSRE  DYMGKQSMYS  FIESHLPAGF  NEYDYIPDSF  .DRETATALI
Ppy    QKIIMDSKT   DYQGFQSMYT  FVTSHLPPGF  NEYDFVPESF  .DRDKTIALI
Lno    QKIVILDSRE  DYMGKQSMYS  FIESHLPAGF  NEYDYIPDSF  .DRETATALI
Ppe1   KKIIILDGKK  DYLGYQSMQS  FMKEHVPANF  NVSAFKPLSF  .DLDR.VACI
Phg    QKLLIIDSMQ  DIGGIECVHS  FVSRYTDEHF  DPLKFVPLDF  .DPREQVALI
GR     KRIIILDAVE  NIHGCESLPN  FISRYSDGNI  A..NFKPLHY  .DPVEQVAAI
YG     KRIIILDTVE  NIHGCESLPN  FISRYSDGNI  A..NFKPLHY  .DPVEQVAAI
Ppe2   ETIIILDLNE  DLGGYQCLNN  FISQNSDINL  DVKKFKPNSF  .NRDDQVALV
49-7C6                                         Y
78-0B10                             S          Y
90-1B5                              S          Y                   I
133-1B2             D               S          Y                   I
146-1H2                             S          Y                  SI
Cons   ----I-D---  ---G------  F---------  ----------  -------A--

201                                                        250
Lcr    MNSSGSTGLP  KGVQLTHENT  VTRFSHARDP  IYGNQVSPGT  AVLTVVPFHH
Lla    MNSSGSTGLP  KGVQLTHENA  VTRFSHARDP  IYGNQVSPGT  AILTVVPFHH
Lmi    MNSSGSTGLP  KGVRITHEGA  VTRFSHAKDP  IYGNQVSPGT  AILTVVPFHH
Pmi    MNSSGSTGLP  KGVDLTHMNV  CVRFSHCRDP  VFGNQIIPDT  AILTVIPFHH
Ppy    MNSSGSTGLP  KGVALPHRTA  CVRFSHARDP  IPGNQIIPDT  AILSVVPFHH
Lno    MNSSGSTGLP  KGVELTHQNV  CVRFSHCRDP  VFGNQIIPDT  AILTVIPFHH
Ppe1   MNSSGSTGLP  KGVPISHRNT  IYRFSHCRDP  VFGNQIIPDT  TILCAVPFHH
Phg    MTSSGTTGLP  KGVMLTHRNI  CVRFVHSRDP  LFGTRFIPET  SILSLVPFHH
GR     LCSSGTTGLP  KGVMQTHRNV  CVRLIHALDP  RVGTQLIPGV  TVLVYLPFFH
YG     LCSSGTTGLP  KGVMQTHQNI  CVRLIHALDP  RAGTQLIPGV  TVLVYLPFFH
Ppe2   MFSSGTTGVS  KGVMLTHKNI  VARFSHCKDP  TFGNAINPTT  AILTVIPFHH
49-7C6                             LA
78-0B10    P                       LA
90-1B5    LP                       LA
133-1B2   LP                       IA                     S
146-1H2   LP                       IA                     S
Cons   --SSG-TG--  KGV---H---  --R--H--DP  --G----P--  --L---PF-H 251                                                        300
Lcr    GFGMFTTLGY  LICGFRVVML  TKFDEETFLK  TLQDYKCTSV  ILVPTLFAIL
Lla    GFGMFTTLGY  LTCGFRIVML  TKFDEETFLK  TLQDYKCSSV  ILVPTLFAIL
Lmi    GFGMFTTLGY  FACGYRVVML  TKFDEELFLR  TLQDYKCTSV  ILVPTLFAIL
Pmi    VFQMFTTLGY  LTCGFRIVLM  YRFEEELFLR  SLQDYKIQSA  LLVPTLFSFF
Ppy    GFGMFTTLGY  LICGFRVVLM  YRFEEELFLR  SLQDYKIQSA  LLVPTLFSFF
Lno    GFGMFTTLGY  LTCGFRIVLM  YRFEEELFLR  SLQDYKIQSA  LLVPTLFSFF
Ppe1   AFGTFTNLGY  LICGFHVVLM  YRFNEHLFLQ  TLQDYKCQSA  LLVPTVLAFL
Phg    AFGMFTTLSY  FIVGLKIVMM  KRFDGELFLK  TIQNYKIPTI  VIAPPVMVFL
GR     AFGFSINLGY  FMVGLRVIML  RRFDQEAFLK  AIQDYEVRSV  INVPAIILFL
YG     AFGFSINLGY  FMVGLRVIML  RRFDQEAFLK  AIQDYEVRSV  INVPAIILFL
Ppe2   GFGMTTTLGY  FTCGFRVALM  HTFEEKLFLQ  SLQDYKVEST  LLVPTLMAFF
49-7C6    M           V                                             L
78-0B10   M           V                                             L
90-1B5    M           V                                             L
133-1B2   M           V                                             L
146-1H2   M           V                                             L
Cons   -F-----L-Y  ---G------  --F----FL-  --Q-Y-----  ---P------
```

FIG. 19A (Continued)

```
        301                                                          350
Lcr   NKSELLNKYD  LSNLVEIASG  GAPLSKEVGE  AVARRFNLPG  VRQGYGLTET
Lla   NRSELLDKYD  LSNLVEIASG  GAPLSKEIGE  AVARRFNLPG  VRQGYGLTET
Lmi   NKSELIDKFD  LSNLTEIASG  GAPLAKEVGE  AVARRFNLPG  VRQGYGLTET
Pmi   AKSTLVDKYD  LSNLHEIASG  GAPLAKEVGE  AVAKRFKLPG  IRQGYGLTET
Ppy   AKSTLIDKYD  LSNLHEIASG  GAPLSKEVGE  AVAKRFHLPG  IRQGYGLTET
Lno   AKSTLVDKYD  LSNLHEIASG  GAPLAKEVGE  AVAKRFKLPG  IRQGYGLTET
Ppe1  AKNPLVDKYD  LSNLHEIASG  GAPLSKEISE  IAAKRFKLPG  IRQGYGLTET
Phg   AKSHLVDKYD  LSSIKEIATG  GAPLGPALAN  AVAKRLKLGG  IIQGYGLTET
GR    SKSPLVDKYD  LSSLRELCCG  AAPLAKEVAE  IAVKRLNLPG  IRCGFGLTES
YG    SKSPLVDKYD  LSSLRELCCG  AAPLAKEVAE  VAVKRLNLPG  IRCGFGLTES
Ppe2  AKSALVEKYD  LSHLKEIASG  GAPLSKEIGE  MVKKRPKLNF  VRQGYGLTET
49-7C6
78-0B10
90-1B5
133-1B2
146-1H2
Cons  ----L---K-D LS---E---G  -APL------  ----R--L--  ---G-GLTE- 351                                                          400
Lcr   TSAIIITPEG  DDKPGASGKV  VPLFKAKVID  LDTKKSLGPN  RRGEVCVKGP
Lla   TSAIIITPEG  DDKPGASGKV  VPLFKAKVID  LDTKKTLGPN  RRGEVCVKGP
Lmi   TSAFIITPEG  DDKPGASGKV  VPLFKVKVID  LDTKKTLGVN  RRGEICVKGP
Pmi   TSAIIITPEG  DDKPGACGKV  VPFFTAKIVD  LDTGKTLGVN  QRGELCVKGP
Ppy   TSAILITPEG  DDKPGAVGKV  VPFFEAKVVD  LDTGKTLGVN  QRGELCVRGP
Lno   TSAIIITPEG  DDKPGACGKV  VPFFSAKIVD  LDTGKTLGVN  QRGELCVKGP
Ppe1  TCAIVITAEG  EFKLGAVGKV  VPFYSLKVLD  LNTGKKLGPN  ERGEICFKGP
Phg   CCAVLITPHN  KIKTGSTGQV  LPYVTAKIVD  TKTGKNLGPN  QTGELCFKSD
GR    TSANIHSLRD  EFKSGSLGRV  TPLMAAKIAD  RETGKALGPN  QVGELCIKGP
YG    TSANIHSLGD  EFKSGSLGRV  TPLMAAKIAD  RETGKALGPN  QVGELCVKGP
Ppe2  TSAVLITPDT  DVRPGSTGKI  VPFHAVKVVD  PTTGKILGPN  ETGELYFKGD
49-7C6            NN                                 P
78-0B10           KG  A                              P           A
90-1B5            KG  AK                             P           P
133-1B2           KG  AK                             P           P
146-1H2           KG  AK           L                 P           P
Cons  --A------- ----G--G--  -P----K--D  --T-K-LG-N  --GE------

401                                                          450
Lcr   MLMKGYVNNP  EATKELIDEE  GWLHTGDIGY  YDEEKHFFIV  DRLKSLIKYK
Lla   MLMKGYVDNP  EATREIIDEE  GWLHTGDIGY  YDEEKHFFIV  DRLKSLIKYK
Lmi   SLMLGYSNNP  EATRETIDEE  GWLHTGDIGY  YDEDEHFFIV  DRLKSLIKYK
Pmi   MIMKGYVNNP  EATNALIDKD  GWLHSGDIAY  YDKDGHFFIV  DRLKSLIKYK
Ppy   MIMSGYVNNP  EATNALIDKD  GWLHSGDIAY  WDEDEHFFIV  DRLKSLIKYK
Lno   MIMKGYVNNP  EATSALIDKD  GWLHSGDIAY  YDKDGHFFIV  DRLKSLIKYK
Ppe1  MIMKGYINNP  EATRELIDEE  GWIHSGDIGY  FDEDGHVYIV  DRLKSLIKYK
Phg   IIMKGYYQNE  EETRLVIDKD  GWLHSGDIGY  YDTDGNFHIV  DRLKELIKYK
GR    MVSKGYVNNV  EATKEAIDDD  GWLHSGDFGY  YDEDEHFYVV  DRYKELIKYK
YG    MVSKGYVNNV  EATKEAIDDD  GWLHSGDFGY  YDEDEHFYVV  DRYKELIKYK
Ppe2  MIMKSYYNNE  EATKAIINKD  GWLRSGDIAY  YDNDGHFYIV  DRLKSLIKYK
49-7C6      G
78-0B10     G                   DN
90-1B5      G                   DN
133-1B2     G                   DN
146-1H2     G                   DN
Cons  -----Y--N-  E-T---I---  GW---GD--Y  -D-------V  DR-K-LIKYK
```

FIG. 19A (Continued)

```
         451                                                        500
Lcr      GYQVPPAELE  SVLLQHPSIF  DAGVAGVPDP  VAGELPGAVV  VLESGKNMTE
Lla      GYQVPPAELE  SVLLQHPNIF  DAGVAGVPDP  IAGELPGAVV  VLEKGKSMTE
Lmi      GYQVPPAELE  SVLLQHPNIF  DAGVAGVPDP  DAGELPGAVV  VMEKGKTMTE
Pmi      GYQVPPAELE  SILLQHPFIF  DAGVAGIPDP  DAGELPAAVV  VLEEGKMMTE
Ppy      GYQVAPAELE  SILLQHPNIF  DAGVAGLPDD  DAGELPAAVV  VLEHGKTMTE
Lno      GYQVPPAELE  SILLQHPFIF  DAGVAGIPDP  DAGELPAAVV  VLEEGKTMTE
Ppe1     GYQVPPAELE  ALLLQHPFIE  DAGVAGVPDE  VAGDLPGAVV  VLKEGKSITE
Phg      AYQVAPAELE  ALLLQHPYIA  DAGVTGIPDE  EAGELPAACV  VLEPGKTMTE
GR       GSQVAPAELE  EILLKNPCIR  DVAVVGIPDL  EAGELPSAFV  VIQPGKEITA
YG       GSQVAPAELE  EILLKNPCIR  DVAVVGIPDL  EAGELPSAFV  VKQPGKEITA
Ppe2     GYQVAPAEIE  GILLQHPYIV  DAGVTGIPDE  AAGELPAAGV  VVQTGKYLNE
49-7C6
78-0B10
90-1B5
133-1B2
146-1H2
Cons     --QV-PAE-E  --LL--P-I-  D--V-G-PD-  -AG-LP-A-V  V---GK----

501                                                        550
Lcr      KEVMDYVASQ  VSNAKRLRGG  VRFVDEVPKG  LTGKIDGRA.  IREILKKPV.
Lla      KEVMDYVASQ  VSNAKRLRGG  VRFVDEVPKG  LTGKIDGKA.  IREILKKPV.
Lmi      KEIVDYVNSQ  VVNHKRLRGG  VRFVDEVPKG  LTGKIDAKV.  IREILKKPQ.
Pmi      QEVMDYVAGQ  VTASKRLRGG  VKFVDEVPKG  LTGKIDSRK.  IREILTMGQK
Ppy      KEIVDYVASQ  VTTAKKLRGG  VVFVDEVPKG  LTGKLDARK.  IREILIKAKK
Lno      QEVMDYVAGQ  VTASKRLRGG  VKFVDEVPKG  LTGKIDGRK.  IREILMMGKK
Ppe1     KEIQDYVAGQ  VTSSKKLRGG  VEFVKEVPKG  FTGKIDTRK.  IKEILIKAQK
Phg      KEVMDYIAER  VTPTKRLRGG  VLFVNNIPKG  ATGKLVRTE.  LRRLLTQRA.
GR       KEVYDYLAER  VSHTKYLRGG  VRFVDSIPRN  VTGKITRKEL  LKQLLEKS..
YG       KEVYDYLAER  VSHTKYLRGG  VRFVDSIPRN  VTGKITRKEL  LKQLLEKS..
Ppe2     QIVQNFVSSQ  VSTAKWLRGG  VKFLDEIPKG  STGKIDRKV.  LRQMFEKH..
49-7C6
78-0B10              D
90-1B5               DY A
133-1B2              DY A                   I                     L
146-1H2              DY A                                         L
Cons     ----------  V---K-LRGG  V-F----P--  -TGK------  ----------

551
Lcr      ......AKM
Lla      ......AKM
Lmi      ......AKM
Pmi      ......SKL
Ppy      G...GKSKL
Lno      ......SKL
Ppe1     GKSKSKAKL
Phg      ......AKL
GR       ......SKL
YG       ......SKL
Ppe2     .....KSKL
49-7C6       TNG*
78-0B10      TNG*
90-1B5       TNG*
133-1B2      TNG*
146-1H2      TNG*
```

FIG. 19A (Continued)

| | | | |
|---|---|---|---|
| Lcr: | Luciola cruciata | Phg: | Phengodes sp. |
| Lla: | Luciola lateralis | Lmi: | Luciola mingrelica |
| Gr: | Pyrophorus plagiophthalamus (green) | | |
| YG: | Pyrophorus plagiophthalamus (yellow green) | | |
| Pmi: | Pyrocoelia miyako | Ppy: | Photinus pyralis |
| Lno: | Lampyris noctiluca | | |
| Ppe-2: | Photuris pennsylvanica (2) | | |
| Ppe-1: | Photuris pennsylvanica (1) | | |
| Cons: | Sites which are strictly conserved | | |

FIG. 19A (Continued)

|         | 1          |            |            |            | 50         |
|---------|------------|------------|------------|------------|------------|
| Lcr     | MENMENDE.N | IVVGPKPFYP | IEEGSAGTQL | RKYMERYAKL | .GAIAFTNAV |
| Lla     | MENMENDE.N | IVYGPEPFYP | IEEGSAGAQL | RKYMDRYAKL | .GAIAFTNAL |
| Lmi     | ME.MEKEE.N | VVYGPLPFYP | IEEGSAGIQL | HKYMHQYAKL | .GAIAFSNAL |
| Pmi     | ...MEDDSKH | IMHGHRHSIL | WEDGTAGEQL | HKAMKRYAQV | PGTIAFTDAH |
| Ppy     | ...MED.AKN | IKKGPAPFYP | LEDGTAGEQL | HKAMKRYALV | PGTIAFTDAH |
| Lno     | ...MED.AKN | IMHGPAPFYP | LEDGTAGEQL | HKAMKRYAQV | PGTIAFTDAH |
| Ppe1    | ...MSI.ENN | ILIGPPPYYP | LEEGTAGEQL | HRAISRYAAV | PGTLAYTDVH |
| Ppe2    | ...MED..KN | ILYGPEPFYP | LADGTAGEQM | FYALSRYADI | SGCIALTNAH |
| Phg     | MIKME..EEH | VMPGAMPRDL | LFEGTAGQQL | HRALYKHSYF | PE...AIVDSH |
| GR      | ...MMKREKN | VVYGPEPLHP | LEDLTAGEML | FRALRKHSHL | PQ..ALVDVY |
| YG      | ...MMKREKN | VIYGPEPLHP | LEDLTAGEML | FRALRKHSHL | PQ..ALVDVF |
| 30-4B02 | ...MMKREKN | VIYGPEPLHP | LEDLTAGEML | FRALRKHSHL | PQ..ALVDVV |
| 81-6G01 | ...MMKREKN | VIYGPEPLHP | LEDLTAGEML | FRALRKHSHL | PQ..ALVDVV |
| Cons    | ---M------ | ---G------ | -----AG--- | ---------- | ----A----- |

|         | 51         |            |            |            | 100        |
|---------|------------|------------|------------|------------|------------|
| Lcr     | TGVDYSYAEY | LEKSCCLGKA | LQNYGLVVDG | RIALCSENCE | EFFIPVIAGL |
| Lla     | TGVDYTYAEY | LEKSCCLGEA | LKNYGLVVDG | RIALCSENCE | EFFIPVLAGL |
| Lmi     | TGVDISYQEY | FDITCRLAEA | MKNFGMKPEE | HIALCSENCE | EFFIPVLAGL |
| Pmi     | AEVNITYSEY | FEMSCRLAET | MKRYGLGLQH | HIAVCSETSL | QFFMPVCGAL |
| Ppy     | IEVNITYAEY | FEMSVRLAEA | MKRYGLNTNH | RIVVCSENSL | QFFMPVLGAL |
| Lno     | AEVNITYSEY | FEMACRLAET | MKRYGLGLQH | HIAVCSENSL | QFFMPVCGAL |
| Ppe1    | TELEVTYKEF | LDVTCRLAEA | MKNYGLGLQH | TISVCSENCV | QFFMPICAAL |
| Ppe2    | TKENVLYEEF | LKLSCRLAES | FKKYGLKQND | TIAVCSENGL | QFFLPLIASL |
| Phg     | THEIISYAKI | LDMSCRLAVS | FQKYGLTQNN | IIGICSENNL | NFFNPVIAAF |
| GR      | GEEWISYKEF | FETTCLLAQS | LHNCGYKMSD | VVSICAENNK | RFFVPIIAAW |
| YG      | GDESLSYKEF | FEATCLLAQS | LHNCGYKMND | VVSICAENNK | RFFIPIIAAW |
| 30-4B02 | GDESLSYKEF | FEATVLLAQS | LHNCGYKMND | VVSICAENNK | RFFIPVIAAW |
| 81-6G01 | GDESLSYKEF | FEATVLLAQS | LHNCGYKMND | VVSICAENNT | RFFIPVIAAW |
| Cons    | ------Y--- | ------L--- | ----G----- | ----C-E--- | -FF-P----- |

|         | 101        |            |            |            | 150        |
|---------|------------|------------|------------|------------|------------|
| Lcr     | FIGVGVAPTN | EIYTLRELVH | SLGISKPTIV | FSSKKGLDKV | ITVQKTVTTI |
| Lla     | FIGVGVAPTN | EIYTLRELVH | SLGISKPTIV | FSSKKGLDKV | ITVQKTVATI |
| Lmi     | YIGVAVAPTN | EIYTLRELNH | SLGIAQPTIV | FSSRKGLPKV | LEVQKTVTCI |
| Pmi     | FIGVGVAPTN | DIYNERELYN | SLFISQPTIV | FCSKRALQKI | LGVQKKLPVI |
| Ppy     | FIGVAVAPAN | DIYNERELLN | SMNISQPTVV | FVSKKGLQKI | LNVQKKLPII |
| Lno     | FIGVGVASTN | DIYNERELYN | SLSISQPTIV | SCSKRALQKI | LGVQKKLPII |
| Ppe1    | YVGVATAPTN | DIYNERELYN | SLSISQPTVV | FTSRNSLQKI | LGVQSRLPII |
| Ppe2    | YLGIIAAPVS | DKYIERELIH | SLGIVKPRII | FCSKNTFQKV | LNVKSKLKYV |
| Phg     | YLGITVATVN | DTYTDRELSE | TLNITKPQML | FCSKQSLPIV | MKTMKIMPYV |
| GR      | YIGMIVAPVN | EGYIPDELCK | VMGISRPQLV | PCTKNILNKV | LEVQSRTDFI |
| YG      | YIGMIVAPVN | ESYIPDELCK | VMGISKPQIV | FCTKNILNKV | LEVQSRTNFI |
| 30-4B02 | YIGMIVAPVN | ESYIPDELCK | VMGISKPQIV | FTTKNILNKV | LEVQSRTNFI |
| 81-6G01 | YIGMIVAPVN | ESYIPDELCK | VMGISKPQIV | FTTKNILNKV | LEVQSRTNFI |
| Cons    | --G---A--- | --Y---EL-- | ---I--P--- | ---------- | ---------- |

FIG. 19B

|        | 151                                                              | 200          |
|--------|------------------------------------------------------------------|--------------|
| Lcr    | KTIVILDSKV DYRGYQCLDT FIKRNTPPGF QASSFKTVEV                      | .DRKEQVALI   |
| Lla    | KTIVILDSKV DYRGYQSMDN FIKKNTPQGF KGSSPKTVEV                      | .NRKEQVALI   |
| Lmi    | KKIVILDSKV NFGGHDCMET FIKKHVELGF QPSSFVPIDV                      | KNRKQHVALL   |
| Pmi    | QKIVILDSRE DYMGKQSMYS FIESHLPAGF NEYDYIPDSF                      | .DRETATALI   |
| Ppy    | QKIIIMDSKT DYQGFQSMYT FVTSHLPPGF NEYDFVPESF                      | .DRDKTIALI   |
| Lno    | QKIVILDSRE DYMGKQSMYS FIESHLPAGF NEYDYIPDSF                      | .DRETATALI   |
| Ppe1   | KKIIILDGKK DYLGYQSMQS FMKEHVPANF NVSAFKPLSF                      | .DLDR.VACI   |
| Ppe2   | ETIIILDLNE DLGGYQCLNN FISQNSDINL DVKKFKPNSF                      | .NRDDQVALV   |
| Phg    | QKLLIIDSMQ DIGGIECVHS FVSRYTDEHF DPLKFVPLDF                      | .DPREQVALI   |
| GR     | KRIIILDAVE NIHGCESLPN FISRYSDGNI A..NFKPLHY                      | .DPVEQVAAI   |
| YG     | KRIIILDTVE NIHGCESLPN FISRYSDGNI A..NFKPLHY                      | .DPVEQVAAI   |
| 30-4B02| KRIIILDTVE NIHGCESLPN FISRYSDGNI A..NFKPLHY                      | .DPVEQVAAI   |
| 81-6G01| KRIIILDTVE NIHGCESLPN FISRYSDGNI A..NFKPLHF                      | .DPVEQVAAI   |
| Cons   | ----I-D--- ---G------ F---------- ----------                     | -------A--   |

|        | 201                                                              | 250          |
|--------|------------------------------------------------------------------|--------------|
| Lcr    | MNSSGSTGLP KGVQLTHENT VTRFSHARDP IYGNQVSPGT                      | AVLTVVPFHH   |
| Lla    | MNSSGSTGLP KGVQLTHENA VTRFSHARDP IYGNQVSPGT                      | AILTVVPFHH   |
| Lmi    | MNSSGSTGLP KGVRITHEGA VTRFSHAKDP IYGNQVSPGT                      | AILTVVPFHH   |
| Pmi    | MNSSGSTGLP KGVDLTHEMNV CVRFSHCRDP VFGNQIIPDT                     | AILTVIPFHH   |
| Ppy    | MNSSGSTGLP KGVALPHRTA CVRFSHARDP IFGNQIIPDT                      | AILSVVPFHH   |
| Lno    | MNSSGSTGLP KGVELTHQNV CVRFSHCRDP VFGNQIIPDT                      | AILTVIPFHH   |
| Ppe1   | MNSSGSTGLP KGVPISHRNT IYRFSHCRDP VFGNQIIPDT                      | TILCAVPFHH   |
| Ppe2   | MFSSGTTGVS KGVMLTHKNI VARFSHCKDP TFGNAINPTT                      | AILTVIPFHH   |
| Phg    | MTSSGTTGLP KGVMLTHRNI CVRFVHSRDP LFGTRFIPET                      | SILSLVPFHH   |
| GR     | LCSSGTTGLP KGVMQTHRNV CVRLIHALDP RVGTQLIPGV                      | TVLVYLPFFH   |
| YG     | LCSSGTTGLP KGVMQTHQNI CVRLIHALDP RAGTQLIPGV                      | TVLVYLPFFH   |
| 30-4B02| LCSSGTTGLP KGVMQTHQNI CVRLIHALDP RAGTQLIPGV                      | TVLVYLPFFH   |
| 81-6G01| LCSSGTTGLP KGVMQTHQNI CVRLIHALDP RAGTQLIPGV                      | TVLVYLPFFH   |
| Cons   | --SSG-TG-- KGV---H--- --R--H--DP --G----P--                      | --L---PF-H   |

|        | 251                                                              | 300          |
|--------|------------------------------------------------------------------|--------------|
| Lcr    | GFGMFTTLGY LICGFRVVML TKFDEETFLK TLQDYKCTSV                      | ILVPTLFAIL   |
| Lla    | GFGMFTTLGY LTCGFRIVML TKFDEETFLK TLQDYKCSSV                      | ILVPTLFAIL   |
| Lmi    | GFGMFTTLGY FACGYRVVML TKFDEELFLR TLQDYKCTSV                      | ILVPTLFAIL   |
| Pmi    | VFQMFTTLGY LTCGFRIVLM YRFEEELFLR SLQDYKIQSA                      | LLVPTLFSFF   |
| Ppy    | GFGMFTTLGY LICGFRVVLM YRFEEELFLR SLQDYKIQSA                      | LLVPTLFSFF   |
| Lno    | GFGMFTTLGY LTCGFRIVLM YRFEEELFLR SLQDYKIQSA                      | LLVPTLFSFF   |
| Ppe1   | AFGTFTNLGY LICGFHVVLM YRFNEHLFLQ TLQDYKCQSA                      | LLVPTVLAFL   |
| Ppe2   | GFGMTTTLGY FTCGFRVALM HTFEEKLFLQ SLQDYKVEST                      | LLVPTLMAFF   |
| Phg    | GFGMFTTLSY FIVGLKIVMM KRFDGELFLK TIQNYKIPTI                      | VIAPPVMVFL   |
| GR     | AFGPSINLGY FMVGLRVIML RRFDQEAFLK AIQDYEVRSV                      | INVPAIILFL   |
| YG     | AFGPSINLGY FMVGLRVIML RRFDQEAFLK AIQDYEVRSV                      | INVPAIILFL   |
| 30-4B02| AFGPSINLGY FMVGLRVIML RRFDQEAFLK AIQDYEVRSV                      | INVPAIILFL   |
| 81-6G01| AFGPSITLGY FMVGLRVIMF RRFDQEAFLK AIQDYEVRSV                      | INVPSVILFL   |
| Cons   | -F-----L-Y ---G------ --F----FL- --Q-Y-----                     | ---P------   |

FIG. 19B (Continued)

|         | 301                                                                  | 350       |
|---------|----------------------------------------------------------------------|-----------|
| Lcr     | NKSELLNKYD LSNLVEIASG GAPLSKEVGE AVARRFNLPG VRQGYGLTET                |           |
| Lla     | NRSELLDKYD LSNLVEIASG GAPLSKEIGE AVARRFNLPG VRQGYGLTET                |           |
| Lmi     | NKSELIDKFD LSNLTEIASG GAPLAKEVGE AVARRFNLPG VRQGYGLTET                |           |
| Pmi     | AKSTLVDKYD LSNLHEIASG GAPLAKEVGE AVAKRFKLPG IRQGYGLTET                |           |
| Ppy     | AKSTLIDKYD LSNLHEIASG GAPLSKEVGE AVAKRFHLPG IRQGYGLTET                |           |
| Lno     | AKSTLVDKYD LSNLHEIASG GAPLAKEVGE AVAKRFKLPG IRQGYGLTET                |           |
| Ppe1    | AKNPLVDKYD LSNLHEIASG GAPLSKEISE IAAKRFKLPG IRQGYGLTET                |           |
| Ppe2    | AKSALVEKYD LSHLKEIASG GAPLSKEIGE MVKKRFKLNF VRQGYGLTET                |           |
| Phg     | AKSHLVDKYD LSSIKEIATG GAPLGPALAN AVAKRLKLGG IIQGYGLTET                |           |
| GR      | SKSPLVDKYD LSSLRELCCG AAPLAKEVAE IAVKRLNLPG IRCGFGLTES                |           |
| YG      | SKSPLVDKYD LSSLRELCCG AAPLAKEVAE VAVKRLNLPG IRCGFGLTES                |           |
| 30-4B02 | SKSPLVDKYD LSSLRELCCG AAPLAKEVAE VAAKRLNLPG IRCGFGLTES                |           |
| 81-6G01 | SKSPLVDKYD LSSLRELCCG AAPLAKEVAE VAAKRLNLPG IRCGFGLTES                |           |
| Cons    | ----L--K-D LS---E---G -APL------ ----R--L-- ---G-GLTE-                |           |

|         | 351                                                                  | 400       |
|---------|----------------------------------------------------------------------|-----------|
| Lcr     | TSAIIITPEG DDKPGASGKV VPLFKAKVID LDTKKSLGPN RRGEVCVKGP                |           |
| Lla     | TSAIIITPEG DDKPGASGKV VPLFKAKVID LDTKKTLGPN RRGEVCVKGP                |           |
| Lmi     | TSAFIITPEG DDKPGASGKV VPLFKVKVID LDTKKTLGVN RRGEICVKGP                |           |
| Pmi     | TSAIIITPEG DDKPGACGKV VPFFTAKIVD LDTGKTLGVN QRGELCVKGP                |           |
| Ppy     | TSAILITPEG DDKPGAVGKV VPFFEAKVVD LDTGKTLGVN QRGELCVRGP                |           |
| Lno     | TSAIIITPEG DDKPGACGKV VPFFSAKIVD LDTGKTLGVN QRGELCVKGP                |           |
| Ppe1    | TCAIVITAEG EFKLGAVGKV VPFYSLKVLD LNTGKKLGPN ERGEICFKGP                |           |
| Ppe2    | TSAVLITPDT DVRPGSTGKI VPFHAVKVVD PTTGKILGPN ETGELYFKGD                |           |
| Phg     | CCAVLITPHN KIKTGSTGQV LPYVTAKIVD TKTGKNLGPN QTGELCFKSD                |           |
| GR      | TSANIHSLRD EFKSGSLGRV TPLMAAKIAD RETGKALGPN QVGELCIKGP                |           |
| YG      | TSANIHSLGD EFKSGSLGRV TPLMAAKIAD RETGKALGPN QVGELCVKGP                |           |
| 30-4B02 | TSANIHSLRD EFKSGSIGRV TPLMAAKIAD RETGKALGPN QVGELCIKGP                |           |
| 81-6G01 | TSANIHSLRD EFKSGSLGRV TPLMAAKIAD RETGKALGPN QVGELCIKGP                |           |
| Cons    | --A------- ----G--G-- -P----K--D --T-K-LG-N --GE------                |           |

|         | 401                                                                  | 450       |
|---------|----------------------------------------------------------------------|-----------|
| Lcr     | MLMKGYVNNP EATKELIDEE GWLHTGDIGY YDEEKHFFIV DRLKSLIKYK                |           |
| Lla     | MLMKGYVDNP EATREIIDEE GWLHTGDIGY YDEEKHFFIV DRLKSLIKYK                |           |
| Lmi     | SLMLGYSNNP EATRETIDEE GWLHTGDIGY YDEDEHFFIV DRLKSLIKYK                |           |
| Pmi     | MIMKGYVNNP EATNALIDKD GWLHSGDIAY YDKDGHFFIV DRLKSLIKYK                |           |
| Ppy     | MIMSGYVNNP EATNALIDKD GWLHSGDIAY WDEDEHFFIV DRLKSLIKYK                |           |
| Lno     | MIMKGYVNNP EATSALIDKD GWLHSGDIAY YDKDGHFFIV DRLKSLIKYK                |           |
| Ppe1    | MIMKGYINNP EATRELIDEE GWIHSGDIGY FDEDGHVYIV DRLKSLIKYK                |           |
| Ppe2    | MIMKSYYNNE EATKAIINKD GWLRSGDIAY YDNDGHFYIV DRLKSLIKYK                |           |
| Phg     | IIMKGYYQNE EETRLVIDKD GWLHSGDIGY YDTDGNFHIV DRLKELIKYK                |           |
| GR      | MVSKGYVNNV EATKEAIDDD GWLHSGDFGY YDEDEHFYVV DRYKELIKYK                |           |
| YG      | MVSKGYVNNV EATKEAIDDD GWLHSGDFGY YDEDEHFYVV DRYKELIKYK                |           |
| 30-4B02 | MVSKGYVNNV EATKEAIDDD GWLHSGDFGY YDEDEHFYVV DRYKELIKYK                |           |
| 81-6G01 | MVSKGYVNNV EATKEAIDDD GWLHSGDFGY YDEDEHFYVV DRYKELIKYK                |           |
| Cons    | -----Y--N- E-T---I--- GW---GD--Y -D-------V DR-K-LIKYK                |           |

FIG. 19B (Continued)

```
             451                                                             500
      Lcr    GYQVPPAELE  SVLLQHPSIF  DAGVAGVPDP  VAGELPGAVV  VLESGKNMTE
      Lla    GYQVPPAELE  SVLLQHPNIF  DAGVAGVPDP  IAGELPGAVV  VLEKGKSMTE
      Lmi    GYQVPPAELE  SVLLQHPNIF  DAGVAGVPDP  DAGELPGAVV  VMEKGKTMTE
      Pmi    GYQVPPAELE  SILLQHPFIF  DAGVAGIPDP  DAGELPAAVV  VLEEGKMMTE
      Ppy    GYQVAPAELE  SILLQHPNIF  DAGVAGLPDD  DAGELPAAVV  VLEHGKTMTE
      Lno    GYQVPPAELE  SILLQHPFIF  DAGVAGIPDP  DAGELPAAVV  VLEEGKTMTE
      Ppe1   GYQVPPAELE  ALLLQHPFIE  DAGVAGVPDE  VAGDLPGAVV  VLKEGKSITE
      Ppe2   GYQVAPAEIE  GILLQHPYIV  DAGVTGIPDE  AAGELPAAGV  VVQTGKYLNE
      Phg    AYQVAPAELE  ALLLQHPYIA  DAGVTGIPDE  EAGELPAACV  VLEPGKTMTE
      GR     GSQVAPAELE  EILLKNPCIR  DVAVVGIPDL  EAGELPSAFV  VIQPGKEITA
      YG     GSQVAPAELE  EILLKNPCIR  DVAVVGIPDL  EAGELPSAFV  VKQPGKEITA
    30-4B02  GSQVAPAELE  EILLTNPCIR  DVAVVGIPDL  EAGELPSAFV  VKQPGKEITA
    81-6G01  GSQVAPAELE  EILLKNPCIR  DVAVVGIPDL  EAGELPSAFV  VKQPGKEITA
      Cons   --QV-PAE-E  --LL--P-I-  D--V-G-PD-  -AG-LP-A-V  V---GK----

501                                                             550
      Lcr    KEVMDYVASQ  VSNAKRLRGG  VRFVDEVPKG  LTGKIDGRA.  IREILKKPV.
      Lla    KEVMDYVASQ  VSNAKRLRGG  VRFVDEVPKG  LTGKIDGKA.  IREILKKPV.
      Lmi    KEIVDYVNSQ  VVNHKRLRGG  VRFVDEVPKG  LTGKIDAKV.  IREILKKPQ.
      Pmi    QEVMDYVAGQ  VTASKRLRGG  VKFVDEVPKG  LTGKIDSRK.  IREILTMGQK
      Ppy    KEIVDYVASQ  VTTAKKLRGG  VVFVDEVPKG  LTGKLDARK.  IREILIKAKK
      Lno    QEVMDYVAGQ  VTASKRLRGG  VKFVDEVPKG  LTGKIDGRK.  IREILMMGKK
      Ppe1   KEIQDYVAGQ  VTSSKKLRGG  VEFVKEVPKG  FTGKIDTRK.  IKEILIKAQK
      Ppe2   QIVQNFVSSQ  VSTAKWLRGG  VKFLDEIPKG  STGKIDRKV.  LRQMFEKH..
      Phg    KEVMDYIAER  VTPTKRLRGG  VLFVNNIPKG  ATGKLVRTE.  LRRLLTQRA.
      GR     KEVYDYLAER  VSHTKYLRGG  VRFVDSIPRN  VTGKITRKEL  LKQLLEKS..
      YG     KEVYDYLAER  VSHTKYLRGG  VRFVDSIPRN  VTGKITRKEL  LKQLLEKS..
    30-4B02  KEVYDYLAER  VSHTKYLRGG  VRFVDSIPRN  VTGKITRKEL  LKQLLEK...
    81-6G01  KEVYDYLAER  VSHTKYLRGG  VRFVDSIPRN  VTGKITRKEL  LKQLLEK...
      Cons   ----------  V---K-LRGG  V-F----P--  -TGK------  ----------

551
      Lcr    ......AKM
      Lla    ......AKM
      Lmi    ......AKM
      Pmi    ......SKL
      Ppy    G...GKSKL
      Lno    ......SKL
      Ppe1   GKSKSKAKL
      Ppe2   .....KSKL
      Phg    ......AKL
      GR     ......SKL
      YG     ......SKL
    30-4B02  .....AGG*
    81-6G01  .....AGG*
      Cons   -------K-
```

FIG. 19B (Continued)

```
         1                                                                50
Lcr   MENMENDE.N  IVVGPKPFYP  IEEGSAGTQL  RKYMERYAKL  .GAIAFTNAV
Lla   MENMENDE.N  IVYGPEPFYP  IEEGSAGAQL  RKYMDRYAKL  .GAIAFTNAL
Lmi   ME.MEKEE.N  VVYGPLPFYP  IEEGSAGIQL  HKYMHQYAKL  .GAIAFSNAL
Pmi   ...MEDDSKH  IMHGHRHSIL  WEDGTAGEQL  HKAMKRYAQV  PGTIAFTDAH
Ppy   ...MED.AKN  IKKGPAPFYP  LEDGTAGEQL  HKAMKRYALV  PGTIAFTDAH
Lno   ...MED.AKN  IMHGPAPFYP  LEDGTAGEQL  HKAMKRYAQV  PGTIAFTDAH
Ppe1  ...MSI.ENN  ILIGPPPYYP  LEEGTAGEQL  HRAISRYAAV  PGTLAYTDVH
Ppe2  ...MED..KN  ILYGPEPFYP  LADGTAGEQM  FYALSRYADI  SGCIALTNAH
Phg   MIKME..EEH  VMPGAMPRDL  LPEGTAGQQL  HRALYKHSYF  PE..AIVDSH
YG    ...MMKREKN  VIYGPEPLHP  LEDLTAGEML  FRALRKHSHL  PQ..ALVDVF
      ---XXOOOOO  XOO-OOOXXO  OOXXO--OXO  XOOXOXXXOO  OXOO-XXOXX 51                                                               100
Lcr   TGVDYSYAEY  LEKSCCLGKA  LQNYGLVVDG  RIALCSENCE  EFFIPVIAGL
Lla   TGVDYTYAEY  LEKSCCLGEA  LKNYGLVVDG  RIALCSENCE  EFFIPVLAGL
Lmi   TGVDISYQEY  FDITCRLAEA  MKNFGMKPEE  HIALCSENCE  EFFIPVLAGL
Pmi   AEVNITYSEY  FEMSCRLAET  MKRYGLGLQH  HIAVCSETSL  QFFMPVCGAL
Ppy   IEVNITYAEY  FEMSVRLAEA  MKRYGLNTNH  RIVVCSENSL  QFFMPVLGAL
Lno   AEVNITYSEY  FEMACRLAET  MKRYGLGLQH  HIAVCSENSL  QFFMPVCGAL
Ppe1  TELEVTYKEF  LDVTCRLAEA  MKNYGLGLQH  TISVCSENCV  QFFMPICAAL
Ppe2  TKENVLYEEF  LKLSCRLAES  FKKYGLKQND  TIAVCSENGL  QFFLPLIASL
Phg   THEIISYAKI  LDMSCRLAVS  FQKYGLTQNN  IIGICSENNL  NFFNPVIAAF
YG    GDESLSYKEF  FEATCLLAQS  LHNCGYKMND  VVSICAEHNK  RFFIPIIAAW
      XOXOXX---X  XOOXOXOOX-  XXOX-XOOOO  OXXO-X-OOX  X--O-XOOOX 101                                                              150
Lcr   FIGVGVAPTN  EIYTLRELVH  SLGISKPTIV  FSSKKGLDKV  ITVQKTVTTI
Lla   FIGVGVAPTN  EIYTLRELVH  SLGISKPTIV  FSSKKGLDKV  ITVQKTVATI
Lmi   YIGVAVAPTN  EIYTLRELNH  SLGIAQPTIV  FSSRKGLPKV  LEVQKTVTCI
Pmi   FIGVGVAPTN  DIYNERELYN  SLFISQPTIV  FCSKRALQKI  LGVQKKLPVI
Ppy   FIGVAVAPAN  DIYNERELLN  SMNISQPTVV  FVSKKGLQKI  LNVQKKLPII
Lno   FIGVGVASTN  DIYNERELYN  SLSISQPTIV  SCSKRALQKI  LGVQKKLPII
Ppe1  YVGVATAPTN  DIYNERELYN  SLSISQPTVV  FTSRNSLQKI  LGVQSRLPII
Ppe2  YLGIIAAPVS  DKYIERELIH  SLGIVKPRII  FCSKNTFQKV  LNVKSKLKYV
Phg   YLGITVATVN  DTYTDRELSE  TLNITKPQML  FCSKQSLPIV  MKTMKIMPYV
YG    YIGMIVAPVN  ESYIPDELCK  VMGISKPQIV  FCTKNILNKV  LEVQSRTNFI
      XO-XOO-OXO  XX-OXX--OO  XXO-OX-XOO  OOXOOOOXOO  OOO-XOXXOO
```

FIG. 19C

```
            151                                                              200
     Lcr  KTIVILDSKV  DYRGYQCLDT  FIKRNTPPGF  QASSFKTVEV  .DRKEQVALI
     Lla  KTIVILDSKV  DYRGYQSMDN  FIKKNTPQGF  KGSSFKTVEV  .NRKEQVALI
     Lmi  KKIVILDSKV  NFGGHDCMET  FIKKEVELGF  QPSSFVPIDV  KNRKQHVALL
     Pmi  QKIVILDSRE  DYMGKQSMYS  FIESHLPAGF  NEYDYIPDSF  .DRETATALI
     Ppy  QKIIIMDSKT  DYQGFQSMYT  FVTSHLPPGF  NEYDFVPESF  .DRDKTIALI
     Lno  QKIVILDSRE  DYMGKQSMYS  FIESHLPAGF  NEYDYIPDSF  .DRETATALI
     Ppe1 KKIIILDGKK  DYLGYQSMQS  FMKEHVPANF  NVSAFKPLSF  .DLDR.VACI
     Ppe2 ETIIILDLNE  DLGGYQCLNN  FISQNSDINL  DVKKFKPNSF  .NRDDQVALV
     Phg  QKLLIIDSMQ  DIGGIECVHS  FVSRYTDEHF  DPLKFVPLDF  .DPREQVALI
     YG   KRIIILDTVE  NIHGCESLPN  FISRYSDGNI  A..NFKPLHY  .DPVEQVAAI
          OXOX-O-XXO  XXO-OXOXOO  -OOOXOXOXX  O--OOOOOXX  -OXOOOO-XO 201                                                              250
     Lcr  MNSSGSTGLP  KGVQLTHENT  VTRFSHARDP  IYGNQVSPGT  AVLTVVPFHH
     Lla  MNSSGSTGLP  KGVQLTHENA  VTRFSHARDP  IYGNQVSPGT  AILTVVPFHH
     Lmi  MNSSGSTGLP  KGVRITHEGA  VTRFSHAKDP  IYGNQVSPGT  AILTVVPFHH
     Pmi  MNSSGSTGLP  KGVDLTHMNV  CVRFSHCRDP  VFGNQIIPDT  AILTVIPFHH
     Ppy  MNSSGSTGLP  KGVALPHRTA  CVRFSHARDP  IFGNQIIPDT  AILSVVPFHH
     Lno  MNSSGSTGLP  KGVELTHQNV  CVRFSHCRDP  VFGNQIIPDT  AILTVIPFHH
     Ppe1 MNSSGSTGLP  KGVPISHRNT  IYRFSHCRDP  VFGNQIIPDT  TILCAVPFHH
     Ppe2 MFSSGTTGVS  KGVMLTHKNI  VARFSHCKDP  TFGNAINPTT  AILTVIPFHH
     Phg  MTSSGTTGLP  KGVMLTHRNI  CVRFVHSRDP  LFGTRFIPET  SILSLVPFHH
     YG   LCSSGTTGLP  KGVMQTHQNI  CVRLIHALDP  RAGTQLIPGV  TVLVYLPFFH
          XX---X--OO  ---OXO-OOO  OO-XX-OX--  OX-XOXO-OX  XX-XXX--X-

251                                                              300
     Lcr  GFGMFTTLGY  LICGFRVVML  TKFDEETFLK  TLQDYKCTSV  ILVPTLFAIL
     Lla  GFGMFTTLGY  LTCGFRIVML  TKFDEETFLK  TLQDYKCSSV  ILVPTLFAIL
     Lmi  GFGMFTTLGY  FACGYRVVML  TKFDEELFLR  TLQDYKCTSV  ILVPTLFAIL
     Pmi  VFQMFTTLGY  LTCGFRIVLM  YRFEEELFLR  SLQDYKIQSA  LLVPTLFSFF
     Ppy  GFGMFTTLGY  LICGFRVVLM  YRFEEELFLR  SLQDYKIQSA  LLVPTLFSFF
     Lno  GFGMFTTLGY  LTCGFRIVLM  YRFEEELFLR  SLQDYKIQSA  LLVPTLFSFF
     Ppe1 AFGTFTNLGY  LICGFHVVLM  YRFNEHLFLQ  TLQDYKCQSA  LLVPTVLAFL
     Ppe2 GFGMTTTLGY  FTCGFRVALM  HTFEEKLFLQ  SLQDYKVEST  LLVPTLMAFF
     Phg  AFGMFTTLSY  FIVGLKIVMM  KRFDGELFLK  TIQNYKIPTI  VIAPPVMVFL
     YG   AFGFSINLGY  FMVGLRVIML  RRFDQEAFLK  AIQDYEVRSV  INVPAIILFL
          X-OXXXX-O-  XOX-XOOXXX  OO-OXOX--O  XX-O-XOOOO  XXO-XXXXOO
```

FIG. 19C (Continued)

```
          301                                                              350
Lcr    NKSELLNKYD  LSNLVEIASG  GAPLSKEVGE  AVARRFNLPG  VRQGYGLTET
Lla    NRSELLDKYD  LSNLVEIASG  GAPLSKEIGE  AVARRFNLPG  VRQGYGLTET
Lmi    NKSELIDKFD  LSNLTEIASG  GAPLAKEVGE  AVARRFNLPG  VRQGYGLTET
Pmi    AKSTLVDKYD  LSNLHEIASG  GAPLAKEVGE  AVAKRFKLPG  IRQGYGLTET
Ppy    AKSTLIDKYD  LSNLHEIASG  GAPLSKEVGE  AVAKRFHLPG  IRQGYGLTET
Lno    AKSTLVDKYD  LSNLHEIASG  GAPLAKEVGE  AVAKRFKLPG  IRQGYGLTET
Ppe1   AKNPLVDKYD  LSNLHEIASG  GAPLSKEISE  IAAKRFKLPG  IRQGYGLTET
Ppe2   AKSALVEKYD  LSHLKEIASG  GAPLSKEIGE  MVKKRFKLNF  VRQGYGLTET
Phg    AKSHLVDKYD  LSSIKEIATG  GAPLGPALAN  AVAKRLKLGG  IIQGYGLTET
YG     SKSPLVDKYD  LSSLRELCCG  AAPLAKEVAE  VAVKRLNLPG  IRCGFGLTES
       XOOO-OO-O-  --XOO-XXX-  X---XOOOXO  XXXO-XX-OO  OOX-X----X 351                                                              400
Lcr    TSAIIITPEG  DDKPGASGKV  VPLFKAKVID  LDTKKSLGPN  RRGEVCVKGP
Lla    TSAIIITPEG  DDKPGASGKV  VPLFKAKVID  LDTKKTLGPN  RRGEVCVKGP
Lmi    TSAFIITPEG  DDKPGASGKV  VPLFKVKVID  LDTKKTLGVN  RRGEICVKGP
Pmi    TSAIIITPEG  DDKPGACGKV  VPFFTAKIVD  LDTGKTLGVN  QRGELCVKGP
Ppy    TSAILITPEG  DDKPGAVGKV  VPFFEAKVVD  LDTGKTLGVN  QRGELCVRGP
Lno    TSAIIITPEG  DDKPGACGKV  VPFFSAKIVD  LDTGKTLGVN  QRGELCVKGP
Ppe1   TCAIVITAEG  EFKLGAVGKV  VPFYSLKVLD  LNTGKKLGPN  ERGEICFKGP
Ppe2   TSAVLITPDT  DVRPGSTGKI  VPFHAVKVVD  PTTGKILGPN  ETGELYFKGD
Phg    CCAVLITPHN  KIKTGSTGQV  LPYVTAKIVD  TKTGKNLGPN  QTGELCFKSD
YG     TSANIHSLGD  EFKSGSLGRV  TPLMAAKIAD  RETGKALGPN  QVGELCVKGP
       OO-XOXXXXX  XXOX-XO-XO  X-XXOO--XX- XX-O-X--O-  OX--OOOOOO 401                                                              450
Lcr    MLMKGYVNNP  EATKELIDEE  GWLHTGDIGY  YDEEKHFFIV  DRLKSLIKYK
Lla    MLMKGYVDNP  EATREIIDEE  GWLHTGDIGY  YDEEKHFFIV  DRLKSLIKYK
Lmi    SLMLGYSNNP  EATRETIDEE  GWLHTGDIGY  YDEDEHFFIV  DRLKSLIKYK
Pmi    MIMKGYVNNP  EATNALIDKD  GWLHSGDIAY  YDKDGHFFIV  DRLKSLIKYK
Ppy    MIMSGYVNNP  EATNALIDKD  GWLHSGDIAY  WDEDEHFFIV  DRLKSLIKYK
Lno    MIMKGYVNNP  EATSALIDKD  GWLHSGDIAY  YDKDGHFFIV  DRLKSLIKYK
Ppe1   MIMKGYINNP  EATRELIDEE  GWIHSGDIGY  FDEDGHVYIV  DRLKSLIKYK
Ppe2   MIMKSYYNNE  EATKAIINKD  GWLRSGDIAY  YDNDGHFYIV  DRLKSLIKYK
Phg    IIMKGYYQNE  EETRLVIDKD  GWLHSGDIGY  YDTDGNFHIV  DRLKELIKYK
YG     MVSKGYVNNV  EATKEAIDDD  GWLHSGDFGY  YDEDEHFYVV  DRYKELIKYK
       OXXOO-OO-X  -O-OOX-OXO  --OOO--XO-  O-OOXOOXX-  --X-X-----
```

FIG. 19C (Continued)

```
       451                                                                    500
Lcr    GYQVPPAELE  SVLLQHPSIF  DAGVAGVPDP  VAGELPGAVV  VLESGKNMTE
Lla    GYQVPPAELE  SVLLQHPNIF  DAGVAGVPDP  IAGELPGAVV  VLEKGKSMTE
Lmi    GYQVPPAELE  SVLLQHPNIF  DAGVAGVPDP  DAGELPGAVV  VMEKGKTMTE
Pmi    GYQVPPAELE  SILLQHPFIF  DAGVAGIPDP  DAGELPAAVV  VLEEGKMMTE
Ppy    GYQVAPAELE  SILLQHPNIF  DAGVAGLPDD  DAGELPAAVV  VLEHGKTMTE
Lno    GYQVPPAELE  SILLQHPFIF  DAGVAGIPDP  DAGELPAAVV  VLEEGKTMTE
Ppe1   GYQVPPAELE  ALLLQHPFIE  DAGVAGVPDE  VAGDLPGAVV  VLKEGKSITE
Ppe2   GYQVAPAEIE  GILLQHPYIV  DAGVTGIPDE  AAGELPAAGV  VVQTGKYLNE
Phg    AYQVAPAELE  ALLLQHPYIA  DAGVTGIPDE  EAGELPAACV  VLEPGKTMTE
YG     GSQVAPAELE  EILLKNPCIR  DVAVVGIPDL  EAGELPSAFV  VKQPGKEITA
       OX--X---O-  XO--XX-O-X  -XX-X-O--X  O--O--X-X-  -XXO--OXOX 501                                                                    550
Lcr    KEVMDYVASQ  VSNAKRLRGG  VRFVDEVPKG  LTGKIDGRA.  IREILKKPV.
Lla    KEVMDYVASQ  VSNAKRLRGG  VRFVDEVPKG  LTGKIDGKA.  IREILKKPV.
Lmi    KEIVDYVNSQ  VVNHKRLRGG  VRFVDEVPKG  LTGKIDAKV.  IREILKKPQ.
Pmi    QEVMDYVAGQ  VTASKRLRGG  VKFVDEVPKG  LTGKIDSRK.  IREILTMGQK
Ppy    KEIVDYVASQ  VTTAKKLRGG  VVFVDEVPKG  LTGKLDARK.  IREILIKAKK
Lno    QEVMDYVAGQ  VTASKRLRGG  VKFVDEVPKG  LTGKIDGRK.  IREILMMGKK
Ppe1   KEIQDYVAGQ  VTSSKKLRGG  VEFVKEVPKG  PTGKIDTRK.  IKEILIKAQK
Ppe2   QIVQNFVSSQ  VSTAKWLRGG  VKFLDEIPKG  STGKIDRKV.  LRQMFEKH..
Phg    KEVMDYIAER  VTPTKRLRGG  VLFVNNIPKG  ATGKLVRTE.  LRRLLTQRA.
YG     KEVYDYLAER  VSHTKYLRGG  VRFVDSIPRN  VTGKITRKEL  LKQLLEKS..
       OOOXOOXOXX  -OOO-X----  -O-OOXX-XX  X---OXOXOO  XXXXOOOOOO

551
Lcr    ......AKM
Lla    ......AKM
Lmi    ......AKM
Pmi    ......SKL
Ppy    G...GKSKL
Lno    ......SKL
Ppe1   GKSKSKAKL
Ppe2   .....KSKL
Phg    ......AKL
YG     ......SKL
       OOOOOOX-O
```

FIG. 19C (Continued)

Key to beetle luciferase sequences:

Lcr    *Luciola cruciata*
Lla    *Luciola lateralis*
Lmi    *Luciola mingrelica*
Pmi    *Pyrocoelia miyako*
Ppy    *Photinus pyralis*
Lno    *Lampyris noctiluca*
Ppe1   *Photuris pennsylvanica* (1)
Ppe2   *Photuris pennsylvanica* (2)
Phg    *Phengodes* sp.
YG     *Pyrophorus plagiophthalamus* – yellow-green luminescence luc49-7C6 (SEQ ID NO:1)

```
GGATCCAATG GCAGATAAAA ATATTTTATA TGGGCCCGAA CCATTTTATC CCTTGGCTGA   60
TGGGACGGCT GGAGAACAGA TGTTTTACGC ATTATCTCGT TATGCAGATA TTTCAGGATG  120
CATAGCATTG ACAAATGCTC ATACAAAAGA AAATGTTTTA TATGAAGAGT TTTTAAAATT  180
GTCGTGTCGT TTAGCGGAAA GTTTTAAAAA GTATGGATTA AAACAAAACG ACACAATAGC  240
GGTGTGTAGC GAAAATGGTT TGCAATTTTT CCTTCCTATA ATTGCATCAT TGTATCTTGG  300
AATAATTGCA GCACCTGTTA GTGATAAATA CATTGAACGT GAATTAATAC ACAGTCTTGG  360
TATTGTAAAA CCACGCATAA TTTTTTGCTC CAAGAATACT TTTCAAAAAG TACTGAATGT  420
AAAATCTAAA TTAAAATATG TAGAAACTAT TATTATATTA GACTTAAATG AAGACTTAGG  480
AGGTTATCAA TGCCTCAACA ACTTTATTTC TCAAAATTCC GATATTAATC TGGACGTAAA  540
AAAATTTAAA CCATATTCTT TTAATCGAGA CGATCAGGTT GCGTTGGTAA TGTTTTCTTC  600
TGGTACAACT GGTGTTTCGA AGGGAGTCAT GCTAACTCAC AAGAATATTG TTGCACGATT  660
TTCTCTTGCA AAAGATCCTA CTTTTGGTAA CGCAATTAAT CCAACGACAG CAATTTTAAC  720
GGTAATACCT TTCCACCATG GTTTTGGTAT GATGACCACA TTAGGATACT TTACTTGTGG  780
ATTCCGAGTT GTTCTAATGC ACACGTTTGA AGAAAAACTA TTTCTACAAT CATTACAAGA  840
TTATAAAGTG GAAAGTACTT TACTTGTACC AACATTAATG GCATTTCTTG CAAAAAGTGC  900
ATTAGTTGAA AAGTACGATT TATCGCACTT AAAAGAAATT GCATCTGGTG GCGCACCTTT  960
ATCAAAAGAA ATTGGGGAGA TGGTGAAAAA ACGGTTTAAA TTAAACTTTG TCAGGCAAGG 1020
GTATGGATTA ACAGAAACCA CTTCGGCTGT TTAATTACA CCGAACAATG ACGTCAGACC 1080
GGGATCAACT GGTAAAATAG TACCATTTCA CGCTGTTAAA GTTGTCGATC CTACAACAGG 1140
AAAAATTTTG GGGCCAAATG AACCTGGAGA ATTGTATTTT AAAGGCGACA TGATAATGAA 1200
AGGTTATTAT AATAATGAAG AAGCTACTAA AGCAATTATT AACAAAGACG GATGGTTGCG 1260
CTCTGGTGAT ATTGCTTATT ATGACAATGA TGGCCATTTT TATATTGTGG ACAGGCTGAA 1320
GTCATTAATT AAATATAAAG GTTATCAGGT TGCACCTGCT GAAATTGAGG AATACTCTT 1380
ACAACATCCG TATATTGTTG ATGCCGGCGT TACTGGTATA CCGGATGAAG CCGCGGGCGA 1440
GCTTCCAGCT GCAGGTGTTG TAGTACAGAC TGGAAAATAT CTAAACGAAC AAATCGTACA 1500
AAATTTTGTT TCCAGTCAAG TTTCAACAGC CAAATGGCTA CGTGGTGGGG TGAAATTTTT 1560
GGATGAAATT CCCAAAGGAT CAACTGGAAA AATTGACAGA AAAGTGTTAA GACAAATGTT 1620
TGAAAAACAC ACCAATGGG                                             1639
```

FIG. 22 luc49-6C10 (SEQ ID NO:2)

```
GGATCCAATG GAAGATAAAA ATATTTTATA TGGACCTGAA CCATTTTATC CCTTGGCTGA    60
TGGGACGGCT GGAGAACAGA TGTTTTACGC ATTATCTCGT TATGCAGATA TTTCAGGATG   120
CATAGCATTG ACAAATGCTC ATACAAAAGC CCCTGTTTTA TATGAAGAGT TGTTAAAATT   180
GTCGTGTCGT TTAGCGGAAA GTTTTAAAAA GTATGGATTA AAACAAAACG ACACAATAGC   240
GGTGTGTAGC GAAAATGGTT TGCAATTTTT CCTTCCTATA ATTGCATCAT TGTATCTTGG   300
AATAATTGCA GCACCTGTTA GTGATAAATA CATTGAACGT GAATTAATAC ACAGTCTTGG   360
TATTGTAAAA CCACGCATAA TTTTTTGCTC CAAGAATACT TTTCAAAAAG TACTGAATGT   420
AAAATCTAAA TTAAAATATG TAGAAACTAT TATTATATTA GACTTAAATG AAGACTTAGG   480
AGGTTATCAA TGCCTCAACA ACTTTATTTC TCAAAATTCC GATATTAATC TGGACGTAAA   540
AAAATTTAAA CCATATTCTT TTAATCGAGA CGATCAGGTT GCGTTGGTAA TGTTTTCTTC   600
TGGTACAACT GGTGTTTCGA AGGGAGTCAT GCTAACTCAC AAGAATATTG TTGCACGATT   660
TTCTCATGCA AAAGATCCTA CTTTTGGTAA CGCAATTAAT CCAACGACAG CAATTTTAAC   720
GGTAATACCT TTCCACCATG GTTTTGGTAT GATGACCACA TTAGGATACT TTACTTGTGG   780
ATTCCGAGTT GTTCTAATGC ACACGTTTGA AGAAAAACTA TTTCTACAAT CATTACAAGA   840
TTATAAAGTG GAAAGTACTT TACTTGTACC AACATTAATG GCATTTTTTG CAAAAAGTGC   900
ATTAGTTGAA AAGTACGATT TATCGCACTT AAAAGAAATT GCATCTGGTG GCGCACCTTT   960
ATCAAAAGAA ATTGGGGAGA TGGTGAAAAA ACGGTTTAAA TTAAACTTTG TCAGGCAAGG  1020
GTATGGATTA ACAGAAACCA CTTCGGCTGT TTTAATTACA CCGAACAATG ACGTCAGACC  1080
GGGATCAACT GGTAAAATAG TACCATTTCA CGCTGTTAAA GTTGTCGATC CTACAACAGG  1140
AAAAATTTTG GGGCCAAATG AAACTGGAGA ATTGTATTTT AAAGGCGACA TGATAATGAA  1200
AGGTTATTAT AATAATGAAG AAGCTACTAA AGCAATTATT AACAAAGACG GATGGTTGCG  1260
CTCTGGTGAT ATTGCTTATT ATGACAATGA TGGCCATTTT TATATTGTGG ACAGGCTGAA  1320
GTCATTAATT AAATATAAAG GTTATCAGGT TGCACCTGCT GAAATTGAGG GAATACTCTT  1380
ACAACATCCG TATATTGTTG ATGCCGGCGT TACTGGTATA CCGGATGAAG CCGCGGGCGA  1440
GCTTCCAGCT GCAGGTGTTA TAGTACAGAC TGGAAAATAT CTAAACGAAC AAATCGTACA  1500
AAATTTTGTT TCCAGTCAAG TTTCAACAGC CAAATGGCTA CGTGGTGGGG TGAAATTTTT  1560
GGATGAAATT CCCAAAGGAT CAACTGGAAA AATTGACAGA AAAGTGTTAA GACAAATGTT  1620
TGAAAAACAC ACCAATGGG                                             1639
```

FIG. 23 luc49-0G12 (SEQ ID NO:3)

```
GGATCCAATG GAAGATAAAA ATATTTTATA TGGACCTGAA CCATTTTATC CCTTGGCTGA    60
TGGGACGGCT GGAGAACAGA TGTTTTACGC ATTATCTCGT TATGCAGATA TTTCAGGATG   120
CATAGCATTG ACAAATGCTC ATACAAAAGC CCCTGTTTTA TATGAAGAGT TTTTAAAATT   180
GTCGTGTCGT TTAGCGGAAA GTTTTAAAAA GTATGGATTA AAACAAAACG ACACAATAGC   240
GGTGTGTAGC GAAAATGGTT TGCAATTTTT CCTTCCTATA ATTGCATCAT TGTATCTTGG   300
AATAATTGCA GCACCTGTTA GTGATAAATA CATTGAACGT GAATTAATAC ACAGTCTTGG   360
TATTGTAAAA CCACGCATAA TTTTTTGCTC CAAGAATACT TTTCAAAAAG TACTGAATGT   420
AAAATCTAAA TTAAAATATG TAGAAACTAT TATTATATTA GACTTAAATG AAGACTTAGG   480
AGGTTATCAA TGCCTCAACA ACTTTATTTC TCAAAATTCC GATATTAATC TTGACGTAAA   540
AAAATTTAAA CCATATTCTT TTAATCGAGA CGATCAGGTT GCGTTGGTAA TGTTTTCTTC   600
TGGTACAACT GGTGTTTCGA AGGGAGTCAT GCTAACTCAC AAGAATATTG TTGTACGATT   660
TTCTTATGCA AAAGATCCTA CTTTTGGTAA CGCAATTAAT CCAACGACAG CAATTTTAAC   720
GGTAATACCT TTCCACCATG GTTTTGGTAT GATGACCACA TTAGGATACT TTACTTGTGG   780
ATTCCGAGTT GTTCTAATGC ACACGTTTGA AGAAAAACTA TTTCTACAAT CATTACAAGA   840
TTATAAAGTG GAAAGTACTT TACTTGTACC AACATTAATG GCATTTGTTG CAAAAAGTGC   900
ATTAGTTGAA AAGTACGATT TATCGCACTT AAAAGAAATT GCATCTGGTG GCGCACCTTT   960
ATCAAAAGAA ATTGGGGAGA TGGTGAAAAA ACGGTTTAAA TTAAACTTTG TCAGGCAAGG  1020
GTATGGATTA ACAGAAACCA CTTCGGCTGT TTTAATTACA CCGAACAATG ACGTCAGACC  1080
GGGATCAACT GGTAAAATAG TACCATTTCA CGCTGTTAAA GTTGTCGATC CTACAACAGG  1140
AAAAATTTTG GGGCCAAATG AAACTGGAGA ATTGTATTTT AAAGGCGACA TGATAATGAA  1200
AGGTTATTAT AATAATGAAG AAGCTACTAA AGCAATTATT AACAAAGACG GATGGTTGCG  1260
CTCTGGTGAT ATTGCTTATT ATGACAATGA TGGCCATTTT TATATTGTGG ACAGGCTGAA  1320
GTCATTAATT AAATATAAAG GTTATCAGGT TGCACCTGCT GAAATTGAGG GAATACTCTT  1380
ACAACATCCG TATATTGTTG ATGCCGGCGT TACTGGTATA CCGGATGAAG CCGCGGGCGA  1440
GCTTCCAGCT GCAGGTGTTG TAGTACAGAC TGGAAAATAT CTAAACGAAC AAATCGTACA  1500
AAATTTTGTT TCCAGTCAAG TTTCAACAGC CAAATGGCTA CGTGGTGGGG TGAAATTTTT  1560
GGATGAAATT CCCAAAGGAT CAACTGGAAA AATTGACAGA AAAGTGTTAA GACAAATGTT  1620
TGAAAAACAC ACCAATGGG                                              1639
```

FIG. 24 luc49-7A5 (SEQ ID NO:4)

```
GGATCCAATG GAAGATAAAA ATATTTTATA TGGACCTGAA CCATTTTATC CCTTGGCTGA    60
TGGGACGGCT GGAGAACAGA TGTTTTACGC ATTATCTCGT TATGCAGATA TTTCAGGATG   120
CATAGCATTG ACAAATGCTC ATACAAAAGC CCCTGTTTTA TATGAAGAGT TTTTAAAATT   180
GTCGTGTCGT TTAGCGGAAA GTTTTAAAAA GTATGGATTA AAACAAAACG ACACAATAGC   240
GGTGTGTAGC GAAAATGGTT TGCAATTTTT CCTTCCTATA ATTGCATCAT TGTATCTTGG   300
AATAATTGCA GCACCTGTTA GTGATAAATA CATTGAACGT GAATTAATAC ACAGTCTTGG   360
TATTGTAAAA CCACGCATAA TTTTTTGCTC CAAGAATACT TTTCAAAAAG TACTGAATGT   420
AAAATCTAAA TTAAAATATG TAGAAACTAT TATTATATTA GACTTAAATG AAGACTTAGG   480
AGGTTATCAA TGCCTCAACA ACTTTATTTC TCAAAATTCC GATATTAATC TTGACGTAAA   540
AAAATTTAAA CCATATTCTT TTAATGAGA CGATCAGGTT GCGTTGGTAA TGTTTTCTTC   600
TGGTACAACT GGTGTTTCGA AGGGAGTCAT GCTAACTCAC AAGAATATTG TTGCACGATT   660
TTCTATTGCA AAAGATCCTA CTTTTGGTAA CGCAATTAAT CCAACGACAG CAATTTTAAC   720
GGTAATACCT TTCCACCATG GTTTTGGTAT GATGACCACA TTAGGATACT TTACTTGTGG   780
ATTCCGAGTT GTTCTAATGC ACACGTTTGA AGAAAAACTA TTTCTACAAT CATTACAAGA   840
TTATAAAGTG GAAAGTACTT TACTTGTACC AACATTAATG GCATTTTTTG CAAAAAGTGC   900
ATTAGTTGAA AAGTACGATT TATCGCACTT AAAAGAAATT GCATCTGGTG GCGCACCTTT   960
ATCAAAAGAA ATTGGGGAGA TGGTGAAAAA ACGGTTTAAA TTAAACTTTG TCAGGCAAGG  1020
GTATGGATTA ACAGAAACCA CTTCGGCTGT TTTAATTACA CCGAACAATG ACGTCAGACC  1080
GGGATCAACT GGTAAAATAG TACCATTTCA CGCTGTTAAA GTTGTCGATC CTACAACAGG  1140
AAAAATTTTG GGGCCAAATG AAACTGGAGA ATTGTATTTT AAAGGCGACA TGATAATGAA  1200
AGGTTATTAT AATAATGAAG AAGCTACTAA AGCAATTATT AACAAAGACG GATGGTTGCG  1260
CTCTGGTGAT ATTGCTTATT ATGACAATGA TGGCCATTTT TATATTGTGG ACAGGCTGAA  1320
GTCATTAATT AAATATAAAG GTTATCAGGT TGCACCTGCT GAAATTGAGG GAATACTCTT  1380
ACAACATCCG TATATTGTTG ATGCCGGCGT TACTGGTATA CCGGATGAAG CCGCGGGCGA  1440
GCTTCCAGCT GCAGGTGTTG TAGTACAGAC TGGAAAAATAT CTAAACGAAC AAATCGTACA  1500
AAATTTTGTT TCCAGTCAAG TTTCAACAGC CAAATGGCTA CGTGGTGGGG TGAAATTTTT  1560
GGATGAAATT CCCAAAGGAT CAACTGGAAA AATTGACAGA AAAGTGTTAA GACAAATGTT  1620
TGAAAAACAC ACCAATGGG                                              1639
```

FIG. 25 luc49-4G11 (SEQ ID NO:5)

```
GGATCCAATG GAAGATAAAA ATATTTTATA TGGACCTGAA CCATTTTATC CCTTGGCTGA   60
TGGGACGGCT GGAGAACAGA TGTTTGACGC ATTATCTCGT TATGCAGATA TTTCAGGATG  120
CATAGCATTG ACAAATGCTC ATACAAAAGC CCCTGTTTTA TATGAAGAGT TGTTAAAATT  180
GTCGTGTCGT TTAGCGGAAA GTTTTAAAAA GTATGGATTA AAACAAAACG ACACAATAGC  240
GGTGTGTAGC GAAAATGGTT TGCAATTTTT CCTTCCTATA ATTGCATCAT TGTATCTTGG  300
AATAATTGCA GCACCTGTTA GTGATAAATA CATTGAACGT GAATTAATAC ACAGTCTTGG  360
TATTGTAAAA CCACGCATAA TTTTTTGCTC CAAGAATACT TTTCAAAAAG TACTGAATGT  420
AAAATCTAAA TTAAAATATG TAGAAACTAT TATTATATTA GACTTAAATG AAGACTTAGG  480
AGGTTATCAA TGCCTCAACA ACTTTATTTC TCAAAATTCC GATATTAATC TTGACGTAAA  540
AAAATTTAAA CCATATTCTT TTAATCGAGA CGATCAGGTT GCGTTGGTAA TGTTTTCTTC  600
TGGTACAACT GGTGTTTCGA AGGGAGTCAT GCTAACTCAC AAGAATATTG TTGCACGATT  660
TTCTCATGCA AAAGATCCTA CTTTTGGTAA CGCAATTAAT CCAACGACAG CAATTTTAAC  720
GGTAATACCT TTCCACCATG GTTTTGGTAT GATGACCACA TTAGGATACT TTACTTGTGG  780
ATTCCGAGTT GTTCTAATGC ACACGTTTGA AGAAAAACTA TTTCTACAAT CATTACAAGA  840
TTATAAAGTG GAAAGTACTT TACTTGTACC AACATTAATG GCATTTTTTG CAAAAAGTGC  900
ATTAGTTGAA AAGTACGATT TATCGCACTT AAAAGAAATT GCATCTGGTG GCGCACCTTT  960
ATCAAAAGAA ATTGGGGAGA TGGTGAAAAA ACGGTTTAAA TTAAACTTTG TCAGGCAAGG 1020
GTATGGATTA ACAGAAACCA CTTCGGCTGT TTTAATTACA CCGAACAATG ACGTCAGACC 1080
GGGATCAACT GGTAAAATAG TACCATTTCA CGCTGTTAAA GTTGTCGATC CTACAACAGG 1140
AAAAATTTTG GGGCCAAATG AAACTGGAGA ATTGTATTTT AAAGGCGACA TGATAATGAA 1200
AGGTTATTAT AATAATGAAG AAGCTACTAA AGCAATTATT AACAAAGACG GATGGTTGCG 1260
CTCTGGTGAT ATTGCTTATT ATGACAATGA TGGCCATTTT TATATTGTGG ACAGGCTGAA 1320
GTCATTAATT AAATATAAAG GTTATCAGGT TGCACCTGCT GAAATTGAGG GAATACTCTT 1380
ACAACATCCG TATATTGTTG ATGCCGGCGT TACTGGTATA CCGGATGAAG CCGCGGGCGA 1440
GCTTCCAGCT GCAGGTGTTG TAGTACAGAC TGGAAAATAT CTAAACGAAC AAATCGTACA 1500
AAATTTTGTT TCCAGTCAAG TTTCAACAGC CAAATGGCTA CGTGGTGGGG TGAAATTTTT 1560
GGATGAAATT CCCAAAGGAT CAACTGGAAA AATTGACAGA AAAGTGTTAA GACAAATGTT 1620
TGAAAAACAC ACCAATGGG                                              1639
```

FIG. 26 luc49-7C6 (SEQ ID NO:14)

Luc49-6C10 (SEQ ID NO:15)

Luc49-0G12 (SEQ ID NO:16)

Luc49-7A5 (SEQ ID NO:17)

Luc49-4G11 (SEQ ID NO:18)

```
              M E D K N I L Y G P E P F Y P L A D  20
G T A G E Q M F D A L S R Y A D I S G C  40
I A L T N A H T K E N V L Y E E F L K L  60
S C R L A E S F K K Y G L K Q N D T I A  80
V C S E N G L Q F F L P I I A S L Y L G  100
I I A A P V S D K Y I E R E L I H S L G  120
I V K P R I I F C S K N T F Q K V L N V  140
K S K L K Y V E T I I I L D L N E D L G  160
G Y Q C L N N F I S Q N S D I N L D V K  180
K F K P Y S F N R D D Q V A L V M F S S  200
G T T G V S K G V M L T H K N I V A R F  220
S H A K D P T F G N A I N P T T A I L T  240
V I P F H H G F G M M T T L G Y F T C G  260
F R V V L M H T F E E K L F L Q S L Q D  280
Y K V E S T L L V P T L M A F F A K S A  300
L V E K Y D L S H L K E I A S G G A P L  320
S K E I G E M V K K R F K L N F V R Q G  340
Y G L T E T T S A V L I T P N N D V R P  360
G S T G K I V P F H A V K V V D P T T G  380
K I L G P N E T G E L Y F K G D M I M K  400
G Y Y N N E E A T K A I I N K D G W L R  420
S G D I A Y Y D N D G H F Y I V D R L K  440
S L I K Y K G Y Q V A P A E I E G I L L  460
Q H P Y I V D A G V T G I P D E A A G E  480
L P A A G V V V Q T G K Y L N E Q I V Q  500
N F V S S Q V S T A K W L R G G V K F L  520
D E I P K G S T G K I D R K V L R Q M F  540
E K H T N G                              546
```

FIG. 31 luc78-0B10 (SEQ ID NO:6)

```
GGATCCAATG GCAGATAAGA ATATTTTATA TGGGCCCGAA CCATTTTATC CCTTGGCTGA    60
TGGGACGGCT GGAGAACAGA TGTTTGACGC ATTATCTCGT TATGCAGATA TTTCCGGATG   120
CATAGCATTG ACAAATGCTC ATACAAAAGA AAATGTTTTA TATGAAGAGT TTTTAAAATT   180
GTCGTGTCGT TTAGCGGAAA GTTTTAAAAA GTATGGATTA AAACAAAACG ACACAATAGC   240
GGTGTGTAGC GAAAATGGTT TGCAATTTTT CCTTCCTGTA ATTGCATCAT TGTATCTTGG   300
AATAATTGCA GCACCTGTTA GTGATAAATA CATTGAACGT GAATTAATAC ACAGTCTTGG   360
TATTGTAAAA CCACGCATAA TTTTTTGCTC CAAGAATACT TTTCAAAAAG TACTGAATGT   420
AAAATCTAAA TTAAAATCTG TAGAAACTAT TATTATATTA GACTTAAATG AAGACTTAGG   480
AGGTTATCAA TGCCTCAACA ACTTTATTTC TCAAAATTCC GATAGTAATC TGGACGTAAA   540
AAAATTTAAA CCATATTCTT TTAATCGAGA CGATCAGGTT GCGTTGGTAA TGTTTTCTTC   600
TGGTACAACT GGTGTTCCGA AGGGAGTCAT GCTAACTCAC AAGAATATTG TTGCACGATT   660
TTCTCTTGCA AAAGATCCTA CTTTTGGTAA CGCAATTAAT CCCACGACAG CAATTTTAAC   720
GGTAATACCT TTCCACCATG GTTTTGGTAT GATGACCACA TTAGGATACT TTACTTGTGG   780
ATTCCGAGTT GTTCTAATGC ACACGTTTGA AGAAAAACTA TTTCTACAAT CATTACAAGA   840
TTATAAAGTG GAAAGTACTT TACTTGTACC AACATTAATG GCATTTCTTG CAAAAAGTGC   900
ATTAGTTGAA AAGTACGATT TATCGCACTT AAAAGAAATT GCATCTGGTG GCGCACCTTT   960
ATCAAAAGAA ATTGGGAGA TGGTGAAAAA ACGGTTTAAA TTAAACTTTG TCAGGCAAGG  1020
GTATGGATTA ACAGAAACCA CTTCGGCTGT TTTAATTACA CCGAAAGGTG ACGCCAGACC  1080
GGGATCAACT GGTAAAATAG TACCATTTCA CGCTGTTAAA GTTGTCGATC CTACAACAGG  1140
AAAAATTTTG GGGCCAAATG AACCTGGAGA ATTGTATTTT AAAGGCGCCA TGATAATGAA  1200
GGGTTATTAT AATAATGAAG AAGCTACTAA AGCAATTATT GATAATGACG GATGGTTGCG  1260
CTCTGGTGAT ATTGCTTATT ATGACAATGA TGGCCATTTT TATATTGTGG ACAGGCTGAA  1320
GTCATTAATT AAATATAAAG GTTATCAGGT TGCACCTGCT GAAATTGAGG GAATACTCTT  1380
ACAACATCCG TATATTGTTG ATGCCGGCGT TACTGGTATA CCGGATGAAG CCGCGGGCGA  1440
GCTTCCAGCT GCAGGTGTTG TAGTACAGAC TGGAAAATAT CTAAACGAAC AAATCGTACA  1500
AGATTTTGTT TCCAGTCAAG TTTCAACAGC CAAATGGCTA CGTGGTGGG TGAAATTTTT  1560
GGATGAAATT CCCAAAGGAT CAACTGGAAA AATTGACAGA AAAGTGTTAA GACAAATGTT  1620
TGAAAAACAC ACCAATGGG                                              1639
```

FIG. 32 luc78-0G8 (SEQ ID NO:7)

```
GGATCCAATG GCAGATAAAA ATATTTTATA TGGGCCCGAA CCATTTTATC CCTTGGCTGA    60
TGGGACGGCT GGAGAACAGA TGTTTTACGC ATTATCTCGT TATGCAGATA TTTCAGGATG   120
CATAGCATTG ACAAATGCTC ATACAAAAGC CCCTGTTTTA TATGAAGAGT TTTTAAAATT   180
GTCGTGTCGT TTAGCGGAAA GTTTTAAAAA GTATGGATTA AAACAAAACG ACACAATAGC   240
GGTGTGTAGC GAAAATGGTT TGCAATTTTT CCTTCCTGTA ATTGCATCAT TGTATCTTGG   300
AATAATTGCA GCACCTGTTA GTGATAAATA CATTGAACGT GAATTAATAC ACAGTCTTGG   360
TATTGTAAAA CCACGCATAA TTTTTTGCTC CAAGAATACT TTTCAAAAAG TACTGAATGT   420
AAAATCTAAA TTAAAATATG TAGAAACTAT TATTATATTA GACTTAAATG AAGACTTAGG   480
AGGTTATCAA TGCCTCAACA ACTTTATTTC TCAAAATTCC GATATTAATC TTGACGTAAA   540
AAAATTTAAA CCATATTCTT TTAATCGAGA CGATCAGGTT GCGTTGGTAA TGTTTTCTTC   600
TGGTACAACT GGTGTTCCGA AGGGAGTCAT GCTAACTCAC AAGAATATTG TTGCACGATT   660
TTCTCTTGCA AAAGATCCTA CTTTTGGTAA CGCAATTAAT CCAACGACAG CAATTTTAAC   720
GGTAATACCT TTCCACCATG GTTTGGTAT GATGACCACA TTAGGATACT TTACTTGTGG   780
ATTCCGAGTT GTTCTAATGC ACACGTTTGA AGAAAAACTA TTTCTACAAT CATTACAAGA   840
TTATAAAGTG GAAAGTACTT TACTTGTACC AACATTAATG GCATTTCTTG CAAAAAGTGC   900
ATTAGTTGAA AAGTACGATT TATCGCACTT AAAAGAAATT GCATCTGGTG GCGCACCTTT   960
ATCAAAAGAA ATTGGGGAGA TGGTGAAAAA ACGGTTTAAA TTAAACTTTG TCAGGCAAGG  1020
GTATGGATTA ACAGAAACCA CTTCGGCTGT TTAATTACA CCGAAAXXXX XXGTCAGACC  1080
GGGATCAACT GGTAAAATAG TACCATTTCA CGCTGTTAAA GTTGTCGATC CTACAACAGG  1140
AAAAATTTTG GGGCCAAATG AACCTGGAGA ATTGTATTTT AAAGGCGACA TGATAATGAA  1200
AGGTTATTAT AATAATGAAG AAGCTACTAA AGCAATTATT GATAAAGACG GATGGTTGCG  1260
CTCTGGTGAT ATTGCTTATT ATGACAATGA TGGCCATTTT TATATTGTGG ACAGGCTGAA  1320
GTCATTAATT AAATATAAAG GTTATCAGGT TGCACCTGCT GAAATTGAGG GAATACTCTT  1380
ACAACATCCG TATATTGTTG ATGCCGGCGT TACTGGTATA CCGGATGAAG CCGCGGGCGA  1440
GCTTCCAGCT GCAGGTGTTG TAGTACAGAC TGGAAAATAT CTAAACGAAC AAATCGTACA  1500
AAATTTTGTT TCCAGTCAAG TTTCAACAGC CAAATGGCTA CGGGGTGGGG TGAAATTTTT  1560
GGATGAAATT CCCAAAGGAT CAACTGGAAA AATTGACAGA AAAGTGTTAA GACAAATGTT  1620
TGAAAAACAC ACCAATGGG                                              1639
```

FIG. 33 luc78-1E1   (SEQ ID NO:8)

```
GGATCCAATG GCAGATAAAA ATATTTTATA TGGGCCCGAA CCATTTTATC CCTTGGCTGA   60
TGGGACGGCT GGAGAACAGA TGTTTTACGC ATTATCTCGT TATGCAGATA TTTCAGGATG  120
CATAGCATTG ACAAATGCTC ATACAAAAGC CCCTGTTTTA TATGAAGAGT TGTTAAAATT  180
GTCGTGTCGT TTAGCGGAAA GTTTTAAAAA GTATGGATTA AAACAAAACG ACACAATAGC  240
GGTGTGTAGC GAAAATGGTT TGCAATATTT CCTTCCTGTA ATTGCATCAT TGTATCTTGG  300
AATAATTGCA GCACCTGTTA GTGATAAATA CATTGAACGT GAATTAATAC ACAGTCTTGG  360
TATTGTAAAA CCACGCATAA TTTTTTGCTC CAAGAATACT TTTCAAAAAG TACTGAATGT  420
AAAATCTAAA TTAAAATATG TAGAAACTAT TATTATATTA GACTTAAATG AAGACTTAGG  480
AGGTTATCAA TGCCTCAACA ACTTTATTTC TCAAAATTCC GATATTAATC TTGACGTAAA  540
AAAATTTAAA CCATATTCTT TTAATCGAGA CGATCAGGTT GCGTTGGTAA TGTTTTCTTC  600
TGGTACAACT GGTGTTCCGA AGGGAGTCAT GCTAACTCAC AAGAATATTG TTGCACGATT  660
TTCTATTGCA AAAGATCCTA CTTTTGGTAA CGCAATTAAT CCAACGACAG CAATTTTAAC  720
GGTAATACCT TTCCACCATG GTTTTGGTAT GATGACCACA TTAGGATACT TTACTTGTGG  780
ATTCCGAGTT GTTCTAATGC ACACGTTTGA AGAAAAACTA TTTCTACAAT CATTACAAGA  840
TTATAAAGTG GAAAGTACTT TACTTGTACC AACATTAATG GCATTTCTTG CAAAAAGTGC  900
ATTAGTTGAA AAGTACGATT TATCGCACTT AAAAGAAATT GCATCTGGTG GCGCACCTTT  960
ATCAAAAGAA ATTGGGGAGA TGGTGAAAAA ACGGTTTAAA TTAAACTTTG TCAGGCAAGG 1020
GTATGGATTA ACAGAAACCA CTTCGGCTGT TTTAATTACA CCGAAXXXXX XXGCCAGACC 1080
GGGATCAACT GGTAAAATAG TACCATTTCA CGCTGTTAAA GTTGTCGATC CTACAACAGG 1140
AAAAATTTTG GGGCCAAATG AAGCTGGAGA ATTGTATTTT AAAGGCGCCA TGATAATGAA 1200
GGGTTATTAT AATAATGAAG AAGCTACTAA AGCAATTATT AACAAAGACG GATGGTTGCG 1260
CTCTGGTGAT ATTGCTTATT ATGACAATGA TGGCCATTTT TATATTGTGG ACAGGCTGAA 1320
GTCATTAATT AAATATAAAG GTTATCAGGT TGCACCTGCT GAAATTGAGG GAATACTCTT 1380
ACAACATCCG TATATTGTTG ATGCCGGCGT TACTGGTATA CCGGATGAAG CCGCGGGCGA 1440
GCTTCCAGCT GCAGGTGTTG TAGTACAGAC TGGAAAATAT CTAAACGAAC AAATCGTACA 1500
AAATTTTGTT TCCAGTCAAG TTTCAACAGC CAAATGGCTA CGTGGTGGGG TGAAATTTTT 1560
GGATGAAATT CCCAAAGGAT CAACTGGAAA AATTGACAGA AAAGTGTTAA GACAAATGTT 1620
TGAAAAACAC ACCAATGGG                                              1639
```

FIG. 34 luc78-2B4 (SEQ ID NO:9)

```
GGATCCAATG GCAGATAAAA ATATTTTATA TGGGCCCGAA CCATTTTATC CCTTGGCTGA   60
TGGGACGGCT GGAGAACAGA TGTTTGACGC ATTATCTCGT TATGCAGATA TTTCAGGATG  120
CATAGCATTG ACAAATGCTC ATACAAAAGC CCCTGTTTTA TATGAAGAGT TGTTAAAATT  180
GTCGTGTCGT TTAGCGGAAA GTTTTAAAAA GTATGGATTA AAACAAAACG ACACAATAGC  240
GGTGTGTAGC GAAAATGGTT TGCAATTTTT CCTTCCTGTA ATTGCATCAT TGTATCTTGG  300
AATAATTGCA GCACCTGTTA GTGATAAATA CGTTGAACGT GAATTAATAC ACAGTCTTGG  360
TATTGTAAAA CCACGCATAA TTTTTTGCTC CAAGAATACT TTTCAAAAAG TACTGAATGT  420
AAAATCTAAA TTAAAATATG TAGAAACTAT TATTATATTA GACTTAAATG AAGACTTAGG  480
AGGTTATCAA TGCCTCAACA ACTTTATTTC TCAAAATTCC GATAGTAATC TGGACGTAAA  540
AAAATTTAAA CCAAATTCTT TTAATCGAGA CGATCAGGTT GCGTTGGTAA TGTTTTCTTC  600
TGGTACAACT GGTGTTTCGA AGGGAGTCAT GCTAACTCAC AAGAATATTG TTGCACGATT  660
TTCTCTTGCA AAAGATCCTA CTTTTGGTAA CGCAATTAAT CCAACGACAG CAATTTTAAC  720
GGTAATACCT TTCCACCATG GTTTTGGTAT GATGACCACA TTAGGATACT TTACTTGTGG  780
ATTCCGAGTT GTTCTAATGC ACACGTTTGA AGAAAAACTA TTTCTACAAT CATTACAAGA  840
TTATAAAGTG GAAAGTACTT TACTTGTACC AACATTAATG GCATTTCTTG CAAAAAGTGC  900
ATTAGTTGAA AAGTACGATT TATCGCACTT AAAAGAAATT GCATCTGGTG GCGCACCTTT  960
ATCAAAAGAA ATTGGGGAGA TGGTGAAAAA ACGGTTTAAA TTAAACTTTG TCAGGCAAGG 1020
GTATGGATTA ACAGAAACCA CTTCGGCTGT TTTAATTACA CCGAACxxxx xxGCAGACC 1080
GGGATCAACT GGTAAAATAG TACCATTTCA CGCTGTTAAA GTTGTCGATC CTACAACAGG 1140
AAAAATTTTG GGGCCAAATG AACCTGGAGA ATTGTATTTT AAAGGCGCCA TGATAATGAA 1200
GGGTTATTAT AATAATGAAG AAGCTACTAA AGCAATTATT GATAAAGACG GATGGTTGCG 1260
CTCTGGTGAT ATTGCTTATT ATGACAATGA TGGCCATTTT TATATTGTGG ACAGGCTGAA 1320
GTCATTAATT AAATATAAAG GTTATCAGGT TGCACCTGCT GAAATTGAGG GAATACTCTT 1380
ACAACATCCG TATATTGTTG ATGCCGGCGT TACTGGTATA CCGGATGAAG CCGCGGGCGA 1440
GCTTCCAGCT GCAGGTGTTG TAGTACAGAC TGGAAAATAT CTAAACGAAC AAATCGTACA 1500
AAATTTTGTT TCCAGTCAAG TTTCAACAGC CAAATGGCTA CGTGGTGGGG TGAAATTTTT 1560
GGATGAAATT CCCAAAGGAT CAACTGGAAA AATTGACAGA AAAGTGTTAA GACAAATGTT 1620
TGAAAAACAC ACCAATGGG                                             1639
```

FIG. 35 luc78-OB10 (SEQ ID NO:19)

Luc78-0G8 (SEQ ID NO:20)

Luc78-1E1 (SEQ ID NO:21)

Luc78-2B4 (SEQ ID NO:22)

```
  M A D K N I L Y G P E P F Y P L A D  20
G T A G E Q M F D A L S R Y A D I P G C  40
I A L T N A H T K E N V L Y E E F L K L  60
S C R L A E S F K K Y G L K Q N D T I A  80
V C S E N G L Q F F L P V I A S L Y L G 100
I I A A P V S D K Y V E R E L I H S L G 120
I V K P R I I F C S K N T F Q K V L N V 140
K S K L K Y V E T I I I L D L N E D L G 160
G Y Q C L N N F I S Q N S D S N L D V K 180
K F K P N S F N R D D Q V A L V M F S S 200
G T T G V P K G V M L T H K N I V A R F 220
S L A K D P T F G N A I N P T T A I L T 240
V I P F H H G F G M M T T L G Y F T C G 260
F R V V L M H T F E E K L F L Q S L Q D 280
Y K V E S T L L V P T L M A F L A K S A 300
L V E K Y D L S H L K E I A S G G A P L 320
S K E I G E M V K K R F K L N F V R Q G 340
Y G L T E T T S A V L I T P K X X A R P 360
G S T G K I V P F H A V K V V D P T T G 380
K I L G P N E T G E L Y F K G A M I M K 400
G Y Y N N E E A T K A I I D K D G W L R 420
S G D I A Y Y D N D G H F Y I V D R L K 440
S L I K Y K G Y Q V A P A E I E G I L L 460
Q H P Y I V D A G V T G I P D E A A G E 480
L P A A G V V V Q T G K Y L N E Q I V Q 500
N F V S S Q V S T A K W L R G G V K F L 520
D E I P K G S T G K I D R K V L R Q M F 540
E K H T N G                             546
```

FIG. 39 luc85-4F12 (SEQ ID NO:10)

```
GGATCCAATG GCAGATAAAA ATATTTTATA TGGGCCCGAA CCATTTTATC CCTTGGCTGA    60
TGGGACGGCT GGAGAACAGA TGTTTTACGC ATTATCTCGT TATGCAGATA TTCCGGGCTG   120
CATAGCATTG ACAAATGCTC ATACAAAAGC CCCTGTTTTA TATGAAGAGT TTTTAAAATT   180
GTCGTGTCGT TTAGCGGAAA GTTTTAAAAA GTATGGATTA AAACAAAACG ACACAATAGC   240
GGTGTGTAGC GAAAATGGTT TGCAATTTTT CCTTCCTGTA ATTGCATCAT TGTATCTTGG   300
AATAATTGTG GCACCTGTTA ACGATAAATA CATTGAACGT GAATTAATAC ACAGTCTTGG   360
TATTGTAAAA CCACGCATAG TTTTTTGCTC CAAGAATACT TTCAAAAAG TACTGAATGT    420
AAAATCTAAA TTAAAATCTG TAGAAACTAT TATTATATTA GACTTAAATG AAGACTTAGG   480
AGGTTATCAA TGCCTCAACA ACTTTATTTC TCAAAATTCC GATATTAATC TTGACGTAAA   540
AAAATTTAAA CCATATTCTT TTAATCGAGA CGATCAGGTT GCGTTGATTA TGTTTTCTTC   600
TGGTACAACT GGTCTGCCGA AGGGAGTCAT GCTAACTCAC AAGAATATTG TTGCACGATT   660
TTCTCTTGCA AAAGATCCTA CTTTTGGTAA CGCAATTAAT CCCACGACAG CAATTTTAAC   720
GGTAATACCT TTCCACCATG GTTTTGGTAT GATGACCACA TTAGGATACT TTACTTGTGG   780
ATTCCGAGTT GTTCTAATGC ACACGTTTGA AGAAAAACTA TTTCTACAAT CATTACAAGA   840
TTATAAAGTG GAAAGTACTT TACTTGTACC AACATTAATG GCATTTCTTG CAAAAAGTGC   900
ATTAGTTGAA AAGTACGATT TATCGCACTT AAAAGAAATT GCATCTGGTG GCGCACCTTT   960
ATCAAAAGAA ATTGGGGAGA TGGTGAAAAA ACGGTTTAAA TTAAACTTTG TCAGGCAAGG  1020
GTATGGATTA ACAGAAACCA CTTCGGCTGT TTTAATTACA CCGAAAXXXX XXGCCAGACC  1080
GGGATCAACT GGTAAAATAG TACCATTTCA CGCTGTTAAA GTTGTCGATC CTACAACAGG  1140
AAAAATTTTG GGCCAAATG AACCTGGAGA ATTGTATTTT AAAGGCCCGA TGATAATGAA   1200
GGGTTATTAT AATAATGAAG AAGCTACTAA AGCAATTATT GATAATGACG GATGGTTGCG  1260
CTCTGGTGAT ATTGCTTATT ATGACAATGA TGGCCATTTT TATATTGTGG ACAGGCTGAA  1320
GTCATTAATT AAATATAAAG GTTATCAGGT TGCACCTGCT GAAATTGAGG GAATACTCTT  1380
ACAACATCCG TATATTGTTG ATGCCGGCGT TACTGGTATT CCGGATGAAG CCGCGGGCGA  1440
GCTTCCAGCT GCAGGTGTTG TAGTACAGAC TGGAAAATAT CTAAACGAAC AAATCGTACA  1500
AAATTTTGTT TCCAGTCAAG TTTCAACAGC CAAATGGCTA CGTGGTGGGG TGAAATTTTT  1560
GGATGAAATT CCCAAAGGAT CAACTGGAAA AATTGACAGA AAAGTGTTAA GACAAATGTT  1620
TGAAAAACAC ACCAATGGG                                              1639
```

FIG. 40

Luc85-4F12 (SEQ ID NO:23)

Luc90-1B5 (SEQ ID NO:11)

```
GGATCCAATG GCAGATAAGA ATATTTTATA TGGGCCCGAA CCATTTTATC CCTTGGAAGA    60
TGGGACGGCT GGAGAACAGA TGTTTGACGC ATTATCTCGT TATGCAGATA TTCCGGGCTG   120
CATAGCATTG ACAAATGCTC ATACAAAGA AAATGTTTTA TATGAAGAGT TTCTGAAACT    180
GTCGTGTCGT TTAGCGGAAA GTTTTAAAAA GTATGGATTA AAACAAAACG ACACAATAGC   240
GGTGTGTAGC GAAAATGGTC TGCAATTTTT CCTTCCTGTA ATTGCATCAT TGTATCTTGG   300
AATAATTGTG GCACCTGTTA ACGATAAATA CATTGAACGT GAATTAATAC ACAGTCTTGG   360
TATTGTAAAA CCACGCATAG TTTTTTGCTC CAAGAATACT TTTCAAAAAG TACTGAATGT   420
AAAATCTAAA TTAAAATCTA TTGAAACTAT TATTATATTA GACTTAAATG AAGACTTAGG   480
AGGTTATCAA TGCCTCAACA ACTTTATTTC TCAAAATTCC GATAGTAATC TGGACGTAAA   540
AAAATTTAAA CCATATTCTT TTAATCGAGA CGATCAGGTT GCGTAGATTA TGTTTTCTTC   600
TGGTACAACT GGTCTGCCGA AGGGAGTCAT GCTAACTCAC AAGAATATTG TTGCACGATT   660
TTCTCTTGCA AAAGATCCTA CTTTTGGTAA CGCAATTAAT CCCACGACAG CAATTTTAAC   720
GGTAATACCT TTCCACCATG GTTTTGGTAT GATGACCACA TTAGGATACT TTACTTGTGG   780
ATTCCGAGTT GTTCTAATGC ACACGTTTGA AGAAAACTA TTTCTACAAT CATTACAAGA    840
TTATAAAGTG GAAAGTACTT TACTTGTACC AACATTAATG GCATTTCTTG CAAAAAGTGC   900
ATTAGTTGAA AAGTACGATT TATCGCACTT AAAAGAAATT GCATCTGGTG GCGCACCTTT   960
ATCAAAAGAA ATTGGGGAGA TGGTGAAAAA ACGGTTTAAA TTAAACTTTG TCAGGCAAGG  1020
GTATGGATTA ACAGAAACCA CTTCGGCTGT TTTAATTACA CCGAAAGGTG ACGCCAAACC  1080
GGGATCAACT GGTAAAATAG TACCATTTCA CGCTGTTAAA GTTGTCGATC CTACAACAGG  1140
AAAAATTTTG GGGCCAAATG AACCTGGAGA ATTGTATTTT AAAGGCCCGA TGATAATGAA  1200
GGGTTATTAT AATAATGAAG AAGCTACTAA AGCAATTATT GATAATGACG GATGGTTGCG  1260
CTCTGGTGAT ATTGCTTATT ATGACAATGA TGGCCATTTT TATATTGTGG ACAGGCTGAA  1320
GTCACTGATT AAATATAAAG GTTATCAGGT TGCACCTGCT GAAATTGAGG GAATACTCTT  1380
ACAACATCCG TATATTGTTG ATGCCGGCGT TACTGGTATA CCGGATGAAG CCGCGGGCGA  1440
GCTTCCAGCT GCAGGTGTTG TAGTACAGAC TGGAAAATAT CTAAACGAAC AAATCGTACA  1500
AGATTATGTT GCCAGTCAAG TTTCAACAGC CAAATGGCTA CGTGGTGGGG TGAAATTTTT  1560
GGATGAAATT CCCAAAGGAT CAACTGGAAA AATTGACAGA AAAGTGTTAA GACAAATGTT  1620
TGAAAAACAC ACCAATGGG                                             1639
```

FIG. 42

Luc90-1B5 (SEQ ID NO:24)

```
            M   A   D   K   N   I   L   Y   G   P   E   P   F   Y   P   L   E   D    20
    G   T   A   G   E   Q   M   F   D   A   L   S   R   Y   A   D   I   P   G   C    40
    I   A   L   T   N   A   H   T   K   E   N   V   L   Y   E   E   F   L   K   L    60
    S   C   R   L   A   E   S   F   K   K   Y   G   L   K   Q   N   D   T   I   A    80
    V   C   S   E   N   G   L   Q   F   F   L   P   V   I   A   S   L   Y   L   G   100
    I   I   Y   A   P   V   N   D   K   Y   I   E   R   E   L   I   H   S   L   G   120
    I   V   K   P   R   I   V   F   C   S   K   N   T   F   Q   K   V   L   N   V   140
    K   S   K   L   K   S   I   E   T   I   I   I   L   D   L   N   E   D   L   G   160
    G   Y   Q   C   L   N   N   F   I   S   Q   N   S   D   S   N   L   D   V   K   180
    K   F   K   P   Y   S   F   N   R   D   D   Q   V   A   L   I   M   F   S   S   200
    G   T   T   G   L   P   K   G   V   M   L   T   H   K   N   I   V   A   R   F   220
    S   L   A   K   D   P   T   F   G   N   A   I   N   P   T   T   A   I   L   T   240
    V   I   P   F   H   H   G   F   G   M   M   T   T   L   G   Y   F   T   C   G   260
    F   R   V   V   L   M   H   T   F   E   E   K   L   F   L   Q   S   L   Q   D   280
    Y   K   V   E   S   T   L   L   V   P   T   L   M   A   F   L   A   K   S   A   300
    L   V   E   K   Y   D   L   S   H   L   K   E   I   A   S   G   G   A   P   L   320
    S   K   E   I   G   E   M   V   K   K   R   F   K   L   N   F   V   R   Q   G   340
    Y   G   L   T   E   T   T   S   A   V   L   I   T   P   K   G   D   A   K   P   360
    G   S   T   G   K   I   V   P   F   H   A   V   K   V   V   D   P   T   T   G   380
    K   I   L   G   P   N   E   P   G   E   L   Y   F   K   G   P   M   I   M   K   400
    G   Y   Y   N   N   E   E   A   T   K   A   I   I   D   N   D   G   W   L   R   420
    S   G   D   I   A   Y   Y   D   N   D   G   H   F   Y   I   V   D   R   L   K   440
    S   L   I   K   Y   K   G   Y   Q   V   A   P   A   E   I   E   G   I   L   L   460
    Q   H   P   Y   I   V   D   A   G   V   T   G   I   P   D   E   A   A   G   E   480
    L   P   A   A   G   V   V   V   Q   T   G   K   Y   L   N   E   Q   I   V   Q   500
    D   Y   V   A   S   Q   V   S   T   A   K   W   L   R   G   V   K   F   L   520
    D   E   I   P   K   G   S   T   G   K   I   D   R   K   V   L   R   Q   M   F   540
    E   K   H   T   N   G                                                             546
```

FIG. 43 lucPpe2 [T249M] (SEQ ID NO:12)

```
GGATCCAATG GAAGATAAAA ATATTTTATA TGGACCTGAA CCATTTTATC CCTTGGCTGA    60
TGGGACGGCT GGAGAACAGA TGTTTTACGC ATTATCTCGT TATGCAGATA TTTCAGGATG   120
CATAGCATTG ACAAATGCTC ATACAAAAGA AAATGTTTTA TATGAAGAGT TTTTAAAATT   180
GTCGTGTCGT TTAGCGGAAA GTTTTAAAAA GTATGGATTA AAACAAAACG ACACAATAGC   240
GGTGTGTAGC GAAAATGGTT TGCAATTTTT CCTTCCTTTA ATTGCATCAT TGTATCTTGG   300
AATAATTGCA GCACCTGTTA GTGATAAATA CATTGAACGT GAATTAATAC ACAGTCTTGG   360
TATTGTAAAA CCACGCATAA TTTTTTGTTC CAAGAATACT TTTCAAAAAG TACTGAATGT   420
AAAATCTAAA TTAAAATATG TAGAAACTAT TATTATATTA GACTTAAATG AAGACTTAGG   480
AGGTTATCAA TGCCTCAACA ACTTTATTTC TCAAAATTCC GATATTAATC TTGACGTAAA   540
AAAATTTAAA CCAAATTCTT TTAATCGAGA CGATCAGGTT GCGTTGGTAA TGTTTTCTTC   600
TGGTACAACT GGTGTTTCGA AGGGAGTCAT GCTAACTCAC AAGAATATTG TTGCACGATT   660
TTCTCATTGC AAAGATCCTA CTTTTGGTAA CGCAATTAAT CCAACGACAG CAATTTTAAC   720
GGTAATACCT TTCCACCATG GTTTTGGTAT GATGACCACA TTAGGATACT TTACTTGTGG   780
ATTCCGAGTT GCTCTAATGC ACACGTTTGA AGAAAAACTA TTTCTACAAT CATTACAAGA   840
TTATAAAGTG GAAAGTACTT TACTTGTACC AACATTAATG GCATTTTTTG CAAAAAGTGC   900
ATTAGTTGAA AAGTACGATT TATCGCACTT AAAAGAAATT GCATCTGGTG GCGCACCTTT   960
ATCAAAAGAA ATTGGGGAGA TGGTGAAAAA ACGGTTTAAA TTAAACTTTG TCAGGCAAGG  1020
GTATGGATTA ACAGAAACCA CTTCGGCTGT TTTAATTACA CCGGACACTG ACGTCAGACC  1080
GGGATCAACT GGTAAAATAG TACCATTTCA CGCTGTTAAA GTTGTCGATC CTACAACAGG  1140
AAAAATTTTG GGGCCAAATG AAACTGGAGA ATTGTATTTT AAAGGCGACA TGATAATGAA  1200
AAGTTATTAT AATAATGAAG AAGCTACTAA AGCAATTATT AACAAAGACG GATGGTTGCG  1260
CTCTGGTGAT ATTGCTTATT ATGACAATGA TGGCCATTTT TATATTGTGG ACAGGCTGAA  1320
GTCATTAATT AAATATAAAG GTTATCAGGT TGCACCTGCT GAAATTGAGG GAATACTCTT  1380
ACAACATCCG TATATTGTTG ATGCCGGCGT TACTGGTATA CCGGATGAAG CCGCGGGCGA  1440
GCTTCCAGCT GCAGGTGTTG TAGTACAGAC TGGAAAATAT CTAAACGAAC AAATCGTACA  1500
AAATTTTGTT TCCAGTCAAG TTTCAACAGC AAATGGCTA CGTGGTGGGG TGAAATTTTT  1560
GGATGAAATT CCCAAAGGAT CAACTGGAAA AATTGACAGA AAAGTGTTAA GACAAATGTT  1620
TGAAAAACAC AAATCTAAGC TG                                          1642
```

FIG. 44

LucPpe2 [T249M] (SEQ ID NO:25)

LucPpL 81-6G1 (SEQ ID NO:26)

LucPpl 81-6G1

```
ATGATGAAGC GAGAGAAAAA TGTTATATAT GGACCCGAAC CCCTACACCC CTTGGAAGAC
TTAACAGCTG GAGAAATGCT CTTCCGTGCC CTTCGAAAAC ATTCTCATTT ACCGCAGGCT
TTAGTAGATG TGGTTGGCGA CGAATCGCTT TCCTATAAAG AGTTTTTTGA AGCGACAGTC
CTCCTAGCGC AAAGTCTCCA CAATTGTGGA TACAAGATGA ATGATGTAGT GTCGATCTGC
GCCGAGAATA ATACAAGATT TTTTATTCCC GTTATTGCAG CTTGGTATAT TGGTATGATT
GTAGCACCTG TTAATGAAAG TTACATCCCA GATGAACTCT GTAAGGTGAT GGGTATATCG
AAACCACAAA TAGTTTTTAC GACAAAGAAC ATTTTAAATA AGGTATTGGA GGTACAGAGC
AGAACTAATT TCATAAAAAG GATCATCATA CTTGATACTG TAGAAAACAT ACACGGTTGT
GAAAGTCTTC CCAATTTTAT TTCTCGTTAT TCGGATGGAA ATATTGCCAA CTTCAAACCT
TTACATTTCG ATCCTGTTGA GCAAGTGGCA GCTATCTTAT GTTCGTCAGG CACTACTGGA
TTACCGAAAG GTGTAATGCA AACTCACCAA AATATTTGTG TCCGACTTAT ACATGCTTTA
GACCCCAGGG CAGGAACGCA ACTTATTCCT GGTGTGACAG TCTTAGTATA TCTGCCTTTT
TTCCATGCTT TTGGGTTCTC TATAACCTTG GGATACTTCA TGGTGGGTCT TCGTGTTATC
ATGTTCAGAC GATTTGATCA AGAAGCATTT CTAAAAGCTA TTCAGGATTA TGAAGTTCGA
AGTGTAATTA ACGTTCCATC AGTAATATTG TTCTTATCGA AAAGTCCTTT GGTTGACAAA
TACGATTTAT CAAGTTTAAG GGAATTGTGT TGCGGTGCGG CACCATTAGC AAAAGAAGTT
GCTGAGGTTG CAGCAAAACG ATTAAACTTG CCAGGAATTC GCTGTGGATT TGGTTTGACA
GAATCTACTT CAGCTAATAT ACACAGTCTT AGGGATGAAT TTAAATCAGG ATCACTTGGA
AGAGTTACTC CTTTAATGGC AGCTAAAATA GCAGATAGGG AAACTGGTAA AGCATTGGGA
CCAAATCAAG TTGGTGAATT ATGCATTAAA GGTCCCATGG TATCGAAAGG TTACGTGAAC
AATGTAGAAG CTACCAAAGA AGCTATTGAT GATGATGGTT GGCTTCACTC TGGAGACTTT
GGATACTATG ATGAGGATGA GCATTTCTAT GTGGTGGACC GTTACAAGGA ATTGATTAAA
TATAAGGGCT CTCAGGTAGC ACCTGCAGAA CTAGAAGAGA TTTTATTGAA AAATCCATGT
ATCAGAGATG TTGCTGTGGT TGGTATTCCT GATCTAGAAG CTGGAGAACT GCCATCTGCG
TTTGTGGTTA AACAGCCCGG AAAGGAGATT ACAGCTAAAG AAGTGTACGA TTATCTTGCC
GAGAGGGTCT CCCATACAAA GTATTTGCGT GGAGGGGTTC GATTCGTTGA TAGCATACCA
AGGAATGTTA CAGGTAAAAT TACAAGAAAG GAACTTCTGA AGCAGTTGCT GGAGAAGGCG
GGAGGT
```

FIG. 47

Luc133-1B2 (SEQ ID NO:42)

```
AGATCCAATG GCAGATAAGA ATATTTTATA TGGGCCCGAA CCATTTTATC CCTTGGAAGA    60
TGGGACGGCT GGAGAACAGA TGTTTGACGC ATTATCTCGT TATGCAGATA TTCCGGGCTG   120
CATAGCATTG ACAAATGCTC ATACAAAAGA AAATGTTTTA TATGAAGAGT TTCTGAAACT   180
GTCGTGTCGT TTAGCGGAAA GTTTTAAAAA GTATGGATTA AAACAAAACG ACACAATAGC   240
GGTGTGTAGC GAAAATAGTC TGCAATTTTT CCTTCCTGTA ATTGCATCAT TGTATCTTGG   300
AATAATTGTG GCACCTGTTA ACGATAAATA CATTGAACGT GAATTAATAC ACAGTCTTGG   360
TATTGTAAAA CCACGCATAG TTTTTTGCTC CAAGAATACT TTTCAAAAAG TACTGAATGT   420
AAAATCTAAA TTAAAATCTA TTGAAACTAT TATTATATTA GACTTAAATG ATGACTTAGG   480
AGGTTATCAA TGCCTCAACA ACTTTATTTC TCAAAATTCC GATAGTAATC TGGACGTAAA   540
AAAATTTAAA CCATATTCTT TTAATCGAGA CGATCAGGTT GCGTTGATTA TGTTTTCTTC   600
TGGTACAACT GGTCTGCCGA AGGGAGTCAT GCTAACTCAC AAGAATATTG TTGCACGATT   660
TTCTATTGCA AAAGATCCTA CTTTTGGTAA CGCAATTAAT CCCACGTCAG CAATTTTAAC   720
GGTAATACCT TTCCACCATG GTTTTGGTAT GATGACCACA TTAGGATACT TTACTTGTGG   780
ATTCCGAGTT GTTCTAATGC ACACGTTTGA AGAAAAACTA TTTCTACAAT CATTACAAGA   840
TTATAAAGTG GAAAGTACTT TACTTGTACC AACATTAATG GCATTTCTTG CAAAAAGTGC   900
ATTAGTTGAA AAGTACGATT TATCGCACTT AAAAGAAATT GCATCTGGTG GCGCACCTTT   960
ATCAAAAGAA ATTGGGGAGA TGGTGAAAAA ACGGTTTAAA TTAAACTTTG TCAGGCAAGG  1020
GTATGGATTA ACAGAAACCA CTTCGGCTGT TTTAATTACA CCGAAAGGTG ACGCCAAACC  1080
GGGATCAACT GGTAAAATAG TACCATTTCA CGCTGTTAAA GTTGTCGATC CTACAACAGG  1140
AAAAATTTTG GGGCCAAATG AACCTGGAGA ATTGTATTTT AAAGGCCCGA TGATAATGAA  1200
GGGTTATTAT AATAATGAAG AAGCTACTAA AGCAATTATT GATAATGACG GATGGTTGCG  1260
CTCTGGTGAT ATTGCTTATT ATGACAATGA TGGCCATTTT TATATTGTGG ACAGGCTGAA  1320
GTCACTGATT AAATATAAAG GTTATCAGGT TGCACCTGCT GAAATTGAGG AATACTCTT  1380
ACAACATCCG TATATTGTTG ATGCCGGCGT TACTGGTATA CCGGATGAAG CCGCGGGCGA  1440
GCTTCCAGCT GCAGGTGTTG TAGTACAGAC TGGAAAATAT CTAAACGAAC AAATCGTACA  1500
AGATTATGTT GCCAGTCAAG TTTCAACAGC CAAATGGCTA CGTGGTGGGG TGATATTTTT  1560
GGATGAAATT CCCAAAGGAT CAACTGGAAA AATTGACAGA AAAGTGTTAA GACAAATGTT  1620
AGAAAAACAC ACCAATGGG                                              1639
```

FIG. 55

Luc146-1H2 (SEQ ID NO:43)

```
GGATCCAATG GCAGATAAGA ATATTTTATA TGGGCCCGAA CCATTTTATC CCTTGGAAGA    60
TGGGACGGCT GGAGAACAGA TGTTTGACGC ATTATCTCGT TATGCAGCTA TTCCGGGCTG   120
CATAGCATTG ACAAATGCTC ATACAAAAGA AAATGTTTTA TATGAAGAGT TTCTGAAACT   180
GTCGTGTCGT TTAGCGGAAA GTTTTAAAAA GTATGGATTA AAACAAAACG ACACAATAGC   240
GGTGTGTAGC GAAAATAGTC TGCAATTTTT CCTTCCTGTA ATTGCATCAT TGTATCTTGG   300
AATAATTGTG GCACCTGTTA ACGATAAATA CATTGAACGT GAATTAATAC ACAGTCTTGG   360
TATTGTAAAA CCACGCATAG TTTTTTGCTC CAAGAATACT TTTCAAAAAG TACTGAATGT   420
AAAATCTAAA TTAAAATCTA TTGAAACTAT TATTATATTA GACTTAAATG AAGACTTAGG   480
AGGTTATCAA TGCCTCAACA ACTTTATTTC TCAAAATTCC GATAGTAATC TGGACGTAAA   540
AAAATTTAAA CCCTATTCTT TTAATCGAGA CGATCAGGTT GCGTCGATTA TGTTTTCTTC   600
TGGTACAACT GGTCTGCCGA AGGGAGTCAT GCTAACTCAC AAGAATATTG TTGCACGATT   660
TTCTATTGCA AAAGATCCTA CTTTTGGTAA CGCAATTAAT CCCACGTCAG CAATTTTAAC   720
GGTAATACCT TTCCACCATG GTTTTGGTAT GATGACCACA TTAGGATACT TTACTTGTGG   780
ATTCCGAGTT GTTCTAATGC ACACGTTTGA AGAAAAACTA TTTCTACAAT CATTACAAGA   840
TTATAAAGTG GAAAGTACTT TACTTGTACC AACATTAATG GCATTTCTTG CAAAAAGTGC   900
ATTAGTTGAA AAGTACGATT TATCGCACTT AAAAGAAATT GCATCTGGTG GCGCACCTTT   960
ATCAAAAGAA ATTGGGGAGA TGGTGAAAAA ACGGTTTAAA TTAAACTTTG TCAGGCAAGG  1020
GTATGGATTA ACAGAAACCA CTTCGGCTGT TTTAATTACA CCGAAAGGTG ACGCCAAACC  1080
GGGATCAACT GGTAAAATAG TACCATTACA CGCTGTTAAA GTTGTCGATC CTACAACAGG  1140
AAAAATTTTG GGGCCAAATG AACCTGGAGA ATTGTATTTT AAAGGCCCGA TGATAATGAA  1200
GGGTTATTAT AATAATGAAG AAGCTACTAA AGCAATTATT GATAATGACG GATGGTTGCG  1260
CTCTGGTGAT ATTGCTTATT ATGACAATGA TGGCCATTTT TATATTGTGG ACAGGCTGAA  1320
GTCACTGATT AAATATAAAG GTTATCAGGT TGCACCTGCT GAAATTGAGG GAATACTCTT  1380
ACAACATCCG TATATTGTTG ATGCCGGCGT TACTGGTATA CCGGATGAAG CCGCGGGCGA  1440
GCTTCCAGCT GCAGGTGTTG TAGTACAGAC TGGAAAATAT CTAAACGAAC AAATCGTACA  1500
AGATTATGTT GCCAGTCAAG TTTCAACAGC CAAATGGCTA CGTGGTGGG TGAAATTTTT  1560
GGATGAAATT CCCAAAGGAT CAACTGGAAA AATTGACAGA AAAGTGTTAA GACAAATGTT  1620
AGAAAAACAC ACCAATGGG                                              1639
```

FIG. 56

Luc133-1B2 (SEQ ID NO:44)

|   |   | M | A | D | K | N | I | L | Y | G | P | E | P | F | Y | P | L | E | D | 20 |
|---|---|---|---|---|---|---|---|---|---|---|---|---|---|---|---|---|---|---|---|---|
| G | T | A | G | E | Q | M | F | D | A | L | S | R | Y | A | D | I | P | G | C | 40 |
| I | A | L | T | N | A | H | T | K | E | N | V | L | Y | E | E | F | L | K | L | 60 |
| S | C | R | L | A | E | S | F | K | K | Y | G | L | K | Q | N | D | T | I | A | 80 |
| V | C | S | E | N | S | L | Q | F | F | L | P | V | I | A | S | L | Y | L | G | 100 |
| I | I | V | A | P | V | N | D | K | Y | I | E | R | E | L | I | H | S | L | G | 120 |
| I | V | K | P | R | I | V | F | C | S | K | N | T | F | Q | K | V | L | N | V | 140 |
| K | S | K | L | K | S | I | E | T | I | I | I | L | D | L | N | D | D | L | G | 160 |
| G | Y | Q | C | L | N | N | F | I | S | Q | N | S | D | S | N | L | D | V | K | 180 |
| K | F | K | P | Y | S | F | N | R | D | D | Q | V | A | L | I | M | F | S | S | 200 |
| G | T | T | G | L | P | K | G | V | M | L | T | H | K | N | I | V | A | R | F | 220 |
| S | I | A | K | D | P | T | F | G | N | A | I | N | P | T | S | A | I | L | T | 240 |
| V | I | P | F | H | H | G | F | G | M | M | T | T | L | G | Y | F | T | C | G | 260 |
| F | R | V | V | L | M | H | T | F | E | E | K | L | F | L | Q | S | L | Q | D | 280 |
| Y | K | V | E | S | T | L | L | V | P | T | L | M | A | F | L | A | K | S | A | 300 |
| L | V | E | K | Y | D | L | S | H | L | K | E | I | A | S | G | G | A | P | L | 320 |
| S | K | E | I | G | E | M | V | K | K | R | F | K | L | N | F | V | R | Q | G | 340 |
| Y | G | L | T | E | T | T | S | A | V | L | I | T | P | K | G | D | A | K | P | 360 |
| G | S | T | G | K | I | V | P | F | H | A | V | K | V | V | D | P | T | T | G | 380 |
| K | I | L | G | P | N | E | P | G | E | L | Y | F | K | G | P | M | I | M | K | 400 |
| G | Y | Y | N | N | E | E | A | T | K | A | I | I | D | N | D | G | W | L | R | 420 |
| S | G | D | I | A | Y | Y | D | N | D | G | H | F | Y | I | V | D | R | L | K | 440 |
| S | L | I | K | Y | K | G | Y | Q | V | A | P | A | E | I | E | G | I | L | L | 460 |
| Q | H | P | Y | I | V | D | A | G | V | T | G | I | P | D | E | A | A | G | E | 480 |
| L | P | A | A | G | V | V | V | Q | T | G | K | Y | L | N | E | Q | I | V | Q | 500 |
| D | Y | V | A | S | Q | V | S | T | A | K | W | L | R | G | G | V | I | F | L | 520 |
| D | E | I | P | K | G | S | T | G | K | I | D | R | K | V | L | R | Q | M | L | 540 |
| E | K | H | T | N | G |   |   |   |   |   |   |   |   |   |   |   |   |   |   |   |

FIG. 57

Luc146-1H2 (SEQ ID NO:45)

LucPpl81-0B11

```
GGATCCCATG ATGAAGCGAG AGAAAAATGT TATATATGGA CCCGAACCCC TACACCCCTT  60
GGAAGACTTA ACAGCTGGAG AAATGCTCTT CCGTGCCCTT CGAAAACATT CTCATTTACC 120
GCAGGCTTTA GTAGATGTGG TTGGCGACGA ATCGCTTTCC TATAAAGAGT TTTTTGAAGC 180
CACAGTCCTC CTAGCGCAAA GTCTCCACAA TTGTGGATAC AAGATGAATG ATGTAGTGTC 240
GATCTGCGCC GAGAATAATA CAAGATTTTT TATTCCCGTT ATTGCAGCTT GGTATATTGG 300
TATGATTGTA GCACCTGTTA ATGAAAGTTA CATCCAGAT GAACTCTGTA AGGTCATGGG 360
TATATCGAAA CCACAAATAG TTTTTACGAC AAAGAACATT TTAAATAAGG TATTGGAGGT 420
ACAGAGCAGA ACTAATTTCA TAAAAAGGAT CATCGTACTT GATACTGTAG AAAACATACA 480
CGGTTGTGAA AGTCTTCCCA ATTTTATTTC TCGTTATTCG GATGGAAATA TTGCCAACTT 540
CAAACCTTTA CATTTCGATC CTGTAGAGCA AGTGGCAGCT ATCTTATGTT CGTCAGGCAC 600
TACTGGATTA CCGAAAGGTG TAATGCAAAC TCACCAAAAT ATTTGTGTCC GACTTATACA 660
TGCTTTAGAC CCCAGGGCAG GAACGCAACT TATTCCTGGT GTGACAGTCT TAGTATATCT 720
GCCTTTTTTC CATGCTTTTG GGTTCTCTAT AACCTTGGGA TACTTCATGG TGGGTCTTCG 780
TGTTATCATG TCAAGACGAT TTGATCCAGA AGCATTTCTA AAAGCTATTC AGGATTATGA 840
AGTTCGAAGT GTAATTAACG TTCCATCAGT AATATTGTTC TTATCGAAAA GTCCTTTGGT 900
TGACAAATAC GATTATCAA GTTTAAGGGA ATTGTGTTGC GGTGCGGCAC CATTAGCAAA 960
AGAAGTTGCT GAGGTTGCAG CAAAACGATT AAACTTGCCA GGAATTCGCT GTGGATTTGG 1020
TTTGACAGAA TCTACTTCAG CTAATATACA CAGTCTTAGG GATGAATTTA AACCAGGATC 1080
ACTTGGAAGA GTTACTCCTT TAATGGCAGC TAAAATAGCA GATAGGGAAA CTGGTAAAGC 1140
ATTGGGACCA AATCAAGTTG GTGAATTATG CATTAAAGGT CCCATGGTAT CGAAAGGTTA 1200
CGTGAACAAT GTAGAAGCTA CCAAAGAAGC TATTGATGAT GATGGTTGGC TTCACTCTGG 1260
AGACTTTGGA TACTATGATG AGGATGAGCA TTTCTATGTG GTGGACCGTT ACAAGGAATT 1320
GATTAAATAT AAGGGCTCTC AGGTAGCACC TGCAGAACTA GAAGAGATTT TATTGAAAAA 1380
TCCATGTATC AGAGATGTTG CTGTGGTTGG TATTCCTGAT CTAGAAGCTG GAGAACTGCC 1440
ATCTGCGTTT GTGGTTAAAC AGCCCGGAAA GGAGATTACA GCTAAAGAAG TGTACGATTA 1500
TCTTGCCGAG AGGGTCTCCC ATACAAAGTA TTTGCGTGGA GGGGTTCGAT TCGTTGATAG 1560
CATACCACGG AATGTTACAG GTAAAATTAC AAGAAAGGAA CTTCTGAAGC AGTTGCTGGA 1620
GAAGGCGGGA GGT
```

FIG. 65

LucPpl 81-OB11

SEQUENCE LISTING

<160> NUMBER OF SEQ ID NOS: 93

<210> SEQ ID NO 1
<211> LENGTH: 1639
<212> TYPE: DNA
<213> ORGANISM: Artificial Sequence
<220> FEATURE:
<223> OTHER INFORMATION: Mutant luciferase

<400> SEQUENCE: 1

| | | | | | |
|---|---|---|---|---|---|
| ggatccaatg | gcagataaaa | atattttata | tgggcccgaa | ccattttatc | ccttggctga | 60 |
| tgggacggct | ggagaacaga | tgttttacgc | attatctcgt | tatgcagata | tttcaggatg | 120 |
| catagcattg | acaaatgctc | atacaaaaga | aaatgtttta | tatgaagagt | ttttaaaatt | 180 |
| gtcgtgtcgt | ttagcggaaa | gttttaaaaa | gtatggatta | aaacaaaacg | acacaatagc | 240 |
| ggtgtgtagc | gaaatggtt | tgcaattttt | ccttcctata | attgcatcat | tgtatcttgg | 300 |
| aataattgca | gcacctgtta | gtgataaata | cattgaacgt | gaattaatac | acagtcttgg | 360 |
| tattgtaaaa | ccacgcataa | ttttttgctc | caagaatact | tttcaaaaag | tactgaatgt | 420 |
| aaaatctaaa | ttaaaatatg | tagaaactat | tattatatta | gacttaaatg | aagacttagg | 480 |
| aggttatcaa | tgcctcaaca | actttatttc | tcaaaattcc | gatattaatc | tggacgtaaa | 540 |
| aaaatttaaa | ccatattctt | ttaatcgaga | cgatcaggtt | gcgttggtaa | tgttttcttc | 600 |
| tggtacaact | ggtgtttcga | agggagtcat | gctaactcac | aagaatattg | ttgcacgatt | 660 |
| ttctcttgca | aaagatccta | cttttggtaa | cgcaattaat | ccaacgacag | caattttaac | 720 |
| ggtaatacct | ttccaccatg | gttttggtat | gatgaccaca | ttaggatact | ttacttgtgg | 780 |
| attccgagtt | gttctaatgc | acacgtttga | agaaaaacta | tttctacaat | cattacaaga | 840 |
| ttataaagtg | gaaagtactt | tacttgtacc | aacattaatg | gcatttcttg | caaaaagtgc | 900 |
| attagttgaa | aagtacgatt | tatcgcactt | aaaagaaatt | gcatctggtg | gcgcaccttt | 960 |
| atcaaaagaa | attgggggaga | tggtgaaaaa | acggtttaaa | ttaaactttg | tcaggcaagg | 1020 |
| gtatggatta | acagaaacca | cttcggctgt | tttaattaca | ccgaacaatg | acgtcagacc | 1080 |
| gggatcaact | ggtaaaatag | taccatttca | cgctgttaaa | gttgtcgatc | ctacaacagg | 1140 |
| aaaaattttg | gggccaaatg | aacctggaga | attgtatttt | aaaggcgaca | tgataatgaa | 1200 |
| aggttattat | aataatgaag | aagctactaa | agcaattatt | aacaaagacg | gatggttgcg | 1260 |
| ctctggtgat | attgcttatt | atgacaatga | tggccatttt | tatattgtgg | acaggctgaa | 1320 |
| gtcattaatt | aaatataaag | gttatcaggt | tgcacctgct | gaaattgagg | gaatactctt | 1380 |
| acaacatccg | tatattgttg | atgccggcgt | tactggtata | ccggatgaag | ccgcgggcga | 1440 |
| gcttccagct | gcaggtgttg | tagtacgac | tggaaaatat | ctaaacgaac | aaatcgtaca | 1500 |
| aaattttgtt | tccagtcaag | tttcaacagc | caaatggcta | cgtggtgggg | tgaaattttt | 1560 |
| ggatgaaatt | cccaaaggat | caactggaaa | aattgacaga | aaagtgttaa | gacaaatgtt | 1620 |
| tgaaaaacac | accaatggg | | | | | 1639 |

<210> SEQ ID NO 2
<211> LENGTH: 1639
<212> TYPE: DNA
<213> ORGANISM: Artificial Sequence
<220> FEATURE:
<223> OTHER INFORMATION: Mutant luciferase

<400> SEQUENCE: 2

```
ggatccaatg gaagataaaa atattttata tggacctgaa ccattttatc ccttggctga      60
tgggacggct ggagaacaga tgttttacgc attatctcgt tatgcagata tttcaggatg     120
catagcattg acaaatgctc atacaaaagc ccctgtttta tatgaagagt tgttaaaatt     180
gtcgtgtcgt ttagcggaaa gttttaaaaa gtatggatta aaacaaaacg acacaatagc     240
ggtgtgtagc gaaaatggtt tgcaattttt ccttcctata attgcatcat tgtatcttgg     300
aataattgca gcacctgtta gtgataaata cattgaacgt gaattaatac acagtcttgg     360
tattgtaaaa ccacgcataa ttttttgctc caagaatact tttcaaaaag tactgaatgt     420
aaaatctaaa ttaaaatatg tagaaactat tattatatta gacttaaatg aagacttagg     480
aggttatcaa tgcctcaaca actttatttc tcaaaattcc gatattaatc tggacgtaaa     540
aaaatttaaa ccatattctt ttaatcgaga cgatcaggtt gcgttggtaa tgttttcttc     600
tggtacaact ggtgtttcga agggagtcat gctaactcac aagaatattg ttgcacgatt     660
ttctcatgca aaagatccta cttttggtaa cgcaattaat ccaacgacag caattttaac     720
ggtaatacct ttccaccatg gttttggtat gatgaccaca ttaggatact ttacttgtgg     780
attccgagtt gttctaatgc acacgtttga agaaaaacta tttctacaat cattacaaga     840
ttataaagtg gaaagtactt tacttgtacc aacattaatg gcattttttg caaaaagtgc     900
attagttgaa aagtacgatt tatcgcactt aaaagaaatt gcatctggtg gcgcaccttt     960
atcaaaagaa attggggaga tggtgaaaaa acggtttaaa ttaaactttg tcaggcaagg    1020
gtatggatta acagaaacca cttcggctgt tttaattaca ccgaacaatg acgtcagacc    1080
gggatcaact ggtaaaatag taccatttca cgctgttaaa gttgtcgatc ctacaacagg    1140
aaaaattttg gggccaaatg aaactggaga attgtatttt aaaggcgaca tgataatgaa    1200
aggttattat aataatgaag aagctactaa agcaattatt aacaaagacg gatggttgcg    1260
ctctggtgat attgcttatt atgacaatga tggccatttt tatattgtgg acaggctgaa    1320
gtcattaatt aaatataaag gttatcaggt tgcacctgct gaaattgagg gaatactctt    1380
acaacatccg tatattgttg atgccggcgt tactggtata ccggatgaag ccgcgggcga    1440
gcttccagct gcaggtgttg tagtacagac tggaaaatat ctaaacgaac aaatcgtaca    1500
aaattttgtt tccagtcaag tttcaacagc caaatggcta cgtggtgggg tgaaattttt    1560
ggatgaaatt cccaaaggat caactggaaa aattgacaga aaagtgttaa gacaaatgtt    1620
tgaaaaacac accaatggg                                                 1639

<210> SEQ ID NO 3
<211> LENGTH: 1639
<212> TYPE: DNA
<213> ORGANISM: Artificial Sequence
<220> FEATURE:
<223> OTHER INFORMATION: Mutant luciferase

<400> SEQUENCE: 3
ggatccaatg gaagataaaa atattttata tggacctgaa ccattttatc ccttggctga      60
tgggacggct ggagaacaga tgttttacgc attatctcgt tatgcagata tttcaggatg     120
catagcattg acaaatgctc atacaaaagc ccctgtttta tatgaagagt ttttaaaatt     180
gtcgtgtcgt ttagcggaaa gttttaaaaa gtatggatta aaacaaaacg acacaatagc     240
ggtgtgtagc gaaaatggtt tgcaattttt ccttcctata attgcatcat tgtatcttgg     300
aataattgca gcacctgtta gtgataaata cattgaacgt gaattaatac acagtcttgg     360
```

-continued

| | |
|---|---|
| tattgtaaaa ccacgcataa ttttttgctc caagaatact tttcaaaaag tactgaatgt | 420 |
| aaaatctaaa ttaaaatatg tagaaactat tattatatta gacttaaatg aagacttagg | 480 |
| aggttatcaa tgcctcaaca actttatttc tcaaaattcc gatattaatc ttgacgtaaa | 540 |
| aaaatttaaa ccatattctt ttaatcgaga cgatcaggtt gcgttggtaa tgttttcttc | 600 |
| tggtacaact ggtgtttcga agggagtcat gctaactcac aagaatattg ttgtacgatt | 660 |
| ttcttatgca aaagatccta cttttggtaa cgcaattaat ccaacgacag caattttaac | 720 |
| ggtaatacct ttccaccatg gttttggtat gatgaccaca ttaggatact ttacttgtgg | 780 |
| attccgagtt gttctaatgc acacgtttga agaaaaacta tttctacaat cattacaaga | 840 |
| ttataaagtg gaaagtactt tacttgtacc aacattaatg gcatttcttg caaaaagtgc | 900 |
| attagttgaa aagtacgatt tatcgcactt aaaagaaatt gcatctggtg gcgcaccttt | 960 |
| atcaaaagaa attggggaga tggtgaaaaa acggtttaaa ttaaactttg tcaggcaagg | 1020 |
| gtatggatta acagaaacca cttcggctgt tttaattaca ccgaacaatg acgtcagacc | 1080 |
| gggatcaact ggtaaaatag taccatttca cgctgttaaa gttgtcgatc ctacaacagg | 1140 |
| aaaaattttg gggccaaatg aaactggaga attgtatttt aaaggcgaca tgataatgaa | 1200 |
| aggttattat aataatgaag aagctactaa agcaattatt aacaaagacg gatggttgcg | 1260 |
| ctctggtgat attgcttatt atgacaatga tggccatttt tatattgtgg acaggctgaa | 1320 |
| gtcattaatt aaatataaag gttatcaggt tgcacctgct gaaattgagg gaatactctt | 1380 |
| acaacatccg tatattgttg atgccggcgt tactggtata ccggatgaag ccgcgggcga | 1440 |
| gcttccagct gcaggtgttg tagtacagac tggaaaatat ctaaacgaac aaatcgtaca | 1500 |
| aaattttgtt tccagtcaag tttcaacagc caaatggcta cgtggtgggg tgaaattttt | 1560 |
| ggatgaaatt cccaaaggat caactggaaa aattgacaga aagtgttaa gacaaatgtt | 1620 |
| tgaaaaacac accaatggg | 1639 |

<210> SEQ ID NO 4
<211> LENGTH: 1639
<212> TYPE: DNA
<213> ORGANISM: Artificial Sequence
<220> FEATURE:
<223> OTHER INFORMATION: Mutant luciferase

<400> SEQUENCE: 4

| | |
|---|---|
| ggatccaatg aagataaaa atattttata tggacctgaa ccatttttatc ccttggctga | 60 |
| tgggacggct ggagaacaga tgttttacgc attatctcgt tatgcagata tttcaggatg | 120 |
| catagcattg acaaatgctc atacaaaagc ccctgtttta tatgaagagt tttttaaaatt | 180 |
| gtcgtgtcgt ttagcggaaa gttttaaaaa gtatggatta aaacaaaacg acacaatagc | 240 |
| ggtgtgtagc gaaaatggtt tgcaatttt ccttcctata attgcatcat tgtatcttgg | 300 |
| aataattgca gcacctgtta gtgataaata cattgaacgt gaattaatac acagtcttgg | 360 |
| tattgtaaaa ccacgcataa ttttttgctc caagaatact tttcaaaaag tactgaatgt | 420 |
| aaaatctaaa ttaaaatatg tagaaactat tattatatta gacttaaatg aagacttagg | 480 |
| aggttatcaa tgcctcaaca actttatttc tcaaaattcc gatattaatc ttgacgtaaa | 540 |
| aaaatttaaa ccatattctt ttaatcgaga cgatcaggtt gcgttggtaa tgttttcttc | 600 |
| tggtacaact ggtgtttcga agggagtcat gctaactcac aagaatattg ttgcacgatt | 660 |
| ttctattgca aaagatccta cttttggtaa cgcaattaat ccaacgacag caattttaac | 720 |
| ggtaatacct ttccaccatg gttttggtat gatgaccaca ttaggatact ttacttgtgg | 780 |

```
attccgagtt gttctaatgc acacgtttga agaaaaacta tttctacaat cattacaaga    840
ttataaagtg gaaagtactt tacttgtacc aacattaatg cattttttg caaaaagtgc    900
attagttgaa aagtacgatt tatcgcactt aaaagaaatt gcatctggtg gcgcaccttt    960
atcaaaagaa attggggaga tggtgaaaaa acggtttaaa ttaaactttg tcaggcaagg    1020
gtatggatta acagaaacca cttcggctgt tttaattaca ccgaacaatg acgtcagacc    1080
gggatcaact ggtaaaatag taccatttca cgctgttaaa gttgtcgatc ctacaacagg    1140
aaaaattttg gggccaaatg aaactggaga attgtatttt aaaggcgaca tgataatgaa    1200
aggttattat aataatgaag aagctactaa agcaattatt aacaaagacg gatggttgcg    1260
ctctggtgat attgcttatt atgacaatga tggccatttt tatattgtgg acaggctgaa    1320
gtcattaatt aaatataaag gttatcaggt tgcacctgct gaaattgagg aatactctt    1380
acaacatccg tatattgttg atgccggcgt tactggtata ccggatgaag ccgcgggcga    1440
gcttccagct gcaggtgttg tagtacagac tggaaaatat ctaaacgaac aaatcgtaca    1500
aaatttttgtt tccagtcaag tttcaacagc caaatggcta cgtggtgggg tgaaattttt    1560
ggatgaaatt cccaaaggat caactggaaa aattgacaga aaagtgttaa gacaaatgtt    1620
tgaaaaacac accaatggg                                                   1639

<210> SEQ ID NO 5
<211> LENGTH: 1639
<212> TYPE: DNA
<213> ORGANISM: Artificial Sequence
<220> FEATURE:
<223> OTHER INFORMATION: Mutant luciferase

<400> SEQUENCE: 5
ggatccaatg aagataaaa atattttata tggacctgaa ccatttttatc ccttggctga    60
tgggacggct ggagaacaga tgtttgacgc attatctcgt tatgcagata tttcaggatg    120
catagcattg acaaatgctc atacaaaagc ccctgtttta tatgaagagt tgttaaaatt    180
gtcgtgtcgt ttagcggaaa gttttaaaaa gtatggatta aaacaaaacg acacaatagc    240
ggtgtgtagc gaaaatggtt tgcaattttt ccttcctata attgcatcat tgtatcttgg    300
aataattgca gcacctgtta gtgataaata cattgaacgt gaattaatac acagtcttgg    360
tattgtaaaa ccacgcataa ttttttgctc caagaatact tttcaaaaag tactgaatgt    420
aaaatctaaa ttaaaatatg tagaaactat tattatatta gacttaaatg aagacttagg    480
aggttatcaa tgcctcaaca actttatttc tcaaaattcc gatattaatc ttgacgtaaa    540
aaaatttaaa ccatattctt ttaatcgaga cgatcaggtt gcgttggtaa tgttttcttc    600
tggtacaact ggtgtttcga agggagtcat gctaactcac aagaatattg ttgcacgatt    660
ttctcatgca aaagatccta cttttggtaa cgcaattaat ccaacgacag caattttaac    720
ggtaatacct ttccaccatg gttttggtat gatgaccaca ttaggatact ttacttgtgg    780
attccgagtt gttctaatgc acacgtttga agaaaaacta tttctacaat cattacaaga    840
ttataaagtg gaaagtactt tacttgtacc aacattaatg cattttttg caaaaagtgc    900
attagttgaa aagtacgatt tatcgcactt aaaagaaatt gcatctggtg gcgcaccttt    960
atcaaaagaa attggggaga tggtgaaaaa acggtttaaa ttaaactttg tcaggcaagg    1020
gtatggatta acagaaacca cttcggctgt tttaattaca ccgaacaatg acgtcagacc    1080
gggatcaact ggtaaaatag taccatttca cgctgttaaa gttgtcgatc ctacaacagg    1140
```

-continued

```
aaaaattttg gggccaaatg aaactggaga attgtatttt aaaggcgaca tgataatgaa      1200
aggttattat aataatgaag aagctactaa agcaattatt aacaaagacg gatggttgcg      1260
ctctggtgat attgcttatt atgacaatga tggccatttt tatattgtgg acaggctgaa      1320
gtcattaatt aaatataaag gttatcaggt tgcacctgct gaaattgagg gaatactctt      1380
acaacatccg tatattgttg atgccggcgt tactggtata ccggatgaag ccgcgggcga      1440
gcttccagct gcaggtgttg tagtacagac tggaaaatat ctaaacgaac aaatcgtaca      1500 aaatttttgtt tccagtcaag tttcaacagc caaatggcta cgtggtgggg tgaaattttt      1560
ggatgaaatt cccaaaggat caactggaaa aattgacaga aaagtgttaa gacaaatgtt      1620
tgaaaaacac accaatggg                                                   1639
```

<210> SEQ ID NO 6
<211> LENGTH: 1639
<212> TYPE: DNA
<213> ORGANISM: Artificial Sequence
<220> FEATURE:
<223> OTHER INFORMATION: Mutant luciferase

<400> SEQUENCE: 6

```
ggatccaatg gcagataaga atatttata tgggcccgaa ccattttatc ccttggctga       60
tgggacggct ggagaacaga tgtttgacgc attatctcgt tatgcagata tttccggatg      120
catagcattg acaaatgctc atacaaaaga aaatgtttta tatgaagagt ttttaaaatt      180
gtcgtgtcgt ttagcggaaa gttttaaaaa gtatggatta aaacaaaacg acacaatagc      240
ggtgtgtagc gaaaatggtt tgcaattttt ccttcctgta attgcatcat tgtatcttgg      300
aataattgca gcacctgtta gtgataaata cattgaacgt gaattaatac acagtcttgg      360
tattgtaaaa ccacgcataa ttttttgctc caagaatact tttcaaaaag tactgaatgt      420
aaaatctaaa ttaaaatctg tagaaactat tattatatta gacttaaatg aagacttagg      480
aggttatcaa tgcctcaaca actttatttc tcaaaattcc gatagtaatc tggacgtaaa      540
aaaatttaaa ccatattctt ttaatcgaga cgatcaggtt gcgttggtaa tgtttctttc      600
tggtacaact ggtgttccga agggagtcat gctaactcac aagaatattg ttgcacgatt      660
ttctcttgca aaagatccta cttttggtaa cgcaattaat cccacgacag caattttaac      720
ggtaatacct ttccaccatg gttttggtat gatgaccaca ttaggatact ttacttgtgg      780
attccgagtt gttctaatgc acacgtttga agaaaaacta tttctacaat cattacaaga      840
ttataaagtg gaaagtactt tacttgtacc aacattaatg gcatttcttg caaaaagtgc      900
attagttgaa aagtacgatt tatcgcactt aaaagaaatt gcatctggtg gcgcaccttt      960
atcaaaagaa attggggaga tggtgaaaaa acggtttaaa ttaaactttg tcaggcaagg     1020
gtatggatta acagaaacca cttcggctgt tttaattaca ccgaaaggtg acgccagacc     1080
gggatcaact ggtaaaatag taccatttca cgctgttaaa gttgtcgatc ctacaacagg     1140
aaaaattttg gggccaaatg aacctggaga attgtatttt aaaggcgcca tgataatgaa     1200
gggttattat aataatgaag aagctactaa agcaattatt gataatacg gatggttgcg     1260 ctctggtgat attgcttatt atgacaatga tggccatttt tatattgtgg acaggctgaa     1320
gtcattaatt aaatataaag gttatcaggt tgcacctgct gaaattgagg gaatactctt     1380
acaacatccg tatattgttg atgccggcgt tactggtata ccggatgaag ccgcgggcga     1440
gcttccagct gcaggtgttg tagtacagac tggaaaatat ctaaacgaac aaatcgtaca     1500 agatttttgtt tccagtcaag tttcaacagc caaatggcta cgtggtgggg tgaaattttt     1560
```

```
ggatgaaatt cccaaaggat caactggaaa aattgacaga aaagtgttaa gacaaatgtt    1620
tgaaaaacac accaatggg                                                 1639

<210> SEQ ID NO 7
<211> LENGTH: 1639
<212> TYPE: DNA
<213> ORGANISM: Artificial Sequence
<220> FEATURE:
<221> NAME/KEY: unsure
<222> LOCATION: (1067)...(1072)
<223> OTHER INFORMATION: Unknown nucleotides
<223> OTHER INFORMATION: Mutant luciferase

<400> SEQUENCE: 7
ggatccaatg gcagataaaa atattttata tgggcccgaa ccatttatc ccttggctga      60 tgggacggct ggagaacaga tgttttacgc attatctcgt tatgcagata tttcaggatg    120
catagcattg acaaatgctc atacaaaagc ccctgtttta tatgaagagt ttttaaaatt    180
gtcgtgtcgt ttagcggaaa gttttaaaaa gtatggatta aaacaaaacg acacaatagc    240
ggtgtgtagc gaaaatggtt tgcaattttt ccttcctgta attgcatcat tgtatcttgg    300
aataattgca gcacctgtta gtgataaata cattgaacgt gaattaatac acagtcttgg    360
tattgtaaaa ccacgcataa ttttttgctc caagaatact tttcaaaaag tactgaatgt    420
aaaatctaaa ttaaaatatg tagaaactat tattatatta gacttaaatg aagacttagg    480
aggttatcaa tgcctcaaca actttatttc tcaaaattcc gatattaatc ttgacgtaaa    540
aaaatttaaa ccatattctt ttaatcgaga cgatcaggtt gcgttggtaa tgttttcttc    600
tggtacaact ggtgttccga agggagtcat gctaactcac aagaatattg ttgcacgatt    660
ttctcttgca aaagatccta cttttggtaa cgcaattaat ccaacgacag caattttaac    720
ggtaataccT ttccaccatg gttttggtat gatgaccaca ttaggatact ttacttgtgg    780
attccgagtt gttctaatgc acacgtttga agaaaaacta tttctacaat cattacaaga    840
ttataaagtg gaaagtactt tacttgtacc aacattaatg gcatttcttg caaaaagtgc    900
attagttgaa aagtacgatt tatcgcactt aaaagaaatt gcatctggtg gcgcaccttt    960
atcaaaagaa attggggaga tggtgaaaaa acggtttaaa ttaaactttg tcaggcaagg   1020
gtatggatta acagaaacca cttcggctgt tttaattaca ccgaaannnn nngtcagacc    1080
gggatcaact ggtaaaatag taccatttca cgctgttaaa gttgtcgatc ctacaacagg   1140
aaaaattttg gggccaaatg aacctggaga attgtatttt aaaggcgaca tgataatgaa   1200
aggttattat aataatgaag aagctactaa agcaattatt gataaagacg gatggttgcg   1260
ctctggtgat attgcttatt atgacaatga tggccatttt tatattgtgg acaggctgaa   1320
gtcattaatt aaatataaag gttatcaggt tgcacctgct gaaattgagg gaatactctt   1380
acaacatccg tatattgttg atgccggcgt tactggtata ccggatgaag ccgcgggcga   1440
gcttccagct gcaggtgttg tagtacagac tggaaaatat ctaaacgaac aaatcgtaca   1500 aaatttgtt tccagtcaag tttcaacagc caaatggcta cggggtgggg tgaaattttt   1560
ggatgaaatt cccaaaggat caactggaaa aattgacaga aaagtgttaa gacaaatgtt   1620
tgaaaaacac accaatggg                                                1639

<210> SEQ ID NO 8
<211> LENGTH: 1639
<212> TYPE: DNA
<213> ORGANISM: Artificial Sequence
```

<220> FEATURE:
<221> NAME/KEY: unsure
<222> LOCATION: (1067)...(1072)
<223> OTHER INFORMATION: Unknown nucleotides
<223> OTHER INFORMATION: Mutant luciferase

<400> SEQUENCE: 8

```
ggatccaatg gcagataaaa atattttata tgggcccgaa ccatttatc ccttggctga      60
tgggacggct ggagaacaga tgttttacgc attatctcgt tatgcagata tttcaggatg    120
catagcattg acaaatgctc atacaaaagc ccctgtttta tatgaagagt tgttaaaatt    180
gtcgtgtcgt ttagcggaaa gttttaaaaa gtatggatta aaacaaaacg acacaatagc    240
ggtgtgtagc gaaaatggtt tgcaatattt ccttcctgta attgcatcat tgtatcttgg    300
aataattgca gcacctgtta gtgataaata cattgaacgt gaattaatac acagtcttgg    360
tattgtaaaa ccacgcataa ttttttgctc caagaatact tttcaaaaag tactgaatgt    420
aaaatctaaa ttaaaatatg tagaaactat tattatatta gacttaaatg aagacttagg    480
aggttatcaa tgcctcaaca actttatttc tcaaaattcc gatattaatc ttgacgtaaa    540
aaaatttaaa ccatattctt ttaatcgaga cgatcaggtt gcgttggtaa tgttttcttc    600
tggtacaact ggtgttccga agggagtcat gctaactcac aagaatattg ttgcacgatt    660
ttctattgca aaagatccta cttttggtaa cgcaattaat ccaacgacag caattttaac    720
ggtaatacct ttccaccatg gttttggtat gatgaccaca ttaggatact ttacttgtgg    780
attccgagtt gttctaatgc acacgtttga agaaaaacta tttctacaat cattacaaga    840
ttataaagtg gaaagtactt tacttgtacc aacattaatg gcatttcttg caaaaagtgc    900
attagttgaa aagtacgatt tatcgcactt aaaagaaatt gcatctggtg gcgcaccttt    960
atcaaaagaa attggggaga tggtgaaaaa acggtttaaa ttaaactttg tcaggcaagg   1020
gtatggatta acagaaacca cttcggctgt tttaattaca ccgaaannnn nngccagacc   1080
gggatcaact ggtaaaatag taccatttca cgctgttaaa gttgtcgatc ctacaacagg   1140
aaaaattttg gggccaaatg aacctggaga attgtatttt aaaggcgcca tgataatgaa   1200
gggttattat aataatgaag aagctactaa agcaattatt aacaaagacg gatggttgcg   1260
ctctggtgat attgcttatt atgacaatga tggccatttt tatattgtgg acaggctgaa   1320
gtcattaatt aaatataaag gttatcaggt tgcacctgct gaaattgagg gaatactctt   1380
acaacatccg tatattgttg atgccggcgt tactggtata ccggatgaag ccgcgggcga   1440
gcttccagct gcaggtgttg tagtacagac tgaaaatat ctaaacgaac aaatcgtaca   1500
aaattttgtt tccagtcaag tttcaacagc caaatggcta cgtggtgggg tgaaattttt   1560
ggatgaaatt cccaaaggat caactggaaa aattgacaga aaagtgttaa gacaaatgtt   1620
tgaaaaacac accaatggg                                                 1639
```

<210> SEQ ID NO 9
<211> LENGTH: 1639
<212> TYPE: DNA
<213> ORGANISM: Artificial Sequence
<220> FEATURE:
<221> NAME/KEY: unsure
<222> LOCATION: (1067)...(1072)
<223> OTHER INFORMATION: Unknown nucleotides
<223> OTHER INFORMATION: Mutant luciferase

<400> SEQUENCE: 9

```
ggatccaatg gcagataaaa atattttata tgggcccgaa ccatttatc ccttggctga      60
```

```
tgggacggct ggagaacaga tgtttgacgc attatctcgt tatgcagata tttcaggatg      120
catagcattg acaaatgctc atacaaaagc ccctgtttta tatgaagagt tgttaaaatt      180
gtcgtgtcgt ttagcggaaa gttttaaaaa gtatggatta aaacaaaacg acacaatagc      240
ggtgtgtagc gaaaatggtt tgcaatttt cctttcctgta attgcatcat tgtatcttgg      300
aataattgca gcacctgtta gtgataaata cgttgaacgt gaattaatac acagtcttgg      360
tattgtaaaa ccacgcataa ttttttgctc caagaatact tttcaaaaag tactgaatgt      420
aaaatctaaa ttaaaatatg tagaaactat tattatatta gacttaaatg aagacttagg      480
aggttatcaa tgcctcaaca actttatttc tcaaaattcc gatagtaatc tggacgtaaa      540
aaaatttaaa ccaaattctt ttaatcgaga cgatcaggtt gcgttggtaa tgttttcttc      600
tggtacaact ggtgtttcga agggagtcat gctaactcac aagaatattg ttgcacgatt      660
ttctcttgca aaagatccta cttttggtaa cgcaattaat ccaacgacag caattttaac      720
ggtaatacct ttccaccatg gttttggtat gatgaccaca ttaggatact ttacttgtgg      780
attccgagtt gttctaatgc acacgtttga agaaaaacta tttctacaat cattacaaga      840
ttataaagtg gaaagtactt tacttgtacc aacattaatg gcatttcttg caaaaagtgc      900
attagttgaa aagtacgatt tatcgcactt aaaagaaatt gcatctggtg gcgcaccttt      960
atcaaaagaa attggggaga tggtgaaaaa acggtttaaa ttaaactttg tcaggcaagg     1020
gtatggatta acagaaacca cttcggctgt tttaattaca ccgaacnnnn nngccagacc     1080
gggatcaact ggtaaaatag taccatttca cgctgttaaa gttgtcgatc ctacaacagg     1140
aaaaattttg gggccaaatg aacctggaga attgtatttt aaaggcgcca tgataatgaa     1200
gggttattat aataatgaag aagctactaa agcaattatt gataaagacg gatggttgcg     1260
ctctggtgat attgcttatt atgacaatga tggccatttt tatattgtgg acaggctgaa     1320
gtcattaatt aaatataaag gttatcaggt tgcacctgct gaaattgagg gaatactctc     1380
acaacatccg tatattgttg atgccggcgt tactggtata ccggatgaag ccgcgggcga     1440
gcttccagct gcaggtgttg tagtacgac tggaaaatat ctaaacgaac aaatcgtaca     1500
aaattttgtt tccagtcaag tttcaacagc caaatggcta cgtggtgggg tgaaattttt     1560
ggatgaaatt cccaaaggat caactggaaa aattgacaga aaagtgttaa gacaaatgtt     1620
tgaaaaacac accaatggg                                                  1639
```

<210> SEQ ID NO 10
<211> LENGTH: 1639
<212> TYPE: DNA
<213> ORGANISM: Artificial Sequence
<220> FEATURE:
<221> NAME/KEY: unsure
<222> LOCATION: (1067)...(1072)
<223> OTHER INFORMATION: Unknown nucleotides
<223> OTHER INFORMATION: Mutant luciferase

<400> SEQUENCE: 10

```
ggatccaatg gcagataaaa atattttata tgggcccgaa ccattttatc ccttggctga       60
tgggacggct ggagaacaga tgttttacgc attatctcgt tatgcagata ttccgggctg      120
catagcattg acaaatgctc atacaaaagc ccctgtttta tatgaagagt ttttaaaatt      180
gtcgtgtcgt ttagcggaaa gttttaaaaa gtatggatta aaacaaaacg acacaatagc      240
ggtgtgtagc gaaaatggtt tgcaatttt cctttcctgta attgcatcat tgtatcttgg      300
aataattgtg gcacctgtta acgataaata cattgaacgt gaattaatac acagtcttgg      360
```

```
tattgtaaaa ccacgcatag ttttttgctc caagaatact tttcaaaaag tactgaatgt      420
aaaatctaaa ttaaaatctg tagaaactat tattatatta gacttaaatg aagacttagg      480
aggttatcaa tgcctcaaca actttatttc tcaaaattcc gatattaatc ttgacgtaaa      540
aaaatttaaa ccatattctt ttaatcgaga cgatcaggtt gcgttgatta tgttttcttc      600
tggtacaact ggtctgccga agggagtcat gctaactcac aagaatattg ttgcacgatt      660
ttctcttgca aaagatccta cttttggtaa cgcaattaat cccacgacag caattttaac      720
ggtaatacct ttccaccatg gttttggtat gatgaccaca ttaggatact ttacttgtgg      780
attccgagtt gttctaatgc acacgtttga agaaaaacta tttctacaat cattacaaga      840
ttataaagtg gaaagtactt tacttgtacc aacattaatg gcatttcttg caaaaagtgc      900
attagttgaa aagtacgatt tatcgcactt aaaagaaatt gcatctggtg gcgcaccttt      960
atcaaaagaa attggggaga tggtgaaaaa acggtttaaa ttaaactttg tcaggcaagg     1020
gtatggatta acagaaacca cttcggctgt tttaattaca ccgaaannnn nngccagacc     1080
gggatcaact ggtaaaatag taccatttca cgctgttaaa gttgtcgatc ctacaacagg     1140
aaaaattttg gggccaaatg aacctggaga attgtatttt aaaggcccga tgataatgaa     1200
gggttattat aataatgaag aagctactaa agcaattatt gataatgacg gatggttgcg     1260
ctctggtgat attgcttatt atgacaatga tggccatttt tatattgtgg acaggctgaa     1320
gtcattaatt aaatataaag gttatcaggt tgcacctgct gaaattgagg aatactctt      1380 acaacatccg tatattgttg atgccggcgt tactggtatt ccggatgaag ccgcgggcga     1440
gcttccagct gcaggtgttg tagtacagac tggaaaatat ctaaacgaac aaatcgtaca     1500
aaattttgtt tccagtcaag tttcaacagc caaatggcta cgtggtgggg tgaaattttt     1560
ggatgaaatt cccaaaggat caactggaaa aattgacaga aagtgttaa gacaaatgtt      1620 tgaaaaacac accaatggg                                                  1639
```

<210> SEQ ID NO 11
<211> LENGTH: 1639
<212> TYPE: DNA
<213> ORGANISM: Artificial Sequence
<220> FEATURE:
<223> OTHER INFORMATION: Mutant luciferase

<400> SEQUENCE: 11

```
ggatccaatg gcagataaga atattttata tgggcccgaa ccatttatc ccttggaaga       60 tgggacggct ggagaacaga tgtttgacgc attatctcgt tatgcagata ttccgggctg     120
catagcattg acaaatgctc atacaaaaga aaatgtttta tatgaagagt ttctgaaact     180
gtcgtgtcgt ttagcggaaa gttttaaaaa gtatggatta aaacaaaacg acacaatagc     240
ggtgtgtagc gaaaatggtc tgcaattttt ccttcctgta attgcatcat tgtatcttgg     300
aataattgtg gcacctgtta acgataaata cattgaacgt gaattaatac acagtcttgg     360
tattgtaaaa ccacgcatag ttttttgctc caagaatact tttcaaaaag tactgaatgt     420
aaaatctaaa ttaaaatcta ttgaaactat tattatatta gacttaaatg aagacttagg     480
aggttatcaa tgcctcaaca actttatttc tcaaaattcc gatagtaatc tggacgtaaa     540
aaaatttaaa ccatattctt ttaatcgaga cgatcaggtt gcgttgatta tgttttcttc     600
tggtacaact ggtctgccga agggagtcat gctaactcac aagaatattg ttgcacgatt     660
ttctcttgca aaagatccta cttttggtaa cgcaattaat cccacgacag caattttaac     720
ggtaatacct ttccaccatg gttttggtat gatgaccaca ttaggatact ttacttgtgg     780
```

```
attccgagtt gttctaatgc acacgtttga agaaaaacta tttctacaat cattacaaga    840
ttataaagtg gaaagtactt tacttgtacc aacattaatg gcatttcttg caaaaagtgc    900
attagttgaa aagtacgatt tatcgcactt aaaagaaatt gcatctggtg gcgcaccttt    960
atcaaaagaa attggggaga tggtgaaaaa acggtttaaa ttaaactttg tcaggcaagg   1020
gtatggatta acagaaacca cttcggctgt tttaattaca ccgaaaggtg acgccaaacc   1080
gggatcaact ggtaaaatag taccatttca cgctgttaaa gttgtcgatc ctacaacagg   1140
aaaaattttg gggccaaatg aacctggaga attgtatttt aaaggcccga tgataatgaa   1200
gggttattat aataatgaag aagctactaa agcaattatt gataatgacg gatggttgcg   1260
ctctggtgat attgcttatt atgacaatga tggccatttt tatattgtgg acaggctgaa   1320
gtcactgatt aaatataaag gttatcaggt tgcacctgct gaaattgagg gaatactctt   1380
acaacatccg tatattgttg atgccggcgt tactggtata ccggatgaag ccgcgggcga   1440
gcttccagct gcaggtgttg tagtacagac tggaaaatat ctaaacgaac aaatcgtaca   1500
agattatgtt gccagtcaag tttcaacagc caaatggcta cgtggtgggg tgaaattttt   1560
ggatgaaatt cccaaaggat caactggaaa aattgacaga aaagtgttaa gacaaatgtt   1620
tgaaaaacac accaatggg                                               1639

<210> SEQ ID NO 12
<211> LENGTH: 1642
<212> TYPE: DNA
<213> ORGANISM: Artificial Sequence
<220> FEATURE:
<223> OTHER INFORMATION: Mutant luciferase

<400> SEQUENCE: 12
ggatccaatg gaagataaaa atattttata tggacctgaa ccattttatc ccttggctga     60
tgggacggct ggagaacaga tgttttacgc attatctcgt tatgcagata tttcaggatg    120
catagcattg acaaatgctc atacaaaaga aaatgtttta tatgaagagt ttttaaaatt    180
gtcgtgtcgt ttagcggaaa gttttaaaaa gtatggatta aacaaaacg acacaatagc    240
ggtgtgtagc gaaaatggtt tgcaattttt ccttcctttta attgcatcat tgtatcttgg    300
aataattgca gcacctgtta gtgataaata cattgaacgt gaattaatac acagtcttgg    360
tattgtaaaa ccacgcataa tttttttgttc caagaatact tttcaaaaag tactgaatgt    420
aaaatctaaa ttaaaatatg tagaaactat tattatatta gacttaaatg aagacttagg    480
aggttatcaa tgcctcaaca actttattc tcaaaattcc gatattaatc ttgacgtaaa    540
aaaatttaaa ccaaattctt ttaatcgaga cgatcaggtt gcgttggtaa tgttttcttc    600
tggtacaact ggtgtttcga agggagtcat gctaactcac aagaatattg ttgcacgatt    660
ttctcattgc aaagatccta cttttggtaa cgcaattaat ccaacgacag caattttaac    720
ggtaatacct ttccaccatg gttttggtat gatgaccaca ttaggatact ttacttgtgg    780
attccgagtt gctctaatgc acacgtttga agaaaaacta tttctacaat cattacaaga    840
ttataaagtg gaaagtactt tacttgtacc aacattaatg gcattttttg caaaaagtgc    900
attagttgaa aagtacgatt tatcgcactt aaaagaaatt gcatctggtg gcgcaccttt    960
atcaaaagaa attggggaga tggtgaaaaa acggtttaaa ttaaactttg tcaggcaagg   1020
gtatggatta acagaaacca cttcggctgt tttaattaca ccggacactg acgtcagacc   1080
gggatcaact ggtaaaatag taccatttca cgctgttaaa gttgtcgatc ctacaacagg   1140
```

-continued

| | |
|---|---|
| aaaaattttg gggccaaatg aaactggaga attgtatttt aaaggcgaca tgataatgaa | 1200 |
| aagttattat aataatgaag aagctactaa agcaattatt aacaaagacg gatggttgcg | 1260 |
| ctctggtgat attgcttatt atgacaatga tggccatttt tatattgtgg acaggctgaa | 1320 |
| gtcattaatt aaatataaag gttatcaggt tgcacctgct gaaattgagg gaatactctt | 1380 |
| acaacatccg tatattgttg atgccggcgt tactggtata ccggatgaag ccgcgggcga | 1440 |
| gcttccagct gcaggtgttg tagtacagac tggaaaatat ctaaacgaac aaatcgtaca | 1500 |
| aaattttgtt tccagtcaag tttcaacagc caaatggcta cgtggtgggg tgaaattttt | 1560 |
| ggatgaaatt cccaaaggat caactggaaa aattgacaga aaagtgttaa gacaaatgtt | 1620 |
| tgaaaaacac aaatctaagc tg | 1642 |

<210> SEQ ID NO 13
<211> LENGTH: 1626
<212> TYPE: DNA
<213> ORGANISM: Artificial Sequence
<220> FEATURE:
<223> OTHER INFORMATION: Mutant luciferase

<400> SEQUENCE: 13

| | |
|---|---|
| atgatgaagc gagagaaaaa tgttatatat ggacccgaac ccctacaccc cttggaagac | 60 |
| ttaacagctg gagaaatgct cttccgtgcc cttcgaaaac attctcattt accgcaggct | 120 |
| ttagtagatg tggttggcga cgaatcgctt cctataaag agtttttga agcgacagtc | 180 |
| ctcctagcgc aaagtctcca caattgtgga tacaagatga atgatgtagt gtcgatctgc | 240 |
| gccgagaata tacaagatt ttttattccc gttattgcag cttggtatat tggtatgatt | 300 |
| gtagcacctg ttaatgaaag ttacatccca gatgaactct gtaaggtgat gggtatatcg | 360 |
| aaaccacaaa tagttttac gacaagaac attttaaata aggtattgga ggtacagagc | 420 |
| agaactaatt tcataaaaag gatcatcata cttgatactg tagaaaacat acacggttgt | 480 |
| gaaagtcttc ccaattttat ttctcgttat tcggatggaa atattgccaa cttcaaacct | 540 |
| ttacatttcg atcctgttga gcaagtggca gctatcttat gttcgtcagg cactactgga | 600 |
| ttaccgaaag gtgtaatgca aactcaccaa aatatttgtg tccgacttat acatgcttta | 660 |
| gaccccaggg caggaacgca acttattcct ggtgtgacag tcttagtata tctgcctttt | 720 |
| ttccatgctt ttgggttctc tataaccttg ggatacttca tggtgggtct tcgtgttatc | 780 |
| atgttcagac gatttgatca agaagcattt ctaaaagcta ttcaggatta tgaagttcga | 840 |
| agtgtaatta acgttccatc agtaatattg ttcttatcga aagtcctttt ggttgacaaa | 900 |
| tacgatttat caagtttaag ggaattgtgt tgcggtgcgg caccattagc aaaagaagtt | 960 |
| gctgaggttg cagcaaaacg attaaacttg ccaggaattc gctgtggatt tggtttgaca | 1020 |
| gaatctactt cagctaatat acacagtctt ggggatgaat ttaaatcagg atcacttgga | 1080 |
| agagttactc ctttaatggc agctaaaata gcagataggg aaactggtaa agcattggga | 1140 |
| ccaaatcaag ttggtgaatt atgcattaaa ggtcccatgg tatcgaaagg ttacgtgaac | 1200 |
| aatgtagaag ctaccaaaga agctattgat gatgatggtt ggcttcactc tggagacttt | 1260 |
| ggatactatg atgaggatga gcatttctat gtggtggacc gttacaagga attgattaaa | 1320 |
| tataagggct ctcaggtagc acctgcagaa ctagaagaga tttatattgaa aaatccatgt | 1380 |
| atcagagatg ttgctgtggt tggtattcct gatctagaag ctggagaact gccatctgcg | 1440 |
| tttgtggtta aacagcccgg aaaggagatt acagctaaag aagtgtacga ttatcttgcc | 1500 |
| gagagggtct cccatacaaa gtatttgcgt ggagggttc gattcgttga tagcatacca | 1560 |

-continued

```
aggaatgtta caggtaaaat tacaagaaag gaacttctga agcagttgct ggagaaggcg    1620
ggaggt                                                              1626
```

<210> SEQ ID NO 14
<211> LENGTH: 544
<212> TYPE: PRT
<213> ORGANISM: Artificial Sequence
<220> FEATURE:
<223> OTHER INFORMATION: Mutant luciferase

<400> SEQUENCE: 14

```
Met Ala Asp Lys Asn Ile Leu Tyr Gly Pro Glu Pro Phe Tyr Pro Leu
 1               5                  10                  15

Ala Asp Gly Thr Ala Gly Glu Gln Met Phe Tyr Ala Leu Ser Arg Tyr
            20                  25                  30

Ala Asp Ile Ser Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Gly Leu Gln Phe Phe Leu Pro Ile Ile Ala Ser Leu Tyr
                85                  90                  95

Leu Gly Ile Ile Ala Ala Pro Val Ser Asp Lys Tyr Ile Glu Arg Glu
            100                 105                 110

Leu Ile His Ser Leu Gly Ile Val Lys Pro Arg Ile Ile Phe Cys Ser
        115                 120                 125

Lys Asn Thr Phe Gln Lys Val Leu Asn Val Lys Ser Lys Leu Lys Tyr
    130                 135                 140

Val Glu Thr Ile Ile Leu Asp Leu Asn Glu Asp Leu Gly Gly Tyr
145                 150                 155                 160

Gln Cys Leu Asn Asn Phe Ile Ser Gln Asn Ser Asp Ile Asn Leu Asp
                165                 170                 175

Val Lys Lys Phe Lys Pro Tyr Ser Phe Asn Arg Asp Asp Gln Val Ala
            180                 185                 190

Leu Val Met Phe Ser Ser Gly Thr Thr Gly Val Ser Lys Gly Val Met
        195                 200                 205

Leu Thr His Lys Asn Ile Val Ala Arg Phe Ser Leu Ala Lys Asp Pro
    210                 215                 220

Thr Phe Gly Asn Ala Ile Asn Pro Thr Thr Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Leu Ala Lys Ser Ala Leu Val Glu Lys Tyr Asp
    290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
```

```
                        340                 345                 350
Asn Asn Asp Val Arg Pro Gly Ser Thr Gly Lys Ile Val Pro Phe His
        355                 360                 365
Ala Val Lys Val Val Asp Pro Thr Thr Gly Lys Ile Leu Gly Pro Asn
    370                 375                 380
Glu Pro Gly Glu Leu Tyr Phe Lys Gly Asp Met Ile Met Lys Gly Tyr
385                 390                 395                 400
Tyr Asn Asn Glu Glu Ala Thr Lys Ala Ile Ile Asn Lys Asp Gly Trp
                405                 410                 415
Leu Arg Ser Gly Asp Ile Ala Tyr Tyr Asp Asn Asp Gly His Phe Tyr
                420                 425                 430
Ile Val Asp Arg Leu Lys Ser Leu Ile Lys Tyr Lys Gly Tyr Gln Val
            435                 440                 445
Ala Pro Ala Glu Ile Glu Gly Ile Leu Leu Gln His Pro Tyr Ile Val
    450                 455                 460
Asp Ala Gly Val Thr Gly Ile Pro Asp Glu Ala Ala Gly Glu Leu Pro
465                 470                 475                 480
Ala Ala Gly Val Val Val Gln Thr Gly Lys Tyr Leu Asn Glu Gln Ile
                485                 490                 495
Val Gln Asn Phe Val Ser Ser Gln Val Ser Thr Ala Lys Trp Leu Arg
                500                 505                 510
Gly Gly Val Lys Phe Leu Asp Glu Ile Pro Lys Gly Ser Thr Gly Lys
            515                 520                 525
Ile Asp Arg Lys Val Leu Arg Gln Met Phe Glu Lys His Thr Asn Gly
        530                 535                 540

<210> SEQ ID NO 15
<211> LENGTH: 544
<212> TYPE: PRT
<213> ORGANISM: Artificial Sequence
<220> FEATURE:
<223> OTHER INFORMATION: Mutant luciferase

<400> SEQUENCE: 15

Met Glu Asp Lys Asn Ile Leu Tyr Gly Pro Glu Pro Phe Tyr Pro Leu
 1               5                  10                  15
Ala Asp Gly Thr Ala Gly Glu Gln Met Phe Tyr Ala Leu Ser Arg Tyr
            20                  25                  30
Ala Asp Ile Ser Gly Cys Ile Ala Leu Thr Asn Ala His Thr Lys Glu
        35                  40                  45
Asn Val Leu Tyr Glu Glu Leu Leu Lys Leu Ser Cys Arg Leu Ala Glu
    50                  55                  60
Ser Phe Lys Lys Tyr Gly Leu Lys Gln Asn Asp Thr Ile Ala Val Cys
65                  70                  75                  80
Ser Glu Asn Gly Leu Gln Phe Phe Leu Pro Ile Ile Ala Ser Leu Tyr
                85                  90                  95
Leu Gly Ile Ile Ala Ala Pro Val Ser Asp Lys Tyr Ile Glu Arg Glu
            100                 105                 110
Leu Ile His Ser Leu Gly Ile Val Lys Pro Arg Ile Ile Phe Cys Ser
        115                 120                 125
Lys Asn Thr Phe Gln Lys Val Leu Asn Val Lys Ser Lys Leu Lys Tyr
    130                 135                 140
Val Glu Thr Ile Ile Ile Leu Asp Leu Asn Glu Asp Leu Gly Gly Tyr
145                 150                 155                 160
Gln Cys Leu Asn Asn Phe Ile Ser Gln Asn Ser Asp Ile Asn Leu Asp
```

```
                    165                 170                 175
Val Lys Lys Phe Lys Pro Tyr Ser Phe Asn Arg Asp Asp Gln Val Ala
            180                 185                 190

Leu Val Met Phe Ser Ser Gly Thr Thr Gly Val Ser Lys Gly Val Met
        195                 200                 205

Leu Thr His Lys Asn Ile Val Ala Arg Phe Ser His Ala Lys Asp Pro
    210                 215                 220

Thr Phe Gly Asn Ala Ile Asn Pro Thr Thr Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Phe Ala Lys Ser Ala Leu Val Glu Lys Tyr Asp
290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

Asn Asn Asp Val Arg Pro Gly Ser Thr Gly Lys Ile Val Pro Phe His
        355                 360                 365

Ala Val Lys Val Val Asp Pro Thr Thr Gly Lys Ile Leu Gly Pro Asn
    370                 375                 380

Glu Thr Gly Glu Leu Tyr Phe Lys Gly Asp Met Ile Met Lys Gly Tyr
385                 390                 395                 400

Tyr Asn Asn Glu Glu Ala Thr Lys Ala Ile Ile Asn Lys Asp Gly Trp
                405                 410                 415

Leu Arg Ser Gly Asp Ile Ala Tyr Tyr Asp Asn Asp Gly His Phe Tyr
            420                 425                 430

Ile Val Asp Arg Leu Lys Ser Leu Ile Lys Tyr Lys Gly Tyr Gln Val
        435                 440                 445

Ala Pro Ala Glu Ile Glu Gly Ile Leu Leu Gln His Pro Tyr Ile Val
    450                 455                 460

Asp Ala Gly Val Thr Gly Ile Pro Asp Glu Ala Ala Gly Glu Leu Pro
465                 470                 475                 480

Ala Ala Gly Val Val Val Gln Thr Gly Lys Tyr Leu Asn Glu Gln Ile
                485                 490                 495

Val Gln Asn Phe Val Ser Ser Gln Val Ser Thr Ala Lys Trp Leu Arg
            500                 505                 510

Gly Gly Val Lys Phe Leu Asp Glu Ile Pro Lys Gly Ser Thr Gly Lys
        515                 520                 525

Ile Asp Arg Lys Val Leu Arg Gln Met Phe Glu Lys His Thr Asn Gly
    530                 535                 540
```

<210> SEQ ID NO 16
<211> LENGTH: 544
<212> TYPE: PRT
<213> ORGANISM: Artificial Sequence
<220> FEATURE:
<223> OTHER INFORMATION: Mutant luciferase

```
<400> SEQUENCE: 16

Met Glu Asp Lys Asn Ile Leu Tyr Gly Pro Glu Pro Phe Tyr Pro Leu
 1               5                  10                  15

Ala Asp Gly Thr Ala Gly Glu Gln Met Phe Tyr Ala Leu Ser Arg Tyr
             20                  25                  30

Ala Asp Ile Ser Gly Cys Ile Ala Leu Thr Asn Ala His Thr Lys Glu
             35                  40                  45

Asn Val Leu Tyr Glu Glu Phe Leu Lys Leu Ser Cys Arg Leu Ala Glu
 50                  55                  60

Ser Phe Lys Lys Tyr Gly Leu Lys Gln Asn Asp Thr Ile Ala Val Cys
 65                  70                  75                  80

Ser Glu Asn Gly Leu Gln Phe Phe Leu Pro Ile Ile Ala Ser Leu Tyr
             85                  90                  95

Leu Gly Ile Ile Ala Ala Pro Val Ser Asp Lys Tyr Ile Glu Arg Glu
            100                 105                 110

Leu Ile His Ser Leu Gly Ile Val Lys Pro Arg Ile Ile Phe Cys Ser
            115                 120                 125

Lys Asn Thr Phe Gln Lys Val Leu Asn Val Lys Ser Lys Leu Lys Tyr
            130                 135                 140

Val Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ile Asn Leu Asp
                165                 170                 175

Val Lys Lys Phe Lys Pro Tyr Ser Phe Asn Arg Asp Asp Gln Val Ala
                180                 185                 190

Leu Val Met Phe Ser Ser Gly Thr Thr Gly Val Ser Lys Gly Val Met
                195                 200                 205

Leu Thr His Lys Asn Ile Val Val Arg Phe Ser Leu Ala Lys Asp Pro
210                 215                 220

Thr Phe Gly Asn Ala Ile Asn Pro Thr Thr Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
                260                 265                 270

Leu Gln Ser Leu Gln Asp Tyr Lys Val Glu Ser Thr Leu Leu Val Pro
                275                 280                 285

Thr Leu Met Ala Phe Phe Ala Lys Ser Ala Leu Val Glu Lys Tyr Asp
290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
                340                 345                 350

Asn Asn Asp Val Arg Pro Gly Ser Thr Gly Lys Ile Val Pro Phe His
                355                 360                 365

Ala Val Lys Val Val Asp Pro Thr Thr Gly Lys Ile Leu Gly Pro Asn
            370                 375                 380

Glu Thr Gly Glu Leu Tyr Phe Lys Gly Asp Met Ile Met Lys Gly Tyr
385                 390                 395                 400

Tyr Asn Asn Glu Glu Ala Thr Lys Ala Ile Ile Thr Lys Asp Gly Trp
                405                 410                 415
```

```
Leu Arg Ser Gly Asp Ile Ala Tyr Tyr Asp Asn Asp Gly His Phe Tyr
            420                 425                 430

Ile Val Asp Arg Leu Lys Ser Leu Ile Lys Tyr Lys Gly Tyr Gln Val
            435                 440                 445

Ala Pro Ala Glu Ile Glu Gly Ile Leu Leu Gln His Pro Tyr Ile Val
            450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
                485                 490                 495

Val Gln Asn Phe Val Ser Ser Gln Val Ser Thr Ala Lys Trp Leu Arg
            500                 505                 510

Gly Gly Val Lys Phe Leu Asp Glu Ile Pro Lys Gly Ser Thr Gly Lys
            515                 520                 525

Ile Asp Arg Lys Val Leu Arg Gln Met Phe Glu Lys His Thr Asn Gly
            530                 535                 540
```

<210> SEQ ID NO 17
<211> LENGTH: 544
<212> TYPE: PRT
<213> ORGANISM: Artificial Sequence
<220> FEATURE:
<223> OTHER INFORMATION: Mutant luciferase

<400> SEQUENCE: 17

```
Met Glu Asp Lys Asn Ile Leu Tyr Gly Pro Glu Pro Phe Tyr Pro Leu
1               5                   10                  15

Ala Asp Gly Thr Ala Gly Glu Gln Met Phe Tyr Ala Leu Ser Arg Tyr
            20                  25                  30

Ala Asp Ile Ser Gly Cys Ile Ala Leu Thr Asn Ala His Thr Lys Glu
            35                  40                  45

Asn Val Leu Tyr Glu Glu Phe Leu Lys Leu Ser Cys Arg Leu Ala Glu
        50                  55                  60

Ser Phe Lys Lys Tyr Gly Leu Lys Gln Asn Asp Thr Ile Ala Val Cys
65                  70                  75                  80

Ser Glu Asn Gly Leu Gln Phe Phe Leu Pro Ile Ile Ala Ser Leu Tyr
                85                  90                  95

Leu Gly Ile Ile Ala Ala Pro Val Ser Asp Lys Tyr Ile Glu Arg Glu
            100                 105                 110

Leu Ile His Ser Leu Gly Ile Val Lys Pro Arg Ile Ile Phe Cys Ser
            115                 120                 125

Lys Asn Thr Phe Gln Lys Val Leu Asn Val Lys Ser Lys Leu Lys Tyr
130                 135                 140

Val Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ile Asn Leu Asp
                165                 170                 175

Val Lys Lys Phe Lys Pro Tyr Ser Phe Asn Arg Asp Asp Gln Val Ala
            180                 185                 190

Leu Val Met Phe Ser Ser Gly Thr Thr Gly Val Ser Lys Gly Val Met
            195                 200                 205

Leu Thr His Lys Asn Ile Val Ala Arg Phe Ser Ile Ala Lys Asp Pro
            210                 215                 220

Thr Phe Gly Asn Ala Ile Asn Pro Thr Thr Ala Ile Leu Thr Val Ile
225                 230                 235                 240
```

```
Pro Phe His His Gly Phe Gly Met Met Thr Thr Leu Gly Tyr Phe Thr
              245                 250                 255

Cys Gly Phe Arg Val Val Leu Met His Thr Phe Glu Glu Lys Leu Phe
              260                 265                 270

Leu Gln Ser Leu Gln Asp Tyr Lys Val Glu Ser Thr Leu Leu Val Pro
              275                 280                 285

Thr Leu Met Ala Phe Leu Ala Lys Ser Ala Leu Val Glu Lys Tyr Asp
              290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
              325                 330                 335

Gln Gly Tyr Gly Leu Thr Glu Thr Thr Ser Ala Val Leu Ile Thr Pro
              340                 345                 350

Asn Asn Asp Val Arg Pro Gly Ser Thr Gly Lys Ile Val Pro Phe His
              355                 360                 365

Ala Val Lys Val Val Asp Pro Thr Thr Gly Lys Ile Leu Gly Pro Asn
              370                 375                 380

Glu Thr Gly Glu Leu Tyr Phe Lys Gly Asp Met Ile Met Lys Gly Tyr
385                 390                 395                 400

Tyr Asn Asn Glu Glu Ala Thr Lys Ala Ile Ile Asn Lys Asp Gly Trp
              405                 410                 415

Leu Arg Ser Gly Asp Ile Ala Tyr Tyr Asp Asn Asp Gly His Phe Tyr
              420                 425                 430

Ile Val Asp Arg Leu Lys Ser Leu Ile Lys Tyr Lys Gly Tyr Gln Val
              435                 440                 445

Ala Pro Ala Glu Ile Glu Gly Ile Leu Leu Gln His Pro Tyr Ile Val
              450                 455                 460

Asp Ala Gly Val Thr Gly Ile Pro Asp Glu Ala Ala Gly Glu Leu Pro
465                 470                 475                 480

Ala Ala Gly Val Val Val Gln Thr Gly Lys Tyr Leu Asn Glu Gln Ile
              485                 490                 495

Val Gln Asn Phe Val Ser Ser Gln Val Ser Thr Ala Lys Trp Leu Arg
              500                 505                 510

Gly Gly Val Lys Phe Leu Asp Glu Ile Pro Lys Gly Ser Thr Gly Lys
              515                 520                 525

Ile Asp Arg Lys Val Leu Arg Gln Met Phe Glu Lys His Thr Asn Gly
              530                 535                 540

<210> SEQ ID NO 18
<211> LENGTH: 544
<212> TYPE: PRT
<213> ORGANISM: Artificial Sequence
<220> FEATURE:
<223> OTHER INFORMATION: Mutant luciferase

<400> SEQUENCE: 18

Met Glu Asp Lys Asn Ile Leu Tyr Gly Pro Glu Pro Phe Tyr Pro Leu
  1               5                  10                  15

Ala Asp Gly Thr Ala Gly Glu Gln Met Phe Asp Ala Leu Ser Arg Tyr
               20                  25                  30

Ala Asp Ile Ser Gly Cys Ile Ala Leu Thr Asn Ala His Thr Lys Glu
               35                  40                  45

Asn Val Leu Tyr Glu Glu Phe Leu Lys Leu Ser Cys Arg Leu Ala Glu
               50                  55                  60
```

-continued

```
Ser Phe Lys Lys Tyr Gly Leu Lys Gln Asn Asp Thr Ile Ala Val Cys
 65                  70                  75                  80

Ser Glu Asn Gly Leu Gln Phe Phe Leu Pro Ile Ile Ala Ser Leu Tyr
                 85                  90                  95

Leu Gly Ile Ile Ala Ala Pro Val Ser Asp Lys Tyr Ile Glu Arg Glu
                100                 105                 110

Leu Ile His Ser Leu Gly Ile Val Lys Pro Arg Ile Ile Phe Cys Ser
            115                 120                 125

Lys Asn Thr Phe Gln Lys Val Leu Asn Val Lys Ser Lys Leu Lys Tyr
130                 135                 140

Val Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ile Asn Leu Asp
                165                 170                 175

Val Lys Lys Phe Lys Pro Tyr Ser Phe Asn Arg Asp Asp Gln Val Ala
                180                 185                 190

Leu Val Met Phe Ser Ser Gly Thr Thr Gly Val Ser Lys Gly Val Met
            195                 200                 205

Leu Thr His Lys Asn Ile Val Ala Arg Phe Ser His Ala Lys Asp Pro
    210                 215                 220

Thr Phe Gly Asn Ala Ile Asn Pro Thr Thr Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
                260                 265                 270

Leu Gln Ser Leu Gln Asp Tyr Lys Val Glu Ser Thr Leu Leu Val Pro
            275                 280                 285

Thr Leu Met Ala Phe Phe Ala Lys Ser Ala Leu Val Glu Lys Tyr Asp
    290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
                340                 345                 350

Asn Asn Asp Val Arg Pro Gly Ser Thr Gly Lys Ile Val Pro Phe His
            355                 360                 365

Ala Val Lys Val Val Asp Pro Thr Thr Gly Lys Ile Leu Gly Pro Asn
    370                 375                 380

Glu Thr Gly Glu Leu Tyr Phe Lys Gly Asp Met Ile Met Lys Gly Tyr
385                 390                 395                 400

Tyr Asn Asn Glu Glu Ala Thr Lys Ala Ile Ile Asn Lys Asp Gly Trp
                405                 410                 415

Leu Arg Ser Gly Asp Ile Ala Tyr Tyr Asp Asn Asp Gly His Phe Tyr
                420                 425                 430

Ile Val Asp Arg Leu Lys Ser Leu Ile Lys Tyr Lys Gly Tyr Gln Val
            435                 440                 445

Ala Pro Ala Glu Ile Glu Gly Ile Leu Leu Gln His Pro Tyr Ile Val
    450                 455                 460

Asp Ala Gly Val Thr Gly Ile Pro Asp Glu Ala Ala Gly Glu Leu Pro
465                 470                 475                 480
```

```
Ala Ala Gly Val Val Gln Thr Gly Lys Tyr Leu Asn Glu Gln Ile
            485                 490                 495

Val Gln Asn Phe Val Ser Ser Gln Val Ser Thr Ala Lys Trp Leu Arg
            500                 505                 510

Gly Gly Val Lys Phe Leu Asp Glu Ile Pro Lys Gly Ser Thr Gly Lys
            515                 520                 525

Ile Asp Arg Lys Val Leu Arg Gln Met Phe Glu Lys His Thr Asn Gly
530                 535                 540

<210> SEQ ID NO 19
<211> LENGTH: 544
<212> TYPE: PRT
<213> ORGANISM: Artificial Sequence
<220> FEATURE:
<223> OTHER INFORMATION: Mutant luciferase

<400> SEQUENCE: 19

Met Ala Asp Lys Asn Ile Leu Tyr Gly Pro Glu Pro Phe Tyr Pro Leu
1               5                   10                  15

Ala Asp Gly Thr Ala Gly Glu Gln Met Phe Asp Ala Leu Ser Arg Tyr
            20                  25                  30

Ala Asp Ile Ser Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Gly Leu Gln Phe Phe Leu Pro Val Ile Ala Ser Leu Tyr
                85                  90                  95

Leu Gly Ile Ile Ala Ala Pro Val Ser Asp Lys Tyr Ile Glu Arg Glu
            100                 105                 110

Leu Ile His Ser Leu Gly Ile Val Lys Pro Arg Ile Ile Phe Cys Ser
        115                 120                 125

Lys Asn Thr Phe Gln Lys Val Leu Asn Val Lys Ser Lys Leu Lys Ser
    130                 135                 140

Val Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Tyr Ser Phe Asn Arg Asp Asp Gln Val Ala
            180                 185                 190

Leu Val Met Phe Ser Ser Gly Thr Thr Gly Val Pro Lys Gly Val Met
        195                 200                 205

Leu Thr His Lys Asn Ile Val Ala Arg Phe Ser Leu Ala Lys Asp Pro
    210                 215                 220

Thr Phe Gly Asn Ala Ile Asn Pro Thr Thr Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Leu Ala Lys Ser Ala Leu Val Glu Lys Tyr Asp
    290                 295                 300
```

-continued

```
Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
                340                 345                 350

Lys Gly Asp Ala Arg Pro Gly Ser Thr Gly Lys Ile Val Pro Phe His
                355                 360                 365

Ala Val Lys Val Val Asp Pro Thr Thr Gly Lys Ile Leu Gly Pro Asn
370                 375                 380

Glu Pro Gly Glu Leu Tyr Phe Lys Gly Ala Met Ile Met Lys Gly Tyr
385                 390                 395                 400

Tyr Asn Asn Glu Glu Ala Thr Lys Ala Ile Ile Asp Asn Asp Gly Trp
                405                 410                 415

Leu Arg Ser Gly Asp Ile Ala Tyr Tyr Asp Asn Asp Gly His Phe Tyr
                420                 425                 430

Ile Val Asp Arg Leu Lys Ser Leu Ile Lys Tyr Lys Gly Tyr Gln Val
                435                 440                 445

Ala Pro Ala Glu Ile Glu Gly Ile Leu Leu Gln His Pro Tyr Ile Val
450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
                485                 490                 495

Val Gln Asp Phe Val Ser Ser Gln Val Ser Thr Ala Lys Trp Leu Arg
                500                 505                 510

Gly Gly Val Lys Phe Leu Asp Glu Ile Pro Lys Gly Ser Thr Gly Lys
                515                 520                 525

Ile Asp Arg Lys Val Leu Arg Gln Met Phe Glu Lys His Thr Asn Gly
                530                 535                 540
```

<210> SEQ ID NO 20
<211> LENGTH: 544
<212> TYPE: PRT
<213> ORGANISM: Artificial Sequence
<220> FEATURE:
<223> OTHER INFORMATION: Mutant luciferase
<220> FEATURE:
<221> NAME/KEY: UNSURE
<222> LOCATION: (354)...(355)
<223> OTHER INFORMATION: Unknown amino acids

<400> SEQUENCE: 20

```
Met Ala Asp Lys Asn Ile Leu Tyr Gly Pro Glu Pro Phe Tyr Pro Leu
1               5                   10                  15

Ala Asp Gly Thr Ala Gly Glu Gln Met Phe Tyr Ala Leu Ser Arg Tyr
                20                  25                  30

Ala Asp Ile Ser Gly Cys Ile Ala Leu Thr Asn Ala His Thr Lys Glu
                35                  40                  45

Asn Val Leu Tyr Glu Glu Phe Leu Lys Leu Ser Cys Arg Leu Ala Glu
        50                  55                  60

Ser Phe Lys Lys Tyr Gly Leu Lys Gln Asn Asp Thr Ile Ala Val Cys
65                  70                  75                  80

Ser Glu Asn Gly Leu Gln Phe Phe Leu Pro Val Ile Ala Ser Leu Tyr
                85                  90                  95

Leu Gly Ile Ile Ala Ala Pro Val Ser Asp Lys Tyr Ile Glu Arg Glu
                100                 105                 110
```

-continued

```
Leu Ile His Ser Leu Gly Ile Val Lys Pro Arg Ile Ile Phe Cys Ser
        115                 120                 125
Lys Asn Thr Phe Gln Lys Val Leu Asn Val Lys Ser Lys Leu Lys Tyr
    130                 135                 140
Val Glu Thr Ile Ile Ile Leu Asp Leu Asn Glu Asp Leu Gly Gly Tyr
145                 150                 155                 160
Gln Cys Leu Asn Asn Phe Ile Ser Gln Asn Ser Asp Ile Asn Leu Asp
                165                 170                 175
Val Lys Lys Phe Lys Pro Tyr Ser Phe Asn Arg Asp Asp Gln Val Ala
            180                 185                 190
Leu Val Met Phe Ser Ser Gly Thr Thr Gly Val Pro Lys Gly Val Met
        195                 200                 205
Leu Thr His Lys Asn Ile Val Ala Arg Phe Ser Leu Ala Lys Asp Pro
    210                 215                 220
Thr Phe Gly Asn Ala Ile Asn Pro Thr Thr Ala Ile Leu Thr Val Ile
225                 230                 235                 240
Pro Phe His His Gly Phe Gly Met Met Thr Thr Leu Gly Tyr Phe Thr
                245                 250                 255
Cys Gly Phe Arg Val Val Leu Met His Thr Phe Glu Glu Lys Leu Phe
            260                 265                 270
Leu Gln Ser Leu Gln Asp Tyr Lys Val Glu Ser Thr Leu Leu Val Pro
        275                 280                 285
Thr Leu Met Ala Phe Leu Ala Lys Ser Ala Leu Val Glu Lys Tyr Asp
    290                 295                 300
Leu Ser His Leu Lys Glu Ile Ala Ser Gly Gly Ala Pro Leu Ser Lys
305                 310                 315                 320
Glu Ile Gly Glu Met Val Lys Lys Arg Phe Lys Leu Asn Phe Val Arg
                325                 330                 335
Gln Gly Tyr Gly Leu Thr Glu Thr Thr Ser Ala Val Leu Ile Thr Pro
            340                 345                 350
Lys Xaa Xaa Val Arg Pro Gly Ser Thr Gly Lys Ile Val Pro Phe His
        355                 360                 365
Ala Val Lys Val Val Asp Pro Thr Thr Gly Lys Ile Leu Gly Pro Asn
    370                 375                 380
Glu Pro Gly Glu Leu Tyr Phe Lys Gly Asp Met Ile Met Lys Gly Tyr
385                 390                 395                 400
Tyr Asn Asn Glu Glu Ala Thr Lys Ala Ile Ile Asp Lys Asp Gly Trp
                405                 410                 415
Leu Arg Ser Gly Asp Ile Ala Tyr Tyr Asp Asn Asp Gly His Phe Tyr
            420                 425                 430
Ile Val Asp Arg Leu Lys Ser Leu Ile Lys Tyr Lys Gly Tyr Gln Val
        435                 440                 445
Ala Pro Ala Glu Ile Glu Gly Ile Leu Leu Gln His Pro Tyr Ile Val
    450                 455                 460
Asp Ala Gly Val Thr Gly Ile Pro Asp Glu Ala Ala Gly Glu Leu Pro
465                 470                 475                 480
Ala Ala Gly Val Val Gln Thr Gly Lys Tyr Leu Asn Glu Gln Ile
                485                 490                 495
Val Gln Asn Phe Val Ser Ser Gln Val Ser Thr Ala Lys Trp Leu Arg
            500                 505                 510
Gly Gly Val Lys Phe Leu Asp Glu Ile Pro Lys Gly Ser Thr Gly Lys
        515                 520                 525
```

```
Ile Asp Arg Lys Val Leu Arg Gln Met Phe Glu Lys His Thr Asn Gly
        530                 535                 540

<210> SEQ ID NO 21
<211> LENGTH: 544
<212> TYPE: PRT
<213> ORGANISM: Artificial Sequence
<220> FEATURE:
<223> OTHER INFORMATION: Mutant luciferase
<220> FEATURE:
<221> NAME/KEY: UNSURE
<222> LOCATION: (354)...(355)
<223> OTHER INFORMATION: Unknown amino acids

<400> SEQUENCE: 21

Met Ala Asp Lys Asn Ile Leu Tyr Gly Pro Glu Pro Phe Tyr Pro Leu
 1               5                  10                  15

Ala Asp Gly Thr Ala Gly Glu Gln Met Phe Asp Ala Leu Ser Arg Tyr
                20                  25                  30

Ala Asp Ile Pro Gly Cys Ile Ala Leu Thr Asn Ala His Thr Lys Glu
            35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
 65                 70                  75                  80

Ser Glu Asn Gly Leu Gln Tyr Phe Leu Pro Val Ile Ala Ser Leu Tyr
                85                  90                  95

Leu Gly Ile Ile Ala Ala Pro Val Ser Asp Lys Tyr Ile Glu Arg Glu
            100                 105                 110

Leu Ile His Ser Leu Gly Ile Val Lys Pro Arg Ile Ile Phe Cys Ser
        115                 120                 125

Lys Asn Thr Phe Gln Lys Val Leu Asn Val Lys Ser Lys Leu Lys Tyr
    130                 135                 140

Val Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ile Asn Leu Asp
                165                 170                 175

Val Lys Lys Phe Lys Pro Asn Ser Phe Asn Arg Asp Asp Gln Val Ala
            180                 185                 190

Leu Val Met Phe Ser Ser Gly Thr Thr Gly Val Pro Lys Gly Val Met
        195                 200                 205

Leu Thr His Lys Asn Ile Val Ala Arg Phe Ser Ile Ala Lys Asp Pro
    210                 215                 220

Thr Phe Gly Asn Ala Ile Asn Pro Thr Thr Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Leu Ala Lys Ser Ala Leu Val Glu Lys Tyr Asp
    290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335
```

```
Gln Gly Tyr Gly Leu Thr Glu Thr Thr Ser Ala Val Leu Ile Thr Pro
            340                 345                 350

Lys Xaa Xaa Ala Arg Pro Gly Ser Thr Gly Lys Ile Val Pro Phe His
        355                 360                 365

Ala Val Lys Val Val Asp Pro Thr Thr Gly Lys Ile Leu Gly Pro Asn
    370                 375                 380

Glu Pro Gly Glu Leu Tyr Phe Lys Gly Ala Met Ile Met Lys Gly Tyr
385                 390                 395                 400

Tyr Asn Asn Glu Glu Ala Thr Lys Ala Ile Ile Asp Lys Asp Gly Trp
                405                 410                 415

Leu Arg Ser Gly Asp Ile Ala Tyr Tyr Asp Asn Asp Gly His Phe Tyr
            420                 425                 430

Ile Val Asp Arg Leu Lys Ser Leu Ile Lys Tyr Lys Gly Tyr Gln Val
        435                 440                 445

Ala Pro Ala Glu Ile Glu Gly Ile Leu Leu Gln His Pro Tyr Ile Val
    450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
                485                 490                 495

Val Gln Asn Phe Val Ser Ser Gln Val Ser Thr Ala Lys Trp Leu Arg
            500                 505                 510

Gly Gly Val Lys Phe Leu Asp Glu Ile Pro Lys Gly Ser Thr Gly Lys
            515                 520                 525

Ile Asp Arg Lys Val Leu Arg Gln Met Phe Glu Lys His Thr Asn Gly
            530                 535                 540

<210> SEQ ID NO 22
<211> LENGTH: 544
<212> TYPE: PRT
<213> ORGANISM: Artificial Sequence
<220> FEATURE:
<223> OTHER INFORMATION: Mutant luciferase
<220> FEATURE:
<221> NAME/KEY: UNSURE
<222> LOCATION: (354)...(355)
<223> OTHER INFORMATION: Unknown amino acids

<400> SEQUENCE: 22

Met Ala Asp Lys Asn Ile Leu Tyr Gly Pro Glu Pro Phe Tyr Pro Leu
1               5                   10                  15

Ala Asp Gly Thr Ala Gly Glu Gln Met Phe Asp Ala Leu Ser Arg Tyr
            20                  25                  30

Ala Asp Ile Pro Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65              70                  75                  80

Ser Glu Asn Gly Leu Gln Phe Leu Pro Val Ile Ala Ser Leu Tyr
            85                  90                  95

Leu Gly Ile Ile Ala Ala Pro Val Ser Asp Lys Tyr Val Glu Arg Glu
                100                 105                 110

Leu Ile His Ser Leu Gly Ile Val Lys Pro Arg Ile Ile Phe Cys Ser
            115                 120                 125

Lys Asn Thr Phe Gln Lys Val Leu Asn Val Lys Ser Lys Leu Lys Tyr
```

```
          130                 135                 140
Val Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Asn Ser Phe Asn Arg Asp Asp Gln Val Ala
                180                 185                 190

Leu Val Met Phe Ser Ser Gly Thr Thr Gly Val Pro Lys Gly Val Met
                195                 200                 205

Leu Thr His Lys Asn Ile Val Ala Arg Phe Ser Leu Ala Lys Asp Pro
            210                 215                 220

Thr Phe Gly Asn Ala Ile Asn Pro Thr Thr Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
                260                 265                 270

Leu Gln Ser Leu Gln Asp Tyr Lys Val Glu Ser Thr Leu Leu Val Pro
            275                 280                 285

Thr Leu Met Ala Phe Leu Ala Lys Ser Ala Leu Val Glu Lys Tyr Asp
290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
                340                 345                 350

Lys Xaa Xaa Ala Arg Pro Gly Ser Thr Gly Lys Ile Val Pro Phe His
            355                 360                 365

Ala Val Lys Val Val Asp Pro Thr Thr Gly Lys Ile Leu Gly Pro Asn
370                 375                 380

Glu Thr Gly Glu Leu Tyr Phe Lys Gly Ala Met Ile Met Lys Gly Tyr
385                 390                 395                 400

Tyr Asn Asn Glu Glu Ala Thr Lys Ala Ile Ile Asp Lys Asp Gly Trp
                405                 410                 415

Leu Arg Ser Gly Asp Ile Ala Tyr Tyr Asp Asn Asp Gly His Phe Tyr
                420                 425                 430

Ile Val Asp Arg Leu Lys Ser Leu Ile Lys Tyr Lys Gly Tyr Gln Val
                435                 440                 445

Ala Pro Ala Glu Ile Glu Gly Ile Leu Leu Gln His Pro Tyr Ile Val
                450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
                485                 490                 495

Val Gln Asn Phe Val Ser Ser Gln Val Ser Thr Ala Lys Trp Leu Arg
                500                 505                 510

Gly Gly Val Lys Phe Leu Asp Glu Ile Pro Lys Gly Ser Thr Gly Lys
                515                 520                 525

Ile Asp Arg Lys Val Leu Arg Gln Met Phe Glu Lys His Thr Asn Gly
                530                 535                 540
```

<210> SEQ ID NO 23

```
<211> LENGTH: 544
<212> TYPE: PRT
<213> ORGANISM: Artificial Sequence
<220> FEATURE:
<223> OTHER INFORMATION: Mutant luciferase
<220> FEATURE:
<221> NAME/KEY: UNSURE
<222> LOCATION: (354)...(355)
<223> OTHER INFORMATION: Unknown amino acids

<400> SEQUENCE: 23

Met Ala Asp Lys Asn Ile Leu Tyr Gly Pro Glu Pro Phe Tyr Pro Leu
 1               5                  10                  15

Ala Asp Gly Thr Ala Gly Glu Gln Met Phe Asp Ala Leu Ser Arg Tyr
            20                  25                  30

Ala Asp Ile Pro Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
 50                  55                  60

Ser Phe Lys Lys Tyr Gly Leu Lys Gln Asn Asp Thr Ile Ala Val Cys
 65                  70                  75                  80

Ser Glu Asn Gly Leu Gln Phe Phe Leu Pro Val Ile Ala Ser Leu Tyr
                85                  90                  95

Leu Gly Ile Ile Val Ala Pro Val Asn Asp Lys Tyr Ile Glu Arg Glu
            100                 105                 110

Leu Ile His Ser Leu Gly Ile Val Lys Pro Arg Ile Ile Phe Cys Ser
        115                 120                 125

Lys Asn Thr Phe Gln Lys Val Leu Asn Val Lys Ser Lys Leu Lys Ser
130                 135                 140

Val Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ile Asn Leu Asp
                165                 170                 175

Val Lys Lys Phe Lys Pro Tyr Ser Phe Asn Arg Asp Asp Gln Val Ala
            180                 185                 190

Leu Ile Met Phe Ser Ser Gly Thr Thr Gly Leu Pro Lys Gly Val Met
        195                 200                 205

Leu Thr His Lys Asn Ile Val Ala Arg Phe Ser Leu Ala Lys Asp Pro
210                 215                 220

Thr Phe Gly Asn Ala Ile Asn Pro Thr Thr Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Leu Ala Lys Ser Ala Leu Val Glu Lys Tyr Asp
290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

Lys Xaa Xaa Ala Arg Pro Gly Ser Thr Gly Lys Ile Val Pro Phe His
```

-continued

```
            355                 360                 365
Ala Val Lys Val Val Asp Pro Thr Thr Gly Lys Ile Leu Gly Pro Asn
            370                 375                 380
Glu Pro Gly Glu Leu Tyr Phe Lys Gly Pro Met Ile Met Lys Gly Tyr
385                 390                 395                 400
Tyr Asn Asn Glu Glu Ala Thr Lys Ala Ile Ile Asp Asn Asp Gly Trp
                405                 410                 415
Leu Arg Ser Gly Asp Ile Ala Tyr Tyr Asp Asn Asp Gly His Phe Tyr
            420                 425                 430
Ile Val Asp Arg Leu Lys Ser Leu Ile Lys Tyr Lys Gly Tyr Gln Val
            435                 440                 445
Ala Pro Ala Glu Ile Glu Gly Ile Leu Leu Gln His Pro Tyr Ile Val
            450                 455                 460
Asp Ala Gly Val Thr Gly Ile Pro Asp Glu Ala Ala Gly Glu Leu Pro
465                 470                 475                 480
Ala Ala Gly Val Val Gln Thr Gly Lys Tyr Leu Asn Glu Gln Ile
                485                 490                 495
Val Gln Asp Phe Val Ser Ser Gln Val Ser Thr Ala Lys Trp Leu Arg
            500                 505                 510
Gly Gly Val Lys Phe Leu Asp Glu Ile Pro Lys Gly Ser Thr Gly Lys
            515                 520                 525
Ile Asp Arg Lys Val Leu Arg Gln Met Phe Glu Lys His Thr Asn Gly
            530                 535                 540

<210> SEQ ID NO 24
<211> LENGTH: 544
<212> TYPE: PRT
<213> ORGANISM: Artificial Sequence
<220> FEATURE:
<223> OTHER INFORMATION: Mutant luciferase

<400> SEQUENCE: 24

Met Ala Asp Lys Asn Ile Leu Tyr Gly Pro Glu Pro Phe Tyr Pro Leu
1               5                   10                  15
Glu Asp Gly Thr Ala Gly Glu Gln Met Phe Asp Ala Leu Ser Arg Tyr
            20                  25                  30
Ala Asp Ile Pro Gly Cys Ile Ala Leu Thr Asn Ala His Thr Lys Glu
        35                  40                  45
Asn Val Leu Tyr Glu Glu Phe Leu Lys Leu Ser Cys Arg Leu Ala Glu
    50                  55                  60
Ser Phe Lys Lys Tyr Gly Leu Lys Gln Asn Asp Thr Ile Ala Val Cys
65                  70                  75                  80
Ser Glu Asn Gly Leu Gln Phe Phe Leu Pro Val Ile Ala Ser Leu Tyr
                85                  90                  95
Leu Gly Ile Ile Val Ala Pro Val Asn Asp Lys Tyr Ile Glu Arg Glu
            100                 105                 110
Leu Ile His Ser Leu Gly Ile Val Lys Pro Arg Ile Val Phe Cys Ser
            115                 120                 125
Lys Asn Thr Phe Gln Lys Val Leu Asn Val Lys Ser Lys Leu Lys Ser
        130                 135                 140
Ile Glu Thr Ile Ile Ile Leu Asp Leu Asn Glu Asp Leu Gly Gly Tyr
145                 150                 155                 160
Gln Cys Leu Asn Asn Phe Ile Ser Gln Asn Ser Asp Ser Asn Leu Asp
                165                 170                 175
Val Lys Lys Phe Lys Pro Tyr Ser Phe Asn Arg Asp Asp Gln Val Ala
```

-continued

```
                    180                 185                 190
Leu Ile Met Phe Ser Ser Gly Thr Thr Gly Leu Pro Lys Gly Val Met
            195                 200                 205
Leu Thr His Lys Asn Ile Val Ala Arg Phe Ser Leu Ala Lys Asp Pro
        210                 215                 220
Thr Phe Gly Asn Ala Ile Asn Pro Thr Ala Ile Leu Thr Val Ile
225                 230                 235                 240
Pro Phe His His Gly Phe Gly Met Met Thr Thr Leu Gly Tyr Phe Thr
                245                 250                 255
Cys Gly Phe Arg Val Val Leu Met His Thr Phe Glu Glu Lys Leu Phe
            260                 265                 270
Leu Gln Ser Leu Gln Asp Tyr Lys Val Glu Ser Thr Leu Leu Val Pro
        275                 280                 285
Thr Leu Met Ala Phe Leu Ala Lys Ser Ala Leu Val Glu Lys Tyr Asp
    290                 295                 300
Leu Ser His Leu Lys Glu Ile Ala Ser Gly Gly Ala Pro Leu Ser Lys
305                 310                 315                 320
Glu Ile Gly Glu Met Val Lys Lys Arg Phe Lys Leu Asn Phe Val Arg
                325                 330                 335
Gln Gly Tyr Gly Leu Thr Glu Thr Thr Ser Ala Val Leu Ile Thr Pro
            340                 345                 350
Lys Gly Asp Ala Lys Pro Gly Ser Thr Gly Lys Ile Val Pro Phe His
        355                 360                 365
Ala Val Lys Val Val Asp Pro Thr Thr Gly Lys Ile Leu Gly Pro Asn
    370                 375                 380
Glu Pro Gly Glu Leu Tyr Phe Lys Gly Pro Met Ile Met Lys Gly Tyr
385                 390                 395                 400
Tyr Asn Asn Glu Glu Ala Thr Lys Ala Ile Ile Asp Asn Asp Gly Trp
                405                 410                 415
Leu Arg Ser Gly Asp Ile Ala Tyr Tyr Asp Asn Asp Gly His Phe Tyr
            420                 425                 430
Ile Val Asp Arg Leu Lys Ser Leu Ile Lys Tyr Lys Gly Tyr Gln Val
        435                 440                 445
Ala Pro Ala Glu Ile Glu Gly Ile Leu Leu Gln His Pro Tyr Ile Val
    450                 455                 460
Asp Ala Gly Val Thr Gly Ile Pro Asp Glu Ala Ala Gly Glu Leu Pro
465                 470                 475                 480
Ala Ala Gly Val Val Gln Thr Gly Lys Tyr Leu Asn Glu Gln Ile
                485                 490                 495
Val Gln Asp Tyr Val Ala Ser Gln Val Ser Thr Ala Lys Trp Leu Arg
            500                 505                 510
Gly Gly Val Lys Phe Leu Asp Glu Ile Pro Lys Gly Ser Thr Gly Lys
        515                 520                 525
Ile Asp Arg Lys Val Leu Arg Gln Met Phe Glu Lys His Thr Asn Gly
    530                 535                 540

<210> SEQ ID NO 25
<211> LENGTH: 545
<212> TYPE: PRT
<213> ORGANISM: Artificial Sequence
<220> FEATURE:
<223> OTHER INFORMATION: Mutant luciferase

<400> SEQUENCE: 25

Met Glu Asp Lys Asn Ile Leu Tyr Gly Pro Glu Pro Phe Tyr Pro Leu
```

-continued

```
  1               5                    10                   15
Ala Asp Gly Thr Ala Gly Glu Gln Met Phe Tyr Ala Leu Ser Arg Tyr
                 20                  25                  30
Ala Asp Ile Ser Gly Cys Ile Ala Leu Thr Asn Ala His Thr Lys Glu
                 35                  40                  45
Asn Val Leu Tyr Glu Glu Phe Leu Lys Leu Ser Cys Arg Leu Ala Glu
 50                  55                  60
Ser Phe Lys Lys Tyr Gly Leu Lys Gln Asn Asp Thr Ile Ala Val Cys
 65                  70                  75                  80
Ser Glu Asn Gly Leu Gln Phe Phe Leu Pro Leu Ile Ala Ser Leu Tyr
                 85                  90                  95
Leu Gly Ile Ile Ala Ala Pro Val Ser Asp Lys Tyr Ile Glu Arg Glu
                100                 105                 110
Leu Ile His Ser Leu Gly Ile Val Lys Pro Arg Ile Ile Phe Cys Ser
                115                 120                 125
Lys Asn Thr Phe Gln Lys Val Leu Asn Val Lys Ser Lys Leu Lys Tyr
    130                 135                 140
Val Glu Thr Ile Ile Ile Leu Asp Leu Asn Glu Asp Leu Gly Gly Tyr
145                 150                 155                 160
Gln Cys Leu Asn Asn Phe Ile Ser Gln Asn Ser Asp Ile Asn Leu Asp
                165                 170                 175
Val Lys Lys Phe Lys Pro Asn Ser Phe Asn Arg Asp Asp Gln Val Ala
                180                 185                 190
Leu Val Met Phe Ser Ser Gly Thr Thr Gly Val Ser Lys Gly Val Met
                195                 200                 205
Leu Thr His Lys Asn Ile Val Ala Arg Phe Ser His Cys Lys Asp Pro
    210                 215                 220
Thr Phe Gly Asn Ala Ile Asn Pro Thr Thr Ala Ile Leu Thr Val Ile
225                 230                 235                 240
Pro Phe His His Gly Phe Gly Met Met Thr Thr Leu Gly Tyr Phe Thr
                245                 250                 255
Cys Gly Phe Arg Val Ala Leu Met His Thr Phe Glu Glu Lys Leu Phe
                260                 265                 270
Leu Gln Ser Leu Gln Asp Tyr Lys Val Glu Ser Thr Leu Leu Val Pro
    275                 280                 285
Thr Leu Met Ala Phe Phe Ala Lys Ser Ala Leu Val Glu Lys Tyr Asp
290                 295                 300
Leu Ser His Leu Lys Glu Ile Ala Ser Gly Gly Ala Pro Leu Ser Lys
305                 310                 315                 320
Glu Ile Gly Glu Met Val Lys Lys Arg Phe Lys Leu Asn Phe Val Arg
                325                 330                 335
Gln Gly Tyr Gly Leu Thr Glu Thr Thr Ser Ala Val Leu Ile Thr Pro
                340                 345                 350
Asp Thr Asp Val Arg Pro Gly Ser Thr Gly Lys Ile Val Pro Phe His
    355                 360                 365
Ala Val Lys Val Val Asp Pro Thr Thr Gly Lys Ile Leu Gly Pro Asn
    370                 375                 380
Glu Thr Gly Glu Leu Tyr Phe Lys Gly Asp Met Ile Met Lys Gly Tyr
385                 390                 395                 400
Tyr Asn Asn Glu Glu Ala Thr Lys Ala Ile Ile Asn Lys Asp Gly Trp
                405                 410                 415
Leu Arg Ser Gly Asp Ile Ala Tyr Tyr Asp Asn Asp Gly His Phe Tyr
                420                 425                 430
```

-continued

```
Ile Val Asp Arg Leu Lys Ser Leu Ile Lys Tyr Lys Gly Tyr Gln Val
            435                 440                 445

Ala Pro Ala Glu Ile Glu Gly Ile Leu Leu Gln His Pro Tyr Ile Val
        450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
                485                 490                 495

Val Gln Asn Phe Val Ser Ser Gln Val Ser Thr Ala Lys Trp Leu Arg
            500                 505                 510

Gly Gly Val Lys Phe Leu Asp Glu Ile Pro Lys Gly Ser Thr Gly Lys
            515                 520                 525

Ile Asp Arg Lys Val Leu Arg Gln Met Phe Glu Lys His Lys Ser Lys
            530                 535                 540

Leu
545
```

<210> SEQ ID NO 26
<211> LENGTH: 542
<212> TYPE: PRT
<213> ORGANISM: Artificial Sequence
<220> FEATURE:
<223> OTHER INFORMATION: Mutant luciferase

<400> SEQUENCE: 26

```
Met Met Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
145                 150                 155                 160

Glu Ser Leu Pro Asn Gly Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Ala
    210                 215                 220

Gly Thr Gln Leu Ile Pro Gly Val Thr Val Leu Val Tyr Leu Pro Phe
225                 230                 235                 240
```

-continued

```
Phe His Ala Phe Gly Phe Ser Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
    290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Asn Ile His Ser Leu Arg Asp
            340                 345                 350

Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
    370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp Glu His Phe Tyr Val Val
            420                 425                 430

Asp Arg Tyr Lys Glu Leu Ile Lys Tyr Lys Gly Ser Gln Val Ala Pro
        435                 440                 445

Ala Glu Leu Glu Glu Ile Leu Leu Lys Asn Pro Cys Ile Arg Asp Val
    450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Glu Lys Ala Gly Gly
    530                 535                 540

<210> SEQ ID NO 27
<211> LENGTH: 548
<212> TYPE: PRT
<213> ORGANISM: Luciola cruciata

<400> SEQUENCE: 27

Met Glu Asn Met Glu Asn Asp Glu Asn Ile Val Val Gly Pro Lys Pro
1               5                   10                  15

Phe Tyr Pro Ile Glu Glu Gly Ser Ala Gly Thr Gln Leu Arg Lys Tyr
            20                  25                  30

Met Glu Arg Tyr Ala Lys Leu Gly Ala Ile Ala Phe Thr Asn Ala Val
        35                  40                  45

Thr Gly Val Asp Tyr Ser Tyr Ala Glu Tyr Leu Glu Lys Ser Cys Cys
    50                  55                  60

Leu Gly Lys Ala Leu Gln Asn Tyr Gly Leu Val Val Asp Gly Arg Ile
```

```
65                   70                   75                   80
Ala Leu Cys Ser Glu Asn Cys Glu Glu Phe Phe Ile Pro Val Ile Ala
                85                   90                   95

Gly Leu Phe Ile Gly Val Gly Val Ala Pro Thr Asn Glu Ile Tyr Thr
                100                  105                  110

Leu Arg Glu Leu Val His Ser Leu Gly Ile Ser Lys Pro Thr Ile Val
            115                  120                  125

Phe Ser Ser Lys Lys Gly Leu Asp Lys Val Ile Thr Val Gln Lys Thr
        130                  135                  140

Val Thr Thr Ile Lys Thr Ile Val Ile Leu Asp Ser Lys Val Asp Tyr
145                  150                  155                  160

Arg Gly Tyr Gln Cys Leu Asp Thr Phe Ile Lys Arg Asn Thr Pro Pro
                165                  170                  175

Gly Phe Gln Ala Ser Ser Phe Lys Thr Val Glu Val Asp Arg Lys Glu
                180                  185                  190

Gln Val Ala Leu Ile Met Asn Ser Ser Gly Ser Thr Gly Leu Pro Lys
            195                  200                  205

Gly Val Gln Leu Thr His Glu Asn Thr Val Thr Arg Phe Ser His Ala
        210                  215                  220

Arg Asp Pro Ile Tyr Gly Asn Gln Val Ser Pro Gly Thr Ala Val Leu
225                  230                  235                  240

Thr Val Val Pro Phe His His Gly Phe Gly Met Phe Thr Thr Leu Gly
                245                  250                  255

Tyr Leu Ile Cys Gly Phe Arg Val Val Met Leu Thr Lys Phe Asp Glu
                260                  265                  270

Glu Thr Phe Leu Lys Thr Leu Gln Asp Tyr Lys Cys Thr Ser Val Ile
            275                  280                  285

Leu Val Pro Thr Leu Phe Ala Ile Leu Asn Lys Ser Glu Leu Leu Asn
        290                  295                  300

Lys Tyr Asp Leu Ser Asn Leu Val Glu Ile Ala Ser Gly Gly Ala Pro
305                  310                  315                  320

Leu Ser Lys Glu Val Gly Glu Ala Val Ala Arg Arg Phe Asn Leu Pro
                325                  330                  335

Gly Val Arg Gln Gly Tyr Gly Leu Thr Glu Thr Thr Ser Ala Ile Ile
                340                  345                  350

Ile Thr Pro Glu Gly Asp Asp Lys Pro Gly Ala Ser Gly Lys Val Val
            355                  360                  365

Pro Leu Phe Lys Ala Lys Val Ile Asp Leu Asp Thr Lys Lys Ser Leu
        370                  375                  380

Gly Pro Asn Arg Arg Gly Glu Val Cys Val Lys Gly Pro Met Leu Met
385                  390                  395                  400

Lys Gly Tyr Val Asn Asn Pro Glu Ala Thr Lys Glu Leu Ile Asp Glu
                405                  410                  415

Glu Gly Trp Leu His Thr Gly Asp Ile Gly Tyr Tyr Asp Glu Glu Lys
                420                  425                  430

His Phe Phe Ile Val Asp Arg Leu Lys Ser Leu Ile Lys Tyr Lys Gly
            435                  440                  445

Tyr Gln Val Pro Pro Ala Glu Leu Glu Ser Val Leu Leu Gln His Pro
        450                  455                  460

Ser Ile Phe Asp Ala Gly Val Ala Gly Val Pro Asp Pro Val Ala Gly
465                  470                  475                  480

Glu Leu Pro Gly Ala Val Val Leu Glu Ser Gly Lys Asn Met Thr
                485                  490                  495
```

Glu Lys Glu Val Met Asp Tyr Val Ala Ser Gln Val Ser Asn Ala Lys
                500                 505                 510

Arg Leu Arg Gly Gly Val Arg Phe Val Asp Glu Val Pro Lys Gly Leu
            515                 520                 525

Thr Gly Lys Ile Asp Gly Arg Ala Ile Arg Glu Ile Leu Lys Lys Pro
        530                 535                 540

Val Ala Lys Met
545

<210> SEQ ID NO 28
<211> LENGTH: 548
<212> TYPE: PRT
<213> ORGANISM: Luciola lateralis

<400> SEQUENCE: 28

Met Glu Asn Met Glu Asn Asp Glu Asn Ile Val Tyr Gly Pro Glu Pro
 1               5                  10                  15

Phe Tyr Pro Ile Glu Glu Gly Ser Ala Gly Ala Gln Leu Arg Lys Tyr
                20                  25                  30

Met Asp Arg Tyr Ala Lys Leu Gly Ala Ile Ala Phe Thr Asn Ala Leu
            35                  40                  45

Thr Gly Val Asp Tyr Thr Tyr Ala Glu Tyr Leu Glu Lys Ser Cys Cys
    50                  55                  60

Leu Gly Glu Ala Leu Lys Asn Tyr Gly Leu Val Val Asp Gly Arg Ile
65                  70                  75                  80

Ala Leu Cys Ser Glu Asn Cys Glu Glu Phe Phe Ile Pro Val Leu Ala
                85                  90                  95

Gly Leu Phe Ile Gly Val Gly Val Ala Pro Thr Asn Glu Ile Tyr Thr
                100                 105                 110

Leu Arg Glu Leu Val His Ser Leu Gly Ile Ser Lys Pro Thr Ile Val
            115                 120                 125

Phe Ser Ser Lys Lys Gly Leu Asp Lys Val Ile Thr Val Gln Lys Thr
        130                 135                 140

Val Ala Thr Ile Lys Thr Ile Val Ile Leu Asp Ser Lys Val Asp Tyr
145                 150                 155                 160

Arg Gly Tyr Gln Ser Met Asp Asn Phe Ile Lys Lys Asn Thr Pro Gln
                165                 170                 175

Gly Phe Lys Gly Ser Ser Phe Lys Thr Val Glu Val Asn Arg Lys Glu
                180                 185                 190

Gln Val Ala Leu Ile Met Asn Ser Ser Gly Ser Thr Gly Leu Pro Lys
            195                 200                 205

Gly Val Gln Leu Thr His Glu Asn Ala Val Thr Arg Phe Ser His Ala
        210                 215                 220

Arg Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
                245                 250                 255

Tyr Leu Thr Cys Gly Phe Arg Ile Val Met Leu Thr Lys Phe Asp Glu
                260                 265                 270

Glu Thr Phe Leu Lys Thr Leu Gln Asp Tyr Lys Cys Ser Ser Val Ile
            275                 280                 285

Leu Val Pro Thr Leu Phe Ala Ile Leu Asn Arg Ser Glu Leu Leu Asp
        290                 295                 300

Lys Tyr Asp Leu Ser Asn Leu Val Glu Ile Ala Ser Gly Gly Ala Pro

```
        305                 310                 315                 320
Leu Ser Lys Glu Ile Gly Glu Ala Val Ala Arg Arg Phe Asn Leu Pro
                325                 330                 335

Gly Val Arg Gln Gly Tyr Gly Leu Thr Glu Thr Thr Ser Ala Ile Ile
                340                 345                 350

Ile Thr Pro Glu Gly Asp Asp Lys Pro Gly Ala Ser Gly Lys Val Val
                355                 360                 365

Pro Leu Phe Lys Ala Lys Val Ile Asp Leu Asp Thr Lys Lys Thr Leu
        370                 375                 380

Gly Pro Asn Arg Arg Gly Glu Val Cys Val Lys Gly Pro Met Leu Met
385                 390                 395                 400

Lys Gly Tyr Val Asp Asn Pro Glu Ala Thr Arg Glu Ile Ile Asp Glu
                405                 410                 415

Glu Gly Trp Leu His Thr Gly Asp Ile Gly Tyr Tyr Asp Glu Glu Lys
                420                 425                 430

His Phe Phe Ile Val Asp Arg Leu Lys Ser Leu Ile Lys Tyr Lys Gly
                435                 440                 445

Tyr Gln Val Pro Pro Ala Glu Leu Glu Ser Val Leu Leu Gln His Pro
        450                 455                 460

Asn Ile Phe Asp Ala Gly Val Ala Gly Val Pro Asp Pro Ile Ala Gly
465                 470                 475                 480

Glu Leu Pro Gly Ala Val Val Leu Glu Lys Gly Lys Ser Met Thr
                485                 490                 495

Glu Lys Glu Val Met Asp Tyr Val Ala Ser Gln Val Ser Asn Ala Lys
                500                 505                 510

Arg Leu Arg Gly Val Arg Phe Val Asp Glu Val Pro Lys Gly Leu
        515                 520                 525

Thr Gly Lys Ile Asp Gly Lys Ala Ile Arg Glu Ile Leu Lys Lys Pro
        530                 535                 540

Val Ala Lys Met
545

<210> SEQ ID NO 29
<211> LENGTH: 548
<212> TYPE: PRT
<213> ORGANISM: Luciola mingrelica

<400> SEQUENCE: 29

Met Glu Met Glu Lys Glu Glu Asn Val Val Tyr Gly Pro Leu Pro Phe
  1               5                  10                  15

Tyr Pro Ile Glu Glu Gly Ser Ala Gly Ile Gln Leu His Lys Tyr Met
                20                  25                  30

His Gln Tyr Ala Lys Leu Gly Ala Ile Ala Phe Ser Asn Ala Leu Thr
                35                  40                  45

Gly Val Asp Ile Ser Tyr Gln Glu Tyr Phe Asp Ile Thr Cys Arg Leu
        50                  55                  60

Ala Glu Ala Met Lys Asn Phe Gly Met Lys Pro Glu Glu His Ile Ala
65                  70                  75                  80

Leu Cys Ser Glu Asn Cys Glu Glu Phe Phe Ile Pro Val Leu Ala Gly
                85                  90                  95

Leu Tyr Ile Gly Val Ala Val Ala Pro Thr Asn Glu Ile Tyr Thr Leu
                100                 105                 110

Arg Glu Leu Asn His Ser Leu Gly Ile Ala Gln Pro Thr Ile Val Phe
        115                 120                 125
```

-continued

```
Ser Ser Arg Lys Gly Leu Pro Lys Val Leu Glu Val Gln Lys Thr Val
    130                 135                 140
Thr Cys Ile Lys Lys Ile Val Ile Leu Asp Ser Lys Val Asn Phe Gly
145                 150                 155                 160
Gly His Asp Cys Met Glu Thr Phe Ile Lys Lys His Val Glu Leu Gly
                165                 170                 175
Phe Gln Pro Ser Ser Phe Val Pro Ile Asp Val Lys Asn Arg Lys Gln
            180                 185                 190
His Val Ala Leu Leu Met Asn Ser Ser Gly Ser Thr Gly Leu Pro Lys
        195                 200                 205
Gly Val Arg Ile Thr His Glu Gly Ala Val Thr Arg Phe Ser His Ala
    210                 215                 220
Lys Asp Pro Ile Tyr Gly Asn Gln Val Ser Pro Gly Thr Ala Ile Leu
225                 230                 235                 240
Thr Val Val Pro Phe His His Gly Phe Gly Met Phe Thr Thr Leu Gly
                245                 250                 255
Tyr Phe Ala Cys Gly Tyr Arg Val Val Met Leu Thr Lys Phe Asp Glu
            260                 265                 270
Glu Leu Phe Leu Arg Thr Leu Gln Asp Tyr Lys Cys Thr Ser Val Ile
        275                 280                 285
Leu Val Pro Thr Leu Phe Ala Ile Leu Asn Lys Ser Glu Leu Ile Asp
    290                 295                 300
Lys Phe Asp Leu Ser Asn Leu Thr Glu Ile Ala Ser Gly Gly Ala Pro
305                 310                 315                 320
Leu Ala Lys Glu Val Gly Glu Ala Val Ala Arg Arg Phe Asn Leu Pro
                325                 330                 335
Gly Val Arg Gln Gly Tyr Gly Leu Thr Glu Thr Thr Ser Ala Phe Ile
            340                 345                 350
Ile Thr Pro Glu Gly Asp Asp Lys Pro Gly Ala Ser Gly Lys Val Val
        355                 360                 365
Pro Leu Phe Lys Val Lys Val Ile Asp Leu Asp Thr Lys Lys Thr Leu
    370                 375                 380
Gly Val Asn Arg Arg Gly Glu Ile Cys Val Lys Gly Pro Ser Leu Met
385                 390                 395                 400
Leu Gly Tyr Ser Asn Asn Pro Glu Ala Thr Arg Glu Thr Ile Asp Glu
                405                 410                 415
Glu Gly Trp Leu His Thr Gly Asp Ile Gly Tyr Tyr Asp Glu Asp Glu
            420                 425                 430
His Phe Phe Ile Val Asp Arg Leu Lys Ser Leu Ile Lys Tyr Lys Gly
        435                 440                 445
Tyr Gln Val Pro Pro Ala Glu Leu Glu Ser Val Leu Leu Gln His Pro
    450                 455                 460
Asn Ile Phe Asp Ala Gly Val Ala Gly Val Pro Asp Pro Asp Ala Gly
465                 470                 475                 480
Glu Leu Pro Gly Ala Val Val Met Glu Lys Gly Lys Thr Met Thr
                485                 490                 495
Glu Lys Glu Ile Val Asp Tyr Val Asn Ser Gln Val Asn His Lys
            500                 505                 510
Arg Leu Arg Gly Gly Val Arg Phe Val Asp Glu Val Pro Lys Gly Leu
        515                 520                 525
Thr Gly Lys Ile Asp Ala Lys Val Ile Arg Glu Ile Leu Lys Lys Pro
    530                 535                 540
Gln Ala Lys Met
```

545

<210> SEQ ID NO 30
<211> LENGTH: 548
<212> TYPE: PRT
<213> ORGANISM: Pyrocoelia miyako

<400> SEQUENCE: 30

| Met | Glu | Asp | Asp | Ser | Lys | His | Ile | Met | His | Gly | His | Arg | His | Ser | Ile |
|---|---|---|---|---|---|---|---|---|---|---|---|---|---|---|---|
| 1 | | | | 5 | | | | | 10 | | | | | 15 | |

| Leu | Trp | Glu | Asp | Gly | Thr | Ala | Gly | Glu | Gln | Leu | His | Lys | Ala | Met | Lys |
| | | | 20 | | | | | 25 | | | | | 30 | | |

| Arg | Tyr | Ala | Gln | Val | Pro | Gly | Thr | Ile | Ala | Phe | Thr | Asp | Ala | His | Ala |
| | | 35 | | | | | 40 | | | | | 45 | | | |

| Glu | Val | Asn | Ile | Thr | Tyr | Ser | Glu | Tyr | Phe | Glu | Met | Ser | Cys | Arg | Leu |
| | 50 | | | | | 55 | | | | | 60 | | | | |

| Ala | Glu | Thr | Met | Lys | Arg | Tyr | Gly | Leu | Gly | Leu | Gln | His | His | Ile | Ala |
| 65 | | | | | 70 | | | | | 75 | | | | | 80 |

| Val | Cys | Ser | Glu | Thr | Ser | Leu | Gln | Phe | Phe | Met | Pro | Val | Cys | Gly | Ala |
| | | | | 85 | | | | | 90 | | | | | 95 | |

| Leu | Phe | Ile | Gly | Val | Gly | Val | Ala | Pro | Thr | Asn | Asp | Ile | Tyr | Asn | Glu |
| | | | | 100 | | | | | 105 | | | | | 110 | |

| Arg | Glu | Leu | Tyr | Asn | Ser | Leu | Phe | Ile | Ser | Gln | Pro | Thr | Ile | Val | Phe |
| | | | 115 | | | | | 120 | | | | | 125 | | |

| Cys | Ser | Lys | Arg | Ala | Leu | Gln | Lys | Ile | Leu | Gly | Val | Gln | Lys | Lys | Leu |
| | | 130 | | | | | 135 | | | | | 140 | | | |

| Pro | Val | Ile | Gln | Lys | Ile | Val | Ile | Leu | Asp | Ser | Arg | Glu | Asp | Tyr | Met |
| 145 | | | | | 150 | | | | | 155 | | | | | 160 |

| Gly | Lys | Gln | Ser | Met | Tyr | Ser | Phe | Ile | Glu | Ser | His | Leu | Pro | Ala | Gly |
| | | | | 165 | | | | | 170 | | | | | 175 | |

| Phe | Asn | Glu | Tyr | Asp | Tyr | Ile | Pro | Asp | Ser | Phe | Asp | Arg | Glu | Thr | Ala |
| | | | 180 | | | | | 185 | | | | | 190 | | |

| Thr | Ala | Leu | Ile | Met | Asn | Ser | Ser | Gly | Ser | Thr | Gly | Leu | Pro | Lys | Gly |
| | | | 195 | | | | | 200 | | | | | 205 | | |

| Val | Asp | Leu | Thr | His | Met | Asn | Val | Cys | Val | Arg | Phe | Ser | His | Cys | Arg |
| | 210 | | | | | 215 | | | | | 220 | | | | |

| Asp | Pro | Val | Phe | Gly | Asn | Gln | Ile | Ile | Pro | Asp | Thr | Ala | Ile | Leu | Thr |
| 225 | | | | | 230 | | | | | 235 | | | | | 240 |

| Val | Ile | Pro | Phe | His | His | Val | Phe | Gln | Met | Phe | Thr | Thr | Leu | Gly | Tyr |
| | | | | 245 | | | | | 250 | | | | | 255 | |

| Leu | Thr | Cys | Gly | Phe | Arg | Ile | Val | Leu | Met | Tyr | Arg | Phe | Glu | Glu | Glu |
| | | | 260 | | | | | 265 | | | | | 270 | | |

| Leu | Phe | Leu | Arg | Ser | Leu | Gln | Asp | Tyr | Lys | Ile | Gln | Ser | Ala | Leu | Leu |
| | | | 275 | | | | | 280 | | | | | 285 | | |

| Val | Pro | Thr | Leu | Phe | Ser | Phe | Phe | Ala | Lys | Ser | Thr | Leu | Val | Asp | Lys |
| | | 290 | | | | | 295 | | | | | 300 | | | |

| Tyr | Asp | Leu | Ser | Asn | Leu | His | Glu | Ile | Ala | Ser | Gly | Gly | Ala | Pro | Leu |
| 305 | | | | | 310 | | | | | 315 | | | | | 320 |

| Ala | Lys | Glu | Val | Gly | Glu | Ala | Val | Ala | Lys | Arg | Phe | Lys | Leu | Pro | Gly |
| | | | | 325 | | | | | 330 | | | | | 335 | |

| Ile | Arg | Gln | Gly | Tyr | Gly | Leu | Thr | Glu | Thr | Thr | Ser | Ala | Ile | Ile | Ile |
| | | | 340 | | | | | 345 | | | | | 350 | | |

| Thr | Pro | Glu | Gly | Asp | Asp | Lys | Pro | Gly | Ala | Cys | Gly | Lys | Val | Val | Pro |
| | | 355 | | | | | 360 | | | | | 365 | | | |

```
Phe Phe Thr Ala Lys Ile Val Asp Leu Asp Thr Gly Lys Thr Leu Gly
        370                 375                 380

Val Asn Gln Arg Gly Glu Leu Cys Val Lys Gly Pro Met Ile Met Lys
385                 390                 395                 400

Gly Tyr Val Asn Asn Pro Glu Ala Thr Asn Ala Leu Ile Asp Lys Asp
                405                 410                 415

Gly Trp Leu His Ser Gly Asp Ile Ala Tyr Tyr Asp Lys Asp Gly His
                420                 425                 430

Phe Phe Ile Val Asp Arg Leu Lys Ser Leu Ile Lys Tyr Lys Gly Tyr
        435                 440                 445

Gln Val Pro Pro Ala Glu Leu Glu Ser Ile Leu Leu Gln His Pro Phe
        450                 455                 460

Ile Phe Asp Ala Gly Val Ala Gly Ile Pro Asp Pro Asp Ala Gly Glu
465                 470                 475                 480

Leu Pro Ala Ala Val Val Val Leu Glu Glu Gly Lys Met Met Thr Glu
                485                 490                 495

Gln Glu Val Met Asp Tyr Val Ala Gly Gln Val Thr Ala Ser Lys Arg
                500                 505                 510

Leu Arg Gly Gly Val Lys Phe Val Asp Glu Val Pro Lys Gly Leu Thr
        515                 520                 525

Gly Lys Ile Asp Ser Arg Lys Ile Arg Glu Ile Leu Thr Met Gly Gln
        530                 535                 540

Lys Ser Lys Leu
545

<210> SEQ ID NO 31
<211> LENGTH: 550
<212> TYPE: PRT
<213> ORGANISM: Photinus pyralis

<400> SEQUENCE: 31

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
                20                  25                  30

Tyr Ala Leu Val Pro Gly Thr Ile Ala Phe Thr Asp Ala His Ile Glu
            35                  40                  45

Val Asn Ile Thr Tyr Ala Glu Tyr Phe Glu Met Ser Val Arg Leu Ala
50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190
```

```
Ala Leu Ile Met Asn Ser Ser Gly Ser Thr Gly Leu Pro Lys Gly Val
            195                 200                 205

Ala Leu Pro His Arg Thr Ala Cys Val Arg Phe Ser His Ala Arg Asp
            210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
            275                 280                 285

Pro Thr Leu Phe Ser Phe Phe Ala Lys Ser Thr Leu Ile Asp Lys Tyr
            290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
            355                 360                 365

Phe Glu Ala Lys Val Val Asp Leu Asp Thr Gly Lys Thr Leu Gly Val
            370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp His Phe
            420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Ala Gly Glu Leu
465                 470                 475                 480

Pro Ala Ala Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
            530                 535                 540

Gly Gly Lys Ser Lys Leu
545                 550

<210> SEQ ID NO 32
<211> LENGTH: 547
<212> TYPE: PRT
<213> ORGANISM: Lampyris noctiluca

<400> SEQUENCE: 32

Met Glu Asp Ala Lys Asn Ile Met His Gly Pro Ala Pro Phe Tyr Pro
```

-continued

```
  1               5                  10                 15
Leu Glu Asp Gly Thr Ala Gly Glu Gln Leu His Lys Ala Met Lys Arg
            20                  25              30
Tyr Ala Gln Val Pro Gly Thr Ile Ala Phe Thr Asp Ala His Ala Glu
        35                  40              45
Val Asn Ile Thr Tyr Ser Glu Tyr Phe Glu Met Ala Cys Arg Leu Ala
    50                  55              60
Glu Thr Met Lys Arg Tyr Gly Leu Gly Leu Gln His His Ile Ala Val
65                  70              75                  80
Cys Ser Glu Asn Ser Leu Gln Phe Phe Met Pro Val Cys Gly Ala Leu
            85                  90              95
Phe Ile Gly Val Gly Val Ala Ser Thr Asn Asp Ile Tyr Asn Glu Arg
            100                 105             110
Glu Leu Tyr Asn Ser Leu Ser Ile Ser Gln Pro Thr Ile Val Ser Cys
        115                 120             125
Ser Lys Arg Ala Leu Gln Lys Ile Leu Gly Val Gln Lys Lys Leu Pro
    130                 135             140
Ile Ile Gln Lys Ile Val Ile Leu Asp Ser Arg Glu Asp Tyr Met Gly
145                 150             155                 160
Lys Gln Ser Met Tyr Ser Phe Ile Glu Ser His Leu Pro Ala Gly Phe
            165                 170             175
Asn Glu Tyr Asp Tyr Ile Pro Asp Ser Phe Asp Arg Glu Thr Ala Thr
            180                 185             190
Ala Leu Ile Met Asn Ser Ser Gly Ser Thr Gly Leu Pro Lys Gly Val
        195                 200             205
Glu Leu Thr His Gln Asn Val Cys Val Arg Phe Ser His Cys Arg Asp
    210                 215             220
Pro Val Phe Gly Asn Gln Ile Ile Pro Asp Thr Ala Ile Leu Thr Val
225                 230             235                 240
Ile Pro Phe His His Gly Phe Gly Met Phe Thr Thr Leu Gly Tyr Leu
            245                 250             255
Thr Cys Gly Phe Arg Ile Val Leu Met Tyr Arg Phe Glu Glu Glu Leu
            260                 265             270
Phe Leu Arg Ser Leu Gln Asp Tyr Lys Ile Gln Ser Ala Leu Leu Val
        275                 280             285
Pro Thr Leu Phe Ser Phe Phe Ala Lys Ser Thr Leu Val Asp Lys Tyr
    290                 295             300
Asp Leu Ser Asn Leu His Glu Ile Ala Ser Gly Gly Ala Pro Leu Ala
305                 310             315                 320
Lys Glu Val Gly Glu Ala Val Ala Lys Arg Phe Lys Leu Pro Gly Ile
            325                 330             335
Arg Gln Gly Tyr Gly Leu Thr Glu Thr Thr Ser Ala Ile Ile Ile Thr
            340                 345             350
Pro Glu Gly Asp Asp Lys Pro Gly Ala Cys Gly Lys Val Val Pro Phe
        355                 360             365
Phe Ser Ala Lys Ile Val Asp Leu Asp Thr Gly Lys Thr Leu Gly Val
    370                 375             380
Asn Gln Arg Gly Glu Leu Cys Val Lys Gly Pro Met Ile Met Lys Gly
385                 390             395                 400
Tyr Val Asn Asn Pro Glu Ala Thr Ser Ala Leu Ile Asp Lys Asp Gly
            405                 410             415
Trp Leu His Ser Gly Asp Ile Ala Tyr Tyr Asp Lys Asp Gly His Phe
            420                 425             430
```

-continued

```
Phe Ile Val Asp Arg Leu Lys Ser Leu Ile Lys Tyr Lys Gly Tyr Gln
            435                 440                 445

Val Pro Pro Ala Glu Leu Glu Ser Ile Leu Leu Gln His Pro Phe Ile
        450                 455                 460

Phe Asp Ala Gly Val Ala Gly Ile Pro Asp Pro Asp Ala Gly Glu Leu
465                 470                 475                 480

Pro Ala Ala Val Val Val Leu Glu Glu Gly Lys Thr Met Thr Glu Gln
                485                 490                 495

Glu Val Met Asp Tyr Val Ala Gly Gln Val Thr Ala Ser Lys Arg Leu
            500                 505                 510

Arg Gly Gly Val Lys Phe Val Asp Glu Val Pro Lys Gly Leu Thr Gly
        515                 520                 525

Lys Ile Asp Gly Arg Lys Ile Arg Glu Ile Leu Met Met Gly Lys Lys
530                 535                 540

Ser Lys Leu
545

<210> SEQ ID NO 33
<211> LENGTH: 552
<212> TYPE: PRT
<213> ORGANISM: Photuris pennsylvanica

<400> SEQUENCE: 33

Met Ser Ile Glu Asn Asn Ile Leu Ile Gly Pro Pro Tyr Tyr Pro
1               5                   10                  15

Leu Glu Glu Gly Thr Ala Gly Glu Gln Leu His Arg Ala Ile Ser Arg
            20                  25                  30

Tyr Ala Ala Val Pro Gly Thr Leu Ala Tyr Thr Asp Val His Thr Glu
        35                  40                  45

Leu Glu Val Thr Tyr Lys Glu Phe Leu Asp Val Thr Cys Arg Leu Ala
    50                  55                  60

Glu Ala Met Lys Asn Tyr Gly Leu Gly Leu Gln His Thr Ile Ser Val
65                  70                  75                  80

Cys Ser Glu Asn Cys Val Gln Phe Phe Met Pro Ile Cys Ala Ala Leu
                85                  90                  95

Tyr Val Gly Val Ala Thr Ala Pro Thr Asn Asp Ile Tyr Asn Glu Arg
            100                 105                 110

Glu Leu Tyr Asn Ser Leu Ser Ile Ser Gln Pro Thr Val Val Phe Thr
        115                 120                 125

Ser Arg Asn Ser Leu Gln Lys Ile Leu Gly Val Gln Ser Arg Leu Pro
    130                 135                 140

Ile Ile Lys Lys Ile Ile Ile Leu Asp Gly Lys Lys Asp Tyr Leu Gly
145                 150                 155                 160

Tyr Gln Ser Met Gln Ser Phe Met Lys Glu His Val Pro Ala Asn Phe
                165                 170                 175

Asn Val Ser Ala Phe Lys Pro Leu Ser Phe Asp Leu Asp Arg Val Ala
            180                 185                 190

Cys Ile Met Asn Ser Ser Gly Ser Thr Gly Leu Pro Lys Gly Val Pro
        195                 200                 205

Ile Ser His Arg Asn Thr Ile Tyr Arg Phe Ser His Cys Arg Asp Pro
    210                 215                 220

Val Phe Gly Asn Gln Ile Ile Pro Asp Thr Thr Ile Leu Cys Ala Val
225                 230                 235                 240

Pro Phe His His Ala Phe Gly Thr Phe Thr Asn Leu Gly Tyr Leu Ile
```

```
                    245                 250                 255
Cys Gly Phe His Val Val Leu Met Tyr Arg Phe Asn Glu His Leu Phe
                260                 265                 270

Leu Gln Thr Leu Gln Asp Tyr Lys Cys Gln Ser Ala Leu Leu Val Pro
                275                 280                 285

Thr Val Leu Ala Phe Leu Ala Lys Asn Pro Leu Val Asp Lys Tyr Asp
                290                 295                 300

Leu Ser Asn Leu His Glu Ile Ala Ser Gly Ala Pro Leu Ser Lys
305                 310                 315                 320

Glu Ile Ser Glu Ile Ala Ala Lys Arg Phe Lys Leu Pro Gly Ile Arg
                325                 330                 335

Gln Gly Tyr Gly Leu Thr Glu Thr Thr Cys Ala Ile Val Ile Thr Ala
                340                 345                 350

Glu Gly Glu Phe Lys Leu Gly Ala Val Gly Lys Val Val Pro Phe Tyr
                355                 360                 365

Ser Leu Lys Val Leu Asp Leu Asn Thr Gly Lys Lys Leu Gly Pro Asn
                370                 375                 380

Glu Arg Gly Glu Ile Cys Phe Lys Gly Pro Met Ile Met Lys Gly Tyr
385                 390                 395                 400

Ile Asn Asn Pro Glu Ala Thr Arg Glu Leu Ile Asp Glu Glu Gly Trp
                405                 410                 415

Ile His Ser Gly Asp Ile Gly Tyr Phe Asp Glu Asp Gly His Val Tyr
                420                 425                 430

Ile Val Asp Arg Leu Lys Ser Leu Ile Lys Tyr Lys Gly Tyr Gln Val
                435                 440                 445

Pro Pro Ala Glu Leu Glu Ala Leu Leu Leu Gln His Pro Phe Ile Glu
                450                 455                 460

Asp Ala Gly Val Ala Gly Val Pro Asp Glu Val Ala Gly Asp Leu Pro
465                 470                 475                 480

Gly Ala Val Val Leu Lys Glu Gly Lys Ser Ile Thr Glu Lys Glu
                485                 490                 495

Ile Gln Asp Tyr Val Ala Gly Gln Val Thr Ser Ser Lys Lys Leu Arg
                500                 505                 510

Gly Gly Val Glu Phe Val Lys Glu Val Pro Lys Gly Phe Thr Gly Lys
                515                 520                 525

Ile Asp Thr Arg Lys Ile Lys Glu Ile Leu Ile Lys Ala Gln Lys Gly
                530                 535                 540

Lys Ser Lys Ser Lys Ala Lys Leu
545                 550

<210> SEQ ID NO 34
<211> LENGTH: 546
<212> TYPE: PRT
<213> ORGANISM: Phengodes sp.

<400> SEQUENCE: 34

Met Ile Lys Met Glu Glu His Val Met Pro Gly Ala Met Pro Arg
  1               5                  10                  15

Asp Leu Leu Phe Glu Gly Thr Ala Gly Gln Gln Leu His Arg Ala Leu
                 20                  25                  30

Tyr Lys His Ser Tyr Phe Pro Glu Ala Ile Val Asp Ser His Thr His
                 35                  40                  45

Glu Ile Ile Ser Tyr Ala Lys Ile Leu Asp Met Ser Cys Arg Leu Ala
                 50                  55                  60
```

-continued

```
Val Ser Phe Gln Lys Tyr Gly Leu Thr Gln Asn Asn Ile Ile Gly Ile
 65                  70                  75                  80

Cys Ser Glu Asn Asn Leu Asn Phe Phe Asn Pro Val Ile Ala Ala Phe
                 85                  90                  95

Tyr Leu Gly Ile Thr Val Ala Thr Val Asn Asp Thr Tyr Thr Asp Arg
            100                 105                 110

Glu Leu Ser Glu Thr Leu Asn Ile Thr Lys Pro Gln Met Leu Phe Cys
            115                 120                 125

Ser Lys Gln Ser Leu Pro Ile Val Met Lys Thr Met Lys Ile Met Pro
130                 135                 140

Tyr Val Gln Lys Leu Leu Ile Ile Asp Ser Met Gln Asp Ile Gly Gly
145                 150                 155                 160

Ile Glu Cys Val His Ser Phe Val Ser Arg Tyr Thr Asp Glu His Phe
                165                 170                 175

Asp Pro Leu Lys Phe Val Pro Leu Asp Phe Asp Pro Arg Glu Gln Val
            180                 185                 190

Ala Leu Ile Met Thr Ser Ser Gly Thr Thr Gly Leu Pro Lys Gly Val
            195                 200                 205

Met Leu Thr His Arg Asn Ile Cys Val Arg Phe Val His Ser Arg Asp
            210                 215                 220

Pro Leu Phe Gly Thr Arg Phe Ile Pro Glu Thr Ser Ile Leu Ser Leu
225                 230                 235                 240

Val Pro Phe His His Ala Phe Gly Met Phe Thr Thr Leu Ser Tyr Phe
                245                 250                 255

Ile Val Gly Leu Lys Ile Val Met Met Lys Arg Phe Asp Gly Glu Leu
            260                 265                 270

Phe Leu Lys Thr Ile Gln Asn Tyr Lys Ile Pro Thr Ile Val Ile Ala
            275                 280                 285

Pro Pro Val Met Val Phe Leu Ala Lys Ser His Leu Val Asp Lys Tyr
            290                 295                 300

Asp Leu Ser Ser Ile Lys Glu Ile Ala Thr Gly Gly Ala Pro Leu Gly
305                 310                 315                 320

Pro Ala Leu Ala Asn Ala Val Ala Lys Arg Leu Lys Leu Gly Gly Ile
                325                 330                 335

Ile Gln Gly Tyr Gly Leu Thr Glu Thr Cys Cys Ala Val Leu Ile Thr
            340                 345                 350

Pro His Asn Lys Ile Lys Thr Gly Ser Thr Gly Gln Val Leu Pro Tyr
            355                 360                 365

Val Thr Ala Lys Ile Val Asp Thr Lys Thr Gly Lys Asn Leu Gly Pro
370                 375                 380

Asn Gln Thr Gly Glu Leu Cys Phe Lys Ser Asp Ile Ile Met Lys Gly
385                 390                 395                 400

Tyr Tyr Gln Asn Glu Glu Glu Thr Arg Leu Val Ile Asp Lys Asp Gly
                405                 410                 415

Trp Leu His Ser Gly Asp Ile Gly Tyr Tyr Asp Thr Asp Gly Asn Phe
            420                 425                 430

His Ile Val Asp Arg Leu Lys Glu Leu Ile Lys Tyr Lys Ala Tyr Gln
            435                 440                 445

Val Ala Pro Ala Glu Leu Glu Ala Leu Leu Leu Gln His Pro Tyr Ile
450                 455                 460

Ala Asp Ala Gly Val Thr Gly Ile Pro Asp Glu Glu Ala Gly Glu Leu
465                 470                 475                 480

Pro Ala Ala Cys Val Val Leu Glu Pro Gly Lys Thr Met Thr Glu Lys
```

```
                        485                 490                 495
Glu Val Met Asp Tyr Ile Ala Glu Arg Val Thr Pro Thr Lys Arg Leu
                500                 505                 510

Arg Gly Gly Val Leu Phe Val Asn Asn Ile Pro Lys Gly Ala Thr Gly
            515                 520                 525

Lys Leu Val Arg Thr Glu Leu Arg Arg Leu Leu Thr Gln Arg Ala Ala
        530                 535                 540

Lys Leu
545

<210> SEQ ID NO 35
<211> LENGTH: 543
<212> TYPE: PRT
<213> ORGANISM: Pyrophorus plagiophthalamus

<400> SEQUENCE: 35

Met Met Lys Arg Glu Lys Asn Val Val Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Tyr Gly Glu Glu
        35                  40                  45

Trp Ile Ser Tyr Lys Glu Phe Phe Glu Thr Thr Cys Leu Leu Ala Gln
    50                  55                  60

Ser Leu His Asn Cys Gly Tyr Lys Met Ser Asp Val Val Ser Ile Cys
65                  70                  75                  80

Ala Glu Asn Asn Lys Arg Phe Phe Val Pro Ile Ile Ala Ala Trp Tyr
                85                  90                  95

Ile Gly Met Ile Val Ala Pro Val Asn Glu Gly Tyr Ile Pro Asp Glu
            100                 105                 110

Leu Cys Lys Val Met Gly Ile Ser Arg Pro Gln Leu Val Phe Cys Thr
        115                 120                 125

Lys Asn Ile Leu Asn Lys Val Leu Glu Val Gln Ser Arg Thr Asp Phe
    130                 135                 140

Ile Lys Arg Ile Ile Ile Leu Asp Ala Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Tyr Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Arg Asn Val Cys Val Arg Leu Ile His Ala Leu Asp Pro Arg Val
    210                 215                 220

Gly Thr Gln Leu Ile Pro Gly Val Thr Val Leu Val Tyr Leu Pro Phe
225                 230                 235                 240

Phe His Ala Phe Gly Phe Ser Ile Asn Leu Gly Tyr Phe Met Val Gly
                245                 250                 255

Leu Arg Val Ile Met Leu Arg Arg Phe Asp Gln Glu Ala Phe Leu Lys
            260                 265                 270

Ala Ile Gln Asp Tyr Glu Val Arg Ser Val Ile Asn Val Pro Ala Ile
        275                 280                 285

Ile Leu Phe Leu Ser Lys Ser Pro Leu Val Asp Lys Tyr Asp Leu Ser
    290                 295                 300
```

-continued

```
Ser Leu Arg Glu Leu Cys Cys Gly Ala Ala Pro Leu Ala Lys Glu Val
305                 310                 315                 320

Ala Glu Ile Ala Val Lys Arg Leu Asn Leu Pro Gly Ile Arg Cys Gly
            325                 330                 335

Phe Gly Leu Thr Glu Ser Thr Ser Ala Asn Ile His Ser Leu Arg Asp
        340                 345                 350

Glu Phe Lys Ser Gly Ser Leu Gly Arg Val Thr Pro Leu Met Ala Ala
    355                 360                 365

Lys Ile Ala Asp Arg Glu Thr Gly Lys Ala Leu Gly Pro Asn Gln Val
370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
            405                 410                 415

Ser Gly Asp Phe Gly Tyr Tyr Asp Glu Asp Glu His Phe Tyr Val Val
        420                 425                 430

Asp Arg Tyr Lys Glu Leu Ile Lys Tyr Lys Gly Ser Gln Val Ala Pro
    435                 440                 445

Ala Glu Leu Glu Glu Ile Leu Leu Lys Asn Pro Cys Ile Arg Asp Val
450                 455                 460

Ala Val Val Gly Ile Pro Asp Leu Glu Ala Gly Glu Leu Pro Ser Ala
465                 470                 475                 480

Phe Val Val Ile Gln Pro Gly Lys Glu Ile Thr Ala Lys Glu Val Tyr
            485                 490                 495

Asp Tyr Leu Ala Glu Arg Val Ser His Thr Lys Tyr Leu Arg Gly Gly
        500                 505                 510

Val Arg Phe Val Asp Ser Ile Pro Arg Asn Val Thr Gly Lys Ile Thr
    515                 520                 525

Arg Lys Glu Leu Leu Lys Gln Leu Leu Glu Lys Ser Ser Lys Leu
530                 535                 540

<210> SEQ ID NO 36
<211> LENGTH: 543
<212> TYPE: PRT
<213> ORGANISM: Pyrophorus plagiophthalamus

<400> SEQUENCE: 36

Met Met Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Phe Gly Asp Glu
        35                  40                  45

Ser Leu Ser Tyr Lys Glu Phe Phe Glu Ala Thr Cys Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Lys Arg Phe Phe Ile Pro Ile Ala Ala Trp Tyr
            85                  90                  95

Ile Gly Met Ile Val Ala Pro Val Asn Glu Ser Tyr Ile Pro Asp Glu
        100                 105                 110

Leu Cys Lys Val Met Gly Ile Ser Lys Pro Gln Ile Val Phe Cys Thr
    115                 120                 125

Lys Asn Ile Leu Asn Lys Val Leu Glu Val Gln Ser Arg Thr Asn Phe
130                 135                 140
```

-continued

```
Ile Lys Arg Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
            165                 170                 175

Asn Phe Lys Pro Leu His Tyr Asp Pro Val Glu Gln Val Ala Ala Ile
            180                 185                 190

Leu Cys Ser Ser Gly Thr Thr Gly Leu Pro Lys Gly Val Met Gln Thr
            195                 200                 205

His Gln Asn Ile Cys Val Arg Leu Ile His Ala Leu Asp Pro Arg Ala
210                 215                 220

Gly Thr Gln Leu Ile Pro Gly Val Thr Val Leu Val Tyr Leu Pro Phe
225                 230                 235                 240

Phe His Ala Phe Gly Phe Ser Ile Asn Leu Gly Tyr Phe Met Val Gly
            245                 250                 255

Leu Arg Val Ile Met Leu Arg Arg Phe Asp Gln Glu Ala Phe Leu Lys
            260                 265                 270

Ala Ile Gln Asp Tyr Glu Val Arg Ser Val Ile Asn Val Pro Ala Ile
            275                 280                 285

Ile Leu Phe Leu Ser Lys Ser Pro Leu Val Asp Lys Tyr Asp Leu Ser
290                 295                 300

Ser Leu Arg Glu Leu Cys Cys Gly Ala Ala Pro Leu Ala Lys Glu Val
305                 310                 315                 320

Ala Glu Val Ala Val Lys Arg Leu Asn Leu Pro Gly Ile Arg Cys Gly
            325                 330                 335

Phe Gly Leu Thr Glu Ser Thr Ser Ala Asn Ile His Ser Leu Gly Asp
            340                 345                 350

Glu Phe Lys Ser Gly Ser Leu Gly Arg Val Thr Pro Leu Met Ala Ala
            355                 360                 365

Lys Ile Ala Asp Arg Glu Thr Gly Lys Ala Leu Gly Pro Asn Gln Val
            370                 375                 380

Gly Glu Leu Cys Val Lys Gly Pro Met Val Ser Lys Gly Tyr Val Asn
385                 390                 395                 400

Asn Val Glu Ala Thr Lys Glu Ala Ile Asp Asp Gly Trp Leu His
            405                 410                 415

Ser Gly Asp Phe Gly Tyr Tyr Asp Glu Asp Glu His Phe Tyr Val Val
            420                 425                 430

Asp Arg Tyr Lys Glu Leu Ile Lys Tyr Lys Gly Ser Gln Val Ala Pro
            435                 440                 445

Ala Glu Leu Glu Glu Ile Leu Leu Lys Asn Pro Cys Ile Arg Asp Val
450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
            485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
            515                 520                 525

Arg Lys Glu Leu Leu Lys Gln Leu Leu Glu Lys Ser Ser Lys Leu
530                 535                 540
```

<210> SEQ ID NO 37
<211> LENGTH: 545

```
<212> TYPE: PRT
<213> ORGANISM: Photuris pennsylvanica

<400> SEQUENCE: 37
```

| | | | | | | | | | | | | | | |
|---|---|---|---|---|---|---|---|---|---|---|---|---|---|---|
| Met | Glu | Asp | Lys | Asn | Ile | Leu | Tyr | Gly | Pro | Glu | Pro | Phe | Tyr | Pro | Leu |
| 1 | | | | 5 | | | | | 10 | | | | | 15 |

Ala Asp Gly Thr Ala Gly Glu Gln Met Phe Tyr Ala Leu Ser Arg Tyr
            20                  25                  30

Ala Asp Ile Ser Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Gly Leu Gln Phe Phe Leu Pro Leu Ile Ala Ser Leu Tyr
                85                  90                  95

Leu Gly Ile Ile Ala Ala Pro Val Ser Asp Lys Tyr Ile Glu Arg Glu
            100                 105                 110

Leu Ile His Ser Leu Gly Ile Val Lys Pro Arg Ile Ile Phe Cys Ser
        115                 120                 125

Lys Asn Thr Phe Gln Lys Val Leu Asn Val Lys Ser Lys Leu Lys Tyr
    130                 135                 140

Val Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ile Asn Leu Asp
                165                 170                 175

Val Lys Lys Phe Lys Pro Asn Ser Phe Asn Arg Asp Asp Gln Val Ala
            180                 185                 190

Leu Val Met Phe Ser Ser Gly Thr Thr Gly Val Ser Lys Gly Val Met
        195                 200                 205

Leu Thr His Lys Asn Ile Val Ala Arg Phe Ser His Cys Lys Asp Pro
    210                 215                 220

Thr Phe Gly Asn Ala Ile Asn Pro Thr Thr Ala Ile Leu Thr Val Ile
225                 230                 235                 240

Pro Phe His His Gly Phe Gly Met Thr Thr Thr Leu Gly Tyr Phe Thr
                245                 250                 255

Cys Gly Phe Arg Val Ala Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Phe Ala Lys Ser Ala Leu Val Glu Lys Tyr Asp
    290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

Asp Thr Asp Val Arg Pro Gly Ser Thr Gly Lys Ile Val Pro Phe His
        355                 360                 365

Ala Val Lys Val Val Asp Pro Thr Thr Gly Lys Ile Leu Gly Pro Asn
    370                 375                 380

Glu Thr Gly Glu Leu Tyr Phe Lys Gly Asp Met Ile Met Lys Ser Tyr
385                 390                 395                 400

```
Tyr Asn Asn Glu Glu Ala Thr Lys Ala Ile Ile Asn Lys Asp Gly Trp
                405                 410                 415
Leu Arg Ser Gly Asp Ile Ala Tyr Tyr Asp Asn Asp Gly His Phe Tyr
            420                 425                 430
Ile Val Asp Arg Leu Lys Ser Leu Ile Lys Tyr Lys Gly Tyr Gln Val
        435                 440                 445
Ala Pro Ala Glu Ile Glu Gly Ile Leu Leu Gln His Pro Tyr Ile Val
    450                 455                 460
Asp Ala Gly Val Thr Gly Ile Pro Asp Glu Ala Ala Gly Glu Leu Pro
465                 470                 475                 480
Ala Ala Gly Val Val Gln Thr Gly Lys Tyr Leu Asn Glu Gln Ile
            485                 490                 495
Val Gln Asn Phe Val Ser Ser Gln Val Ser Thr Ala Lys Trp Leu Arg
            500                 505                 510
Gly Gly Val Lys Phe Leu Asp Glu Ile Pro Lys Gly Ser Thr Gly Lys
        515                 520                 525
Ile Asp Arg Lys Val Leu Arg Gln Met Phe Glu Lys His Lys Ser Lys
    530                 535                 540
Leu
545

<210> SEQ ID NO 38
<211> LENGTH: 38
<212> TYPE: DNA
<213> ORGANISM: Artificial Sequence
<220> FEATURE:
<223> OTHER INFORMATION: A primer

<400> SEQUENCE: 38
gtactgagac gacgccagcc caagcttagg cctgagtg                    38

<210> SEQ ID NO 39
<211> LENGTH: 38
<212> TYPE: DNA
<213> ORGANISM: Artificial Sequence
<220> FEATURE:
<223> OTHER INFORMATION: A primer

<400> SEQUENCE: 39
ggcatgagcg tgaactgact gaactagcgg ccgccgag                    38

<210> SEQ ID NO 40
<211> LENGTH: 18
<212> TYPE: DNA
<213> ORGANISM: Artificial Sequence
<220> FEATURE:
<223> OTHER INFORMATION: A primer

<400> SEQUENCE: 40
gtactgagac gacgccag                                          18

<210> SEQ ID NO 41
<211> LENGTH: 19
<212> TYPE: DNA
<213> ORGANISM: Artificial Sequence
<220> FEATURE:
<223> OTHER INFORMATION: A primer

<400> SEQUENCE: 41
ggcatgagcg tgaactgac                                         19
```

<210> SEQ ID NO 42
<211> LENGTH: 1639
<212> TYPE: DNA
<213> ORGANISM: Artificial Sequence
<220> FEATURE:
<223> OTHER INFORMATION: Mutant luciferase

<400> SEQUENCE: 42

```
agatccaatg gcagataaga atattttata tgggcccgaa ccatttatc ccttggaaga      60
tgggacggct ggagaacaga tgtttgacgc attatctcgt tatgcagata ttccgggctg    120
catagcattg acaaatgctc atacaaaaga aaatgtttta tatgaagagt ttctgaaact    180
gtcgtgtcgt ttagcggaaa gttttaaaaa gtatggatta aaacaaaacg acacaatagc    240
ggtgtgtagc gaaaatagtc tgcaatttt ccttcctgta attgcatcat tgtatcttgg     300
aataattgtg gcacctgtta acgataaata cattgaacgt gaattaatac acagtcttgg    360
tattgtaaaa ccacgcatag ttttttgctc caagaatact tttcaaaaag tactgaatgt    420
aaaatctaaa ttaaaatcta ttgaaactat tattatatta gacttaaatg atgacttagg    480
aggttatcaa tgcctcaaca actttatttc tcaaaattcc gatagtaatc tggacgtaaa    540
aaaatttaaa ccatattctt ttaatcgaga cgatcaggtt gcgttgatta tgttttcttc    600
tggtacaact ggtctgccga agggagtcat gctaactcac aagaatattg ttgcacgatt    660
ttctattgca aaagatccta cttttggtaa cgcaattaat cccacgtcag caattttaac    720
ggtaatacct ttccaccatg gttttggtat gatgaccaca ttaggatact ttacttgtgg    780
attccgagtt gttctaatgc acacgtttga agaaaaacta tttctacaat cattacaaga    840
ttataaagtg gaaagtactt tacttgtacc aacattaatg gcatttcttg caaaaagtgc    900
attagttgaa aagtacgatt tatcgcactt aaaagaaatt gcatctggtg gcgcaccttt    960
atcaaaagaa attggggaga tggtgaaaaa acggtttaaa ttaaactttg tcaggcaagg   1020
gtatggatta acagaaacca cttcggctgt tttaattaca ccgaaaggtg acgccaaacc   1080
gggatcaact ggtaaaatag taccatttca cgctgttaaa gttgtcgatc ctacaacagg   1140
aaaaattttg gggccaaatg aacctggaga attgtatttt aaaggcccga tgataatgaa   1200
gggttattat aataatgaag aagctactaa agcaattatt gataatgacg gatggttgcg   1260
ctctggtgat attgcttatt atgacaatga tggccatttt tatattgtgg acaggctgaa   1320
gtcactgatt aaatataaag gttatcaggt tgcacctgct gaaattgagg gaatactctt   1380
acaacatccg tatattgttg atgccggcgt tactggtata ccggatgaag ccgcgggcga   1440
gcttccagct gcaggtgttg tagtacgac tggaaaatat ctaaacgaac aaatcgtaca   1500
agattatgtt gccagtcaag tttcaacagc caaatggcta cgtggtgggg tgatattttt   1560
ggatgaaatt cccaaaggat caactggaaa aattgacaga aaagtgttaa gacaaatgtt   1620
agaaaaacac accaatggg                                                1639
```

<210> SEQ ID NO 43
<211> LENGTH: 1639
<212> TYPE: DNA
<213> ORGANISM: Artificial Sequence
<220> FEATURE:
<223> OTHER INFORMATION: Mutant luciferase

<400> SEQUENCE: 43

```
ggatccaatg gcagataaga atattttata tgggcccgaa ccatttatc ccttggaaga      60
tgggacggct ggagaacaga tgtttgacgc attatctcgt tatgcagcta ttccgggctg    120
```

```
catagcattg acaaatgctc atacaaaaga aaatgtttta tatgaagagt ttctgaaact    180
gtcgtgtcgt ttagcggaaa gttttaaaaa gtatggatta aaacaaaacg acacaatagc    240
ggtgtgtagc gaaaatagtc tgcaattttt ccttcctgta attgcatcat tgtatcttgg    300
aataattgtg gcacctgtta acgataaata cattgaacgt gaattaatac acagtcttgg    360
tattgtaaaa ccacgcatag ttttttgctc caagaatact tttcaaaaag tactgaatgt    420
aaaatctaaa ttaaaatcta ttgaaactat tattatatta gacttaaatg aagacttagg    480
aggttatcaa tgcctcaaca actttatttc tcaaaattcc gatagtaatc tggacgtaaa    540
aaaatttaaa ccctattctt ttaatcgaga cgatcaggtt gcgtcgatta tgttttcttc    600
tggtacaact ggtctgccga agggagtcat gctaactcac aagaatattg ttgcacgatt    660
ttctattgca aagatcctac ttttggtaa cgcaattaat cccacgtcag caattttaac    720
ggtaatacct ttccaccatg gttttggtat gatgaccaca ttaggatact ttacttgtgg    780
attccgagtt gttctaatgc acacgtttga agaaaaacta tttctacaat cattacaaga    840
ttataaagtg gaaagtactt tacttgtacc aacattaatg gcatttcttg caaaaagtgc    900
attagttgaa aagtacgatt tatcgcactt aaaagaaatt gcatctggtg gcgcaccttt    960
atcaaaagaa attggggaga tggtgaaaaa acggtttaaa ttaaactttg tcaggcaagg   1020
gtatggatta acagaaacca cttcggctgt tttaattaca ccgaaaggtg acgccaaacc   1080
gggatcaact ggtaaaatag taccattaca cgctgttaaa gttgtcgatc ctacaacagg   1140
aaaaattttg gggccaaatg aacctggaga attgtatttt aaaggcccga tgataatgaa   1200
gggttattat aataatgaag aagctactaa agcaattatt gataatgacg gatggttgcg   1260
ctctggtgat attgcttatt atgacaatga tggccatttt tatattgtgg acaggctgaa   1320
gtcactgatt aaatataaag gttatcaggt tgcacctgct gaaattgagg gaatactctt   1380
acaacatccg tatattgttg atgccggcgt tactggtata ccggatgaag ccgcgggcga   1440
gcttccagct gcaggtgttg tagtacgac tggaaaatat ctaaacgaac aaatcgtaca   1500
agattatgtt gccagtcaag tttcaacagc caaatggcta cgtggtgggg tgaaattttt   1560
ggatgaaatt cccaaaggat caactggaaa aattgacaga aaagtgttaa gacaaatgtt   1620
agaaaaacac accaatggg                                                 1639
```

<210> SEQ ID NO 44
<211> LENGTH: 544
<212> TYPE: PRT
<213> ORGANISM: Artificial Sequence
<220> FEATURE:
<223> OTHER INFORMATION: Mutant luciferase

<400> SEQUENCE: 44

```
Met Ala Asp Lys Asn Ile Leu Tyr Gly Pro Glu Pro Phe Tyr Pro Leu
 1               5                  10                  15

Glu Asp Gly Thr Ala Gly Glu Gln Met Phe Asp Ala Leu Ser Arg Tyr
            20                  25                  30

Ala Asp Ile Pro Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Ser Leu Gln Phe Phe Leu Pro Val Ile Ala Ser Leu Tyr
```

```
                        85                    90                       95
Leu Gly Ile Ile Val Ala Pro Val Asn Asp Lys Tyr Ile Glu Arg Glu
            100                 105                 110
Leu Ile His Ser Leu Gly Ile Val Lys Pro Arg Ile Val Phe Cys Ser
            115                 120                 125
Lys Asn Thr Phe Gln Lys Val Leu Asn Val Lys Ser Lys Leu Lys Ser
            130                 135                 140
Ile Glu Thr Ile Ile Ile Leu Asp Leu Asn Asp Asp Leu Gly Gly Tyr
145                 150                 155                 160
Gln Cys Leu Asn Asn Phe Ile Ser Gln Asn Ser Asp Ser Asn Leu Asp
                165                 170                 175
Val Lys Lys Phe Lys Pro Tyr Ser Phe Asn Arg Asp Asp Gln Val Ala
            180                 185                 190
Leu Ile Met Phe Ser Ser Gly Thr Thr Gly Leu Pro Lys Gly Val Met
            195                 200                 205
Leu Thr His Lys Asn Ile Val Ala Arg Phe Ser Ile Ala Lys Asp Pro
210                 215                 220
Thr Phe Gly Asn Ala Ile Asn Pro Thr Ser Ala Ile Leu Thr Val Ile
225                 230                 235                 240
Pro Phe His His Gly Phe Gly Met Met Thr Thr Leu Gly Tyr Phe Thr
                245                 250                 255
Cys Gly Phe Arg Val Val Leu Met His Thr Phe Glu Glu Lys Leu Phe
            260                 265                 270
Leu Gln Ser Leu Gln Asp Tyr Lys Val Glu Ser Thr Leu Leu Val Pro
            275                 280                 285
Thr Leu Met Ala Phe Leu Ala Lys Ser Ala Leu Val Glu Lys Tyr Asp
            290                 295                 300
Leu Ser His Leu Lys Glu Ile Ala Ser Gly Gly Ala Pro Leu Ser Lys
305                 310                 315                 320
Glu Ile Gly Glu Met Val Lys Lys Arg Phe Lys Leu Asn Phe Val Arg
                325                 330                 335
Gln Gly Tyr Gly Leu Thr Glu Thr Thr Ser Ala Val Leu Ile Thr Pro
            340                 345                 350
Lys Gly Asp Ala Lys Pro Gly Ser Thr Gly Lys Ile Val Pro Phe His
            355                 360                 365
Ala Val Lys Val Val Asp Pro Thr Thr Gly Lys Ile Leu Gly Pro Asn
370                 375                 380
Glu Pro Gly Glu Leu Tyr Phe Lys Gly Pro Met Ile Met Lys Gly Tyr
385                 390                 395                 400
Tyr Asn Asn Glu Glu Ala Thr Lys Ala Ile Ile Asp Asn Asp Gly Trp
                405                 410                 415
Leu Arg Ser Gly Asp Ile Ala Tyr Tyr Asp Asn Asp Gly His Phe Tyr
            420                 425                 430
Ile Val Asp Arg Leu Lys Ser Leu Ile Lys Tyr Lys Gly Tyr Gln Val
            435                 440                 445
Ala Pro Ala Glu Ile Glu Gly Ile Leu Leu Gln His Pro Tyr Ile Val
450                 455                 460
Asp Ala Gly Val Thr Gly Ile Pro Asp Glu Ala Ala Gly Glu Leu Pro
465                 470                 475                 480
Ala Ala Gly Val Val Gln Thr Gly Lys Tyr Leu Asn Glu Gln Ile
                485                 490                 495
Val Gln Asp Tyr Val Ala Ser Gln Val Ser Thr Ala Lys Trp Leu Arg
            500                 505                 510
```

```
Gly Gly Val Ile Phe Leu Asp Glu Ile Pro Lys Gly Ser Thr Gly Lys
            515                 520                 525

Ile Asp Arg Lys Val Leu Arg Gln Met Leu Glu Lys His Thr Asn Gly
            530                 535                 540

<210> SEQ ID NO 45
<211> LENGTH: 544
<212> TYPE: PRT
<213> ORGANISM: Artificial Sequence
<220> FEATURE:
<223> OTHER INFORMATION: Mutant luciferase

<400> SEQUENCE: 45

Met Ala Asp Lys Asn Ile Leu Tyr Gly Pro Glu Pro Phe Tyr Pro Leu
 1               5                  10                  15

Glu Asp Gly Thr Ala Gly Glu Gln Met Phe Asp Ala Leu Ser Arg Tyr
             20                  25                  30

Ala Ala Ile Pro Gly Cys Ile Ala Leu Thr Asn Ala His Thr Lys Glu
             35                  40                  45

Asn Val Leu Tyr Glu Glu Phe Leu Lys Leu Ser Cys Arg Leu Ala Glu
 50                  55                  60

Ser Phe Lys Lys Tyr Gly Leu Lys Gln Asn Asp Thr Ile Ala Val Cys
 65                  70                  75                  80

Ser Glu Asn Ser Leu Gln Phe Phe Leu Pro Val Ile Ala Ser Leu Tyr
             85                  90                  95

Leu Gly Ile Ile Val Ala Pro Val Asn Asp Lys Tyr Ile Glu Arg Glu
            100                 105                 110

Leu Ile His Ser Leu Gly Ile Val Lys Pro Arg Ile Val Phe Cys Ser
            115                 120                 125

Lys Asn Thr Phe Gln Lys Val Leu Asn Val Lys Ser Lys Leu Lys Ser
130                 135                 140

Ile Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
            165                 170                 175

Val Lys Lys Phe Lys Pro Tyr Ser Phe Asn Arg Asp Asp Gln Val Ala
            180                 185                 190

Ser Ile Met Phe Ser Ser Gly Thr Thr Gly Leu Pro Lys Gly Val Met
            195                 200                 205

Leu Thr His Lys Asn Ile Val Ala Arg Phe Ser Ile Ala Lys Asp Pro
210                 215                 220

Thr Phe Gly Asn Ala Ile Asn Pro Thr Ser Ala Ile Leu Thr Val Ile
225                 230                 235                 240

Pro Phe His His Gly Phe Gly Met Met Thr Thr Leu Gly Tyr Phe Thr
            245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
            275                 280                 285

Thr Leu Met Ala Phe Leu Ala Lys Ser Ala Leu Val Glu Lys Tyr Asp
            290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
            325                 330                 335
```

```
Gln Gly Tyr Gly Leu Thr Glu Thr Thr Ser Ala Val Leu Ile Thr Pro
            340                 345                 350
Lys Gly Asp Ala Lys Pro Gly Ser Thr Gly Lys Ile Val Pro Leu His
        355                 360                 365
Ala Val Lys Val Val Asp Pro Thr Thr Gly Lys Ile Leu Gly Pro Asn
    370                 375                 380
Glu Pro Gly Glu Leu Tyr Phe Lys Gly Pro Met Ile Met Lys Gly Tyr
385                 390                 395                 400
Tyr Asn Asn Glu Glu Ala Thr Lys Ala Ile Ile Asp Asn Asp Gly Trp
                405                 410                 415
Leu Arg Ser Gly Asp Ile Ala Tyr Tyr Asp Asn Asp Gly His Phe Tyr
            420                 425                 430
Ile Val Asp Arg Leu Lys Ser Leu Ile Lys Tyr Lys Gly Tyr Gln Val
        435                 440                 445
Ala Pro Ala Glu Ile Glu Gly Ile Leu Leu Gln His Pro Tyr Ile Val
    450                 455                 460
Asp Ala Gly Val Thr Gly Ile Pro Asp Glu Ala Ala Gly Glu Leu Pro
465                 470                 475                 480
Ala Ala Gly Val Val Gln Thr Gly Lys Tyr Leu Asn Glu Gln Ile
                485                 490                 495
Val Gln Asp Tyr Val Ala Ser Gln Val Ser Thr Ala Lys Trp Leu Arg
            500                 505                 510
Gly Gly Val Lys Phe Leu Asp Glu Ile Pro Lys Gly Ser Thr Gly Lys
        515                 520                 525
Ile Asp Arg Lys Val Leu Arg Gln Met Leu Glu Lys His Thr Asn Gly
    530                 535                 540

<210> SEQ ID NO 46
<211> LENGTH: 1633
<212> TYPE: DNA
<213> ORGANISM: Artificial Sequence
<220> FEATURE:
<223> OTHER INFORMATION: Mutant luciferase

<400> SEQUENCE: 46
ggatcccatg atgaagcgag agaaaaatgt tatatatgga cccgaacccc tacaccccct      60
ggaagactta acagctggag aaatgctctt ccgtgccctt cgaaaacatt ctcatttacc     120
gcaggcttta gtagatgtgg ttggcgacga atcgctttcc tataaagagt tttttgaagc     180
gacagtcctc ctagcgcaaa gtctccacaa ttgtggatac aagatgaatg atgtagtgtc     240
gatctgcgcc gagaataata caagattttt tattcccgtt attgcagctt ggtatattgg     300
tatgattgta gcacctgtta atgaaagtta catcccagat gaactctgta aggtcatggg     360
tatatcgaaa ccacaaatag tttttacgac aaagaacatt ttaaataagg tattggaggt     420
acagagcaga actaatttca taaaaaggat catcgtactt gatactgtag aaaacataca     480
cggttgtgaa agtcttccca attttatttc tcgttattcg gatggaaata ttgccaactt     540
caaaccttta catttcgatc ctgtagagca agtggcagct atcttatgtt cgtcaggcac     600
tactggatta ccgaaaggtg taatgcaaac tcaccaaaat atttgtgtcc gacttataca     660
tgctttagac cccagggcag gaacgcaact tattcctggt gtgacagtct tagtatatct     720
gccttttttc catgctttg ggttctctat aaccttggga tacttcatgg tgggtcttcg     780
tgttatcatg tcaagacgat tgatccaga agcatttcta aaagctattc aggattatga     840
agttcgaagt gtaattaacg ttccatcagt aatattgttc ttatcgaaaa gtccttggt     900
```

```
tgacaaatac gatttatcaa gtttaaggga attgtgttgc ggtgcggcac cattagcaaa      960
agaagttgct gaggttgcag caaaacgatt aaacttgcca ggaattcgct gtggatttgg     1020
tttgacagaa tctacttcag ctaatataca cagtcttagg gatgaattta aaccaggatc     1080
acttggaaga gttactcctt taatggcagc taaaatagca gatagggaaa ctggtaaagc     1140
attgggacca aatcaagttg gtgaattatg cattaaaggt cccatggtat cgaaaggtta     1200
cgtgaacaat gtagaagcta ccaaagaagc tattgatgat gatggttggc ttcactctgg     1260
agactttgga tactatgatg aggatgagca tttctatgtg gtggaccgtt acaaggaatt     1320
gattaaatat aagggctctc aggtagcacc tgcagaacta gaagagattt tattgaaaaa     1380
tccatgtatc agagatgttg ctgtggttgg tattcctgat ctagaagctg agaactgcc      1440 atctgcgttt gtggttaaac agcccggaaa ggagattaca gctaaagaag tgtacgatta     1500
tcttgccgag agggtctccc atacaaagta tttgcgtgga ggggttcgat tcgttgatag     1560
cataccacgg aatgttacag gtaaaattac aagaaaggaa cttctgaagc agttgctgga     1620
gaaggcggga ggt                                                        1633
```

<210> SEQ ID NO 47
<211> LENGTH: 542
<212> TYPE: PRT
<213> ORGANISM: Artificial Sequence
<220> FEATURE:
<223> OTHER INFORMATION: Mutant luciferase

<400> SEQUENCE: 47

```
Met Met Lys Arg Glu Lys Asn Val Ile Tyr Gly Pro Glu Pro Leu His
 1               5                  10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Val Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Ala
    210                 215                 220
```

-continued

```
Gly Thr Gln Leu Ile Pro Gly Val Thr Val Leu Val Tyr Leu Pro Phe
225                 230                 235                 240

Phe His Ala Phe Gly Phe Ser Ile Thr Leu Gly Tyr Phe Met Val Gly
                245                 250                 255

Leu Arg Val Ile Met Ser Arg Arg Phe Asp Pro Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
    290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Asn Ile His Ser Leu Arg Asp
            340                 345                 350

Glu Phe Lys Pro Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
    370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp Glu His Phe Tyr Val Val
            420                 425                 430

Asp Arg Tyr Lys Glu Leu Ile Lys Tyr Lys Gly Ser Gln Val Ala Pro
        435                 440                 445

Ala Glu Leu Glu Glu Ile Leu Leu Lys Asn Pro Cys Ile Arg Asp Val
    450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Glu Lys Ala Gly Gly
    530                 535                 540
```

<210> SEQ ID NO 48
<211> LENGTH: 23
<212> TYPE: DNA
<213> ORGANISM: Artificial Sequence
<220> FEATURE:
<223> OTHER INFORMATION: A primer

<400> SEQUENCE: 48
ttatcccttg gaagatggga cgg                                    23

<210> SEQ ID NO 49
<211> LENGTH: 22
<212> TYPE: DNA
<213> ORGANISM: Artificial Sequence
<220> FEATURE:
<223> OTHER INFORMATION: A primer

<400> SEQUENCE: 49
ctggagaaca gctgtttgac gc                                    22

<210> SEQ ID NO 50
<211> LENGTH: 32
<212> TYPE: DNA
<213> ORGANISM: Artificial Sequence
<220> FEATURE:
<223> OTHER INFORMATION: A primer

<400> SEQUENCE: 50
gttatgcaga tattccgggc tgcatagcat tg                         32

<210> SEQ ID NO 51
<211> LENGTH: 40
<212> TYPE: DNA
<213> ORGANISM: Artificial Sequence
<220> FEATURE:
<223> OTHER INFORMATION: A primer

<400> SEQUENCE: 51
cttggaataa ttgtggcacc tgttaacgat aaatacattg                 40

<210> SEQ ID NO 52
<211> LENGTH: 23
<212> TYPE: DNA
<213> ORGANISM: Artificial Sequence
<220> FEATURE:
<223> OTHER INFORMATION: A primer

<400> SEQUENCE: 52
aaccacgcat agttttttgc tcc                                   23

<210> SEQ ID NO 53
<211> LENGTH: 31
<212> TYPE: DNA
<213> ORGANISM: Artificial Sequence
<220> FEATURE:
<223> OTHER INFORMATION: A primer

<400> SEQUENCE: 53
aagtactgaa tgtacagtct aaattaaaat c                          31

<210> SEQ ID NO 54
<211> LENGTH: 31
<212> TYPE: DNA
<213> ORGANISM: Artificial Sequence
<220> FEATURE:
<223> OTHER INFORMATION: A primer

<400> SEQUENCE: 54
ttaaaatcta ttgaaactat tattatatta g                          31

<210> SEQ ID NO 55
<211> LENGTH: 23
<212> TYPE: DNA
<213> ORGANISM: Artificial Sequence
<220> FEATURE:
<223> OTHER INFORMATION: A primer

<400> SEQUENCE: 55
gttgcgttga ttatgttttc ttc                                   23

<210> SEQ ID NO 56

<211> LENGTH: 26
<212> TYPE: DNA
<213> ORGANISM: Artificial Sequence
<220> FEATURE:
<223> OTHER INFORMATION: A primer

<400> SEQUENCE: 56
gtacaactgg tctgccgaag ggagtc                                          26

<210> SEQ ID NO 57
<211> LENGTH: 29
<212> TYPE: DNA
<213> ORGANISM: Artificial Sequence
<220> FEATURE:
<223> OTHER INFORMATION: A primer

<400> SEQUENCE: 57
caagaatatt gttgtgcgat tttctcttg                                       29

<210> SEQ ID NO 58
<211> LENGTH: 29
<212> TYPE: DNA
<213> ORGANISM: Artificial Sequence
<220> FEATURE:
<223> OTHER INFORMATION: A primer

<400> SEQUENCE: 58
ctacttttgg taaccagatt aatcccacg                                       29

<210> SEQ ID NO 59
<211> LENGTH: 32
<212> TYPE: DNA
<213> ORGANISM: Artificial Sequence
<220> FEATURE:
<223> OTHER INFORMATION: A primer

<400> SEQUENCE: 59
ccaccatggc tttggtatga cgaccacatt ag                                   32

<210> SEQ ID NO 60
<211> LENGTH: 43
<212> TYPE: DNA
<213> ORGANISM: Artificial Sequence
<220> FEATURE:
<223> OTHER INFORMATION: A primer

<400> SEQUENCE: 60
ttgttctaat gcaccgcttt gaagaagaac tatttctaca atc                       43

<210> SEQ ID NO 61
<211> LENGTH: 31
<212> TYPE: DNA
<213> ORGANISM: Artificial Sequence
<220> FEATURE:
<223> OTHER INFORMATION: A primer

<400> SEQUENCE: 61
aagtgcatta gttgataagt acgatttatc g                                    31

<210> SEQ ID NO 62
<211> LENGTH: 28
<212> TYPE: DNA
<213> ORGANISM: Artificial Sequence
<220> FEATURE:
<223> OTHER INFORMATION: A primer

<400> SEQUENCE: 62
cggtttaaat taccgggtgt caggcaag                                                    28

<210> SEQ ID NO 63
<211> LENGTH: 19
<212> TYPE: DNA
<213> ORGANISM: Artificial Sequence
<220> FEATURE:
<223> OTHER INFORMATION: A primer

<400> SEQUENCE: 63
aagacgccaa accgggatc                                                              19

<210> SEQ ID NO 64
<211> LENGTH: 28
<212> TYPE: DNA
<213> ORGANISM: Artificial Sequence
<220> FEATURE:
<223> OTHER INFORMATION: A primer

<400> SEQUENCE: 64
atcaactggt aaagtagtac catttcac                                                    28

<210> SEQ ID NO 65
<211> LENGTH: 28
<212> TYPE: DNA
<213> ORGANISM: Artificial Sequence
<220> FEATURE:
<223> OTHER INFORMATION: A primer

<400> SEQUENCE: 65
tattttaaag gcccgatgat aatgaagg                                                    28

<210> SEQ ID NO 66
<211> LENGTH: 25
<212> TYPE: DNA
<213> ORGANISM: Artificial Sequence
<220> FEATURE:
<223> OTHER INFORMATION: A primer

<400> SEQUENCE: 66
ggatggttgc actctggtga tattg                                                       25

<210> SEQ ID NO 67
<211> LENGTH: 23
<212> TYPE: DNA
<213> ORGANISM: Artificial Sequence
<220> FEATURE:
<223> OTHER INFORMATION: A primer

<400> SEQUENCE: 67
cagctgcagt tgttgtagta cag                                                         23

<210> SEQ ID NO 68
<211> LENGTH: 23
<212> TYPE: DNA
<213> ORGANISM: Artificial Sequence
<220> FEATURE:
<223> OTHER INFORMATION: A primer

<400> SEQUENCE: 68
gaaaatatct aaccgaacaa atc                                                         23

<210> SEQ ID NO 69
<211> LENGTH: 33
<212> TYPE: DNA

<213> ORGANISM: Artificial Sequence
<220> FEATURE:
<223> OTHER INFORMATION: A primer

<400> SEQUENCE: 69
aatcgtacaa gattatgttg ccagtcaagt ttc     33

<210> SEQ ID NO 70
<211> LENGTH: 24
<212> TYPE: DNA
<213> ORGANISM: Artificial Sequence
<220> FEATURE:
<223> OTHER INFORMATION: A primer

<400> SEQUENCE: 70
gggtgaaatt tgtggatgaa attc     24

<210> SEQ ID NO 71
<211> LENGTH: 26
<212> TYPE: DNA
<213> ORGANISM: Artificial Sequence
<220> FEATURE:
<223> OTHER INFORMATION: A primer

<400> SEQUENCE: 71
ttaagacaaa tgctggaaaa acacac     26

<210> SEQ ID NO 72
<211> LENGTH: 28
<212> TYPE: DNA
<213> ORGANISM: Artificial Sequence
<220> FEATURE:
<223> OTHER INFORMATION: A primer

<400> SEQUENCE: 72
ataaaaatat tctgtatggt cccgaacc     28

<210> SEQ ID NO 73
<211> LENGTH: 28
<212> TYPE: DNA
<213> ORGANISM: Artificial Sequence
<220> FEATURE:
<223> OTHER INFORMATION: A primer

<400> SEQUENCE: 73
atgtttgacg cactgtctcg ttatgcag     28

<210> SEQ ID NO 74
<211> LENGTH: 23
<212> TYPE: DNA
<213> ORGANISM: Artificial Sequence
<220> FEATURE:
<223> OTHER INFORMATION: A primer

<400> SEQUENCE: 74
atagcattga ccaatgctca tac     23

<210> SEQ ID NO 75
<211> LENGTH: 43
<212> TYPE: DNA
<213> ORGANISM: Artificial Sequence
<220> FEATURE:
<223> OTHER INFORMATION: A primer

<400> SEQUENCE: 75
aagaaaatgt tctgtatgaa gagtttctga aactgtcgtg tcg     43

<210> SEQ ID NO 76
<211> LENGTH: 28
<212> TYPE: DNA
<213> ORGANISM: Artificial Sequence
<220> FEATURE:
<223> OTHER INFORMATION: A primer

<400> SEQUENCE: 76
taaaaagtat ggactgaaac aaaacgac                               28

<210> SEQ ID NO 77
<211> LENGTH: 22
<212> TYPE: DNA
<213> ORGANISM: Artificial Sequence
<220> FEATURE:
<223> OTHER INFORMATION: A primer

<400> SEQUENCE: 77
cgaaaatggt ctgcaatttt tc                                     22

<210> SEQ ID NO 78
<211> LENGTH: 29
<212> TYPE: DNA
<213> ORGANISM: Artificial Sequence
<220> FEATURE:
<223> OTHER INFORMATION: A primer

<400> SEQUENCE: 78
aattgcatca ctgtatctgg gaataattg                              29

<210> SEQ ID NO 79
<211> LENGTH: 39
<212> TYPE: DNA
<213> ORGANISM: Artificial Sequence
<220> FEATURE:
<223> OTHER INFORMATION: A primer

<400> SEQUENCE: 79
ttgaacgtga actgatacac agtctgggta ttgtaaaac                   39

<210> SEQ ID NO 80
<211> LENGTH: 36
<212> TYPE: DNA
<213> ORGANISM: Artificial Sequence
<220> FEATURE:
<223> OTHER INFORMATION: A primer

<400> SEQUENCE: 80
aaactattat tatactggac ctgaatgaag acttag                      36

<210> SEQ ID NO 81
<211> LENGTH: 28
<212> TYPE: DNA
<213> ORGANISM: Artificial Sequence
<220> FEATURE:
<223> OTHER INFORMATION: A primer

<400> SEQUENCE: 81
gttatcaatg cctgaacaac tttatttc                               28

<210> SEQ ID NO 82
<211> LENGTH: 22
<212> TYPE: DNA
<213> ORGANISM: Artificial Sequence
<220> FEATURE:

```
<223> OTHER INFORMATION: A primer

<400> SEQUENCE: 82
tcttttaatc gtgacgatca gg                                           22

<210> SEQ ID NO 83
<211> LENGTH: 25
<212> TYPE: DNA
<213> ORGANISM: Artificial Sequence
<220> FEATURE:
<223> OTHER INFORMATION: A primer

<400> SEQUENCE: 83
cgacagcaat tctgacggta atacc                                        25

<210> SEQ ID NO 84
<211> LENGTH: 25
<212> TYPE: DNA
<213> ORGANISM: Artificial Sequence
<220> FEATURE:
<223> OTHER INFORMATION: A primer

<400> SEQUENCE: 84
tgtggattcc gcgttgttct aatgc                                        25

<210> SEQ ID NO 85
<211> LENGTH: 39
<212> TYPE: DNA
<213> ORGANISM: Artificial Sequence
<220> FEATURE:
<223> OTHER INFORMATION: A primer

<400> SEQUENCE: 85
tggaaagtac tctgctggta ccaacactga tggcatttc                         39

<210> SEQ ID NO 86
<211> LENGTH: 30
<212> TYPE: DNA
<213> ORGANISM: Artificial Sequence
<220> FEATURE:
<223> OTHER INFORMATION: A primer

<400> SEQUENCE: 86
cgatttatcg cacctgaaag aaattgcatc                                   30

<210> SEQ ID NO 87
<211> LENGTH: 30
<212> TYPE: DNA
<213> ORGANISM: Artificial Sequence
<220> FEATURE:
<223> OTHER INFORMATION: A primer

<400> SEQUENCE: 87
ggtggcgcac ctctgtcaaa agaaattggg                                   30

<210> SEQ ID NO 88
<211> LENGTH: 27
<212> TYPE: DNA
<213> ORGANISM: Artificial Sequence
<220> FEATURE:
<223> OTHER INFORMATION: A primer

<400> SEQUENCE: 88
agggtatgga ctgaccgaaa ccacttc                                      27
```

-continued

```
<210> SEQ ID NO 89
<211> LENGTH: 18
<212> TYPE: DNA
<213> ORGANISM: Artificial Sequence
<220> FEATURE:
<223> OTHER INFORMATION: A primer

<400> SEQUENCE: 89
aggaaaaatt ctggggcc                                                 18

<210> SEQ ID NO 90
<211> LENGTH: 28
<212> TYPE: DNA
<213> ORGANISM: Artificial Sequence
<220> FEATURE:
<223> OTHER INFORMATION: A primer

<400> SEQUENCE: 90
ggctgaagtc actgattaaa tataaagg                                      28

<210> SEQ ID NO 91
<211> LENGTH: 23
<212> TYPE: DNA
<213> ORGANISM: Artificial Sequence
<220> FEATURE:
<223> OTHER INFORMATION: A primer

<400> SEQUENCE: 91
agggaatact gctgcaacat ccg                                           23

<210> SEQ ID NO 92
<211> LENGTH: 38
<212> TYPE: DNA
<213> ORGANISM: Artificial Sequence
<220> FEATURE:
<223> OTHER INFORMATION: A primer

<400> SEQUENCE: 92
cagtcaagtt tcaaccgcca aatggctgcg tggtgggg                           38

<210> SEQ ID NO 93
<211> LENGTH: 25
<212> TYPE: DNA
<213> ORGANISM: Artificial Sequence
<220> FEATURE:
<223> OTHER INFORMATION: A primer

<400> SEQUENCE: 93
gaaaaattga ccgtaaagtg ttaag                                         25
```

THERMOSTABLE LUCIFERASES AND METHODS OF PRODUCTION

CROSS-REFERENCE TO RELATED APPLICATIONS

This application is a continuation-in-part application of U.S. application Ser. No. 09/156,946, filed Sep. 18, 1998 now abandoned, and of PCT/US98/19494, filed Sep. 18, 1998, both of which claim priority from U.S. application Ser. No. 60/059,379, filed Sep. 19, 1997, the disclosures of which are incorporated by reference herein.

STATEMENT OF GOVERNMENT RIGHTS

The invention was made with grants from the Government of the United States of America (grants 1R43 GM506 23-01 and 2R44 GM506 23-02 from the National Institutes of Health and grants ISI-9160613 and III-9301865 from the National Science Foundation). The Government may have certain rights to the invention.

FIELD OF THE INVENTION

The invention is directed to mutant luciferase enzymes having greatly increased thermostability compared to natural luciferases or to luciferases from which they are derived as measured, e.g., by half-lives of at least 2 hours at 50° C. in aqueous solution. The invention includes mutant luciferase enzymes that are resistant to inhibition by a substrate inhibitor, e.g., a substrate analog. The invention is also drawn to polynucleotides encoding the novel luciferases, and to hosts transformed to express the luciferases. The invention is further drawn to methods of producing luciferases with increased thermostability and the use of these luciferases in any method in which previously known luciferases are conventionally employed. Some of the uses employ kits. The invention also provides a method of producing a polynucleotide sequence encoding an enzyme that is resistant to inhibition by an inhibitor, and a method which yields a polynucleotide sequence encoding an enzyme having enhanced enzymological properties.

BACKGROUND OF THE INVENTION

Luciferases are defined by their ability to produce luminescence. Beetle luciferases form a distinct class with unique evolutionary origins and chemical mechanisms (Wood, 1995).

Although the enzymes known as beetle luciferases are widely recognized for their use in highly sensitive luminescent assays, their general utility has been limited due to low thermostability. Beetle luciferases having amino acid sequences encoded by cDNA sequences cloned from luminous beetles are not stable even at moderate temperatures. For example, even the most stable of the luciferases, LucPpe2, obtained from a firefly has very little stability at the moderate temperature of 37° C. Firefly luciferases are a sub-group of the beetle luciferases. Historically, the term "firefly luciferase" referred to the enzyme LucPpy from a single species *Photinus pyralis* (Luc+is a mutant version of LucPpy, see U.S. Pat. No. 5,670,356).

Attempts have been reported to mutate natural cDNA sequences encoding luciferase and to select mutants for improved thermostability (White et al., 1994; from *P. pyralis,* and Kajiyama and Nekano, 1993; from *Luciola lateralis.*) However, there is still a need to improve the characteristics and versatility of this important class of enzymes.

SUMMARY OF THE INVENTION

The invention is drawn to novel and remarkably thermostable luciferases, including luciferase enzymes with half-lives of at least 2 hours at 50° C., or at least 5 hours at 50° C., in an aqueous solution. As described hereinbelow, after 2 hours at 50° C. in an aqueous solution, a thermostable luciferase of the invention lost less than 5% luminescence activity. The mutant luciferases of the present invention display remarkable and heretofore unrealized thermostability at 22° C. in an aqueous solution and at temperatures at least as high as 60° C. in an aqueous solution. For example, the luciferases of the invention are thermostable for at least 10 hours at 50° C.; for at least 2 hours, preferably at least 5 hours, more preferably at least 10 hours, and even more preferably at least 24 hours, at 60° C.; and/or for at least 100 days, preferably at least 200 days, more preferably at least 500 days, and even more preferably at least 800 days, at 22° C., in aqueous solution. For example, after 30 days at 22° C. in an aqueous solution, a thermostable luciferase of the invention lost less than 5% luminescence activity. Preferably, the thermostable luciferases of the invention have enhanced luminescence intensity, enhanced signal stability, enhanced substrate utilization, and/or decreased Km, relative to a reference, e.g., a native wild-type, luciferase. The invention is further directed to the mutant luciferase genes (e.g., cDNA or RNA) which encode the novel luciferase enzymes. The terminology used herein is, e.g., for the mutants isolated in experiment 90, plate number 1, well B5, the *E. coli* strain is 90-1B5, the mutant gene is luc90-1B5, and the mutated luciferase is Luc90-1B5.

As defined herein, a "thermostable" enzyme, e.g., a luciferase, or an enzyme which has "thermostability", is an enzyme which under certain conditions, e.g., at certain temperature, in aqueous solution and/or for certain periods of time, has an increased retention of activity relative to a reference enzyme. For example, for a thermostable luciferase, a reference luciferase may be native wild-type luciferase or recombinant wild-type luciferase. Preferably, for beetle luciferases, the activity is luminescence under conditions of saturation with luciferin and ATP. One measure of thermostability of an enzyme is the half-life of the enzyme in an aqueous solution (the time over which 50% of the activity is lost) at a stated temperature.

The invention further encompasses expression vectors and other genetic constructs containing the mutant luciferases, as well as hosts, bacterial and otherwise, transformed to express the mutant luciferases. The invention is also drawn to compositions and kits which contain the novel luciferases, and use of these luciferases in any methodology where luciferases are employed.

Various means of random mutagenesis were applied to a luciferase gene (nucleotide sequence), most particularly gene synthesis using an error-prone polymerase, to create libraries of modified luciferase genes. This library was expressed in colonies of *E. coli* and visually screened for efficient luminescence to select a subset library of modified luciferases. Lysates of these *E. coli* strains were then made, and quantitatively measured for luciferase activity and thermostability. From this, a smaller subset of modified luciferases was chosen, and the selected mutations were combined to make composite modified luciferases. New libraries were made from the composite modified luciferases by random mutagenesis and the process was repeated. The luciferases with the best overall performance were selected after several cycles of this process.

Methods of producing improved luciferases include directed evolution using a polynucleotide sequence encoding a first beetle luciferase as a starting (parent) sequence, to produce a polynucleotide sequence encoding a second luciferase with increased thermostability, compared to the first luciferase, while maintaining other characteristics of the enzymes. A cDNA designated lucPpe2 encodes a firefly luciferase derived from *Photuris pennsylvanica* that displays increased thermostability as compared to the widely utilized luciferase designated LucPpy from *Photinus pyralis*. The cDNA encoding LucPpe2 was isolated, sequenced and cloned (see Leach et al., 1997). A mutant of this gene encodes a first luciferase LucPpe2 [T249M]. However, the methods of the invention are not limited to use with a polynucleotide sequence encoding a beetle luciferase, i.e., the methods of the invention may be employed with a polynucleotide sequence encoding other enzymes.

In an embodiment of a mutant luciferase, the amino acid sequence is that of LucPpe2 shown in FIG. 45 with the exception that at residue 249 there is a M (designated T249M) rather than the T reported by Leach et al. The underlined residue (249) shows mutation from T to M. This enzyme produced approximately 5-fold more light in vivo when expressed in *E. coli*.

Diluted extracts of recombinant *E. coli* that expressed mutant luciferases made by the methods of the invention were simultaneously screened for a plurality of characteristics including light intensity, signal stability, substrate utilization ($K_m$), and thermostability. A fully automated robotic system was used to screen large numbers of mutants in each generation of the evolution. After several cycles of mutagenesis and screening, thereby creating mutant libraries of luciferases, an increased thermostability compared to LucPpe2 [T249M] of about 35° C. was achieved for clone Luc90-1B5 which also essentially maintained enzymatic activity (there was only negligible loss in activity of 5%) when kept in aqueous solution over 2 hours at 50° C., 5 hours at 65° C., or over 6 weeks at 22° C.

Mutant luciferases of the present invention display increased thermostability for at least 2 hours at 50° C., preferably at least 5 hours at 50° C., and in the range of at least 2 hours, preferably at least 24 hours, and more preferably at least 50 hours, at temperatures including 50° C., 60° C., and/or at temperatures up to 65° C. In particular, the present invention comprises thermostable mutant luciferases which, when solubilized in a suitable aqueous solution, have a thermostability greater than about 2 hours at about 50° C., more preferably greater than about 10 hours at 50° C., and more preferably still greater than 5 hours at 50° C. The present invention also comprises mutant luciferases which, when solubilized in a suitable aqueous solution, have a thermostability greater than about 2 hours, more preferably at least 5 hours, even more preferably greater than about 10 hours, and even more preferably still greater than about 24 hours, at about 60° C. The present invention further comprises mutant luciferases which when solubilized in a suitable aqueous solution have a thermostability greater than about 3 months at about 22° C., and more preferably a thermostability of at least 6 months at 22° C. An embodiment of the invention is a luciferase mutant having thermostability at 65° C., wherein a loss of activity of about 5–6% was found after 6 hours (equivalent to a half-life of 2 days). The half-lives of enzymes from the most stable clones of the present invention, extrapolated from data showing small relative changes, is greater than 2 days at 65° C. (corresponding to 6% loss over 6 hours), and about 2 years at 22° C. (corresponding to 5% loss over 9 weeks).

In particular, the invention comprises luciferase enzymes with embodiments of amino acid sequences disclosed herein (e.g., mutant luciferases designated Luc49-7C6, Luc78-0B10; Luc90-1B5, Luc133-1B2, and Luc146-1H2, as well as all other beetle luciferases that have thermostability as measured in half-lives of at least 2 hours at 50° C. The invention also comprises mutated polynucleotide sequences encoding luciferase enzymes containing any single mutation or any combination of mutations of the type which convert an amino acid of the reference beetle luciferase into a consensus amino acid. Conserved amino acids are defined as those that occur at a particular position in all sequences in a given set of related enzymes. Consensus amino acids are defined as those that occur at a particular position in more than 50% of the sequences in a given set of enzymes. An example is the set of beetle luciferase sequences shown in FIG. 19, excluding LucPpe2.

Nucleotide sequences encoding beetle luciferases are aligned in FIG. 19. Eleven sequences found in nature in various genera, and species within genera, are aligned, including lucPpe2. There are at least three mutations present in each mutant luciferase that show increased thermostability. In general, mutations are not of a conserved amino acid residue. The mutations in the mutant luciferases are indicated in FIGS. 22–47 by underlining.

The invention also provides methods to prepare enzymes having one or more desired properties, e.g., resistance to inhibition by a substrate analog of the enzyme or enhanced enzymological properties. The method comprises selecting at least one isolated polynucleotide sequence encoding an enzyme with the desired property, e.g., an enzymological property, from a first population of mutated polynucleotide sequences. The selected, isolated polynucleotide sequence is then mutated to yield a second population of mutated polynucleotide sequences. Preferably, a mixture of selected isolated polynucleotide sequences are mutated to yield a second population of mutated polynucleotide sequences. The process may be repeated until a further polynucleotide sequence is obtained, e.g., selected and/or isolated, which further polynucleotide sequence encodes an enzyme which has at least one of the desired properties. As used herein, the terms "isolated and/or "purified" refer to in vitro isolation of a RNA, DNA or polypeptide molecule from its natural cellular environment, and from association with other components of the cell, such as nucleic acid or polypeptide, e.g., so that it can be sequenced, replicated, and/or expressed.

BRIEF DESCRIPTION OF THE DRAWINGS

FIG. 19A presents alignment of the amino acid sequence (SEQ ID Nos:27–37) for luciferases from various beetle species (Lcr, Lla, Lmi, Pmi, Ppy, Lno, Ppe1, Phg, GR, YG, Ppe2, respectively) and luciferases of the present invention (Luc49-7C6; Luc78-0B10; Luc90-1B5, Luc133-1B2; and Luc146-1H2, SEQ ID Nos. 14, 19, 24, 44, and 45, respectively); the sequences are aligned, spaces where sequences cannot be aligned are shown by dots (e.g., . . . ); only amino acids that differ in the luciferases of the present invention from those of some beetle species are shown, not the full sequences. "Cons" is a sequence showing conserved amino acids by single letters, and indicates non-conserved amino acids by "-".

FIG. 19B presents alignment of the amino acid sequence (SEQ ID Nos:27–37) for luciferases from various beetle species (Lcr, Lla, Lmi, Pmi, Ppy, Lno, Ppe1, Phg, GR, YG, Ppe2) and luciferases of the present invention (Luc30-4B02 and Luc81-6G01, SEQ ID Nos. 47 and 26, respectively); the sequences are aligned, spaces where sequences cannot be aligned are shown by dots (e.g., . . . ); amino acids that differ in the luciferases of the present invention from those of some beetle species are shown in bold.

FIG. 19C presents alignment of the amino acid sequence (SEQ ID NOs:27–34 and 36–37) for luciferases from various beetle species (Lcr, Lla, Lmi, Pmi, Ppy, Lno, Ppe1, Phg, YG, Ppe2, Ppl); the sequences are aligned, spaces where sequences cannot be aligned are shown by dots (e.g., . . . ); in the line beneath YG, X indicates positions in YG where mutations could yield a consensus amino acid; O indicates positions in YG where mutations could not yield a consensus amino acid.

FIG. 22 is a nucleotide (DNA) sequence (SEQ ID NO:1) encoding mutant luciferase enzyme Luc49-7C6; mutations are indicated by underlining.

FIG. 23 is a nucleotide (DNA) sequence (SEQ ID NO:2) encoding mutant luciferase enzyme Luc49-6C10, mutations are indicated by underlining.

FIG. 24 is a nucleotide (DNA) sequence (SEQ ID NO:3) encoding a mutant luciferase enzyme Luc49-0G12; mutations are indicated by underlining.

FIG. 25 is a nucleotide (DNA) sequence (SEQ ID NO:4) encoding a mutant luciferase enzyme Luc49-7A5; mutations are indicated by underlining.

FIG. 26 is a nucleotide (DNA) sequence (SEQ ID NO:5) encoding a mutant luciferase enzyme Luc49-4G11; mutations are indicated by underlining.

FIG. 27 is an amino acid sequence (SEQ ID NO:14) of the mutant luciferase designated Luc49-7C6; mutations are indicated by underlining.

FIG. 28 is an amino acid sequence (SEQ ID NO:15) of mutant luciferase enzyme Luc49-6C10; mutations are indicated by underlining.

FIG. 29 is an amino acid sequence (SEQ ID NO:16) of mutant luciferase enzyme Luc49-0G12; mutations are indicated by underlining.

FIG. 30 is an amino acid sequence (SEQ ID NO:17) of mutant luciferase enzyme Luc49-7A5; mutations are indicated by underlining.

FIG. 31 is an amino acid sequence (SEQ ID NO:18) of mutant luciferase enzyme Luc49-4G11; mutations are indicated by underlining.

FIG. 32 is a nucleotide (DNA) sequence (SEQ ID NO:6) encoding mutant luciferase enzyme Luc78-0B10; mutations are indicated by underlining.

FIG. 33 is a nucleotide (DNA) sequence (SEQ ID NO:7) encoding mutant luciferase enzyme Luc78-0G8; mutations are indicated by underlining; X's signify unknown identities of nucleotides at certain positions.

FIG. 34 is a nucleotide (DNA) sequence (SEQ ID NO:8) encoding mutant luciferase enzyme Luc78-1E1; mutations are by underlining; X's signify that the identity of a nucleotide at a position is unknown.

FIG. 35 is a nucleotide (DNA) sequence (SEQ ID NO:9) encoding a mutant luciferase Luc78-2B4; underlined nucleotides are mutations; X's signify unknown identities of nucleotides at certain positions.

FIG. 36 is an amino acid sequence (SEQ ID NO:19) of the mutant luciferase Luc78-0B10; underlined amino acids are mutations.

FIG. 37 is an amino acid sequence (SEQ ID NO:20) of the mutant luciferase enzyme Luc78-0G8; underlined amino acids are mutations; X's signify unknown amino acids at a position.

FIG. 38 is an amino acid sequence (SEQ ID NO:21) for mutant luciferase enzyme Luc78-1E1; underlined amino acids are mutations; X's signify an unknown amino acid at a position.

FIG. 39 is an amino acid sequence (SEQ ID NO:22) for mutant luciferase enzyme Luc78-2B4; underlined amino acids are mutations; X's signify an unknown amino acid at a position.

FIG. 40 is a nucleotide (DNA) sequence (SEQ ID NO:10) for encoding a mutant luciferase enzyme Luc85-4F12; underlined nucleotides are mutations; X's signify an unknown amino acid at that position.

FIG. 41 is an amino acid listing (SEQ ID NO:23) for a mutant luciferase enzyme Luc85-4F12; underlined amino acids are mutations; X's signify an unknown amino acid at that position.

FIG. 42 is a nucleotide (DNA) sequence (SEQ ID NO:11) encoding mutant luciferase enzyme Luc90-1B5; underlined nucleotides are mutations.

FIG. 43 is an amino acid sequence (SEQ ID NO:24) for the mutant luciferase designated Luc90-1B5; underlined amino acids are mutated positions.

FIG. 44 is a nucleotide (DNA) sequence (SEQ ID NO:12) encoding luciferase enzyme LucPpe2 [T249M].

FIG. 45 is an amino acid sequence (SEQ ID NO:25) for LucPpe2 [T249M]; the underlined amino acid is a mutation from Thr to Met at residue 249.

FIG. 46 is an amino acid sequence (SEQ ID NO:26) for luciferase enzyme LucPpl81-6G1; underlined amino acids are mutations from a starting sequence; X shows ambiguity.

FIG. 47 is a nucleotide (DNA) sequence (SEQ ID NO:13) encoding luciferase enzyme Luc81-6G1; underlined nucleotides are mutations.

FIG. 55 is a nucleotide (DNA) sequence (SEQ ID NO:42) encoding a luciferase enzyme Luc133-1B2; mutations are indicated by underlining.

FIG. 56 is a nucleotide (DNA) sequence (SEQ ID NO:43) encoding a luciferase enzyme Luc146-1H2; mutations are indicated by underlining.

FIG. 57 is an amino acid sequence (SEQ ID NO:44) of mutant luciferase Luc133-1B2; mutations are indicated by underlining.

FIG. 58 is an amino acid sequence (SEQ ID NO:45) of mutant luciferase Luc146-1H2; mutations are indicated by underlining.

FIG. 65 is a nucleotide (DNA) sequence (SEQ ID NO:46) encoding a luciferase enzyme Luc81-0B11; mutations are indicated by underlining.

Figure 66:
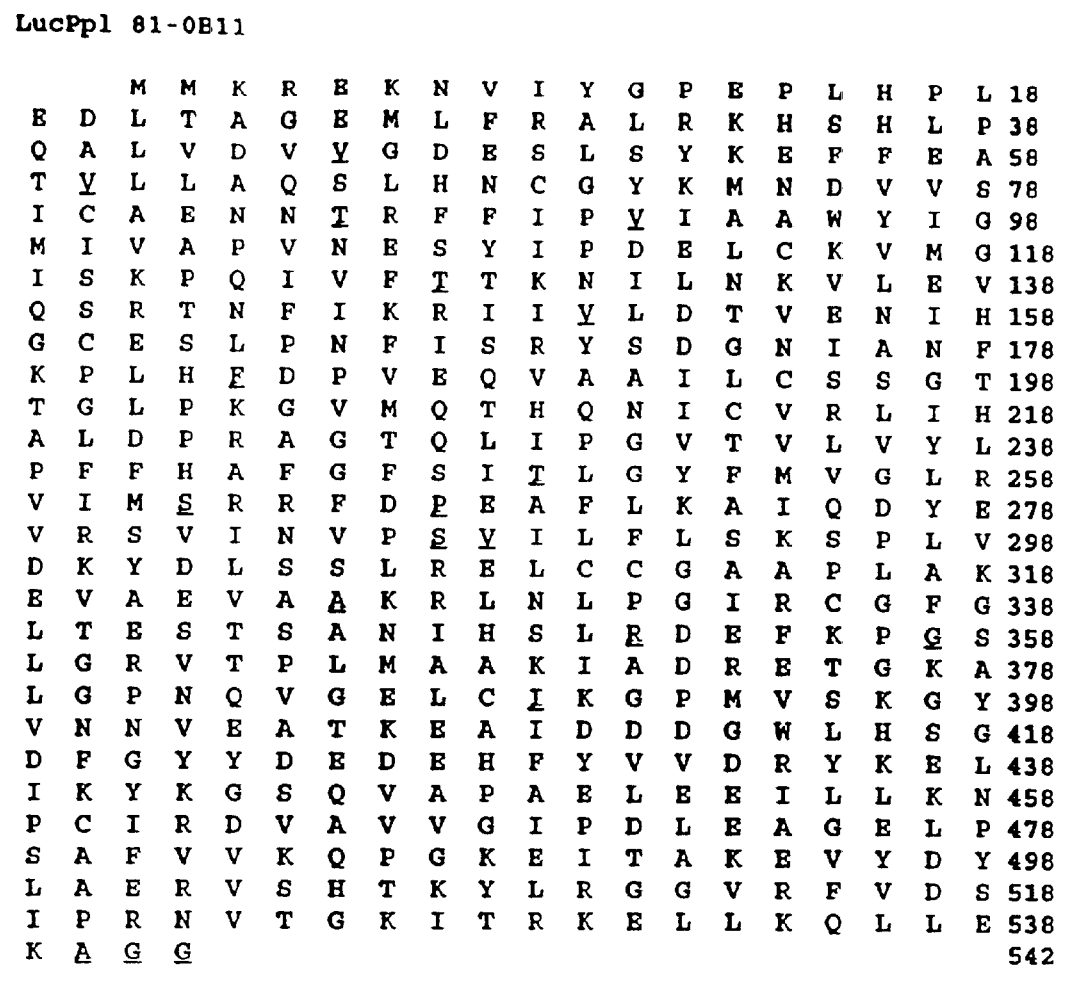

FIG. 66 is an amino acid SEQ ID NO:47 sequence of mutant luciferase Luc81-0B11; mutations are indicated by underlining.

DETAILED DESCRIPTION OF THE INVENTION

Figure 1:
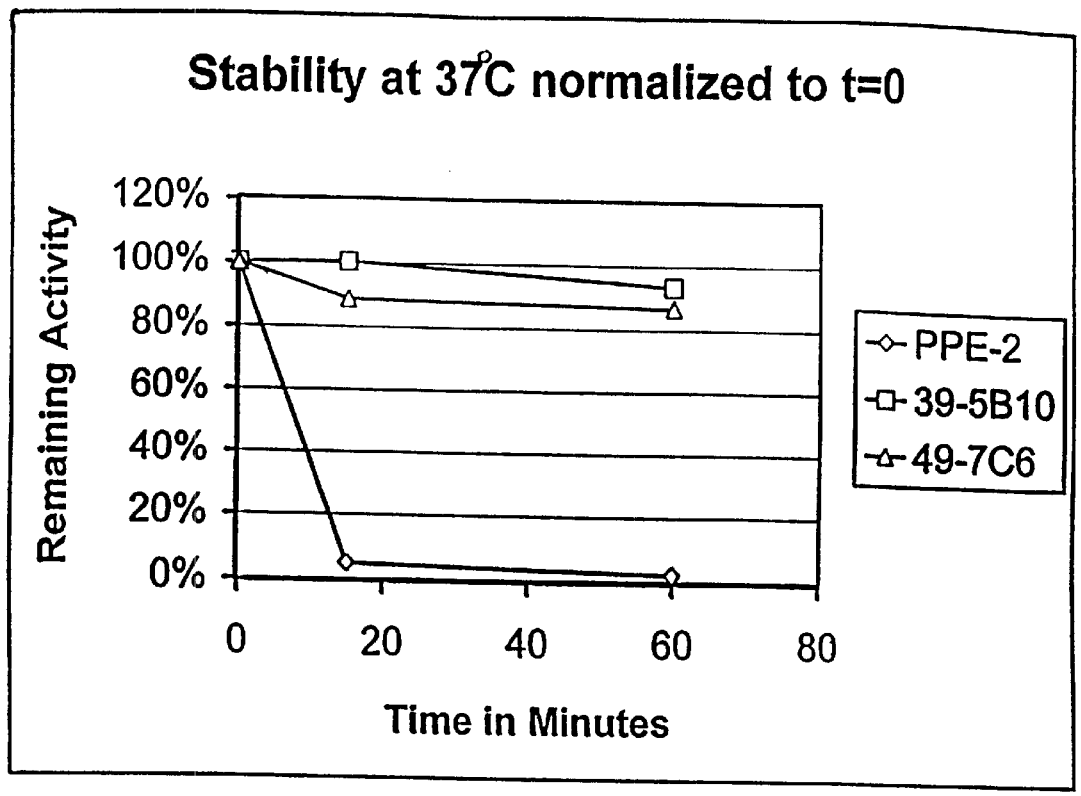
FIG. 1 is a graphical representation of thermostability at 37° C. of LucPpe2[T249M]; Luc39-5B10; and Luc49-7C6, normalized to t=0 [the X-axis is time in minutes; the Y-axis is % remaining activity; and "t" is time].
Figure 2:
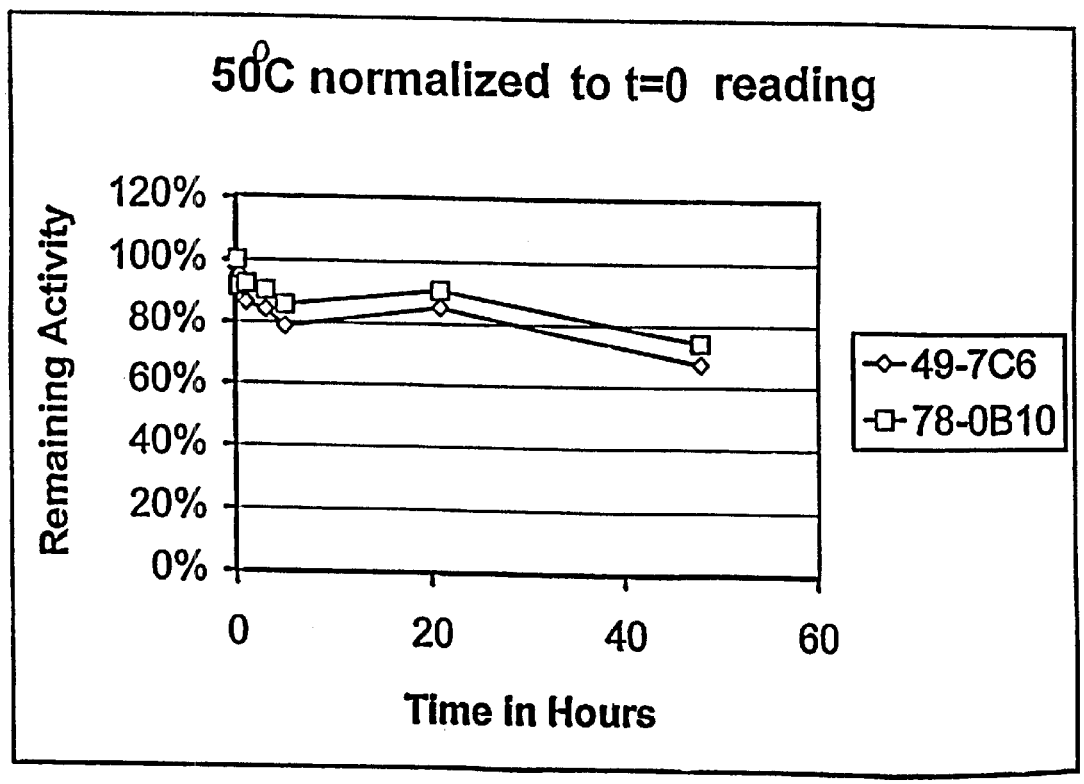
FIG. 2 is a graphical representation of the remaining activity of Luc49-7C6 and Luc78-0B10 at 50° C. normalized to a t=0 reading [the X-axis is time in hours; the Y-axis is % remaining activity; and t is time].
Figure 3:
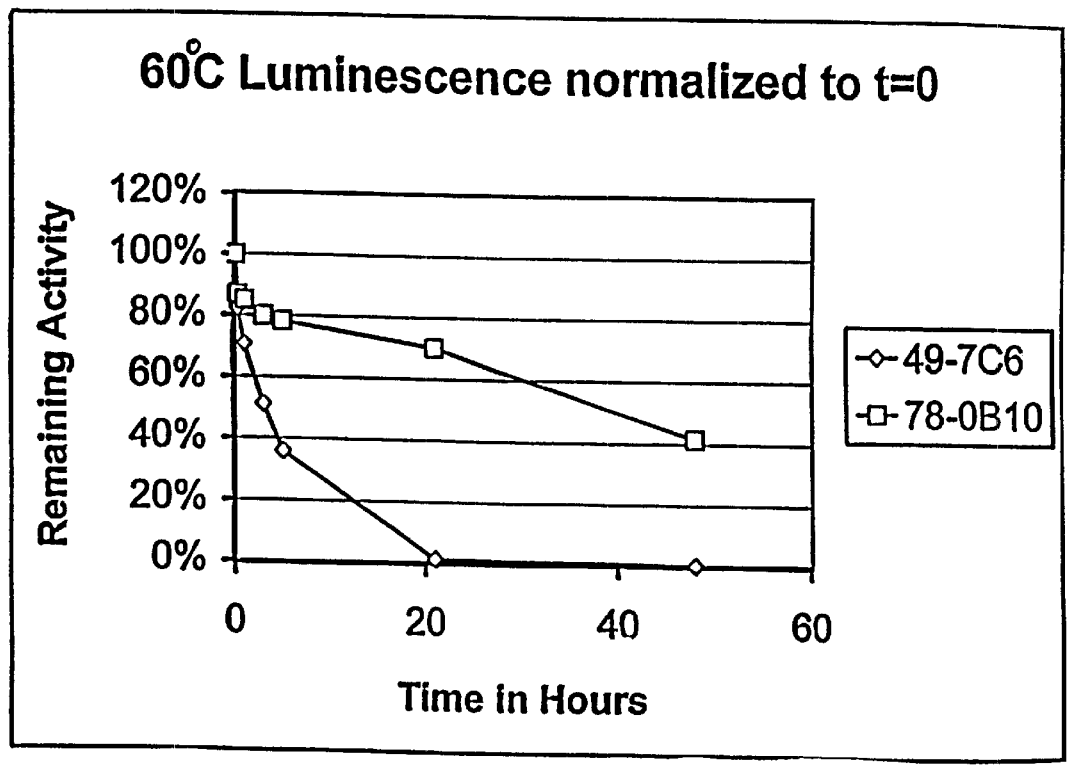
FIG. 3 is a graphical representation of the luminescence produced by Luc49-7C6 and Luc78-0B10 at 60° C. normalized to t=0 [the X-axis is time in hours; the Y-axis is % remaining activity; and t is time].
Figure 4:
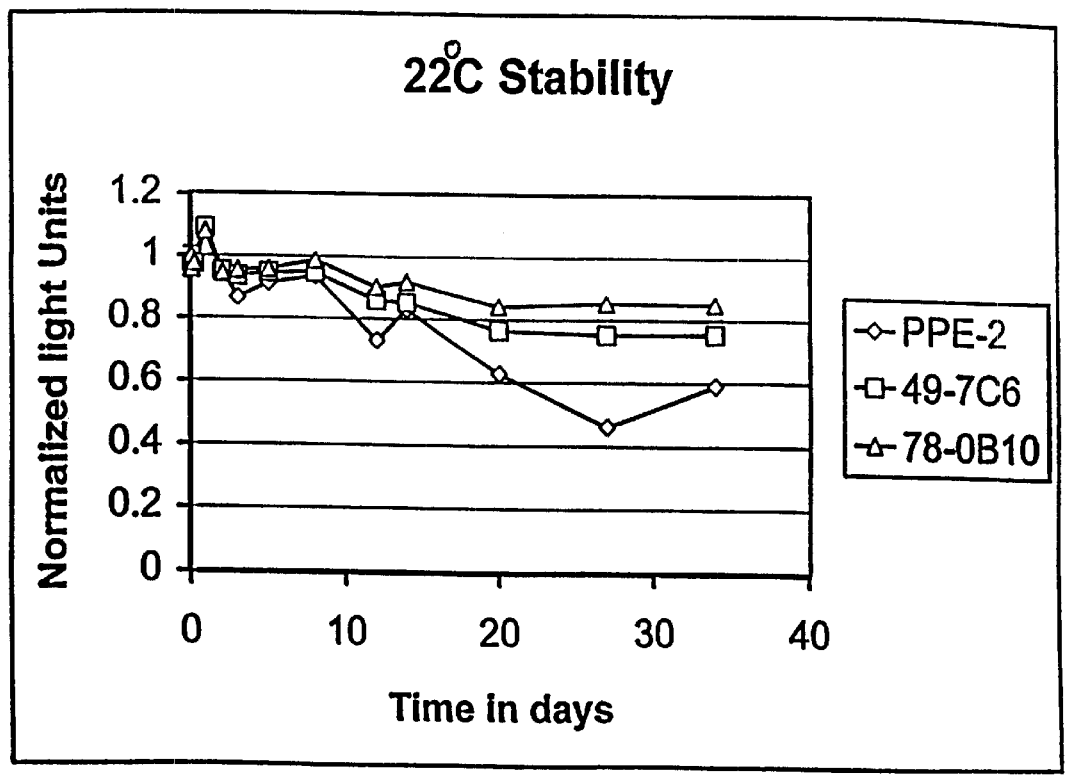
FIG. 4 is a graphical representation of thermostability of luciferases, LucPpe2[T249M]; Luc49-7C6; and Luc78-0B10 thermostability at 22° C. [the X-axis is time in days; the Y-axis is normalized light units].
Figure 5:
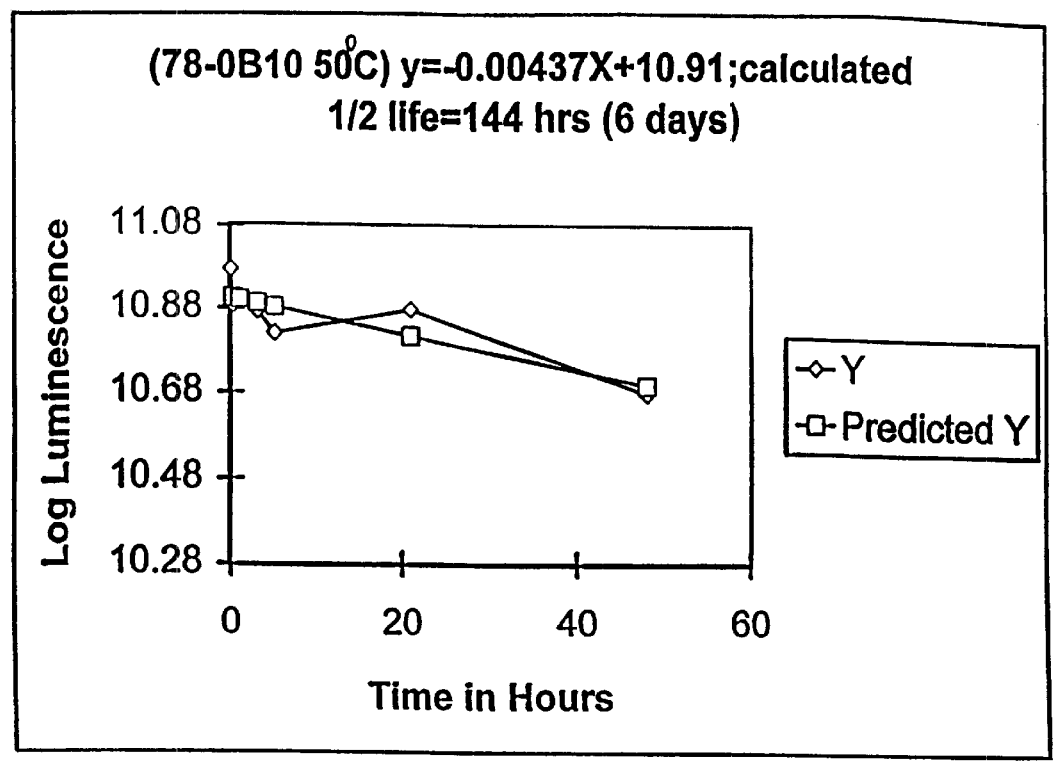
FIG. 5 is a graphical representation of the observed log luminescence produced by (Y) Luc78-0B10 compared to log luminescence predicted by the regression equation Y=0.0043X+10.91; the half life of the enzyme is calculated as 144 hours (6 days) [the X-axis is time in hours; the Y-axis is log luminescence].
Figure 6:
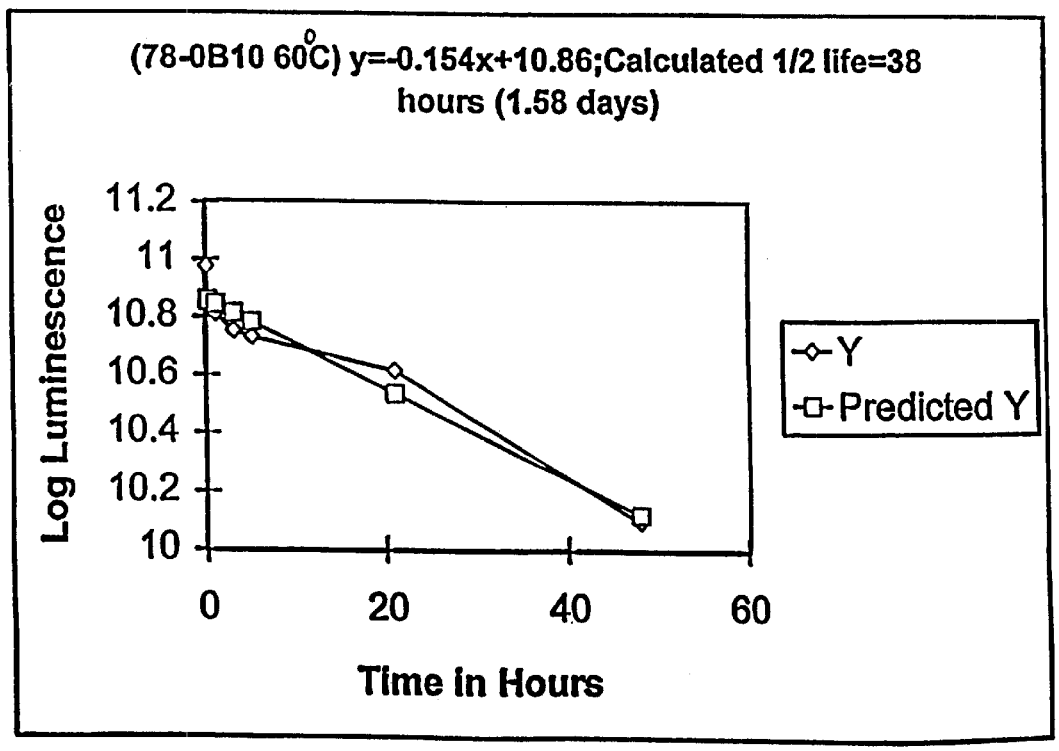
FIG. 6 is a graphical representation of the observed log luminescence produced by Luc78-0B10 at 60° C. compared to the log luminescence calculated by the regression equation Y=0.154X+10.86; the half life of the enzyme is calculated as 38 hours (1.58 days) [the X-axis is time in hours; the Y-axis is log luminescence].
Figure 7:
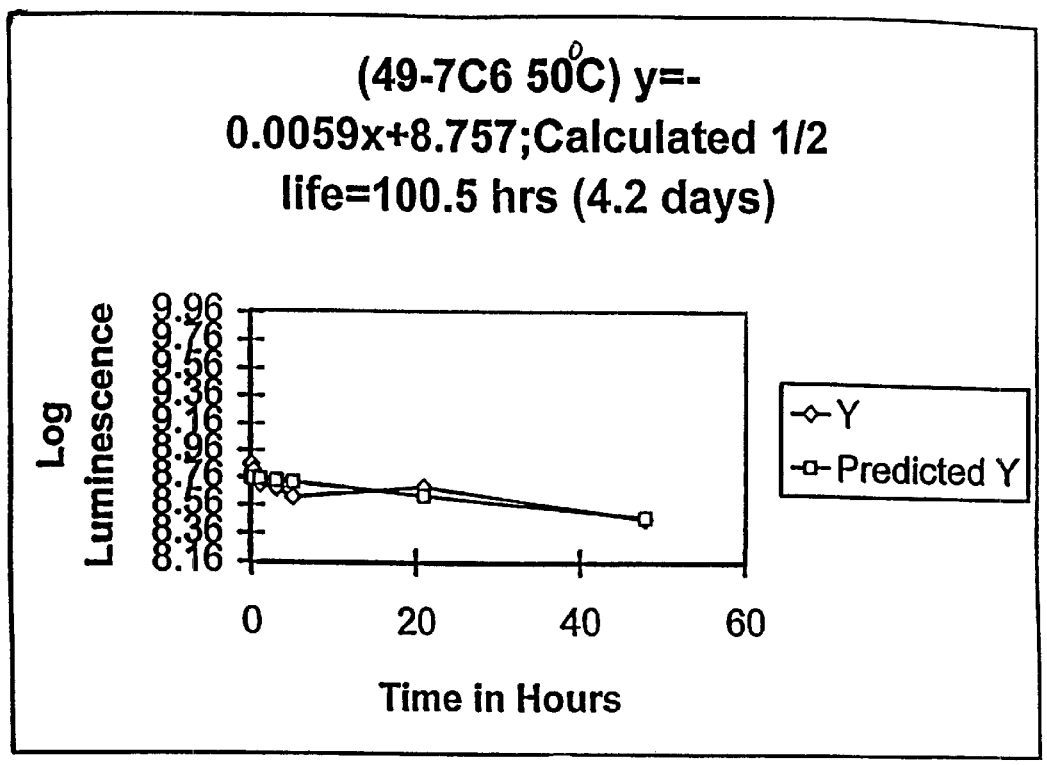
FIG. 7 is a graphical representation of the observed log luminescence produced by Luc49-7C6 at 50° C. compared to log luminescence predicted by the regression equation Y=−0.0059X+8.757; the half-life of the enzyme is calculated as 100.5 hours (4.2 days) [the X-axis is time in hours; the Y-axis is log luminescence].
Figure 8:
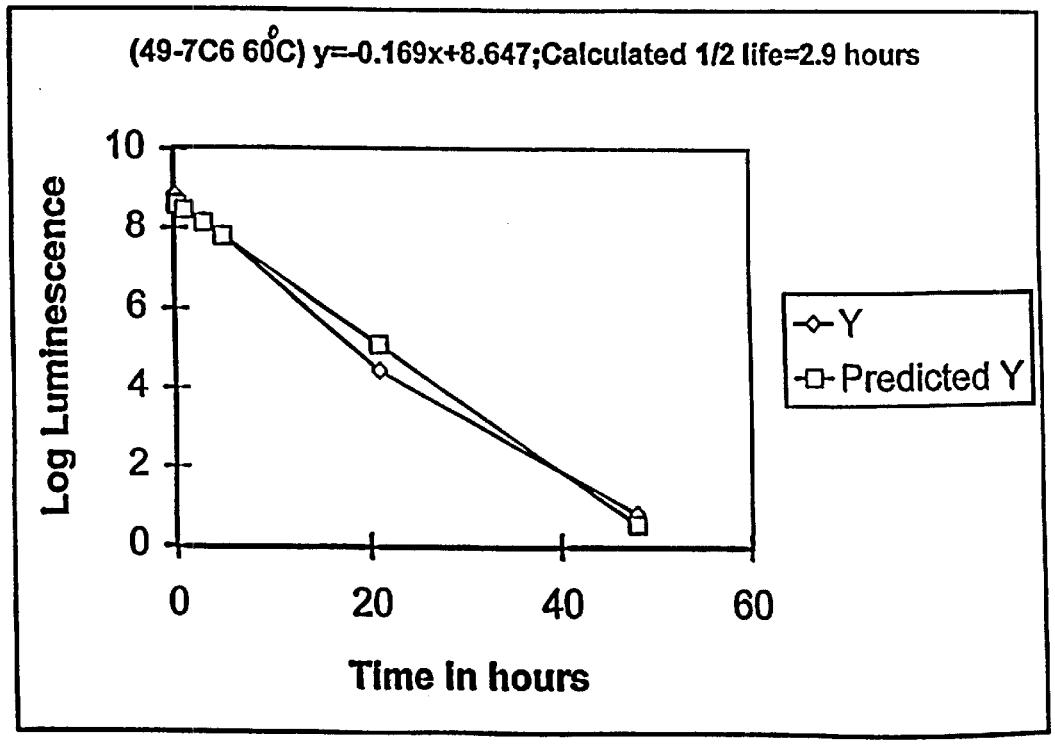
FIG. 8 is a graphical representation of the observed log luminescence produced by Luc49-7C6 at 60° C. compared to the log luminescence calculated by the regression equation Y=−0.169X+8.647; the calculated half-life of the enzymes is 2.9 hours (the X-axis is time in hours; the Y-axis is log luminescence).
Figure 9:
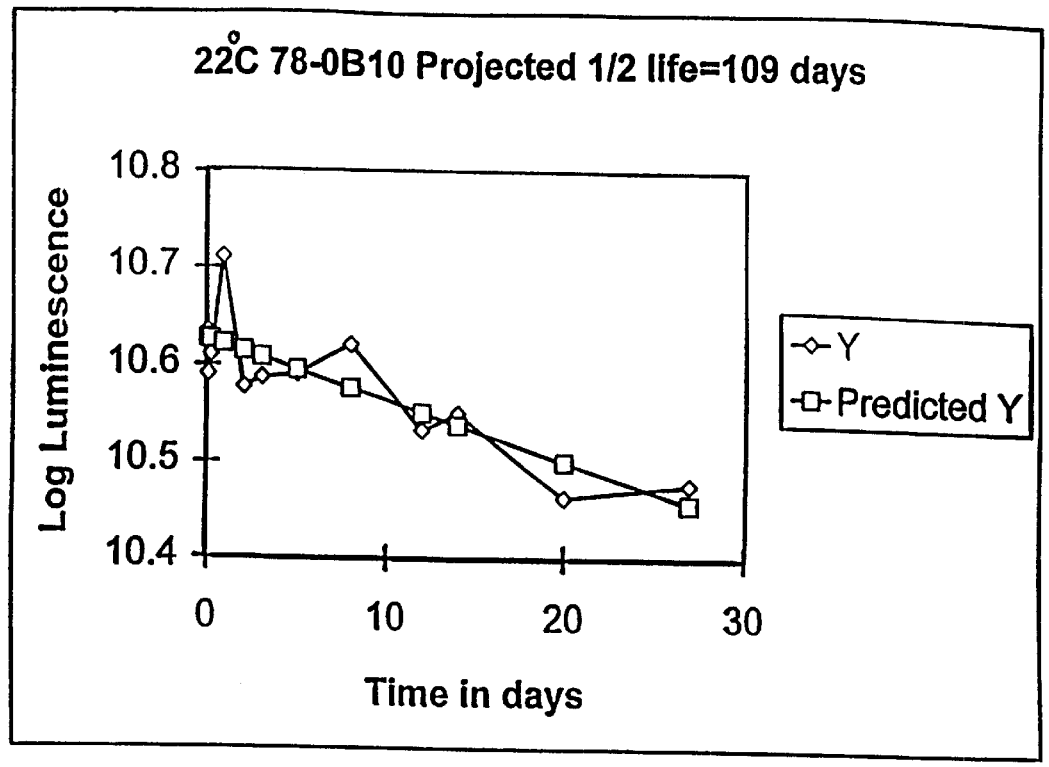
FIG. 9 is a graphical representation of the observed log luminescence produced by Luc78-0B10 at 22° C. compared to a predicted log luminescence, the half-life of the enzyme is 109 days [the X-axis is time in days; the Y-axis is log luminescence].
Figure 10:
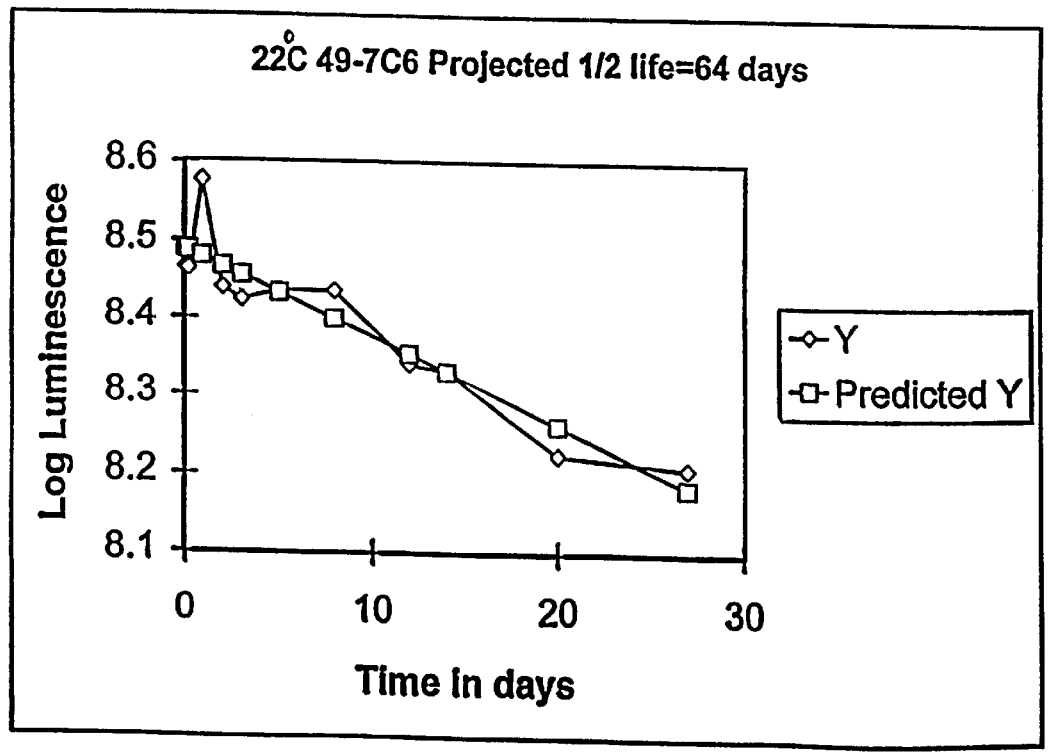
FIG. 10 is a graphical representation of the observed luciferase log luminescence produced by Luc49-7C6 at 22° C. compared to a predicted log luminescence; the half-life of the enzyme is 64 days [the X-axis is time in days; the Y-axis is log luminescence].
Figure 11:
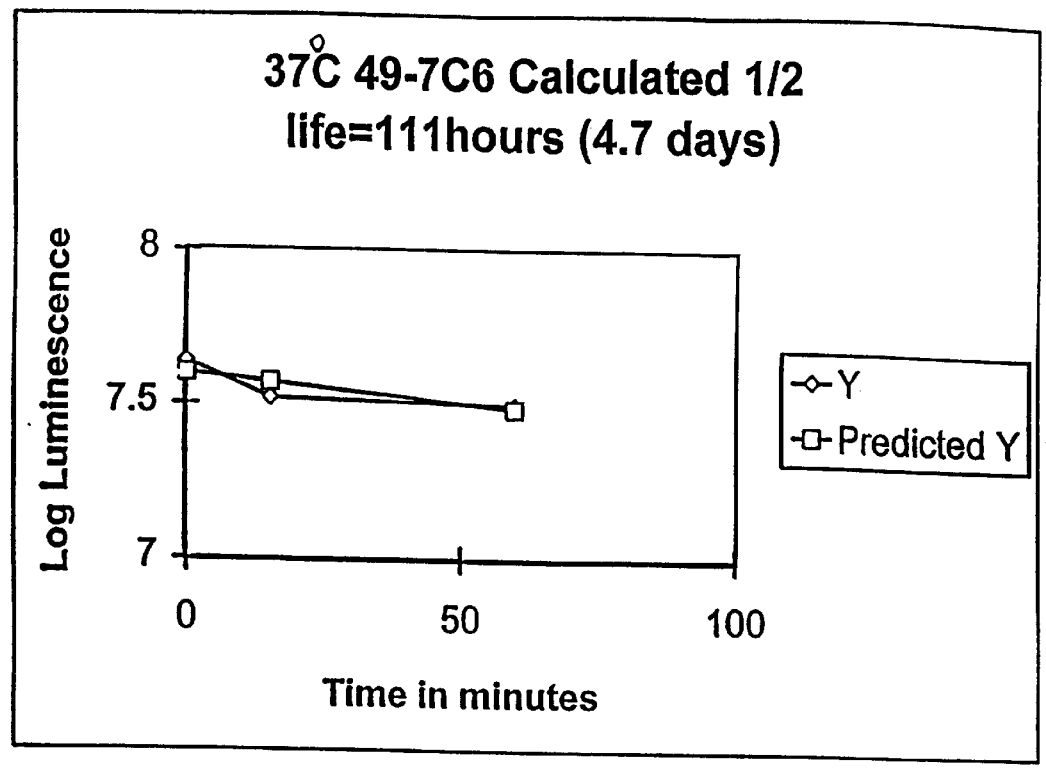
FIG. 11 is a graphical representation of the observed log luminescence produced by luciferase Luc49-7C6 at 37° C. compared to predicted log luminescence [the X-axis is time in minutes; the Y-axis is log luminescence].
Figure 12:
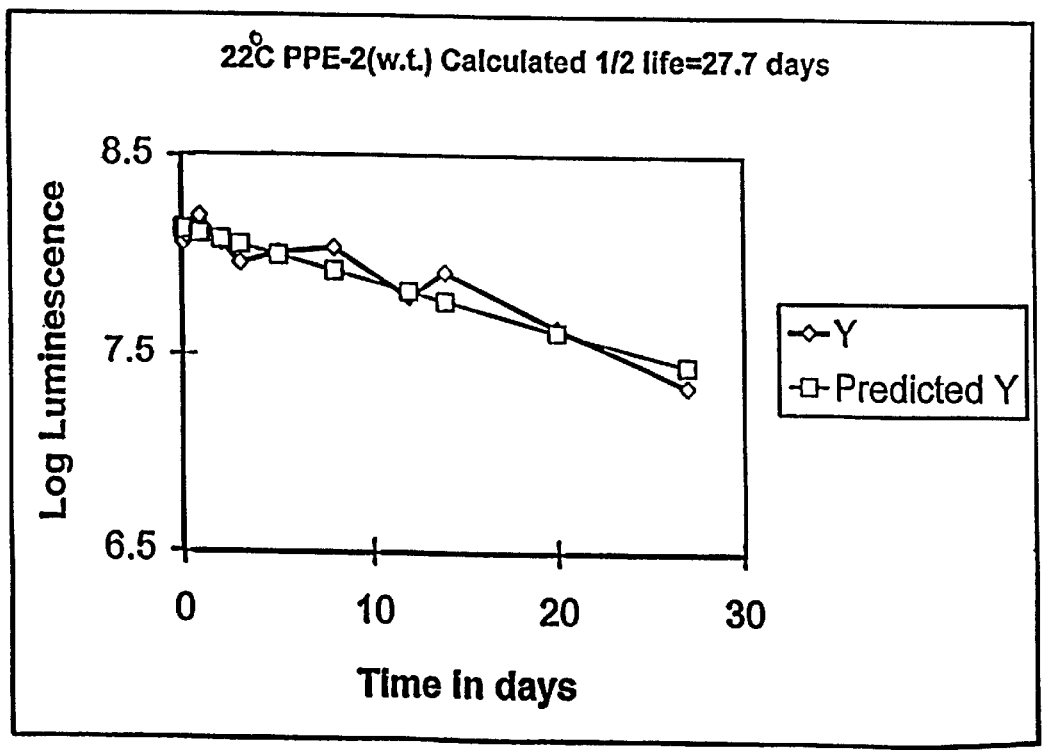
FIG. 12 is a graphical representation of the observed log luminescence produced by luciferase LucPpe2 [T249M] at 22° C. compared to predicted log luminescence [the X-axis is time in days; the Y-axis is log luminescence].
Figure 13:
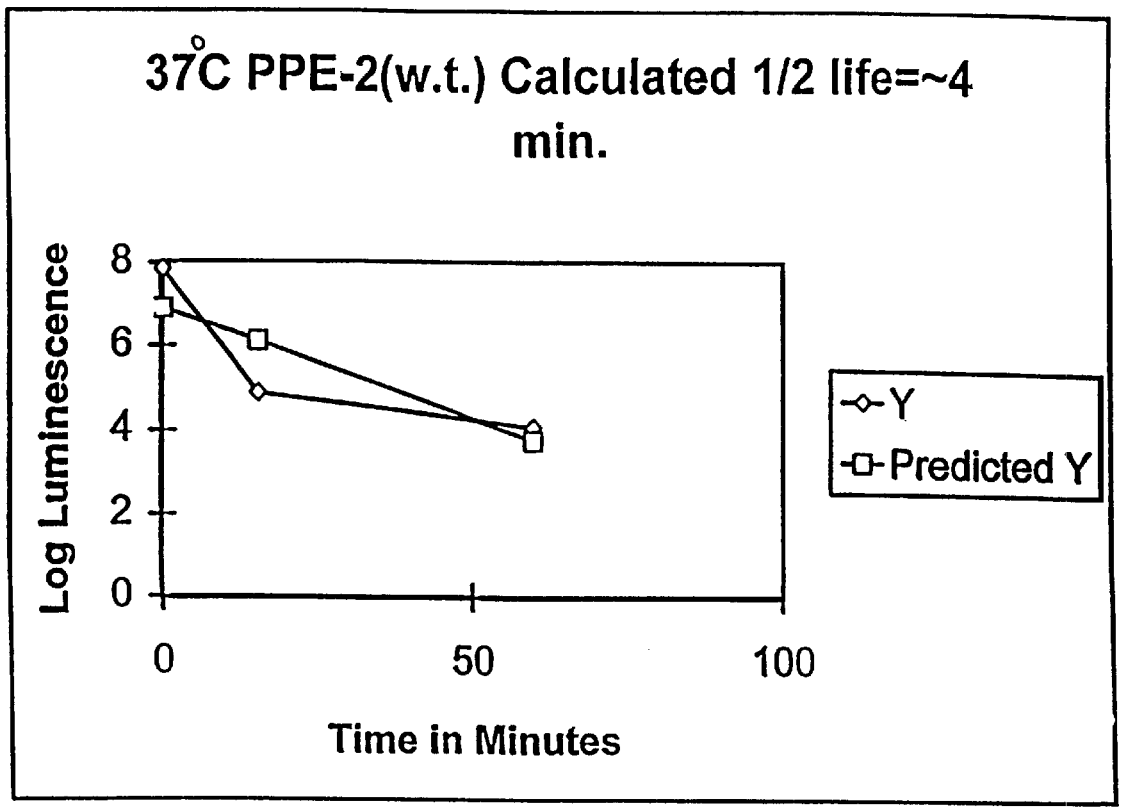
FIG. 13 is a graphical representation of the observed log luminescence produced by luciferase LucPpe2 [T249M] at 37° C. compared to predicted log luminescence [X-axis is time in minutes; Y-axis is log luminescence].

The invention relates to enzymes, e.g., beetle luciferases, that are created by mutations made in the encoding genes, generally by recursive mutagenesis, which mutated enzymes have one or more desired properties, for example, increases thermostability, increased resistance to inhibitors, and/or enhanced enzymological properties, relative to a reference enzyme, e.g., the wild-type enzyme. The polynucleotide sequence which encodes an enzyme of the invention comprises mutations that encode a plurality of amino acid substitutions relative to the polynucleotide sequence encoding the enzyme from which the enzyme of the invention was derived. For example, the invention relates to enzymes, e.g., luciferases, that are thermostable. The increased thermostability allows storage of enzymes such as luciferases without altering its activity, and improves reproducibility and accuracy of assays using the mutated luciferases. Thus, one embodiment of the invention comprises isolated polynucleotide sequences (cDNAs) which encode mutant luciferases with increased thermostability, vectors containing the polynucleotide sequences, and hosts transformed to express the polynucleotide sequences. Table 1 shows results of about 250 clones and characteristics of the luciferases from the clones including thermostability. The invention also encompasses the use of the mutant luciferases in any application where luciferases are conventionally utilized, and kits useful for some of the applications.

Unexpectedly, beetle luciferases with the sought after improved thermostability were achieved in the present invention through a process of recursive mutagenesis and selection (sometimes referred to as "directed evolution"). A strategy of recursive mutagenesis and selection is an aspect of the present invention, in particular the use of multi-parameter automated screens. Thus, instead of screening for only a single attribute such as thermostability, simultaneous screening was done for additional characteristics of enzyme activity and efficiency. By this method, one property is less likely to "evolve" at the expense of another, resulting in increased thermostability, but decreased activity, for example.

Table 1 presents examples of parameter values (Li, Tau, $K_m$ and S, see below) derived from experiments using different luciferases as starting (parent) sequences. The subtitles refer to designations of the temperature at which the enzyme stability was measured and the starting luciferase, e.g., Luc39-5B10 at 51° C. and so forth. All parameters in each experiment are recorded as relative values to the respective starting sequence, e.g., the parameter values for the starting sequence in any experiment equals "1." (See Example 2 herein for definitions.)

Thermostability has evolved in nature for various enzymes, as evidenced by thermostable isozymes found in thermophilic bacteria. Natural evolution works by a process of random mutagenesis (base substitutions, gene deletions, gene insertions), followed by selection of those mutants with improved characteristics. The process is recursive over time. Although the existence of thermostable enzymes in nature suggests that thermostability can be achieved through mutagenesis on an evolutionary scale, the feasibility of achieving a given level of thermostability for a particular class of enzymes by using short term laboratory methods was unpredictable. The natural process of evolution, which generally involves extremely large populations and many millions of generations and genes, by mutation and selection cannot be used to predict the capabilities of a modern laboratory to produce improved genes by directed evolution until such mutants are produced.

Figure 17:
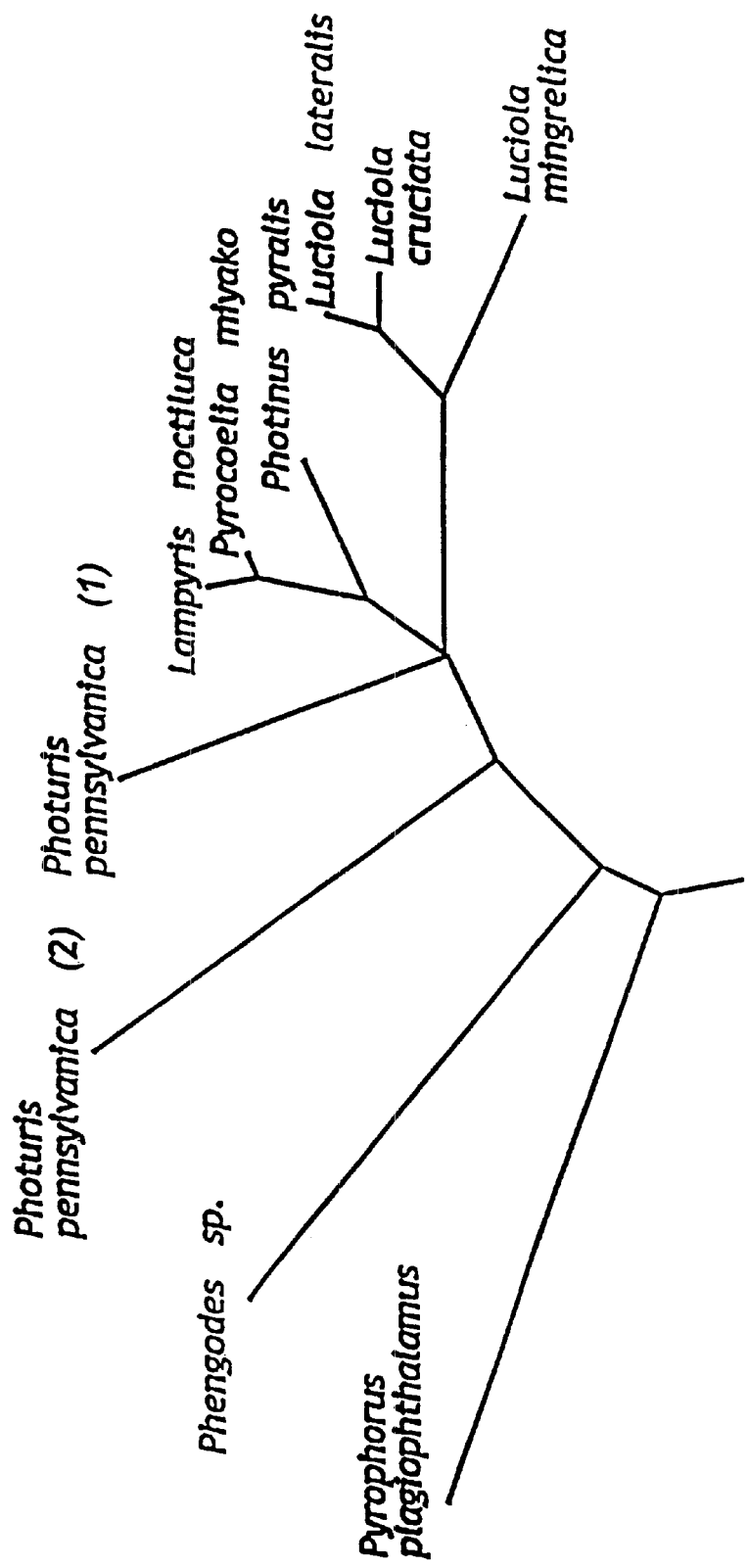
FIG. 17 is a diagram showing the evolutionary relationships among beetle luciferases based on amino acid sequences.
Figure 18A:
FIG. 18A is a representation of the secondary structures of beetle luciferase enzymes (helices are symbolized by cylinders, sheets by collections of arrows, loops connect helices with sheets).
Figure 18B:
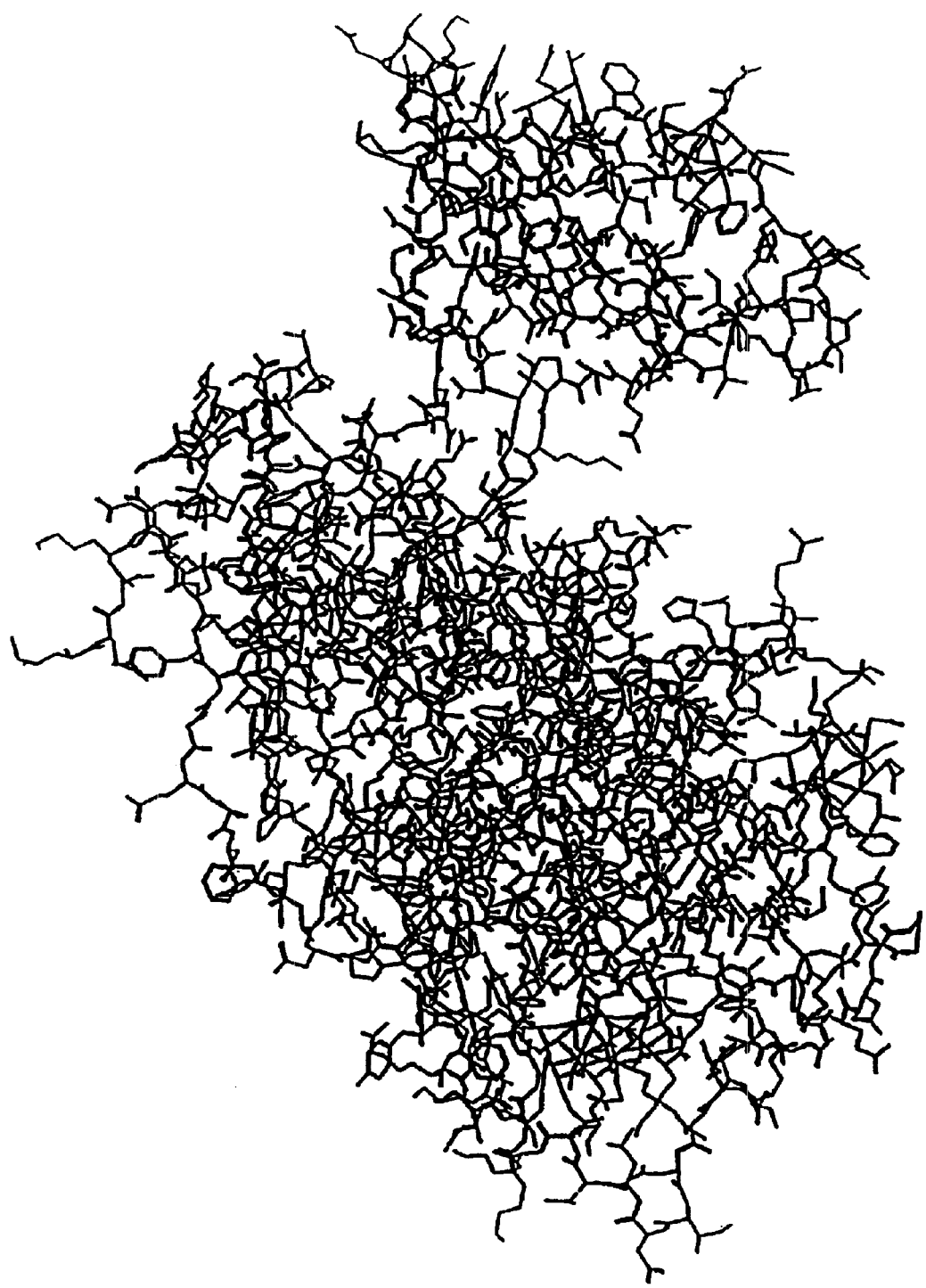
FIG. 18B shows the amino acids (tertiary structures) of the LucPpe2 luciferase, wherein small spirals correspond to cylinders of FIG. 18A.
Figure 18C:
FIG. 18C shows that the general beetle architecture matches (is superimposed on) that of Luc90-1B5.

After such success, because the overall three-dimensional structure of all beetle luciferases are quite similar, having shown it possible for one member of this class makes it predictable that high thermostability can be achieved for other beetle luciferases by similar methods. FIG. 17 shows an evolutionary relationship among beetles luciferases, all of which have a similar overall architecture. The structural class to which the beetle luciferases belong is determined by the secondary structure (e.g. helices are symbolized by cylinders, sheets by collections of arrows, loops connect helices with sheets (FIG. 18A). FIG. 18B shows the amino acids of the LucPpe2 luciferase wherein small spirals correspond to cylinders of FIG. 18A; FIG. 18C shows that the general beetle architecture matches (is superimposed on) that of LucPpe2. This is support for the expectation that the methods of the present invention can be generalized to all beetles luciferases.

Enzymes belong to different structural classes based on the three-dimensional arrangement of secondary elements such as helices, sheets, and loops. Thermostability is determined by how efficiently the secondary elements are packed together into a three-dimensional structure. For each structural class, there also exists a theoretical limit for thermostability. All beetle luciferases belong to a common structural class as evident by their common ancestry (FIG. 17), homologous amino acid sequences, and common catalytic mechanisms.

The application of a limited number of amino acid substitutions by mutagenesis is unlikely to significantly affect the overall three-dimensional architecture (i.e., the structural class for mutant luciferases is not expected to change.) Because the theoretical limit for thermostability for any structural class is not known, the potential thermostability of beetle luciferases was not known until demonstrations of the present invention.

A priori difficulties in achieving the goals of the present invention included:

1. The types of mutations which can be made by laboratory methods are limited.
   i) By random point mutation (e.g. by error-prone PCR), more than one base change per codon is rare. Thus, most potential amino acid changes are rare.
   ii) Other types of random genetic changes are difficult to achieve for areas greater than 100 bp (e.g., random gene deletions or insertions).
2. The number of possible luciferase mutants that can be screened is limited.
   i) Based on sequence comparisons of natural luciferases, ignoring deletions and insertions, more than $10^{189}$ functional enzyme sequences may be possible.
   ii) If 100,000 clones could be screened per day, it would require more than $10^{179}$ centuries to screen all possible mutants assuming same mutant was never screened twice (actual screening rate for the present invention was less than 5000 per day).
3. The probability of finding functional improvement requiring cooperative mutations is rare (the probability of finding a specific cooperative pair is 1 out of $10^8$ clones).

Thus, even if the theoretical limits of thermostability were known, because only a very small number of the possible luciferase mutants can be screened, the a priori probability of finding such a thermostable enzyme was low.

Figures 19D, 20:
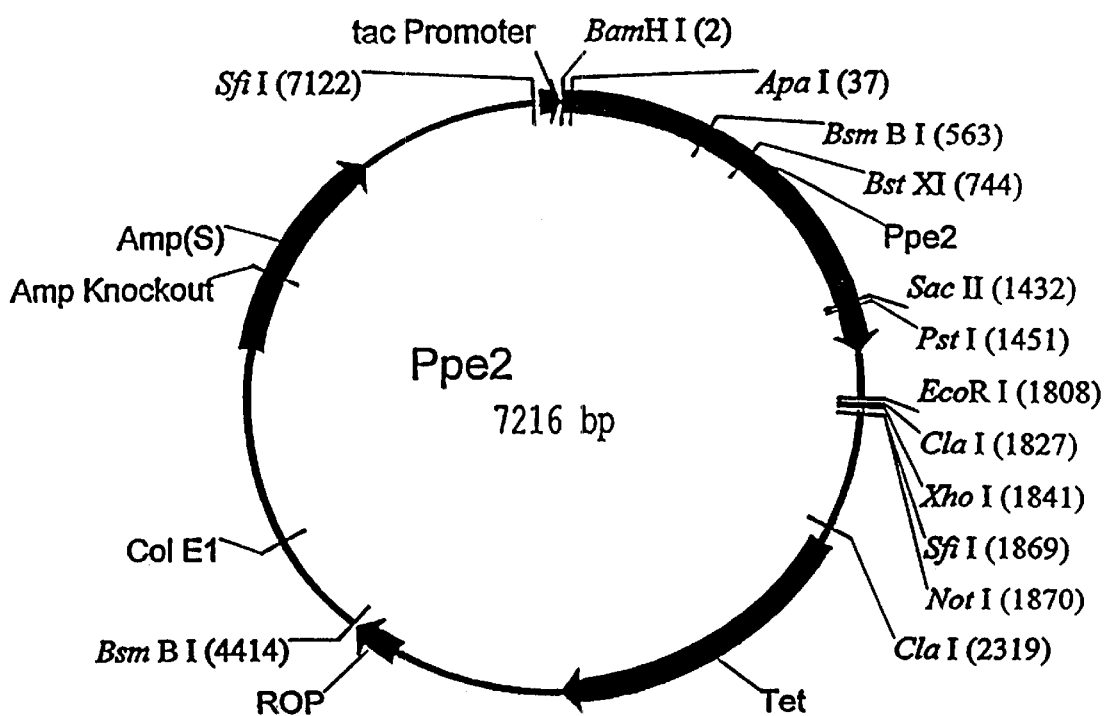
FIG. 19D provides the key to abbreviations for beetle luciferase sequences.
FIG. 20 is the 7216 bp Ppe2 vector map in a pRAM backbone.

However, the present invention now shows that it is possible and feasible to create novel beetle luciferases having high thermostability.

a) The approximately 250 mutants produced by methods of the present invention wherein the initial sequence was from lucPpe2 or lucPplYG demonstrate that it is possible and feasible for at least one member of this enzyme class to achieve high thermostability.
b) Any beetle luciferase can be improved by similar means because the luciferases belong to the same structural class.
   i) Because all beetle luciferases belong to the same structural class, they also share in the same pool of potentially stabilizing mutations (this conclusion is supported by observation that a high percentage of the stabilizing mutations found in the clones of the present invention were conversions to "consensus amino acids" in other beetle luciferases that is, amino acids that appear in the majority of beetle luciferase sequences (see FIG. 19).
   ii) Similar results were achieved using beetle luciferase, consisting largely of a different amino acid sequence, from the luminous beetle *Pyrophorus plagiophthalamus* (LucPplYG). The wild-type lucPplYG has 48% nucleotide sequence identity to the wild type lucPpe2. The LucPplYG mutants were subjected to fewer cycles of directed evolution than the LucPpe2 mutants described herein. Also, in some instances, mutants were selected with less emphasis placed on their relative thermostability. The most stable clone resulting from this evolution (Luc80-5E5) has a half-life of roughly 3.8 hours at 50° C. in solution.

To compensate for a statistical effect caused by the large number of deleterious random mutations expected relative to the beneficial mutations, methods were employed to maximize assay precision and to re-screen previously selected mutations in new permutations. Among the methods for maximizing assay precision were closely controlling culture conditions by using specialized media, reducing growth rates, controlling heat transfer, and analyzing parameters from mid-logarithmic phase growth of the culture. The robotic processes maximized for precision include controlling mixing, heat transfers, and evaporation of samples in the robotic screening process; and normalizing data to spatially distributed control samples. New permutations of the selected mutations were created by a method of DNA shuffling using proof-reading polymerases.

Figure 21:
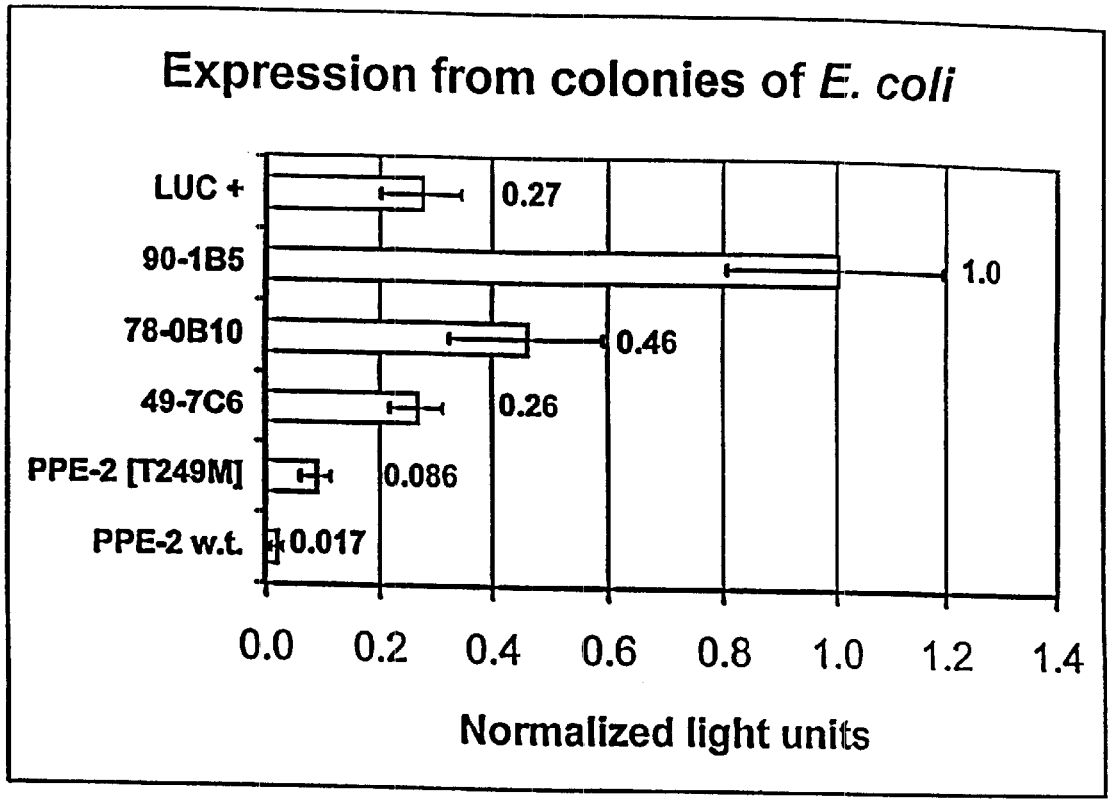
FIG. 21 is a bar graph comparing luminescence as expressed in recombinant colonies of E. coli; the colonies differ in the identity of the luciferase encoding vector (Luc+; Luc90-1B5; Luc78-1B10; Luc49-7C6; LucPpe2 [T249M] and LucPpe2); in the recombinant colony shown in the Y-axis [the X-axis is normalized light units].
Figure 48:
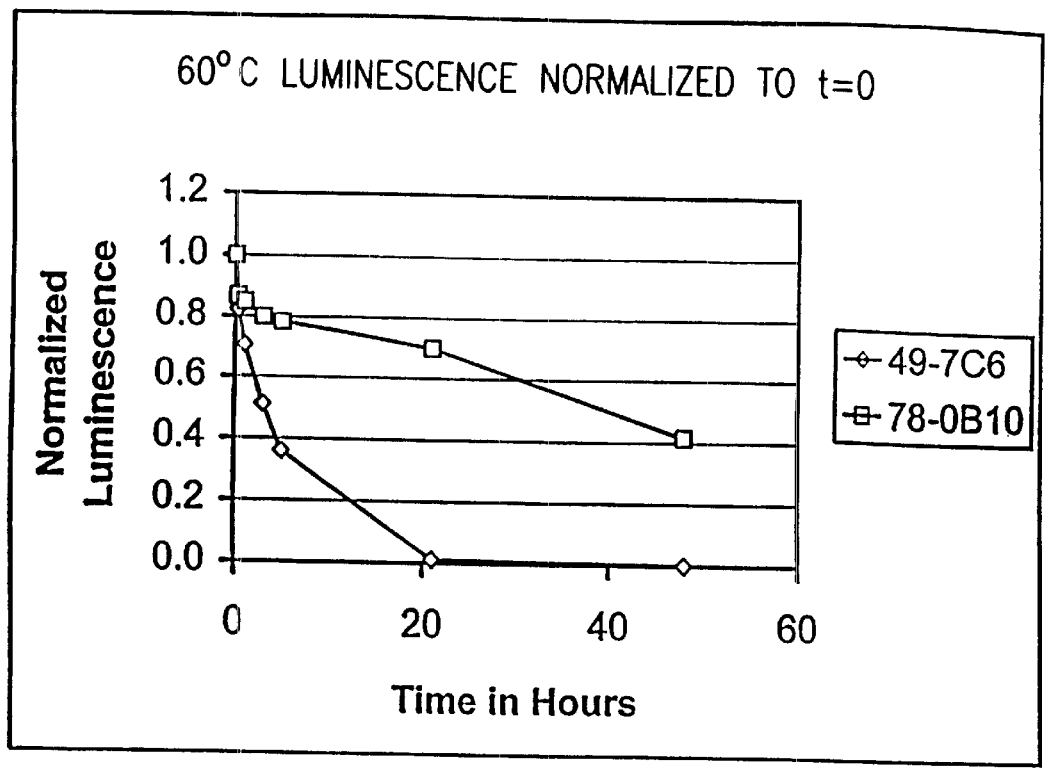
FIG. 48 is a graphical representation of mutant luciferases Luc49-7C6 and Luc78-0B10 luminescence at 60° C. normalized to t=0 [the X-axis is time in hours, the Y-axis is log normalized luminescence].

The difficulty in predicting the outcome of the recursive process is exemplified by the variable success with the other characteristics of luciferase that were also selected for. Although the primary focus was on the enzyme thermostability, selection for mutants producing brighter luminescence, with more efficient substrate utilization, and an extended luminescence signal was also attempted. The definitions are given by equations herewith. The selection process was determined by changes relative to the parent clones for each iteration of the recursive process. The amount of the change was whatever was observed during the screening process. The expression of luciferase in *E. coli* was relatively inefficient, for LucPpe2, compared to Luc+. Other luciferases varied (see FIG. 21).

To improve the overall efficiency of substrate utilization, reduction in the composite apparent utilization constant (i.e., Km[ATP+luciferin]) for both luciferin and ATP was sought. Although there was an unexpected systematic change in each utilization constant (Km[ATP], Km[luciferin]), there was little overall change. Finally, the luminescence signal could only be moderately affected without substantially reducing enzyme efficiency. Thus, although the enzyme thermostability was greatly increased by methods of the present invention, other characteristics of the enzyme were much less affected.

FIGS. 1–13, 16, 48–53, 60 and 62 present measurements of thermostability of mutant luciferases. FIGS. 48–53 present other results of the mutant luciferases. Compositions of the invention include luciferases having greater than the natural level of thermostability. Each mutant luciferase is novel, because its individual characteristics have not been reported. Specific luciferases are known by both their protein and gene sequences. Many other luciferases were isolated that have increased, high thermostability, but whose sequences are not known. These luciferases were identified during the directed evolution process, and were recognized as distinct by their enzymological characteristics. The mutant luciferases of the present invention, e.g., Luc90-1B5, can display remarkable and heretofore unrealized thermostability at temperatures ranging from 22° C. to at least as high as 60° C.

Other aspects of the invention include methods that incorporate the thermostable luciferases, specifically beetle luciferases having high thermostability, as well as methods to prepare an enzyme, including a luciferase, having one or more desired properties, e.g., resistance to inhibition by a substrate inhibitor, or enhanced enzymological properties. Thus, the invention also provides a method to prepare an enzyme which has at least one enhanced enzymological property. From a population of polynucleotide sequences encoding the enzyme which is derived from a first polynucleotide sequence encoding the enzyme which is subject to mutation, at least one polynucleotide sequence encoding an enzyme which has the enhanced enzymological activity is selected and isolated. In one embodiment, oligonucleotide-mediated mutagenesis is then employed to introduce at least one codon which encodes a consensus amino acid to at least one of the selected, isolated polynucleotide sequences encoding the enzymes to yield a further polynucleotide sequence encoding the enzyme and having the codon which encodes the consensus amino acid, wherein the codon which is introduced is not present in the first polynucleotide sequence.

Production of Luciferases of the Present Invention

The method of making luciferases with increased thermostability is recursive mutagenesis followed by selection. Embodiments of the highly thermostable mutant luciferases of the invention were generated by a reiterative process of random point mutations beginning with a source nucleotide sequence, e.g., the lucPpe2 [T249M] cDNA. Recombination mutagenesis is a part of the mutagenesis process, along with point mutagenesis. Both recombination mutagenesis and point mutagenesis are performed recursively. Because the mutation process causes recombination of individual mutants in a fashion similar to the recombination of genetic elements during sexual reproduction, the process is sometimes referred to as the sexual polymerase chain reaction (sPCR). See, for instance, Stemmer, U.S. Pat. No. 5,605,793, issued Feb. 25, 1997.

Taking the lucPpe2 cDNA sequence as a starting point, the gene was mutated to yield mutant luciferases which are far more thermostable. A single point mutation to the lucPpe2 sequence yielded the luciferase whose sequence is depicted as T249M. This mutant is approximately 5 times brighter in vivo than that of lucPpe2, it was utilized as a template for further mutation. It was also used a baseline for measuring the thermostability of the other mutant luciferases described herein.

Embodiments of Sequences of Luciferases of the Present Invention

FIG. 45 shows the amino acid sequence of the LucPpe2 luciferase (T249M). The sequence contains a single mutation at position 249 from T to M (underlined) which distinguishes it from the sequence reported by Leach et al. (1997). This luciferase has a spectral maximum of 552 nm, which is yellow shifted from that of the luciferase of Leach et al. This mutant was selected for use as an original template in some of the Examples because it is approximately 5 times brighter in vivo, than the form reported by Leach et al. which allowed for more efficient screening by the assay. These sequences show changes from the starting sequence (T249M) by underlining. Note that "x" in the sequence denotes an ambiguity in the sequence.

Directed Evolution, A Recursive Process

Directed evolution is a recursive process of creating diversity through mutagenesis and screening for desired changes. For enzymological properties that result from the cumulative action of multiple amino acids, directed evolution provides a means to alter these properties. Each step of the process typically produces small changes in enzyme function, but the cumulative effect of many rounds of this process can lead to substantial overall change.

The characteristic, "thermostability" is a candidate for directed evolution because it is determined by the combined action of many of the amino acids making up the enzyme structure. Luminescence output and efficiency of substrate binding of the modified luciferase were also screened. This was to ensure that changes in thermostability did not also produce undesirable changes in other important enzymological properties.

Because the frequency of deleterious mutations is much greater than useful mutations, it is likely that undesirable clones are selected in each screen within the precision limits of the present invention. To compensate for this, the screening strategy incorporated multiple re-screens of the initially selected mutations. However, before re-screening, the selected mutations were "shuffled" to create a library of random intragenetic recombinations. This process allows beneficial mutations among different clones to be recombined together into fewer common coding sequences, and unlinks deleterious mutations to be segregated and omitted. Thus, although essentially the same set of selected mutations was screened again, they were screened under different permutations as a result of the recombination or shuffling.

Although results of each step of the evolutionary process were assayed by quantitative measurements, these measurements were mutually made in cell lysates rather than in purified enzymes. Furthermore, each step only measured changes in enzyme performance relative to the prior step, so global changes in enzyme function were difficult to judge.

Table 1 summarizes the characteristics of various clones obtained using the methods of the invention.

TABLE 1

| Experiment | Clone ID | Luminescence (Li) | Enzyme stability (tau) | Substrate binding (Km) | Signal stability (S) |
|---|---|---|---|---|---|
| Control is Luc39-5B10 at 51° C. | | | | | |
| 40 | 0a7 | 1.04 | 4.5 | 0.78 | 1 |
| 40 | 5h4 | 1.29 | 1.61 | 1.16 | 0.953 |
| 40 | 0c2 | 1.13 | 1.54 | 0.91 | 0.998 |
| 40 | 5g4 | 1 | 1.4 | 0.85 | 1 |
| 40 | 6d3 | 1.02 | 1.37 | 0.79 | 1 |
| 40 | 1g4 | 1.06 | 1.28 | 0.77 | 0.985 |
| 40 | 1d4 | 1.69 | 1.23 | 0.73 | 1 |
| 40 | 0h9 | 1.26 | 1.21 | 0.63 | 0.998 |
| 40 | 2f6 | 3 | 1.07 | 0.49 | 0.981 |
| 40 | 7d6 | 3.09 | 1.058 | 1.09 | 1.013 |
| 40 | 5a7 | 4.3 | 1.025 | 0.93 | 1.008 |
| 40 | 4c8 | 1 | 1 | 0.33 | 1.004 |
| 41 | 7h7 | 0.73 | 2.4 | 2.1 | 0.995 |
| 41 | 5a5 | 0.77 | 1.93 | 2.7 | 1.002 |
| 41 | 2c12 | 1.06 | 1.7 | 0.91 | 1.003 |
| 41 | 6e5- | 1.16 | 1.62 | 1.53 | 0.997 |
| 41 | 4e5- | 1.08 | 1.37 | 1.4 | 1.004 |
| 41 | 6g7 | 1.3 | 1.27 | 1.39 | 0.999 |
| 41 | 1h4 | 1.36 | 1.24 | 0.56 | 0.994 |
| 41 | 0c11 | 4.1 | 1.23 | 1.24 | 0.996 |
| 41 | 2h9 | 5.3 | 1.01 | 0.83 | 0.986 |
| 42 | 6b10 | 0.97 | 3.6 | 0.97 | 0.997 |
| 42 | 1c3 | 0.91 | 2.1 | 0.6 | 0.998 |
| 42 | 7h9 | 0.8 | 1.8 | 0.8 | 0.982 |
| 42 | 6b2 | 0.77 | 1.72 | 0.8 | 0.978 |
| 42 | 6d6 | 0.83 | 1.7 | 0.733 | 0.975 |
| 42 | 4e10- | 0.77 | 1.63 | 1.8 | 0.954 |
| 42 | 1b5 | 0.83 | 1.41 | 1.05 | 0.955 |
| 42 | 6e6- | 0.71 | 1.16 | 0.89 | 0.955 |
| 42 | 3a9 | 0.85 | 1.3 | 0.86 | 0.997 |
| 42 | 6b6 | 2.7 | 1.3 | 0.91 | 1.02 |
| 42 | 6e9- | 1.5 | 1.27 | 0.98 | 1.01 |
| 42 | 3h11 | 1.73 | 1.21 | 0.63 | 0.985 |
| 42 | 1a2 | 1.11 | 1.17 | 0.77 | 1.005 |
| 42 | 3f7 | 0.49 | 1.16 | 1.13 | 0.944 |
| 42 | 1a4 | 2 | 1.01 | 0.76 | 0.996 |
| Control is Luc40-0A7 at 54° C. | | | | | |
| 46 | 2h3 | 0.86 | 6.4 | 0.37 | 0.96 |
| 46 | 4a9 | 0.67 | 5.7 | 0.66 | 0.997 |
| 46 | 2g4 | 0.65 | 5.3 | 0.78 | 0.96 |
| 46 | 5d12 | 0.94 | 4.9 | 0.94 | 1.002 |
| 46 | 1h11 | 1.02 | 4.8 | 0.84 | 0.998 |
| 46 | 5a10 | 1.23 | 4.4 | 0.81 | 0.9842 |
| 46 | 0a8 | 1.35 | 4.3 | 0.89 | 1 |
| 46 | 4d3 | 0.51 | 3.6 | 0.65 | 0.975 |
| 46 | 2a3 | 1.17 | 2.9 | 0.57 | 0.988 |
| 46 | 3b11 | 1.39 | 2.5 | 0.63 | 1.02 |
| 46 | 7g12 | 1.49 | 2.5 | 0.91 | 1.02 |
| 46 | 0g9 | 1.86 | 2.25 | 0.5 | 0.998 |
| 46 | 7h8 | 1.07 | 1.36 | 0.52 | 0.99 |
| 46 | 1g8 | 0.3 | 1.31 | 0.72 | 0.92 |
| 46 | 1d3 | 1.74 | 1.13 | 1.02 | 1.001 |
| 46 | 0c3 | 1.68 | 1.01 | 0.74 | 1.01 |
| 46 | 5c11 | 0.82 | 1.01 | 0.6 | 0.95 |
| Control is Luc46-2H3 at 54° C. | | | | | |
| 49 | 6c10 | 0.57 | 2.2 | 0.98 | 1 |
| 49 | 7c6 | 1.12 | 1.9 | 0.93 | 1.01 |
| 49 | 0g12 | 1 | 1.58 | 0.69 | 1.08 |
| 49 | 7a5 | 1.08 | 1.44 | 1.1 | 0.99 |
| 49 | 1f6 | 0.66 | 1.13 | 1.04 | 1.006 |
| 49 | 0b5 | 0.76 | 1.07 | 1.03 | 0.98 |
| 49 | 4a3 | 0.94 | 1.06 | 0.77 | 1 |
| Control is Luc49-7C6 at 56° C. | | | | | |
| 56 | 2d12 | 0.97 | 2.9 | 0.29 | 1.006 |
| 56 | 5g10 | 1.01 | 2.77 | 0.64 | 1.007 |
| 56 | 3d5 | 1.32 | 2.25 | 1.85 | 1.0 |
| 57 | 3d1 | 1.06 | 2.9 | 1.05 | 1.02 |
| 57 | 6g12 | 1 | 2.7 | 0.87 | 1.004 |
| 57 | 4c1 | 0.79 | 2.6 | 0.93 | 1.014 |
| 57 | 5f10 | 0.72 | 1.9 | 0.64 | 1.03 |
| 57 | 1e6- | 0.84 | 1.49 | 0.984 | 0.9871 |
| 57 | 1h2 | 0.94 | 1.43 | 0.68 | 0.991 |
| 57 | 2a6 | 1.08 | 1.08 | 0.89 | 0.9976 |
| 58 | 1g6 | 1.57 | 8.9 | 1.78 | 1.02 |
| 58 | 0a5 | 1.53 | 8.5 | 1.56 | 1.05 |
| 58 | 1b1 | 0.84 | 8.5 | 0.6 | 1.04 |
| 58 | 3g1 | 1 | 7.34 | 0.62 | 1.006 |

TABLE 1-continued

| Experiment | Clone ID | Luminescence (Li) | Enzyme stability (tau) | Substrate binding (Km) | Signal stability (S) |
|---|---|---|---|---|---|
| 58 | 0f3 | 1.31 | 6.9 | 0.57 | 0.98 |
| 58 | 3e12- | 1.06 | 6.3 | 0.47 | 0.996 |
| 58 | 0c7 | 1.9 | 4 | 0.64 | 1.06 |
| 58 | Od1 | 1.03 | 3.76 | 0.49 | 1.03 |
| 58 | 3c7 | 1.49 | 3.4 | 0.55 | 1.04 |
| 58 | 2a2 | 1.4 | 2.2 | 0.5 | 1.05 |
| 58 | 2a8 | 3.2 | 2 | 0.81 | 1.05 |
| 58 | 0f2 | 2.2 | 1.92 | 0.45 | 1.04 |
| 58 | 1b4 | 5.1 | 1.87 | 1.08 | 1.09 |
| 58 | 2b3 | 2.7 | 1.55 | 0.57 | 1.04 |
| 58 | 4g1 | 4.9 | 1.2 | 0.72 | 1.06 |
| Control is Luc58-0A5 at 58° C. | | | | | |
| 61 | 4e9- | 1.03 | 1.84 | 0.76 | 1.01 |
| 61 | 1f1 | 1.02 | 1.43 | 0.7 | 1 |
| 61 | 2e12- | 1.56 | 1.34 | 0.48 | 1.003 |
| 61 | 2f2 | 1.5 | 1.3 | 0.32 | 1.01 |
| 61 | 6b4 | 1.2 | 1.26 | 0.88 | 0.98 |
| 61 | 4c10 | 1.46 | 1.12 | 1.06 | 0.99 |
| 61 | 4g11 | 1.31 | 1.03 | 1.43 | 1.03 |
| 61 | 2f1 | 1.41 | 1.02 | 0.79 | 0.995 |
| 61 | 2g1 | 1.3 | 1 | 1.17 | 1 |
| 65 | 6g12 | 0.87 | 2.3 | 0.73 | 0.9605 |
| 65 | 1h6 | 0.84 | 2.2 | 1.62 | 0.9598 |
| 65 | 7f5 | 1.2 | 1.56 | 2.07 | 1.0087 |
| 65 | 5g5 | 2.3 | 1.49 | 0.45 | 0.9985 |
| 65 | 7h2 | 1.56 | 1.27 | 0.91 | 1.0658 |
| 65 | 7b2 | 1.98 | 1.16 | 0.6 | 0.9289 |
| 65 | 0g9 | 1.36 | 1.09 | 1.46 | 0.9927 |
| 65 | 6c7 | 1.48 | 1.06 | 0.86 | 0.9967 |
| 65 | 1e12- | 1.59 | 1.05 | 1.03 | 0.9582 |
| 65 | 4e2- | 1.21 | 1.05 | 1.11 | 0.943 |
| 65 | 6a10 | 1.7 | 1.04 | 0.93 | 0.992 |
| 65 | 4b9 | 1.48 | 1.04 | 1.61 | 1.0009 |
| 65 | 6c1 | 1.36 | 1.02 | 0.72 | 0.9978 |
| 68 | 2g6 | 1.39 | 3.9 | 1.17 | 0.9955 |
| 68 | 4g3 | 2 | 2.5 | 0.27 | 0.9927 |
| 68 | 5a3 | 1.04 | 1.64 | 0.65 | 0.8984 |
| 68 | 2b7 | 1.04 | 1.64 | 5.2 | 0.9237 |
| 68 | 5d10 | 2.75 | 1.36 | 0.73 | 1.0078 |
| 68 | 7d12 | 1.85 | 1.32 | 0.66 | 1.0084 |
| 68 | 7b9 | 1.8 | 1.19 | 0.56 | 1.0052 |
| 68 | 7b3 | 1.2 | 1.16 | 0.55 | 0.9951 |
| 68 | 1g10 | 1.48 | 1.05 | 1.22 | 1.0025 |
| 70 | 2a7 | 1.94 | 4.6 | 0.7 | 1.0015 |
| 70 | 3d6 | 3.5 | 4.2 | 0.18 | 1.03 |
| 70 | 4f8 | 1.87 | 4.2 | 0.69 | 0.9979 |
| 70 | 7h5 | 2.4 | 2.6 | 0.18 | 1 |
| 70 | 5h6 | 3.1 | 2.3 | 0.6 | 0.999 |
| 70 | 7d6 | 3 | 2.2 | 2.29 | 0.9989 |
| 70 | 5a3 | 3.1 | 1.5 | 0.18 | 1.0058 |
| 70 | 7d2 | 2.5 | 1.4 | 0.66 | 1.0126 |
| 70 | 3h7 | 3.2 | 1.22 | 0.23 | 1.002 |
| 70 | 0h5 | 2.5 | 1.15 | 0.36 | 0.9992 |
| 70 | 0d7 | 1.86 | 1 | 1.83 | 0.993 |
| 70 | 1g12 | 2.42 | 1 | 0.26 | 0.965 |
| 71 | 1d10 | 1.6 | 4.5 | 1.06 | 1.0065 |
| 71 | 6f11 | 1.8 | 4.3 | 0.98 | 0.953 |
| 71 | 7h4 | 3.4 | 3.6 | 0.56 | 1.0045 |
| 71 | 4h3 | 3.1 | 3.1 | 0.42 | 1.0171 |
| 71 | 1h5 | 1.31 | 3.01 | 1.31 | 0.9421 |
| 71 | 5e4- | 5.4 | 2.3 | 0.35 | 0.994 |
| 71 | 5c1 | 2.2 | 2.3 | 0.89 | 0.9746 |
| 71 | 0h7 | 3.6 | 1.8 | 0.59 | 1.0197 |
| 71 | 6h9 | 23.7 | 1.71 | 0.91 | 1.0064 |
| 71 | 7e3- | 5.3 | 1.7 | 0.7 | 1.0028 |
| 71 | 5d4 | 11.1 | 1.48 | 0.35 | 1.0213 |
| 71 | 2e3- | 4 | 1.47 | 0.45 | 0.9654 |
| 71 | 6h11 | 17.7 | 1.15 | 2.8 | 1.0064 |
| 71 | 2e10- | 3 | 1.1 | 0.66 | 0.9588 |
| 71 | 2g2 | 4.4 | 1.01 | 0.44 | 1.0046 |
| Control is Luc71-5D4 at 60° C. | | | | | |
| 72 | 2g6 | 0.38 | 3.1 | 1.58 | 1.0052 |
| 72 | 5f12 | 0.81 | 1.53 | 1.02 | 0.9678 |
| 72 | 0d7 | 0.76 | 1.44 | 1.4 | 0.9838 |
| 72 | 5c12 | 0.87 | 1.43 | 1.04 | 0.9718 |
| 72 | 1e1- | 1.04 | 1.41 | 1.15 | 0.9956 |
| 72 | 5b12 | 0.83 | 1.41 | 1.02 | 0.9731 |
| 72 | 0b7 | 1.11 | 1.04 | 0.91 | 1.0049 |
| 72 | 3b4 | 0.49 | 1.03 | 2.2 | 0.9581 |
| 73 | 2h8 | 0.85 | 1.9 | 1.08 | 1.0123 |
| 73 | 4e6- | 0.95 | 1.76 | 0.94 | 0.9939 |
| 73 | 3g8 | 0.86 | 1.53 | 1.04 | 1 |
| 73 | 1g3 | 1.7 | 1.14 | 0.97 | 0.9921 |
| 74 | 2a9 | 0.96 | 1.77 | 0.86 | 0.999 |
| 74 | 4e10- | 0.8 | 1.36 | 1.33 | 0.09897 |
| 74 | 0d5 | 1.69 | 1.28 | 0.61 | 0.9927 |
| 74 | 6g7 | 1.75 | 1.07 | 1.33 | 1.0022 |
| 74 | 5d8 | 0.46 | 1.06 | 0.95 | 0.899 |
| 74 | 5e7- | 1.22 | 1.05 | 0.87 | 0.9977 |
| 74 | 6e1- | 1.19 | 1.02 | 0.96 | 0.999 |
| 76 | 6c3 | 2.3 | 6.4 | 1.2 | 0.9865 |
| 76 | 2a9 | 0.93 | 4.7 | 1.08 | 0.999 |
| 76 | 3h9 | 1.26 | 2.6 | 1.02 | 0.9973 |
| 76 | 0b10 | 1.52 | 2.4 | 1.4 | 0.992 |
| 76 | 0h9 | 1.71 | 1.44 | 1.05 | 1.018 |
| 76 | 2e9- | 0.44 | 1.15 | 1.2 | 0.9318 |
| 76 | 0e10- | 1.67 | 1.1 | 1.02 | 1.014 |
| 76 | 0c10 | 1.13 | 1.05 | 1 | 0.9974 |
| 76 | 3e8- | 1.35 | 1.03 | 1.1 | 0.9894 |
| 76 | 0d12 | 0.69 | 1 | 0.92 | 0.932 |
| 76 | 0f10 | 0.62 | 1 | 1.2 | 0.9478 |
| 78 | 1e1- | 0.54 | 8.9 | 1.15 | 0.9877 |
| 78 | 0h7 | 1.4 | 5 | 0.97 | 1.014 |
| 78 | 0a6 | 1 | 4.3 | 1.5 | 0.9967 |
| 78 | 0b10 | 1.93 | 2 | 1 | 0.9926 |
| 78 | 0f11 | 1.6 | 2 | 0.91 | 0.9905 |
| 78 | 3f1 | 2.4 | 1.7 | 1.09 | 0.9936 |
| 78 | 2b4 | 1.97 | 1.36 | 0.98 | 1.0094 |
| 78 | 5b3 | 3.2 | 1.19 | 1.03 | 0.9735 |
| 78 | 2g12 | 2.5 | 1.03 | 1 | 1.0134 |
| 78 | 0h2 | 1.6 | 1 | 1.15 | 1.0168 |
| Control is Luc78-0B10 at 62° C. | | | | | |
| 82 | 2g12 | 0.9811 | 2.09 | 0.8851 | 0.9939 |
| 82 | 4b9 | 1.0845 | 1.8419 | 0.8439 | 1.0078 |
| 82 | 0d1 | 0.7622 | 1.5171 | 1.11 | 0.9998 |
| 82 | 3g1 | 0.8805 | 1.504 | 0.9629 | 0.9927 |
| 82 | 1d1 | 0.9741 | 1.4497 | 0.8936 | 0.9986 |
| 82 | 1e8- | 0.8206 | 1.4433 | 0.9876 | 0.9968 |
| 82 | 0h9 | 1.1355 | 1.3626 | 0.9171 | 1.0094 |
| 82 | 2c6 | 1.0931 | 1.3402 | 0.9482 | 1.0022 |
| 82 | 3g9 | 1.0364 | 1.251 | 0.968 | 1.0009 |
| 82 | 4h8 | 0.8816 | 1.1667 | 0.9165 | 1.0045 |
| 82 | 0a10 | 1.0535 | 1.1128 | 1.0413 | 1 |
| 82 | 4g1 | 1.4305 | 1.0862 | 1.1734 | 1.0059 |
| 84(121) | 6h7 | 0.3755 | 29.3639 | 2.3636 | 0.8905 |
| 84(121) | 2h9 | 0.4264 | 28.7958 | 1.819 | 0.904 |
| 84(121) | 3f7 | 0.4161 | 25.3058 | 1.8079 | 0.8988 |
| 84(121) | 2h10 | 0.9667 | 14.4658 | 0.8073 | 0.9947 |
| 84(121) | 3a2 | 0.3329 | 12.6 | 2.5444 | 0.855 |
| 84(121) | 3a6 | 1.2299 | 7.2384 | 0.7866 | 1.0046 |
| 84(121) | 5b12 | 1.0535 | 6.0315 | 0.7824 | 1.0056 |
| 84(121) | 5a7 | 1.0413 | 4.9054 | 0.8864 | 1.0071 |
| 84(121) | 3d2 | 0.2032 | 4.8 | 2.4623 | 0.7973 |
| 84(121) | 2a9 | 1.0847 | 4.7486 | 0.7746 | 1.0051 |
| 84(121) | 5e11- | 1.1918 | 4.0988 | 0.872 | 1.008 |
| 84(121) | 7b2 | 0.9115 | 3.9929 | 0.909 | 1.0077 |
| 84(121) | 3b5 | 1.2014 | 3.8251 | 0.7509 | 1.0086 |
| 84(121) | 1f8 | 1.07 | 3.06 | 0.8276 | 1.0093 |
| 84(121) | 2e2- | 1.4356 | 1.9315 | 0.7863 | 1.0175 |
| Control is Luc84-3A6 at 64° C. | | | | | |
| 85(86) | 2a2 | 0.2266 | 12.9013 | 3.326 | 0.8705 |
| 85(86) | 4f12 | 1.1167 | 4.7851 | 0.7439 | 1.0092 |
| 85(86) | 4e9- | 1.0869 | 4.4953 | 0.8539 | 1.0068 |
| 85(86) | 1f11 | 0.6994 | 4.0976 | 0.842 | 1.0124 |
| 85(86) | 5a4 | 1.2273 | 4.09 | 0.9683 | 1.0098 |
| 85(86) | 3e10- | 0.8902 | 3.5342 | 0.8106 | 1.0069 |

TABLE 1-continued

| Experiment | Clone ID | Luminescence (Li) | Enzyme stability (tau) | Substrate binding (Km) | Signal stability (S) |
|---|---|---|---|---|---|
| 85(86) | 3e12- | 1.0512 | 3.4883 | 0.853 | 1.0054 |
| 85(86) | 5e4- | 0.9562 | 3.3886 | 1.0328 | 1.0069 |
| 85(86) | 0e6- | 0.1494 | 3.0145 | 3.6293 | 0.8269 |
| 85(86) | 6b1 | 0.7615 | 2.5712 | 0.8695 | 1.0055 |
| 85(86) | 6h7 | 1.0285 | 2.5401 | 0.8963 | 1.0057 |
| 85(86) | 4b11 | 0.9816 | 2.3899 | 0.7927 | 1.0063 |
| 85(86) | 6d7 | 1.1087 | 2.0607 | 0.9042 | 1.0088 |
| 85(86) | 2e10- | 0.3028 | 2.0603 | 1.9649 | 0.8738 |
| 85(86) | 2a9 | 1.448 | 1.1819 | 0.9722 | 1.0046 |
| Control is Luc85-4F12 at 65° C. | | | | | |
| 88 | 3c1 | 1.4439 | 2.0938 | 0.9874 | 0.9976 |
| 88 | 6g1 | 1.0184 | 1.2665 | 1.2184 | 1.0019 |
| 88 | 3e4- | 1.331 | 1.0996 | 1.0669 | 0.9983 |
| 89 | 1a4 | 1.2565 | 2.4796 | 1.0338 | 0.997 |
| 89 | 3b1 | 0.7337 | 1.9976 | 0.9628 | 1.0001 |
| 89 | 2b12 | 1.0505 | 1.8496 | 1.0069 | 1.0012 |
| 89 | 0b5 | 1.5671 | 1.1362 | 1.0912 | 0.9995 |
| 89 | 1f1 | 1.378 | 1.1018 | 0.9804 | 0.996 |
| 89 | 2f1 | 1.4637 | 1.0894 | 0.9189 | 0.9992 |
| 90 | 0f1 | 1.4081 | 1.3632 | 1.027 | 0.9987 |
| 90 | 1b5 | 1.4743 | 1.1154 | 1.0812 | 1.0011 |
| 90 | 6g5 | 1.2756 | 1.0605 | 1.0462 | 1.0012 |
| 90 | 5e6- | 1.0556 | 1.0569 | 1.1037 | 1.0011 |
| 90 | 4e3- | 1.2934 | 1.0291 | 1.0733 | 1.0002 |

To evaluate the impact of directed evolution on enzyme function, clones from the beginning, middle and end of the process (Table 2) were purified and analyzed. The clones selected for this analysis were Luc[T249M], Luc49-7C6, and Luc78-0B10. Another clone, Luc90-1B5, created by a subsequent strategy of oligonucleotide-directed mutagenesis and screening was also purified for analysis.

TABLE 2

Thermostability Of Luciferase Activity At Different Temperatures (Half-Life In Hours)

| | Room Temperature* | 37° C. | 50° C. | 60° C. |
|---|---|---|---|---|
| Luc[T249M] | 110 | 0.59 | 0.01 | |
| Luc49-7C6 | 430 | 68 | 31 | 6.3 |
| Luc78-0B10 | 3000 | 220 | 47 | 15 |

*about 25° C.

Figure 16A:
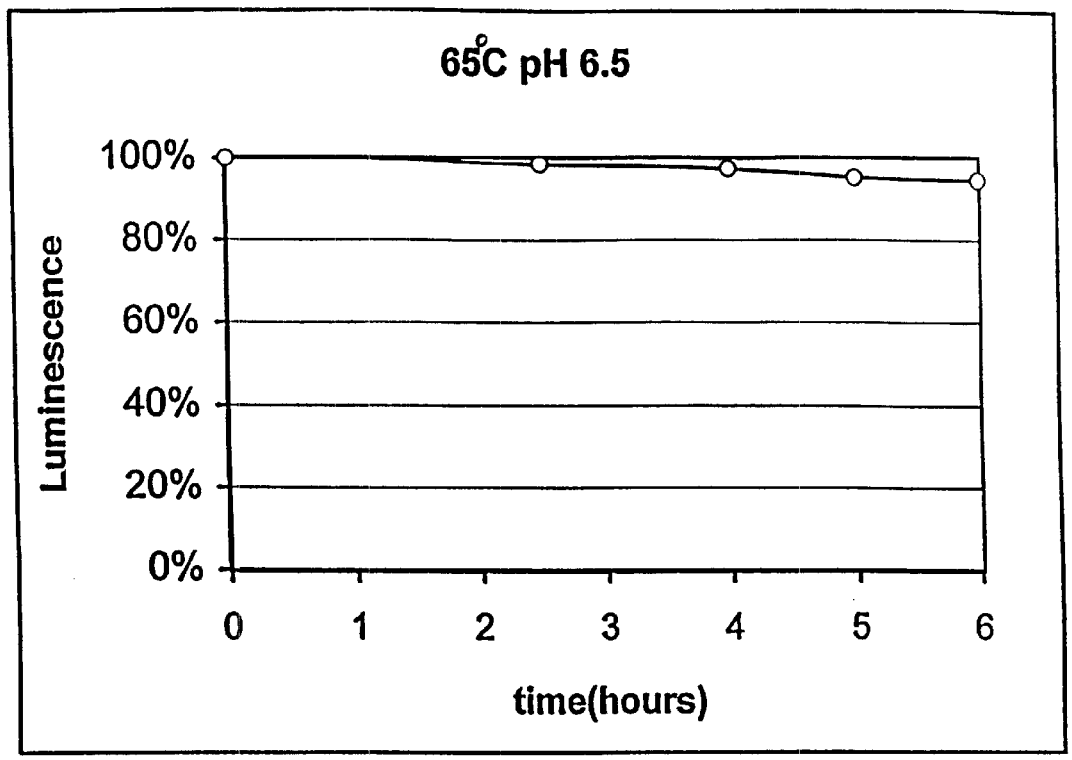
FIG. 16A is a graphical representation of luciferase mutant Luc90-1B5 luminescence measured at 65° C., pH 6.5 (the X-axis is time in hours; the Y-axis is % luminescence).
Figure 16B:
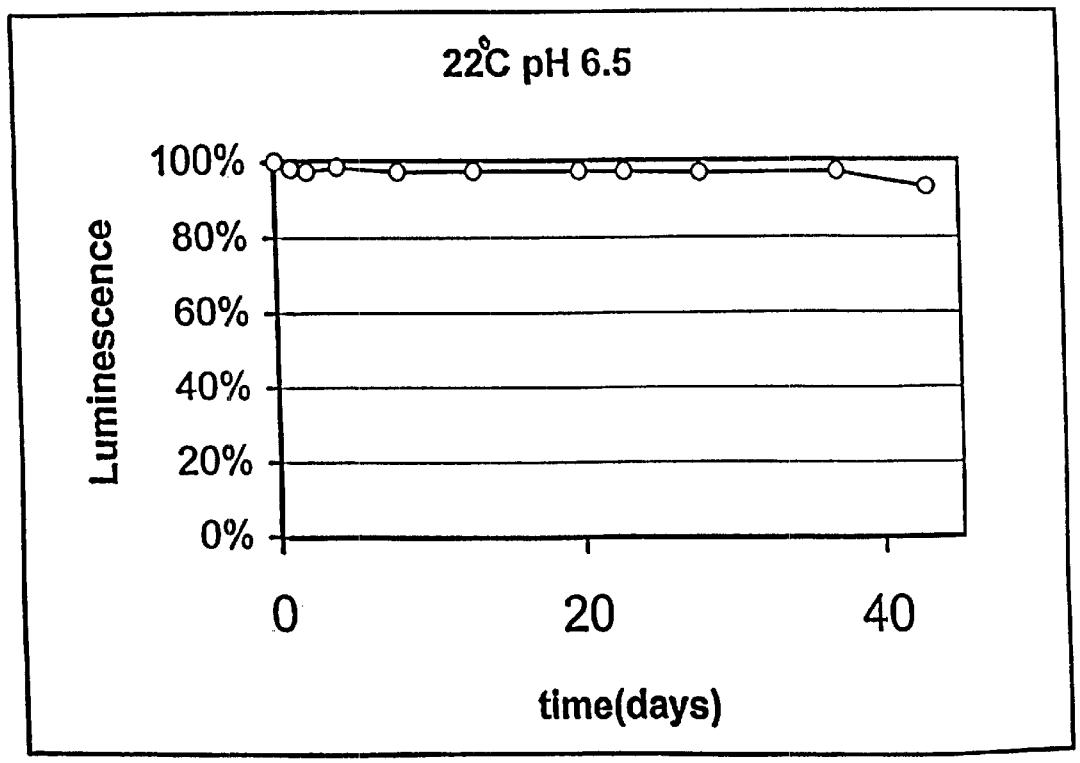
FIG. 16B is a graphical representation of luciferase mutant Luc90-1B5 luminescence at 22° C., pH 6.5 (the X-axis is time in days; the Y-axis is % luminescence).
Figure 49:
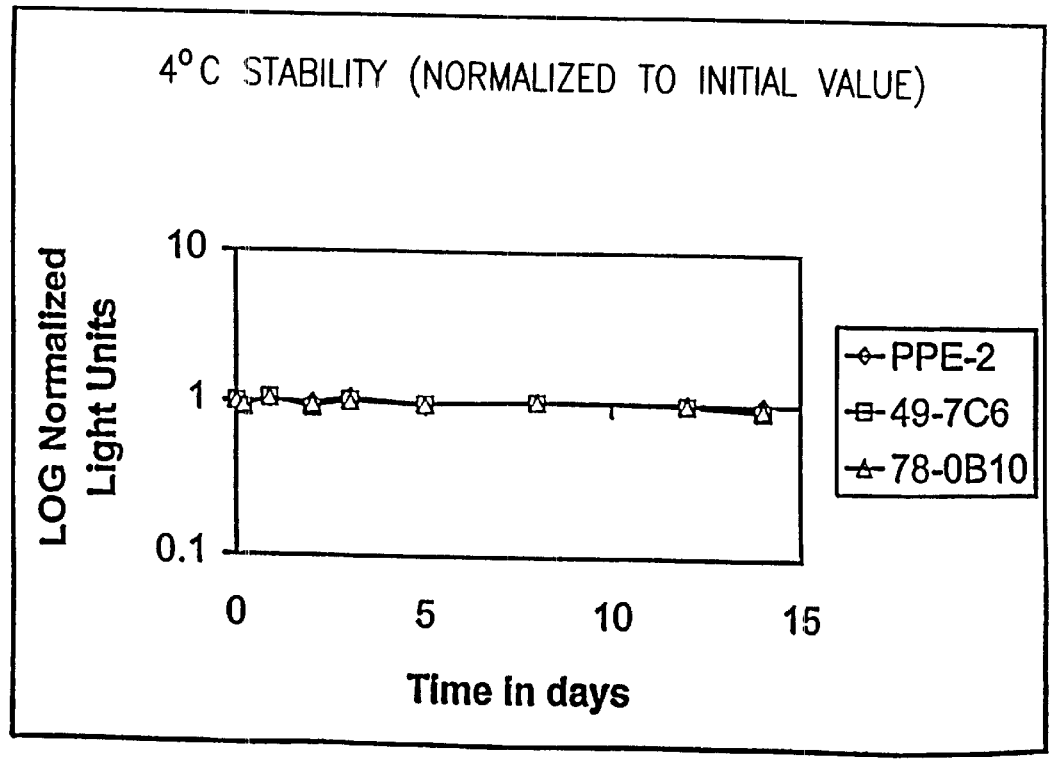
FIG. 49 is a graphical representation of luciferases LucPpe2 [T249M], Luc49-7C6, and Luc78-0B10, thermostability at 4° C., normalized to initial values [the X-axis is time in days; Y is log normalized light units].
Figure 50:
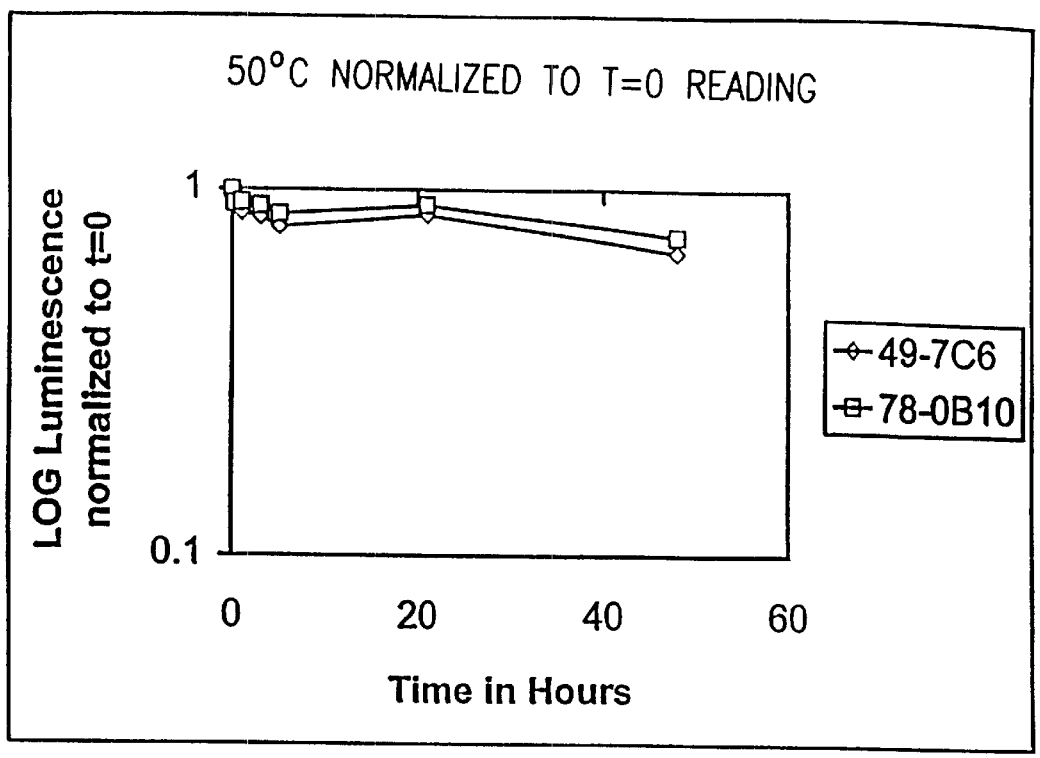
FIG. 50 is a graphical representation of mutant luciferases Luc49-7C6 and Luc78-0B10 luminescence at 50° C. normalized to t=0 [the X-axis is time in hours; the Y-axis is log luminescence].
Figure 51:
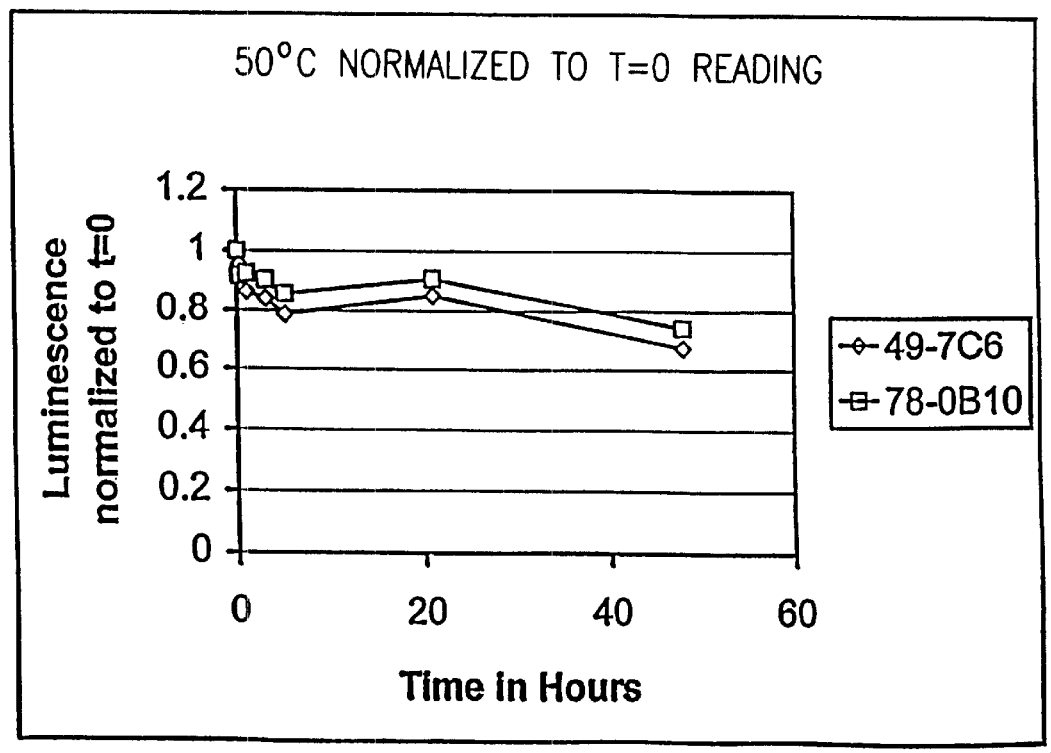
FIG. 51 is a graphical representation of mutant luciferases Luc49-7C6 and Luc78-0B10 luminescence at 50° C. normalized at t=0.
Figure 52:
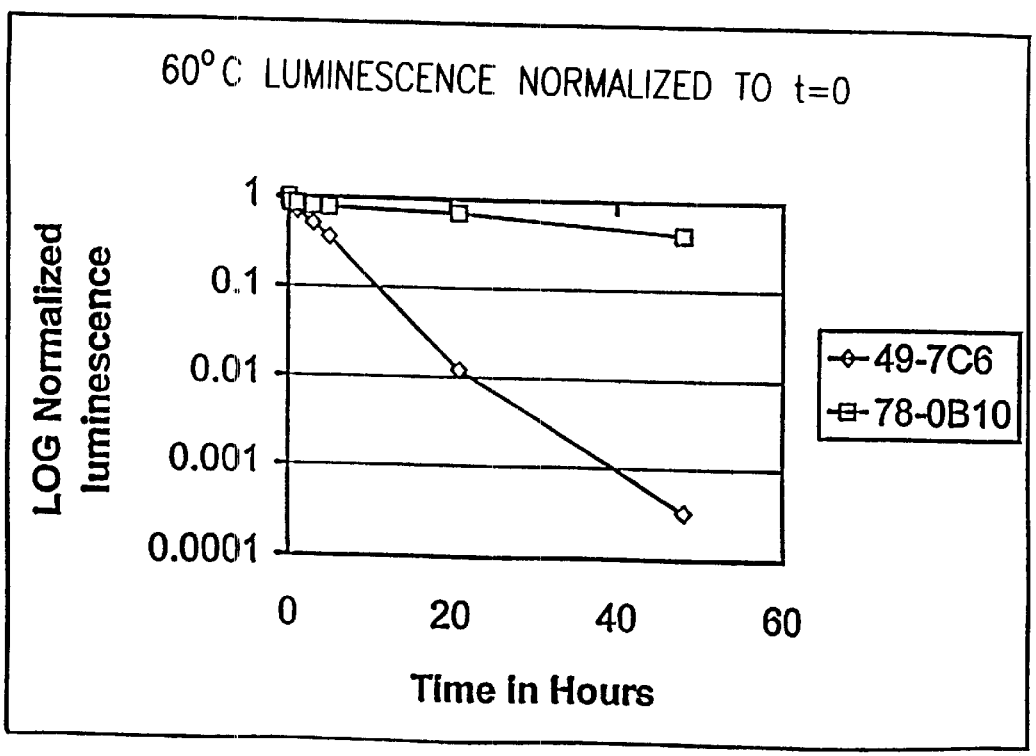
FIG. 52 is a graphical representation of mutant luciferases Luc49-7C6 and Luc78-0B10 luminescence at 60° C. normalized to t=0 [the X-axis is time in hours; the Y-axis is luminescence].
Figure 53:
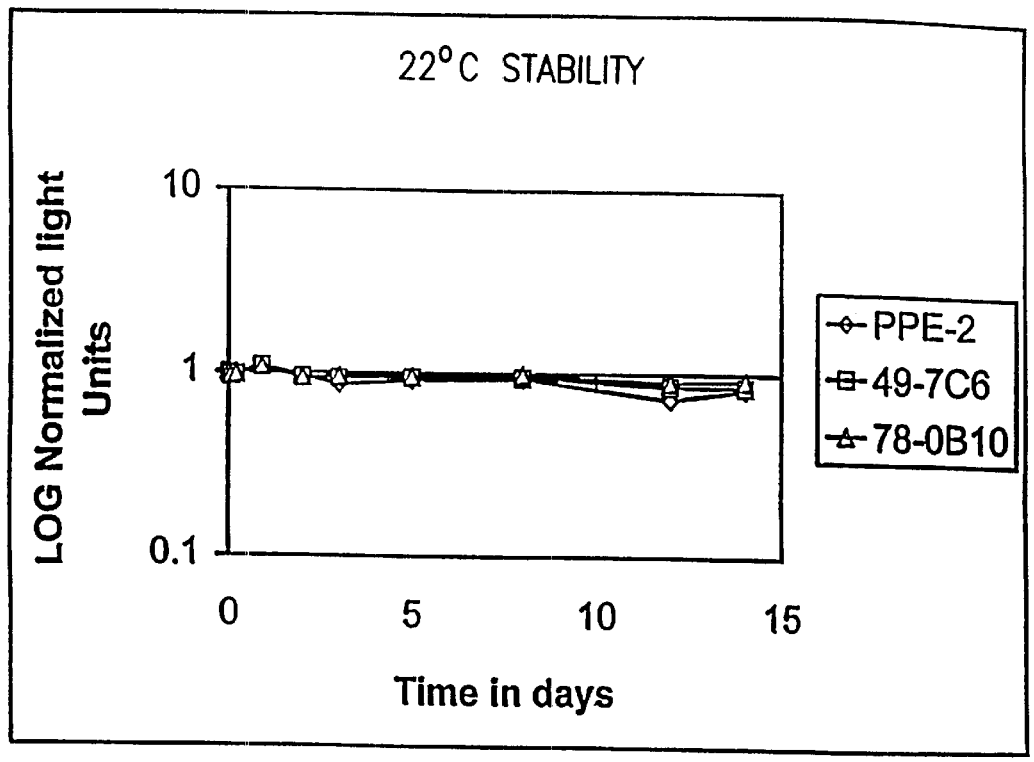
FIG. 53 is a graphical representation of luciferases LucPpe2 [T249M], Luc49-7C6, and Luc78-0B10 thermostability at 22° C. [the X-axis is time in days; the Y-axis is log luminescence].
Figure 54A:
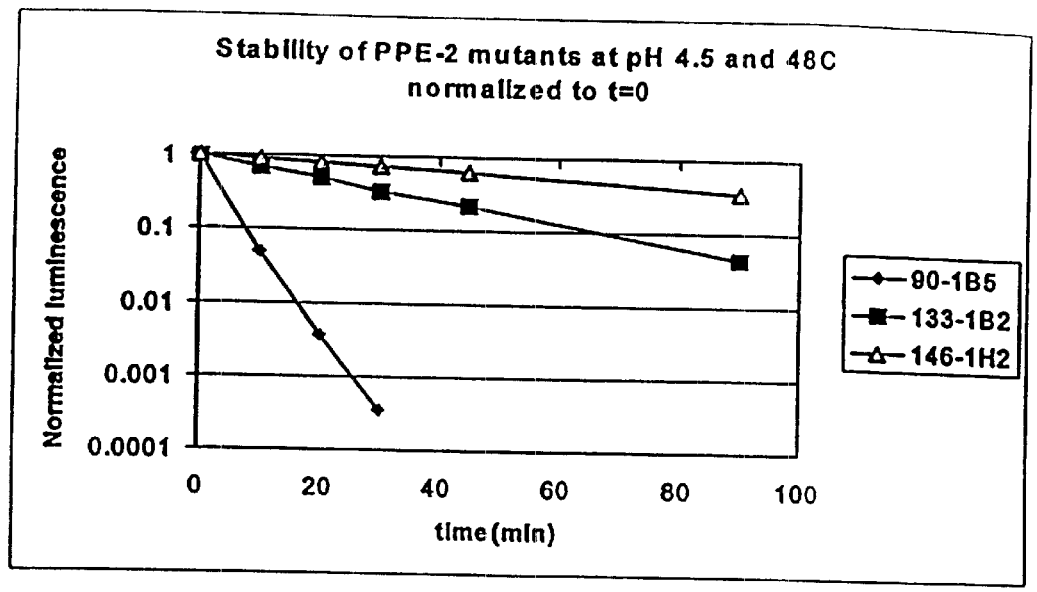
FIG. 54A is a graphical representation of luminescence of Luc90-1B5; Luc133-1B2; and Luc146-1H2, at pH 4.5 and 48° C., normalized to t=0.
Figure 54B:
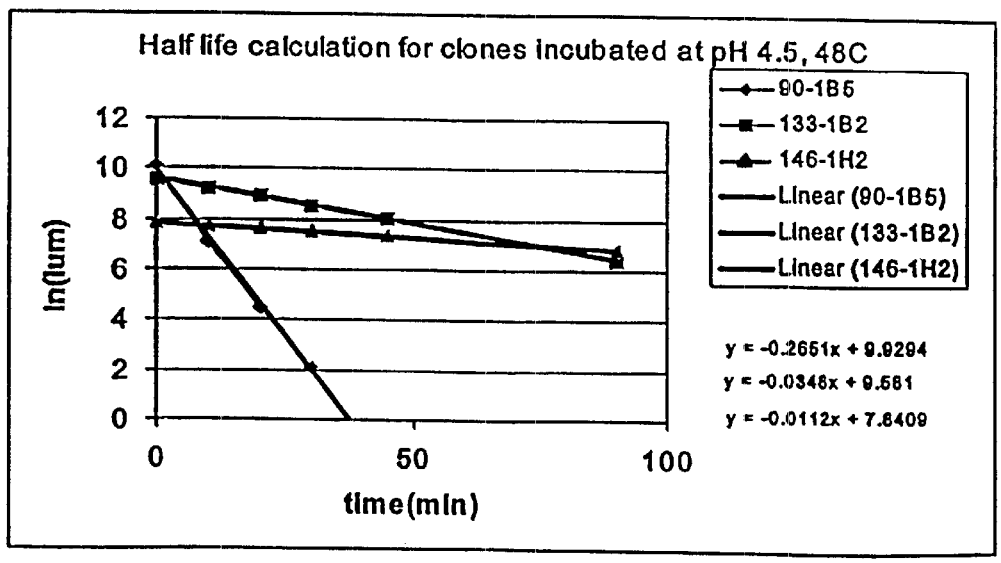
FIG. 54B is a graphical representation of the half-life of Luc90-1B5; Luc133-1B2; and Luc146-1H2, at pH 4.5 and 48° C. The half-life of Luc90-1B5 under these conditions is about 3 minutes, Luc133-1B2 about 20 minutes, and Luc146-1H2 about 62 minutes.

The effect of directed evolution on thermostability was dramatic. At high temperatures, where the parent clone was inactivated almost instantaneously, the mutant enzymes from the related clones showed thermostability over several hours (see also Table 1, and FIGS. 1–3, 5–8, 11, 13, 50–52 and 60). Even at room temperature, these mutants are several fold more thermostable than the parent enzyme (see also FIGS. 4, 9–10, 12, 53, and 62). Subsequent analysis of Luc90-1B5 showed this enzyme to be even more thermostable, having a half-life of 27 hours at 65° C. when tested under the same buffer conditions (FIG. 16A). With some optimization of buffer conditions, this enzyme showed very little activity loss at 65° C. over several hours (citrate buffer at pH 6.5; FIG. 16A). This luciferase was stable at 22° C. over several weeks when incubated at pH 6.5 (FIG. 16B). At times over 100 days at 4° C., the mutant enzymes had increased thermostability. At times of less than 15 days at 4° C., the thermostabilities of the mutants Luc49-7C6 and Luc78-0B10 were not distinguishable from the parent enzyme (FIG. 49).

Kajiyama and Nakamo (1993) showed that a single amino acid substitution of A at position 217; to either I, L, or V, in the firefly luciferase from *Luciola lateralis,* resulted in a luciferase having increased thermostability. Substitution with leucine produced a luciferase that maintained 70% of its activity after incubation for 1 hour at 50° C. All of the enzymes of the present invention created through directed evolution, are much more stable than this *L. lateralis* mutant. One clone, Luc90-1B5, maintains 75% activity after 120 hours (5 days) incubation under similar conditions (50° C., 25 mol/L citrate pH 6.5, 150 mmol/L NaCl, 1 mg/mL BSA, 0.1 mmol/L EDTA, 5% glycerol). Interestingly, the LucPpe2 reported by Leach et al. already contains isoleucine at the homologous position described for the *L. lateralis* mutant.

Although thermostability was the characteristic of interest, clones were selected based on the other enzymological parameters in the screens. By selecting clones having greater luminescence expression, mutants were found that yielded greater luminescence intensity in colonies of *E. coli.* However, the process showed little ability to alter the kinetic profile of luminescence by the enzymes. This failure suggests that the ability to support steady-state luminescence is integral to the catalytic mechanism, and is not readily influenced by a cumulative effect of many amino acids.

Substrate binding was screened by measuring an apparent composite $K_m$ (see Example 2) for luciferin and ATP. Although the apparent composite $K_m$ remained relatively constant, later analysis showed that the individual $K_m$'s systematically changed. The $K_m$ for luciferin rose while the $K_m$ for ATP declined (Table 3). The reason for this change is unknown, although it can be speculated that more efficient release of oxyluciferin or luciferin inhibitors could lead to more rapid enzyme turnover.

Each point mutation, on its own, increases (to a greater or lesser extent) the thermostability of the mutant enzyme relative to the wild-type luciferase. The cumulative effect of combining individual point mutations yields mutant luciferases whose thermostability is greatly increased from the wild-type, often on the order of a magnitude or more.

TABLE 3

Michaelis-Menten Constants for Mutants Created by Directed Evolution

| | $K_m$-luciferin | $K_m$-ATP |
|---|---|---|
| Luc[T249M] | 0.32 μM | 18 μM |
| Luc49-7C6 | 0.99 μM | 14 μM |
| Luc78-0B10 | 1.6 μM | 3.4 μM |
| Luc90-1B5 | 2.2 μM | 3.0 μM |

The following examples illustrate the methods and compositions of the present invention and their embodiments.

EXAMPLE 1

Producing Thermostable Luciferases of the Present Invention

Mutagenesis Method

An illustrative mutagenesis strategy is as follows: From the "best" wild-type luciferase clone, that is a clone with increased thermostability and not appreciably diminished values for other parameters, random mutagenesis was performed by three variations of error-prone PCR. From each cycle of random mutagenesis, 18 of the best clones were selected. DNA was prepared from these clones yielding a total of 54 clones. These clones represent new genetic diversity.

These 54 clones were combined and recombination mutagenesis was performed. The 18 best clones from this population were selected.

These 18 clones were combined with the 18 clones of the previous population and recombination mutagenesis was performed. From this screening, a new luciferase population of 18 clones was selected representing 6 groups of functional properties.

In this screening the new mutations of the selected 54 clones, either in their original sequence configurations or in recombinants thereof, were screened a second time. Each mutation was analyzed on the average about 10 times. Of the 90 clones used in the recombination mutagenesis, it was likely that at least 10 were functionally equivalent to the best clone. Thus, the best clone or recombinants thereof should be screened at least 100 times. Since this was greater than the number of clones used in the recombination, there was significant likelihood of finding productive recombination of the best clone with other clones.

Robotic Processing Methods

Heat transfers were controlled in the robot process by using thick aluminum at many positions where the 96-well plates were placed by the robotic arm. For example, all shelves in the incubators or refrigerator were constructed from ¼ inch aluminum. One position in particular, located at room temperature, was constructed from a block of aluminum of dimensions 4.5×7×6.5 inches. When any 96-well plate was moved from a high temperature (e.g., incubators) or low temperature (e.g., refrigerator) to a device at room temperature, it was first placed on the large aluminum block for temperature equilibration. By this means, the entire plate would rapidly reach the new temperature, thus minimizing unequal evaporation for the various wells in the plate due to temperature differences. Heat transfers in a stack of 96-well plates placed in an incubator (e.g., for overnight growth of *E. coli*) were controlled by placing 1 mm thick sheets of aluminum between the plates. This allowed for more efficient heat transfer from the edges of the stack to the center. Mixing in the robotic process was controlled by having the plate placed on a shaker for several second after each reagent addition.

Figure 14:
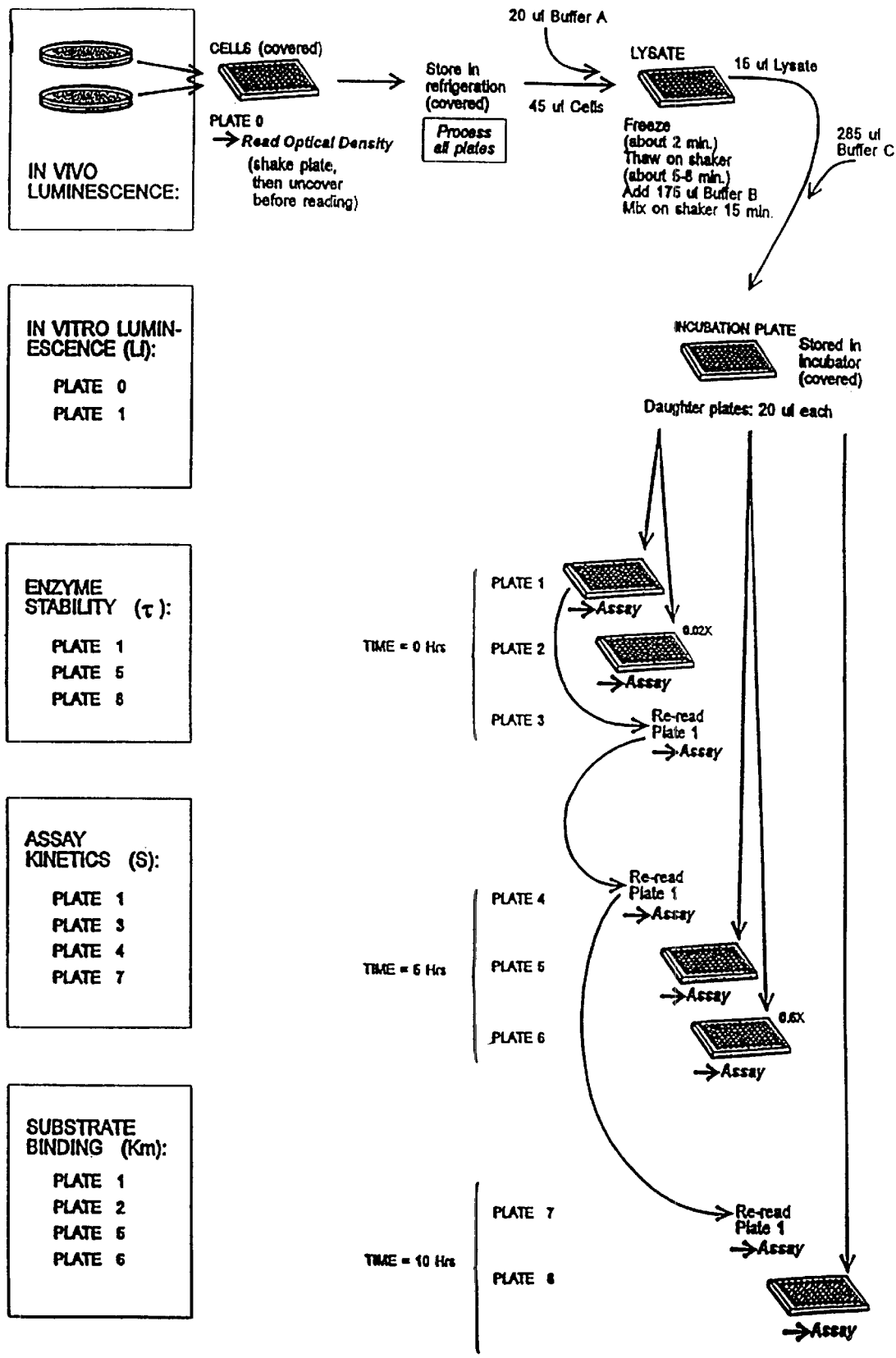
FIG. 14 is a flow chart showing steps for an assay of in vivo and in vitro luciferase luminescence (Li); enzyme stability (τ); assay kinetics (S); and substrate binding (Km).
Figure 15:
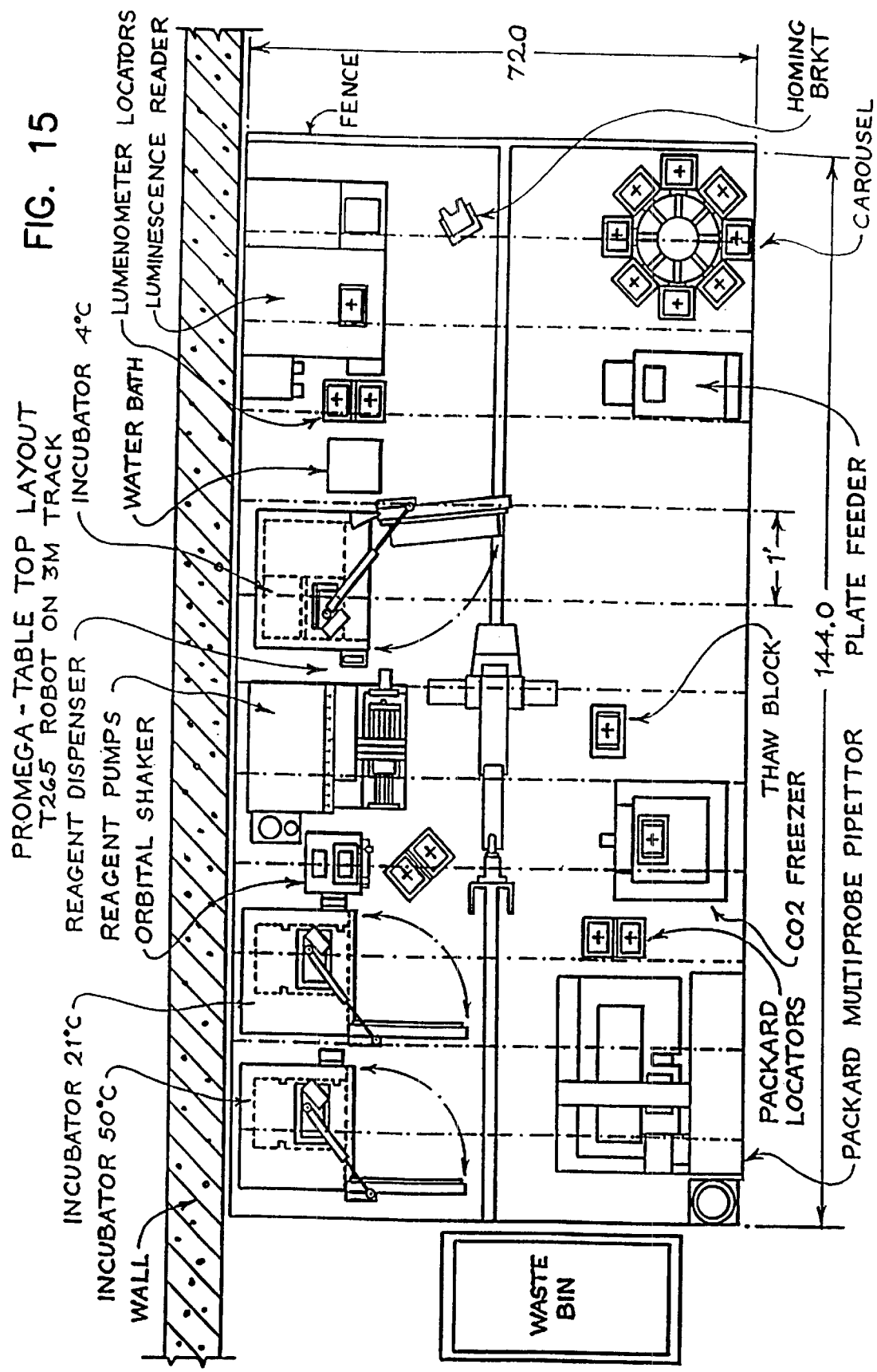
FIG. 15 is a schematic representation of a table top layout robot.

Please refer to FIG. 14 for a schematic of the order in which the plates are analyzed and to FIG. 15 for a robotic apparatus which can be programmed to perform the following functions:

1. Culture Dilution Method

A plate with lid (Falcon 3075) containing cells (*E. coli* JM109) is placed on a shaker and mixed for 3–5 minutes.

A plate (with lid) is obtained from a carousel and placed in the reagent dispenser. 180 $\mu$l of media (M9 minimal media) is added after removing the lid and placing on the locator near the pipetter. The plate is then placed in the pipetter.

The plate on the shaker is placed in the pipetter, and the lid removed and placed on the locator. Cells are transferred to the new plate using pipetting procedure (see "Dilution of Cells into New Cell Plate").

The lids are replaced onto both plates. The new plate is placed in the refrigerator and the old plate is returned to the carousel.

2. Luminescence Assay Method

A plate containing cells is retrieved from the carousel and placed on the shaker for 3–5 minutes to fully mix the cells. The cells tend to settle from solution upon standing.

To measure Optical Density (O.D.), the plate is moved from the shaker to the locator near the luminometer; the lid is removed and the plate placed into the luminometer. The O.D. is measured using a 620 nm filter.

When it is finished, the plate is then placed in the refrigerator for storage.

The above steps are completed for all plates before proceeding with subsequent processing.

To prepare a cell lysate, the plate of cells is first retrieved from the refrigerator and mixed on the shaker to resuspend the cells. A new plate from the carousel without a lid is placed in the reagent dispenser and 20 $\mu$l of Buffer A is added to each well. This is placed in the pipetting station.

The plate of cells in the shaker is placed in the pipetting station. A daughter plate is prepared using pipetting procedure (see "Pipetting Cells into the Lysis Plate") to prepare a daughter plate of cells.

After pipetting, the new daughter plate is placed on the shaker for mixing.

After mixing, the Lysate Plate is placed into a solid $CO_2$ freezing station to freeze the samples. The plate is then moved to the thaw block to thaw for 10 minutes.

The plate is then moved to the reagent dispenser to add 175 $\mu$l of Buffer B, and then mixed on the shaker for about 15 minutes or more. The combination of the freeze/thaw and Buffer B will cause the cells to lyse.

A new plate with a lid from the carousel is used to prepare the dilution plate from which all assays will be derived. The plate is placed in the reagent dispenser and the lid removed to the locator near the pipetter. 285 $\mu$l of Buffer C is added to each well with the reagent dispenser, then the plate is placed in the pipetting station.

The Lysate Plate in the shaker is moved to the pipetting station and pipetting procedure (see "Dilution from Lysis Plate to Incubation Plate") is used. After pipetting, the new daughter plate is placed on the shaker for mixing. The Lysate Plate is discarded.

Two white assay plates (Labsystems #9502887) are obtained from the plate feeder and placed in the pipetter. The incubation plate from the shaker is placed in the pipetter, and the lid removed and placed on the nearby locator. Two daughter plates are made using the pipetting procedure (see "Create Pair of Daughter Plates from Incubation Plate"). Afterwards, the lid is replaced on the parent plate, and the plate is placed in a high temperature incubator. [ranging from 31 ° C. to about 65° C. depending on the clone.]

One daughter plate is placed in the luminometer and the 1× assay method is used. After the assay, the plate is placed in the ambient incubator, and the second daughter plate is placed in the luminometer. For the second plate, the 0.02× assay method is used. This plate is discarded, and the first plate is returned from the incubator to the luminometer. The repeat assay method is used (i.e., no reagent is injected). Afterwards, the plate is again returned to the ambient incubator.

The above steps are completed for all plates before proceeding with processing.

To begin the second set of measurements, the plate from the high temperature incubator is placed in the shaker to mix.

The plate in the ambient incubator is returned to the luminometer and the repeat assay method is again used. The plate is returned afterwards to the ambient incubator.

Two white assay plates again are obtained from the plate feeder and placed in the pipetter. The plate on the shaker is placed in the pipetter, and the lid removed and placed on the nearby locator. Two daughter plates are again made using the pipetting procedure (see "Create Pair of Daughter Plates from Incubation Plate"). Afterwards, the lid is replaced on the parent plate, and the plate is returned to the high temperature incubator.

One daughter plate is placed in the luminometer and the 1× assay method is again used. The plate is discarded after the assay. The second daughter plate is then placed in the luminometer and the 0.06× assay method is used. This plate is also discarded.

The above steps are completed for all plates before proceeding with processing.

In the final set of measurements, the plate from the high temperature incubator is again placed in the shaker to mix.

The plate in the ambient incubator is returned to the luminometer and the repeat assay method is again used. The plate is discarded afterwards.

One white assay plate is taken from the plate feeder and placed in the pipetter. The plate from the shaker is placed in the pipetter, and the lid removed and placed on the nearby locator. One daughter plate is made using the pipetting procedure (see "Create Single Daughter Plate from Incubation Plate"). The lid is replaced on the parent plate and the plate is discarded.

The daughter plate is placed in the luminometer and the 1× assay method is used. The plate is discarded after the assay.

Buffers and Assay Reagents

Buffer A: 325 mM $K_2HPO_2$; 6.5 mM CDTA; 0.1% Triton X-100

Buffer B: 1×CCLR (Promega E153A); 1.25 mg/ml lysozyme; 0.04% gelatin

Buffer C: 10 mM HEPES; 150 mM NaCl; 1 mg/ml BSA; 5% glycerol; 0.1 mM EDTA

1×Assay reagent: 5 $\mu$M Luciferin; 175 $\mu$M ATP; 20 mM Tricine, pH 8.0; 0.1 mM EDTA 0.02×Assay reagent: 1:50 dilution of 1× Assay reagent 0.06×Assay reagent: 1:16.7 dilution of 1× Assay reagent Pipetting Procedures A. Pipetting Cells Into the Lysis Plate Non-aseptic procedure using fixed tips On the pipetter deck:

place a plate containing approximately 200 $\mu$l JM109 cells per well without lid Lysate Plate containing 20 $\mu$l of Buffer A Procedure:

1. Move the tips to the washing station and wash with 1 ml.
2. Move to the cell plate and withdraw 60 $\mu$l.
3. Move to the Lysate Plate and dispense 45 $\mu$l.
4. Repeat steps 1–3 for all 96 samples.
5. At the conclusion of the procedure, step 1 is repeated to clean the tips.

Post-procedure:

Place Lysate Plate onto the shaker.

Place lid on plate with cells and place on carousel.

Place Lysate Plate into the $CO_2$ freezer.

B. Dilution From Lysis Plate to Incubation Plate

On the pipetter deck:

Lysate Plate containing 240 $\mu$l of lysate

Incubation Plate without lid containing 285 $\mu$l of Buffer C

Procedure:

1. Move the tips to the washing station and wash with 0.5 ml.
2. Move to the Lysate Plate and withdraw 30 $\mu$l.
3. Move to the Incubation Plate and dispense 15 $\mu$l by direct contact with the buffer solution.
4. Repeat steps 1–3 for all 96 samples.
5. At the conclusion of the procedure, step 1 is repeated to clean the tips.

Post procedure:

Place Incubation Plate on shaker.

Discard Lysate Plate.

C. Create Pair of Daughter Plates From Incubation Plate

This procedure is done twice

On the pipetter deck:

Incubation Plate containing 100–300 $\mu$l of solution without lid

Two empty Assay Plates (white)

Procedure:

1. Move the tips to the washing station and wash with 0.5 ml.
2. Move to the Incubation Plate and withdraw 50 $\mu$l.
3. Move to the first Assay Plate and dispense 20 $\mu$l.
4. Move to the second Assay Plate and dispense 20 $\mu$l.
5. Repeat steps 1–4 for all 96 samples.
6. At the conclusion of the procedure, step 1 is repeated to clean the tips.

Post-procedure:

1. Replace lid on Incubation Plate.
2. Place Incubation Plate in incubator.
3. Place first Assay Plate in luminometer.
4. Place second Assay Plate on carousel.

D. Create Single Daughter Plate From Incubation Plate

On the pipetter deck:

Place incubation Plate containing 100–300 $\mu$l of solution without lid and

Empty Assay Plate (white)

Procedure:

1. Move the tips to the washing station and wash with 0.5 ml.
2. Move to the Incubation Plate and withdraw 40 $\mu$l.
3. Move to the Assay Plate and dispense 20 $\mu$l.
4. Repeat steps 1–3 for all 96 samples.
5. At the conclusion of the procedure, step 1 is repeated to clean the tips.

Post-procedure:

Discard Incubation Plate and lid on Incubation Plate.

Place Assay Plate in luminometer.

E. Dilution of Cells Into New Cell Plate

Aseptic procedure using fixed tips

On the pipetter deck:

plate containing approximately 200 $\mu$l of cells without lid new cell plate containing 180 $\mu$l of Growth Medium without lid Procedure:

1. Move to the cell plate and withdraw 45 $\mu$l.
2. Move to the Cell Plate and dispense 20 $\mu$l volume by direct liquid-to-liquid transfer.
3. Move to waste reservoir and expel excess cells.
4. Move to isopropanol wash station aspirate isopropanol to sterilize tips.
5. Move to wash station, expel isopropanol and wash tips.
6. Repeat steps 1–4 for all 96 samples.

Post-procedure:

Replace lid on original plate of cells and place onto carousel.

Replace lid on new cell plate and place into refrigerator.

Notes

This procedure is used to prepare the cell plates used in the main analysis procedure. 180 $\mu$l of M9 minimal growth medium is added by the reagent dispenser to each of the new cell plates just prior to initiating the pipetting procedure. The dispenser is flushed with 75% isopropanol before priming with medium. The medium also contains selective antibiotics to reduce potential contamination.

Luminometer Procedures

A. 1×Assay Method
1. Place plate into luminometer.
2. Inject 100 μl of 1×Assay reagent.
3. Measure luminescence for 1 to 3 seconds.
4. Repeat for next well.
5. Continue until all wells are measured.

B. 0.02×Assay Method
1. Place plate into luminometer.
2. Inject 100 μl of 0.02×Assay reagent.
3. Measure luminescence for 1 to 3 seconds.
4. Repeat for next well.
5. Continue until all wells are measured.

C. 0.06×Assay Method
1. Place plate into luminometer.
2. Inject 100 μl of 0.06×Assay reagent.
3. Measure luminescence for 1 to 3 seconds.
4. Repeat for next well.
5. Continue until all wells are measured.

D. Repeat Assay
1. Place plate into luminometer.
2. Measure luminescence for 1 to 3 seconds.
3. Repeat for next well.
4. Continue until all wells are measured.

In Vivo Selection Method

Five to seven nitrocellulose disks having 200–500 colonies per disk (1000–3500 colonies total) are screened per 2 microplates (176 clones) (Wood and DeLuca, 1987). The clones are screened at high temperatures using standard screening conditions.

Eight positions in each microplate are reserved from a reference clone using the "best" luciferase (the parent clone for random mutagenesis and codon mutagenesis). The positions of the reserved wells is shown as "X" below.

Xooooooooooo X
oooooooooooo
oooXooooXooo
oooooooooooo
oooooooooooo
oooXooooXooo
oooooooooooo
Xooooooooooo X The reference clones are made by placing colonies from DNA transformed from the parent clone into the reference wells. To identify these wells prior to inoculation of the microplate, the wells are marked with a black marking pen on the bottom of each well.

Screening Selection Criteria

The following criteria were used for screening purposes. The temperature chosen for the enzyme stability parameter was such that the parent enzyme would decay 100 to 1000 fold over 10 hours (see Table 1). Criteria 1 is achieved manually; data for criteria 2–6 is generated by robotic analysis. For all criteria, the maximum value as described is selected.

1. In vivo screen. The brightest clones are selected at a given temperature.

2. Expression/specific activity. The value for normalized luminescence is calculated as the ratio of luminescence to optical density. The value is reported as the ratio with the reference value.

3. Enzyme stability. Measurements of normalized luminescence of the incubated samples (3 taken over about 15 hours) are fitted to $\ln(L)=\ln(L_0)-(t/\tau)$, where L is normalized luminescence and t is time. $\tau$ is a measure of the enzyme stability. The value is reported as the ratio with the reference value, and the correlation coefficients are calculated.

4. Substrate binding. Measurements of normalized luminescence with 1× and 0.02× are taken at the initial reading set, and 1× and 0.06× are taken at the 5 hour set. The ratio of the 0.02×:1× and 0.06×:1× gives the relative luminescence at 0.02× and 0.06× concentrations. These values, along with the relative luminescence at 1×(i.e., 1), are fitted to a Lineweaver-Burk plot to yield the Km:app,total for the substrates ATP, luciferin, and CoA. The values are reported as the inverse ratio with the reference value, and the correlation coefficients are calculated.

5. Signal stability. The luminescence of the initial 1× luminescent reactions are re-measured 3 additional times over about 15 hours. These values are fitted to $\ln(L)=\ln(L_0)-(t/\tau)$ and the integral over t (15 hours) is calculated. Signal stability is then calculated as $S=(1-\text{int}(L)/L_0 t)^2$. The values are reported as the inverse ratio with the reference value, and the correlation coefficients are calculated.

6. Composite fitness. The values of criteria 2 through 5 are combined into a single composite value of fitness (or commercial utility). This value is based on a judgment of the relative importance of the other criteria. This judgment is given below:

| Criteria | Relative Value |
| --- | --- |
| Enzyme Stability | 5 |
| Signal Stability | 2 |
| Substrate Binding | 2 |
| Expression/Activity | 1 |

The composite, C=Sum(criteria 2–5 weighted by relative value, e.g., more weight is on stability because that was a major goal).

EXAMPLE 2

Software

Organize Data into SQL Database

Each file created by a luminometer (96 well, Anthos, Austria) represents the data from one microplate. These files are stored in the computer controlling the luminometer, and connected to the database computer by a network link. From each microplate of samples, nine microplates are read by the luminometer (the original microplate for optical density and eight daughter microplates for luminescence).

Ninety files are created in total; each containing data sets for 96 samples. Each data set contains the sample number, time of each measurement relative to the first measurement of the plate, luminometer reading, and background corrected luminometer reading. Other file header information is also given. The time that each microplate is read is also needed for analysis. This can be obtained from the robot log or the file creation time. A naming convention for the files is used by the robot during file creation that can be recognized by SQL (e.g. YYMMDDPR.DAT where YY is the year, MM is the month, DD is the day, P is the initial plate [0–9], and R is the reading [0–8]).

Data Reduction and Organization

Normalize luminescence data: For each measurement of luminescence in the eight daughter plates, the normalized luminescence is calculated by dividing the relative light units by the optical density of the original plate. If any value of normalized luminescence is less than zero, assign the value of 0.1 sL where sL is the standard deviation for measurements of normalized luminescence.

Calculate relative measurement time: For each normalized luminescence measurement, the time of the measurement is calculated relative to the first measurement of the sample. For example, the times of all luminescence measurements of sample B6 in plate 7 (i.e., 7:B06) are calculated relative to the first reading of 7:B06. This time calculation involves both the time when the plate is read and the relative time of when the sample is read in the plate.

Calculate enzyme stability ($\tau$): For each sample, use linear regression to fit $\ln(L_{Ix})=\ln(L_0)-(t/\tau)$ using the three luminescence measurements with 1×substrate concentrations (Plates 1, 5, 8). Also calculate the regression coefficient.

Calculate substrate binding ($K_{m:app,total}$): Using microplates from the first set of readings (Plates 1 and 2), calculate the $L_{0.2x,rel}$ by dividing measurements made with substrate concentrations of 0.02× by those of 1×. Similarly, calculate the $L_{0.06x,rel}$ using microplates of the second set of readings (Plates 5 and 6), by dividing measurements made with substrate concentrations of 0.06× by those of 1×.

For each sample, use linear regression to fit $1/L=(K_{m:app,total}/L_{max:app})(1/[S])+(1/L_{max:app})$ using

| L | [S] |
|---|---|
| $L_{0.02x,rel}$ | 0.02 |
| $L_{0.06x,rel}$ | 0.06 |
| 1 ($L_{1x,rel}$) | 1 |

$K_{m:app,total}$ is calculated as the slope/intercept. Also calculate the regression coefficient.

Calculate signal stability (S): For each sample, use linear regression to fit $\ln(L)=\ln(L_0)-(t/\tau)$ using the four luminescence measurements of the initial microplate with 1×substrate concentrations (Plates 1, 3, 4, and 7). Also calculate the regression coefficient. From the calculated values of $\tau$ and $L_0$, calculate the integral of luminescence by $\text{int}(L)=\tau L_0 (1-\exp(-t/\tau))$, where $t_f$ is the average time of the last measurement (e.g., 15 hours). The signal stability is calculated as $S=(1-\text{int}(L)/L_i t_f)^2$, where $L_i$ is the initial measurement of normalized luminescence with 1× substrate concentration (Plate 1).

[Note: To correct for evaporation, an equation $S=(1+K-\text{int}(L)/L_i t_f)^2$, may be used where $1/K=2$(relative change of liquid volume at $t_f$).]

Calculate the reference value surfaces: A three dimensional coordinate system can be defined by using the grid positions of the samples within a microplate as the horizontal coordinates, and the calculated values for the samples ($L_i$, $\tau$, $K_{m:app,total}$, or S) as the vertical coordinates. This three dimensional system is referred to as a "plate map". A smooth surface in the plate maps representing a reference level can be determined by least squares fit of the values determined for the 8 reference clones in each microplate. For each of the 10 initial microplates of samples, respective reference surfaces are determined for the criteria parameters $L_i$, $\tau$ $K_{m:app,total}$, and S (40 surfaces total).

In the least squares fit, the vertical coordinates (i.e., the criteria parameters) are the dependent variables, the horizontal coordinates are the independent variables. A first order surface (i.e., $z=ax+by+c$) is fitted to the values of the reference clones. After the surface is calculated, the residuals to each reference clone are calculated. If any of these residuals is outside of a given cutoff range, the reference surface is recalculated with omission of the aberrant reference clone.

If a first order surface does not sufficiently represent the values of the reference clones, a restricted second order surface is used (i.e., $z=a(x^2+ky^2)+bx+cy+d$, where k is a constant).

Calculate the reference-normalized values: For the criteria parameter of each sample, a reference-normalized value is determined by calculating the ratio or inverse ratio with the respective reference value. The reference-normalized values are $L_i/L_{ir}$, $\tau/\tau_r$, $K_{mr}/K_{m:app,total}$, and $S_r/S$, where reference values are calculated from the equations of the appropriate reference surface.

Calculate the composite scores: For each sample, calculate $C=5(\tau/\tau_r)+2(S_r/S)+2(K_{mr}/K_{m:app,total})+(L_i/L_{ir})$.

Determine subgroupings: For the criteria parameters $L_i$, $\tau$, $K_{m:app,total}$, S, and C, delimiting values (i.e., bin sizes) for subgroupings are defined as gL, g$\tau$, gKm, gS, and gC. Starting with the highest values for $L_i$, $\tau$, or C, or the lowest values of $K_{m:app,total}$ or S, the samples are assigned to bins for each criteria parameter (the first bin being #1, and so on).

Display sorted table of reference-normalized values: Present a table of data for each sample showing in each row the following data:
sample identification number (e.g., 7:B06)
composite score (C)
reference-normalized enzyme stability ($\tau/\tau_r$)
correlation coefficient for enzyme stability
bin number for enzyme stability
reference-normalized signal stability ($S_r/S$)
correlation coefficient for signal stability
bin number for signal stability
reference-normalized substrate binding ($K_{mr}/K_{m:app,total}$)
correlation coefficient for substrate binding
bin number for substrate binding
reference-normalized expression/specific activity ($L_i/L_{ir}$)
bin number for expression/specific activity
The table is sorted by the composite score (C).

Present sorted table of criteria parameters
Present a table of data for each sample showing in each row the following data:
sample identification number
composite score (C)
enzyme stability ($\tau$)
correlation coefficient for enzyme stability
bin number for enzyme stability
signal stability (S)
correlation coefficient for signal stability
bin number for signal stability
substrate binding ($K_{m:app,total}$)
correlation coefficient for substrate binding
bin number for substrate binding
expression/specific activity ($L_i$)
bin number for expression/specific activity
The table is sorted by the composite score (C); the reference clones are excluded from the table. Same entry coding by standard deviation as described above.

Present sorted table of reference-normalized values

This is the same procedure as the final step of the data reduction procedure. The table will show:
  sample identification number
  composite score (C)
  reference-normalized enzyme stability ($\tau/\tau_r$)
  correlation coefficient for enzyme stability
  bin number for enzyme stability
  reference-normalized signal stability ($S_r/S$)
  correlation coefficient for signal stability
  bin number for signal stability
  reference-normalized substrate binding ($K_{mr}/K_{m:app,total}$)
  correlation coefficient for substrate binding
  bin number for substrate binding
  reference-normalized expression/specific activity ($L_i/L_{ir}$)
  bin number for expression/specific activity The table is sorted by the composite score (C); the reference clones are excluded from the table. Same entry coding by standard deviation as described above.

Present Sorted Table of Criteria Parameters for Reference Clones

This is the same procedure as described above for criteria parameters, except for only the reference clones. The table will show:
  sample identification number
  composite score (C)
  enzyme stability ($\tau$)
  correlation coefficient for enzyme stability
  bin number for enzyme stability
  signal stability (S)
  correlation coefficient for signal stability
  bin number for signal stability
  substrate binding ($K_{m:app,total}$)
  correlation coefficient for substrate binding
  bin number for substrate binding
  expression/specific activity ($L_i$)
  bin number for expression/specific activity The table is sorted by the composite score (C). Same entry coding by standard deviation as described above.

Present Sorted Table of Reference-normalized Values

This is the same procedure as described above for reference-normalized values, except for only the reference clones. The table will show:
  sample identification number
  composite score (C)
  reference-normalized enzyme stability ($\tau/\tau_r$)
  correlation coefficient for enzyme stability
  bin number for enzyme stability
  reference-normalized signal stability ($S_r/S$)
  correlation coefficient for signal stability
  bin number for signal stability
  reference-normalized substrate binding ($K_{mr}/K_{m:app,total}$)
  correlation coefficient for substrate binding
  bin number for substrate binding
  reference-normalized expression/specific activity ($L_i/L_{ir}$)
  bin number for expression/specific activity The table is sorted by the composite score (C). Same entry coding by standard deviation as described above.

Sort Table

Any table may be sorted by any entries as primary and secondary key.

Display Histogram of Table

For any table, a histogram of criteria parameter vs. bin number may be displayed for any criteria parameter.

Display Plate Map

For any plate, a plate map may be displayed showing a choice of:
  any luminescence or optical density measurement
  $L_i$
  $L_i$ reference surface
  $L_i/L_{ir}$
  $\tau$
  $\tau$ reference surface
  $\tau/\tau_r$
  correlation coefficient of $\tau$
  S
  S reference surface
  $S_r/S$
  correlation coefficient of S
  $K_{m:app,total}$
  $K_m$ reference surface
  $K_{mr}/K_{m:app,total}$
  correlation coefficient for $K_{m:app,total}$
  composite score (C)

The plate maps are displayed as a three dimensional bar chart. Preferably, the bars representing the reference clones are indicated by color or some other means.

Display Drill-down Summary of Each Entry

For $L_i$, $\tau$, $K_{m:app,total}$ and S, any entry value in a table may be selected to display the luminescence and optical density reading underlying the value calculation, and a graphical representation of the curve fit where appropriate. Preferably the equations involved and the final result and correlation coefficient will also be displayed.

$L_i$ or $L_i/L_r$. Display the optical density and luminescence value from the chosen sample in Plate 0 and Plate 1.

$\tau$ or $\tau/\tau_r$. Display the optical density and luminescence value from the chosen sample in Plate 0, Plate 1, Plate 5, and Plate 8. Display graph of ln(L1X) vs. t, showing data points and best line.

S or $S_r/S$. Display the optical density and luminescence value from the chosen sample in Plate 0, Plate 1, Plate 3, Plate 4, and Plate 7. Display graph of ln(L) vs. t, showing data points and best line.

$K_{m:app,total}$ or $K_{mr}/K_{m:app,total}$. Display the optical density and luminescence value from the chosen sample in Plate 0, Plate 1, Plate 2, Plate 5, and Plate 6. Display graph of 1/L vs. 1/[S], showing data points and best line.

EXAMPLE 3

Preparation of Novel Luciferases

The gene shown in FIG. 45 contains a single base pair mutation which encodes an amino acid substitution at position 249, T to M. This clone has a spectral maximum of 552 nm which is yellow shifted from the sequence of Luc. This mutant was selected as an original template because it produces about 5 times brighter luminosity in vivo which allowed for more efficient screening.

C-terminus Mutagenesis

To eliminate the peroxisome targeting signal (SKL), the L was mutated to a STOP codon and the 3 codons immediately upstream were randomized according to the oligonucleotide mutagenesis procedure described herein. The mutagenic oligonucleotide designed to accomplish this also introduces a unique SpeI site to allow mutant identification without sequencing. The mutants were screened in vivo and 13 colonies picked, 12 of which contained the SpeI site.

N-terminus Mutagenesis

To test if expression could be improved, the 3 codons immediately downstream from the initiation Met were randomized as described herein. The mutagenic oligo designed to accomplish this also introduces a unique ApaI site to allow mutant identification without sequencing. Seven clones were selected, and six of the isolated plasmids were confirmed to be mutants.

Shuffling of C- and N-terminus Mutants

The C- and N-terminus mutagenesis were performed side-by-side. To combine the N- and C-terminus mutations, selected clones from each mutagenesis experiment were combined with the use of recombination mutagenesis according to the recombination mutagenesis protocol described herein. The shuffled mutants were subcloned into amp$^s$ pRAM backbone and screened in DH5 F'IQ (BRL; Hanahan, 1985). A total of 24 clones were picked, only 4 contained both the N- and C- terminus mutations. These 4 clones were used as templates for randomization of the cysteine positions in the gene.

Mutagenesis to Randomize Cysteine Positions/Random Mutagenesis and Recombination Mutagenesis in the Luc Gene There are 7 cysteine positions in LucPpe2. It is known that these positions are susceptible to oxidation which could cause destabilization of the protein. Seven oligonucleotides were ordered to randomize the cysteine positions.

The oligonucleotides were organized into two groups based upon the conservation of cysteine in other luciferase genes from different families. Group 1 randomizes the conserved cysteine positions C-60, C-80, and C-162. Group 2 randomizes cysteines that are not strictly conserved at positions C-38, C-127, C-221, and C-257.

The four selected templates from the N- and C-terminus mutagenesis were sub-cloned into an ampicillin-sensitive backbone and single-stranded DNA was prepared for each of the templates. These templates were combined in equal amounts and oligonucleotide mutagenesis was completed as described herein. It was determined by plating an aliquot of the mutS transformation prior to overnight incubation that each of the 2 groups contained $2 \times 10^4$ independent transformants. MutS-DNA was prepared for the 2 groups and was then transformed into JM109 cells for screening. Mutants from group 1 were screened in vivo and picks were made for a full robotic run. Five clones were selected that had improved characteristics. Mutants from group 2 were screened in vivo and picks were made for a full robotic run. The temperature incubator on the robot was set at 33° C. for this set of experiments. Ten clones were selected that had improved characteristics. The fifteen best picks from both groups of the cysteine mutagenesis experiments were shuffled together as described herein and 18 of the best clones were selected after robotic processing.

The "best" clone from the above experiment (Luc31-1G8) was selected as a template for subsequent rounds of mutagenesis. (The high temperature robot incubator temperature was set to 42° C.) Another complete round of mutagenesis was completed.

The 18 best clones from the above mutagenesis were picked and clone (Luc39-5B10) was selected as the best clone and was used as a template for another round of mutagenesis. (The high temperature robot incubator temperature was set at 49° C.).

After this cycle, 6 of the best clones were selected for sequencing (the nucleotide sequence and inferred amino acid sequence of five of the clones is shown in FIGS. 22–26 and 27–31, respectively). Based upon the sequence data, nine positions were selected for randomization and seven oligos were designed to cover these positions. Based upon data generated from the robot, it was determined that the best clone from the group of six clones that were sequenced was clone (Luc49-7C6, FIGS. 22 and 27). The luciferase gene from this clone was sub-cloned into an ampicillin-sensitive pRAM backbone and single stranded DNA was prepared. The randomization of the selected positions was completed according to the oligonucleotide mutagenesis procedure listed herein.

The randomization oligonucleotides were divided into 4 groups, and transformants from these experiments were picked and two robotic runs were completed. Ten clones were selected from the two experiments. (The high temperature robot incubator temperature on robot was set at 56° C.).

The best 10 picks from the above two experiments, and the best 18 picks from the previous population of clones were shuffled together (recombination mutagenesis protocol).

The 18 best clones were selected and clone Luc58-0A5 was determined to be the best clone. This clone was then used as a template for another round of mutagenesis. The high temperature robot incubator temperature was set at 58° C. Clone Luc71-504 was selected as a new lead clone and another round of mutagenesis was completed. Incubator set at 60° C.

The best 18 picks were selected. The nucleotide sequence and inferred amino acid sequence of 4 clones from experiment 78 are shown in FIGS. 32–35 and 36–39, respectively, and the best clone from this group was determined to be clone Luc78-0B10. The thermostability of clones at various temperatures is presented in the Figures.

EXAMPLE 4

Mutagenesis Strategy from Clone Luc78-0B10 to Luc90-1B5

Twenty-three oligonucleotides were prepared to change 28 positions to consensus. All of the oligonucleotides were tested individually using oligonucleotide directed mutagenesis with single stranded DNA from clone luc78-0B10 as a template to determine which oligonucleotides gave an improvement in thermostability. Table 4 lists the mutagenic oligonucleotides.

TABLE 4

| Description | OLIGO SYNTHESIS NUMBER | SEQ ID NO. |
| --- | --- | --- |
| A17 to T | 6215 | 48 |
| M25 to L | 6216 | 49 |
| S36 to P; remove Nsi I site | 6217 | 50 |
| A101 to V, S105 to N | 6218 | 51 |
| I125 to V | 6219 | 52 |
| K139 to Q | 6220 | 53 |
| V145 to I | 6221 | 54 |
| V194 to I | 6222 | 55 |
| V203 to L, S204 to P | 6231 | 56 |
| A216 to V | 6232 | 57 |
| A229 to Q | 6233 | 58 |
| M249 to T (reversion) | 6234* | 59 |
| T266 to R, K270 to E | 6235 | 60 |
| E301 to D | 6236 | 61 |
| N333 to P, F334 to G | 6237 | 62 |
| R356 to K | 6238 | 63 |
| I363 to V | 6246 | 64 |
| A393 to P | 6247 | 65 |

TABLE 4-continued

| Description | OLIGO SYNTHESIS NUMBER | SEQ ID NO. |
|---|---|---|
| R417 to H | 6248 | 66 |
| G482 to V | 6249 | 67 |
| N492 to T | 6250 | 68 |
| F499 to Y, S501 to A | 6251 | 69 |
| L517 to V | 6252 | 70 |
| F537 to L | 6253 | 71 |

*Note that oligonucleotide #6234 does not change a consensus position. This oligonucleotide causes a reversion of position 249 to the wild-type Ppe-2 codon. Although reversion of this position was shown to increase thermostability at 62° C., reversion of this position decreased light output.

Three oligonucleotide-directed mutagenesis experiments with clone luc78-0B10 as a template were completed. The oligonucleotides for these experiments were divided in the following manner:

a. 6215, 6234, 6236, 6248 (found to give increased thermostability)
b. 6215, 6217, 6218, 6219, 6220, 6221, 6222, 6231, 6233, 6234, 6236, 6238, 6247, 6248, 6249, 6251, 6253 (found to be neutral or have increased thermostability).
c. All 23 oligonucleotides.

Selections from the three experiments listed above were screened with the robotic screening procedure (experiment 84, see Table 1) using luc78-0B10 as a control. Selections from experiment 84 were recombined using the recombination mutagenesis procedure and then screened with the robotic screening procedure (experiment 85).

Single stranded DNA was prepared from three clones, luc85-3E12, luc85-4F12, luc85-5A4. The nucleotide sequence and inferred amino acid sequence of luc85-4F12 are shown in FIGS. 40 and 41, respectively. These clones were used as templates for oligonucleotide-directed mutagenesis to improve codon usage. Positions were selected based upon a codon usage table published in *Nucleic Acids Research*, vol. 18 (supplement) 1990, page 2402. The table below lists oligonucleotides that were used to improve codon usage in *E. coli*.

TABLE 5

| Description | Oligo Synthesis # | SEQ ID NO. |
|---|---|---|
| L7(tta-ctg), remove Apa I site | 6258 | 72 |
| L29(tta-ctg) | 6259 | 73 |
| T42(aca-acc) | 6260 | 74 |
| L51, L56(tta-ctg), L58(ttg-ctg) | 6261 | 75 |
| L71(tta-ctg) | 6262 | 76 |
| L85(ttg-ctg) | 6263 | 77 |
| L95(ttg-ctg), L97(ctt-ctg) | 6273 | 78 |
| L113, L117(tta-ctg) | 6274 | 79 |
| L151, L153(tta-ctg) | 6275 | 80 |
| L163(ctc-ctg) | 6276 | 81 |
| R187(cga-cgt) | 6277 | 82 |
| L237(tta-ctg) | 6279 | 83 |
| R260(cga-cgc) | 6280 | 84 |
| L285, L290(tta-ctg), L286(ctt-ctg) | 6281 | 85 |
| L308(tta-ctg) | 6282 | 86 |
| L318(tta-ctg) | 6283 | 87 |
| L341(tta-ctg), T342(aca-acc) | 6284 | 88 |
| L380(ttg-ctg) | 6285 | 89 |
| L439(tta-ctg) | 6286 | 90 |
| L456(ctc-ctg), L457(tta-ctg) | 6293 | 91 |
| T506(aca-acc), L510(cta-ctg) | 6305 | 92 |
| R530(aga-cgt) | 6306 | 93 |

In the first experiment, the three templates listed above from experiment 85 were combined and used as a templates for oligonucleotide-directed mutagenesis. All of the oligonucleotides were combined in one experiment and clones resulting from oligonucleotide-directed mutagenesis were screened using the robotic screening procedure as experiment 88. There were a low percentage of luminescent colonies that resulted from this experiment, so another oligonucleotide-directed mutagenesis experiment was completed in which the oligonucleotides were combined in the following groups:

a. 6258, 6273, 6280, 6286
b. 6259, 6274, 6281, 6293
c. 6260, 6275, 6282, 6294
d. 6261, 6276, 6283, 6305
e. 6262, 6277, 6284, 9306
f. 6263, 6279, 6285

It was discovered that samples from group b had a low number of luminescent colonies, and it was hypothesized that one of the oligonucleotides in group b was causing problems. Selections were made from all of the experiments with the exception of experiment b. Samples were then run through the robotic screening procedure (experiment 89). Selections from experiments 88 and 89 were shuffled together with the recombination mutagenesis protocol and were then screened with the robotic screening procedure (experiment 90).

Materials and Methods

A. Mutagenesis Protocol

The mutant luciferases disclosed herein were produced via random mutagenesis with subsequent in vivo screening of the mutated genes for a plurality of characteristics including light output and thermostability of the encoded luciferase gene product. The mutagenesis was achieved by generally following a three-step method:

1. Creating genetic diversity through random mutagenesis. Here, error-prone PCR of a starting sequence was used to create point mutations in the nucleotide sequence. Because error-prone PCR yields almost exclusively single point mutations in a DNA sequence, a theoretical maximum of 7 amino acid changes are possible per nucleotide mutation. In practice, however, approximately 6.1 amino acid changes per nucleotide is achievable. For the 550 amino acids in luciferase, approximately 3300 mutants are possible through point mutagenesis.

2. Consolidating single point mutations through recombination mutagenesis. The genetic diversity created by the initial mutagenesis is recombined into a smaller number of clones by sPCR. This process not only reduces the number of mutant clones, but because the rate of mutagenesis is high, the probability of linkage to negative mutations is significant. Recombination mutagenesis unlinks positive mutations from negative mutations. The mutations are "re-linked" into new genes by recombination mutagenesis to yield the new permutations. Then, after re-screening the recombination mutants, the genetic permutations that have the "negative mutations" are eliminated by not being selected. Recombination mutagenesis also serves as a secondary screen of the initial mutants prepared by error-prone PCR.

3. Broadening genetic diversity through random mutagenesis of selected codons. Because random point mutagenesis can only achieve a limited number of amino acid substitutions, complete randomization of selected codons is achieved by oligonucleotides mutagenesis. The codons to be mutated are selected from the results of the preceding mutagenesis processes on the assumption that for any given beneficial substitution, other alternative amino acid substitutions at the same positions may produce even greater benefits. The positions to be mutated are identified by DNA sequencing of selected clones.

B. Initial Mutagenesis Experiments

Both the N-terminus and the C-terminus of the starting sequence were modified by oligonucleotide-directed mutagenesis to optimize expression and remove the peroxisomal targeting sequence. At the N-terminus, nine bases downstream of the initiation codon were randomized. At the C-terminus, nine bases upstream of the termination codon were randomized. Mutant s were analyzed using an in vivo screen, resulting in no significant change in expression.

Six clones from this screen were pooled, and used to mutate the codons for seven cysteines. These codons were randomized using oligonucleotide-directed mutagenesis, and the mutants were screened using the robotic screening procedure. From this screen, fifteen clones were selected for directed evolution.

C. Generating and Testing Clones

Several very powerful and widely known protocols are used to generate and test the clones of the present invention. Unless noted otherwise, these laboratory procedures are well known to one of skill in the art. Particularly noted as being well known to the skilled practitioner is the polymerase chain reaction (PCR) devised by Mullis and various modifications to the standard PCR protocol (error-prone PCR, sPCR, and the like), DNA sequencing by any method (Sanger or Maxxam & Gilbert's methodology), amino acid sequencing by any method (e.g., the Edman degradation), and electrophoretic separation of polynucleotides and polypeptides/proteins.

D. Vector Design

A preferred vector (pRAM) (see FIG. 20) used for the mutagenesis procedure contains several unique features that allow for the mutagenesis strategy to work efficiently:

The pRAM vector contains a filamentous phage origin, f1, which is necessary for the production of single-stranded DNA.

Two SfiI sites flank the gene. These sites were designed by so that the gene to be subcloned can only be inserted in the proper orientation.

The vector contains a tac promoter.

Templates to be used for oligonucleotide mutagenesis contain a 4 base-pair deletion in the bla gene which makes the vector ampicillin-sensitive. The oligonucleotide mutagenesis procedure uses a mutant oligonucleotide as well as an ampicillin repair oligonucleotide that restores function to the bla gene. This allows for the selection of a high percentage of mutants. (If selection is not used, it is difficult to obtain a high percentage of mutants.)

E. Uses of Luciferases

The mutant luciferases of the present invention are suitable for use in any application for which previously known luciferases were used, including the following:

ATP Assays. The greater enzyme stability means that reagents designed for detection of ATP have a greater shelf-life and operational-life at higher temperatures (e.g., room temperature). Therefore, a method of detecting ATP using luciferases with increased thermostability is novel and useful.

Luminescent labels for nucleic acids, proteins, or other molecules. Analogous to advantages of the luciferases of the present invention for ATP assays, their greater shelf-life and operational-life is a benefit to the reliability and reproducibility of luminescent labels. This is particularly advantageous for labeling nucleic acids in hybridization procedures where hybridization temperatures can be relatively high (e.g., greater than 40° C.). Therefore, a method of labeling nucleic acids, proteins, or other molecules using luciferases of the present invention is novel and useful.

Genetic reporter. In the widespread application of luciferase as a genetic reporter, where detection of the reporter is used to infer the presence of another gene or process of interest, the increased thermostability of the luciferases provides less temperature dependence of its expression in living cells and in cell-free translations and transcription/translation systems. Therefore, a method using the luciferases of the present invention as genetic reporters is novel and useful.

Enzyme immobilization. Enzymes in close proximity to physical surfaces can be denatured by their interaction with that surface. The high density immobilization of luciferases onto a surface to provide strong localized luminescence is improved by using thermostable luciferases. Therefore, a method of immobilizing luciferases onto a solid surface using luciferases of the present invention is novel and useful.

Hybrid proteins. Hybrid proteins made by genetic fusion genes encoding luciferases and of other genes, or through a chemical coupling process, benefit by having a greater shelf-life and operational-life. Therefore, a method of producing hybrid proteins through genetic means or chemical coupling using the luciferases of the present invention is novel and useful.

High temperature reactions. The light intensity of a luciferase reaction increases with temperature until the luciferase begins to denature. Because the use of thermostable luciferases allows for use at greater reaction temperatures, the luciferases of the present invention are novel and useful for performing high temperature reactions.

Luminescent solutions. Luminescence has many general uses, including educational, demonstrational, and entertainment purposes. These applications benefit from having enzymes with greater shelf-life and operational-life. Therefore, a method of making luminescent solutions using the luciferases of the present invention is novel and useful.

F. Firefly Luciferase

The firefly luciferase gene chosen for directed evolution was LucPpe2 isolated from *Photuris pennsylvanica*. The luciferase was cloned from fireflies collected in Maryland by Wood et al. and later was independently cloned by Dr. Leach using fireflies collected in Oklahoma (Ye et al., 1997). A mutant of this luciferase (T249M) was made by Wood et al. and used in the present invention because it produced approximately 5-fold more light when expressed in colonies of *E. coli*.

Overview of Evolution Process: Directed evolution was achieved through a recursive process, each step consisting of multiple cycles of 1) creating mutational libraries of firefly luciferase followed by 2) screening the libraries to identify new mutant clones having a plurality of desired enzymological characteristics.

To begin the process, three mutational libraries were created using error-prone PCR (Fromant et al., 1995). Each library was screened first by visual evaluation of luminescence in colonies of *E. coli* (Wood and De Luca, 1987), and then by quantitative measurements of enzymological properties in *E. coli* cell lysates. Approximately 10,000 colonies were examined in the visual screen, from which 704 were selected for quantitative analysis. From each quantitative screen 18 clones were selected. The three sets of 18 clones each were pooled together, and a new mutational library was created using DNA shuffling to generate intragenetic recombinations (sPCR; Stemmer, 1994). The results were screened to yield another set of 18 clones. The entire process was completed by combining this set of 18 clones with 18 clones from the previous round of evolution, creating another mutational library by DNA shuffling, and screening as before.

Screening method: In the qualitative visual screen, colonies were selected only for their ability to sustain relatively bright luminescence. The thermal stability of the luciferase within the colonies of E. coli was progressively challenged in successive rounds of evolution by increasing the temperature of the screen. The selected colonies were inoculated into wells of 96-well plates each containing 200 µg of growth medium.

In the quantitative screens, lysates of the E. coli cultures were measured for 1) luminescence activity, 2) enzyme stability, 3) sustained enzymatic turnover, and 4) substrate binding.

"Luminescence activity" was measured as the ratio of luminescence intensity to the optical density of the cell culture.

"Enzyme stability" was determined by the rate of activity loss from cell lysates over 10 hours. In successive rounds of evolution the incubation temperature of the lysates was increased.

"Sustained enzymatic turnover" was determined by the rate of luminescence loss of a signal enzymatic reaction over 10 hours at room temperature.

"Substrate binding" was determined by the relative activity of the lysate when assayed with diluted substrate mixtures. Of these four parameters, the highest priority for selection was placed on thermostability.

Robotic Automation: Robotic automation was used in the quantitative screens to accurately perform the large number of required quantitative assays on the cultured cells. Overnight cultures were first diluted into fresh medium and grown for 3 hours to produce cultures in mid-log phase growth. The optical densities of each culture was then measured, and aliquots of the cultures were lysed by freeze/thaw and lysozyme. The resulting lysates were further diluted before analysis and incubated at elevated temperatures. Luminescence was measured from aliquots of the diluted lysates, taken at various times, and measured under various conditions as prescribed by the analytical method (see Example 2). Computer analysis of this data yielded the quantitative selection criteria described herein.

Summary of evolutionary progression: After mutagenesis of the N- and C-termini, and randomization of the cysteine codons, a pool of 15 clones was subjected to two rounds of directed evolution as described herein. Five of the 18 clones resulting from this process were sequenced to identify mutations. One of these clones designated, Luc49-7C6, was chosen for more detailed analysis and further mutagenesis. This clone contained 14 new amino acid substitutions compared to the luciferase Luc[T249M].

To assess the potential for other amino acid replacements at the sites of these substitutions, oligonucleotide-directed mutagenesis was used to randomize these codons. The resulting clones were screened as described herein, and 18 selected clones were used to initiate two new rounds of directed evolution. Of the 18 clones resulting from this second set of rounds, the clone designated Luc78-0B10 was chosen for additional study and mutagenesis. This clone encoded a luciferase that contained 23 new amino acid substitutions compared to Luc[T249M].

Using oligonucleotide directed mutagenesis with Luc78-0B10 as the template, codons were selected for substitution to consensus amino acids previously known among beetle luciferases. Selections from this mutagenesis experiment were shuffled together and three clones, determined to be the most stable were then used as templates for oligonucleotide mutagenesis to improve codon usage in E. coli. A clone designated Luc90-1B5 selected from this experiment, contained 34 amino acid substitutions relative to Luc[T249M] (see FIGS. 42 and 43 for the nucleotide sequence and inferred amino acid sequence of luc90-1B5, and FIGS. 44 and 45 for the nucleotide sequence encoding and the inferred amino acid sequence of Luc[T249M]). Out of 25 codons selected for change to consensus amino acids, 11 were replaced in the clone designated Luc90-1B5. Only five out of the 30 positions that were selected for improved codon usage were substituted and had little effect on enzyme expression.

Protein purification: Four mutants that are described herein (Luc[T249M], Luc49-7C6, Luc78-0B10, and Luc90-1B5) were purified using a previously published procedure (Hastings et al., 1996).

Enzymological characterization: Purified proteins were diluted in 25 mmol/L HEPES pH 7.8, 150 mmol/L NaCl, 0.1 mmol/L EDTA, 1 mg/ml BSA. Enzyme stability was determined from diluted proteins incubated at different temperatures, and aliquots were removed at different time points. A linear regression of the natural log of the luminescence and time was calculated. Half-life was calculated as the ln(0.5)/slope of the regression.

G. PCR Mutagenesis Protocol (Random Mutagenesis)

PCR Mutagenesis Reactions

1. Prepare plasmid DNA from a vector containing the gene of interest, estimate DNA concentration from a gel.
2. Set up two 50 µg reactions per group:

There are three groups of mutagenic conditions using different skewed nucleotide concentrations.

The conditions listed herein yield in the range of from 8–10% wild-type Luc colonies after subcloning phenotypic for each generated parent clone. The rate of mutagenesis is estimated by the number of luminescent colonies that are present after mutagenesis. Based upon results of clones mutated in the range of 8–10%, it was determined that this level of mutagenesis produces on average approximately 2–3 amino acid changes per gene. If the mutagenesis rate is selected so that on average there is one amino acid change per gene, then on average 50% of the clones will have no mutations. (Bowie et al., 1990).

For the master mix: add all components (see Table 6) except polymerase, vortex, spin briefly, add polymerase, and mix gently.

TABLE 6

| Component | A to T/T to A | A to C/T to G | G to A/C to T |
|---|---|---|---|
| dATP | 0.3 mM | 0.1 mM | 0.25 mM |
| dCTP | 2.75 mM | 4 mM | 1 mM |
| dGTP | 0.06 mM | 0.02 mM | 0.05 mM |
| dTTP | 0.625 mM | 0.3 mM | 0.6 mM |
| ++pRAMtailUP | 0.4 pmol/µl | 0.4 pmol/µl | 0.4 pmol/µl |
| ++pRAMtailDN | 0.4 pmol/µl | 0.4 pmol/µl | 0.4 pmol/µl |
| *Taq Polymerase | 1 U/µl | 1 U/µl | 1 U/µl |
| °MgCl$_2$ | 6.77 mM | 5.12 mM | 2.7 mM |
| °MnCl$_2$ | 0.5 mM | 0.5 mM | 0.3 mM |
| DNA | 50 ng total | 50 ng total | 50 ng total |
| 10X PCR buffer | 1X | 1X | 1X |

TABLE 6-continued

| Component | A to T/T to A | A to C/T to G | G to A/C to T |
|---|---|---|---|
| Autoclaved nanopure water | To 50 µl | To 50 µl | To 50 µl |

*Taq Polymerase is purchased from Perkin Elmer (N808-0101).
°MnCl$_2$ and MgCl$_2$ are made fresh from 1 M stocks. The stocks are filter sterilized and mixed with sterile water to make the 10 mM and 25 mM stocks which are then stored in Polystyrene Nalgene containers at 4° C.
++pRAMtailUP: 5'-gtactgagacgacgccagcccaagcttaggcctgagtg-3' (SEQ ID NO:38); pRAMtailDN: 5'-ggcatgagcgtgaactgactgaactagcggccgccgag-3' (SEQ ID NO:39)

10×PCR Polymerase Buffer
  100 mM Tris-HCl pH 8.4 from 1 M stock
  500 mM Kcl
  Primers are diluted from a 1 nmol/µl stock to a 20 pmol/µl working stock.
  Cycle in thermal cycler: 94° C. for 1 minute (94° C. for 1 minute, 72° C. for 10 minutes) 10×
3. Purify reaction products with Wizard PCR purification kit (Promega Corporation, Madison, Wis., part#A718c):
  transfer PCR reaction into a new tube containing Promega 100 µl Direct Purification buffer (Promega part#A724a)
  add 1 ml of Wizard PCR Purification Resin (Promega part#A718c) Promega and incubate at room temperature for 1 minute
  pull resin though Wizard minicolumn
  wash with 80% ethanol
  spin in microcentrifuge to remove excess ethanol
  elute into 50 µl sterile nanopure water (allow water to remain on column for at least 1 minute)

Amplification[1] of Mutagenesis Reaction
1. Set up five 50 µl reactions (see Table 7) per group.

This amplification step with Pfu polymerase was incorporated for 2 reasons: (a) To increase DNA yields for the production of large numbers of transformants. (b) To reduce the amount of template DNA that is carried over from the mutagenic PCR reaction: (Primers for the second amplification reaction are nested within the mutagenic primers. The mutagenic primers were designed with non-specific tails of 11 and 12 bases respectively for the upstream and downstream primers. The nested primers will amplify DNA that was previously amplified with the mutagenic primers, but cannot amplify pRAM template DNA.)

TABLE 7

| Components | Concentration | Amount in 50 µl | Final concentration |
|---|---|---|---|
| dATP | 10 mM | 1 µl | 0.2 mM |
| dCTP | 10 mM | 1 µl | 0.2 mM |
| dGTP | 10 mM | 1 µl | 0.2 mM |
| dTTP | 10 mM | 1 µl | 0.2 mM |
| +tpRAM18UP | 20 pmol/µl | 1 µl | 0.4 pmol/µl |
| +pRAM19DN | 20 pmol/µl | 1 µl | 0.4 pmol/µl |
| Pfu polymerase | 2 U/ul | 1 µl | 0.04 µl/µL |
| °10X buffer | 10X | 5 µl | 1X |
| DNA | | 10 µl | |
| Water | | 24.6 µl | |

To master mix: add all components, except polymerase, vortex, spin briefly, add polymerase, mix gently.
°10× reaction buffer for Native Pfu polymerase contains 20 mM MgCl$_2$, so no additional MgCl$_2$ needs to be added
+ primers:
  pRAM18UP -5'-gtactgagacgacgccag-3' (SEQ ID NO:40)
  pRAM19DN -5'-ggcatgagcgtgaactgac-3' (SEQ ID NO:41)

Cycling conditions: 94° C. for 30 seconds (94° C. for 20 seconds, 65° C. for 1 minute, 72° C. for 3 minutes) 25× (Perkin-Elmer Gene Amp® PCR System 2400)
2. Load 1 µl on a gel to check amplification products
3. Purify amplification reaction products with Wizard PCR purification kit (Promega Corporation, part#A718c):
  transfer PCR reaction into a new tube containing 100 µl Direct Purification buffer (Promega, Part#A724a)
  add 1 ml of Wizard PCR Purification Resin (Promega Part#A718c) and incubate at room temperature for 1 min
  pull resin though Wizard minicolumn
  wash with 80% Ethanol
  spin in microcentrifuge to remove excess Ethanol
  elute with 88 µl sterile nanopure water (allow water to remain on column for at least 1 min)

Subcloning of Amplified PCR Mutagenesis Products
1. Digest the DNA with Sfi I as follows:
  2 µl Sfi I (Promega Part #R639a)
  10 µl 10×buffer B (Promega Part #R002a)
  88 µl of DNA from Wizard PCR prep (see step 3 above)
  mix components and overlay with 2 drops of mineral oil; incubate at 50° C. for 1 hour
2. Remove salts and Sfi I ends with Wizard PCR purification as described herein, and elute into 50 µl sterile nanopure water
3. Ligation into pRAM (+/r) backbone (set up 4 ligations per group):
  0.025 pmol pRAM backbone
  0.05 pmol insert (usually in the range of 6 to 12 µl of insert)
  1 µl of T4 DNA Ligase (Promega part M180a)
  2 µl of 10× ligase buffer (Promega part C126b, divide into 25 µl aliquots, do not freeze/thaw more than twice)
  water to 20 µl
  ligate for 2 hours at room temperature
  heat reactions for 15 minutes at 70° C. to inactivate ligase Transformation and Plating
1. Butanol precipitate samples to remove excess salts (n-Butanol from Sigma, St. Louis, Mis., part #BT-105):
  (if ethanol precipitation is used instead of butanol, a wash with 70% ethanol as needed. Excess salt will cause arcing during the electroporation which causes the reaction to fail.)
  add water to 50 µl
  add 500 µl of n-butanol
  mix until butanol/ligation mix is clear and then spin for 20 min at room temperature
  drain butanol into waste container in fume hood
  resuspend in 12 µl water, spin 30 sec at full speed
2. Preparation of cell/DNA mix (set up 4 transformations plus one with reference clone DNA):
  while DNA is precipitating, place electroporation cuvettes on ice
  fill 15 ml Falcon snap-cap tubes with 3 ml S.O.C. medium and place on ice
  thaw JM109 electrocompetent cells on ice (50 µl per ligation reaction)
  pipette 10 µl of the bottom layer from step 1 (or 0.5 µl ref.clone DNA) into competent cells
  (small amounts of butanol carry-over do not adversely effect the transformation efficiency)
  place cell/DNA mix on ice 3. Electroporation:
   carry tubes, cuvettes, and cell/DNA mix on ice to electroporation device
   pipette cell-DNA mix into a cuvette and zap. Instrument settings:
   Cuvette gap: 0.2 cm
   Voltage: 2.5 kV
   Capacitance: 25 µF
   Resistance: 200 Ohms
   Time constant: 4.5 msec
   pipette 1 ml SOC (contains KCl; media prep #KCLM) into cuvette, quickly pour into recovery tube (transformation efficiency is reduced if cells are allowed to sit in cuvette)
   place the recovery tube on ice until all samples are processed
   allow the cells to recover at 37° C. for 30–60 minutes
   plate on LB+amp plates with nitrocellulose filters (# of colonies is about 20% higher if cells recover 60 minutes, possibly due to cell replication.)
   (Best colony density for screening is 500 per plate. For the current batch of cells plate about 500 to 750 µl)

H. Recombination Mutagenesis Protocol or DNA Shuffling
DNase I Digestion of Plasmid DNA
1. Prepare 2% low melting point gel
   use 0.8 g agarose in 40 ml (NuSieve #50082)
   use large prep comb
   make sure it is solidified prior to digesting
2. Prepare 4 µg of pooled plasmid DNA for digest
3. Prepare 1 U/µl DNase dilution on ice according to the table below:

TABLE 8

| DNase I[+] | 0.74 µl |
|---|---|
| 10X DnaseI buffer | 10 µl |
| 1% gelatin* | 10 µl |
| Water to 100 µl | |

[+]DNase I from Sigma (D5791)
*Gelatin was added to keep the DNase I from sticking to the walls of the tubes.

This dilution can be kept on ice for at least 30 min without loss in activity.
4. Digest (set up at room temperature):
   prepare two digests with 1.0 U and 1.5 U DNase I per 100 µl reaction:
   10 µl of 10× DNase I buffer (500 mM Tris, 10 mM MgCl$_2$ pH 7.8)
   x µl DNA (2 µg of pooled plasmid DNA from step 2)
   1 or 1.5 µl of the 1 U/µl enzyme dilution
   sterile nanopure water to 100 µl
   incubate at room temperature for 10 minutes
   stop reaction by addition of 1 µl of 100 mM CDTA
Purification from Agarose Gel
1. Run DNase digested fragments on gel
   add 10 µl of 10× loading buffer to each DNase I digest
   load all on a 2% Low melting point agarose gel
   run about 30 min at 120–150 V
   load pGEM DNA marker in middle lane
2. Isolate fragments
   cut out agarose slice containing fragments in the size range of 600–1000 bp using a razor blade
   cut into pieces that weigh about 0.3 g
   melt the gel slices at 70° C.
   add 300 µl of Phenol (NaCl/Tris equilibrated) to the melted agarose, vortex for about 1 minute at max speed
   spin for 10 min at 4° C.
   remove the top layer into a tube containing an equal volume of Phenol/Chloroform/Isoamyl (saturated with 300 mM NaCl/100 mM Tris pH 8.0), vortex and centrifuge for 5 minutes at RT
   remove the top layer into a tube containing chloroform and vortex and centrifuge.
   remove the top layer into a tube with 2 vol. of 95% cold Ethanol; place in −70° C. freezer for 10 min (no additional salts are needed because of the High Salt Phenol)
   spin at 4° C. for 15 minutes.
   wash with 70% Ethanol, drain and air dry for ~10 min
   resuspend in 25 to 50 µl of sterile nanopure water
   store at −70° C. until ready for use
Assembly Reaction
   Set up 4 reactions (see Table 9) and pool when completed.

TABLE 9

| Component | Concentration | Amount in µl | Final concentration |
|---|---|---|---|
| dATP | 10 mM | 1 | 200 µM |
| dCTP | 10 mM | 1 | 200 µM |
| dGTP | 10 mM | 1 | 200 µM |
| dTTP | 10 mM | 1 | 200 µM |
| DNA* | 1–10 ng | 5 | |
| Tli | 3 U/µl | 0.4 | 0.24 U/µl |
| 10X Thermo buffer | 10X | 5 | 1X |
| MgCl$_2$ | 25 mM | 4 | 2 mM |
| gelatin | 1% | 5 | 0.1% |
| water | | To 50 µl | |

*Because the DNA used for this reaction has been fragmented, it is difficult to estimate a concentration. The easiest way is to load 5 µl of the DNaseI digested DNA to an agarose gel and run the gel until the dye enters the wells (1–2 min). Fragments from a typical 2 µg DNA digest which were resuspended in 100 µl of water give a DNA concentration of about 1 to 10 ng/µl.

Cycling conditions: 94° C. for 30 seconds (94° C. for 20 seconds, 65° C. for 1 minute, 72° C. for 2 minutes) 25×
Amplification of Assembly
   Usually 5 amplification reactions (see Table 10) will produce enough DNA for a full 8 plate robotic run.

TABLE 10

| Component | Concentration | Amount in µml | Final concentration |
|---|---|---|---|
| dATP | 10 mM | 1 | 200 µM |
| dCTP | 10 mM | 1 | 200 µM |
| dGTP | 10 mM | 1 | 200 µM |
| dTTP | 10 mM | 1 | 200 µM |
| pRAMtailUP* | 20 pmol/µl | 2 | 0.8 pmol/µl |
| pRAMtailDN* | 20 pmol/µl | 2 | 0.8 pmol/µl |
| Pfu native polymerase[+] | 2 U/µl | 1 | 0.04 U/µl |
| 10X native Pfu buffer° | 1X | 5 | 1X |
| DNA | 1–10 ng | 5 | |
| water | | water to 50 µl | |

*Note that the concentration of primers is twice as high as in a typical amplification reaction.
°The Pfu 10X buffer contains 20 mM MgCl$_2$, so it is not necessary to add MgCl$_2$.
[+]Pfu polymerase is ordered from Stratagene part #600135. Cycling conditions: 94° C. for 30 seconds (94° C. for 20 seconds, 65° C. for 1 minute, 72° C. for 3 minutes) 25x Subcloning of Assembly Amplification
   Purify amplification products with Wizard PCR purification:
   pool 5 amplification reactions
   transfer into a new tube that contains 100 µl of Direct Purification buffer add 1 ml of Wizard PCR Purification Resin, incubate at RT for 1 minute pull Resin though Wizard minicolumn wash with 80% ethanol and spin in microcentrifuge to remove excess ethanol elute with 88 μl of sterile nanopure water (allow water to remain on column for at least 1 minute)

2. Digest with Sfi I:

2 μl Sfi I

10 μl 10×buffer B

88 μl of DNA from Wizard PCR prep mix components and overlay with 2 drops of mineral oil; incubate at 50° C. for 1 hour 3. Band isolation:

Sometimes after amplification of the assembly reaction a band that is smaller than the gene-sized fragment is produced. This small fragment has been shown to subclone about 10-fold more frequently than the gene sized fragment if the sample is not band isolated. When this contaminating band is present, it is necessary to band isolate after Sfi I digestion.

load the DNA to a 0.7% agarose gel band isolate and purify with the Gene Clean kit from Bio 101 elute DNA with 50 μl sterile nanopure water, check concentration on gel (This type of purification with standard agarose produced the highest number of transformants after subcloning. Other methods tried: Low melt with Phenol chloroform, Gene clean with low melt, Wizard PCR resin with standard agarose, Pierce Xtreme spin column with Low melt (did not work with standard agarose)).

4. Ligate into pRAM [+/r] backbone: (See ligation and transformation protocol above)

Large Scale Preparation of pRAM Backbone

1. Streak an LB amp plate with pRAMMCS [+/r] (This vector contains a synthetic insert with a Sac II site in place of a gene. This vector contains the new ribosome binding site, but it will be cut out when the vector is digested with Sfi I.

2. Prepare a 10 ml overnight culture in LB supplemented with amp.

3. The next day inoculate 1 L of LB supplemented with amp and grow for 16–20 hours.

4. Purify the DNA with the Wizard Maxi Prep kit. (Promega #A7270) (use 4 preps for 1 L of cells)

5. Digest the Plasmid with Sfi I. (Use 5 U per microgram) Overlay with mineral oil and digest for at least two hours.

6. Ethanol precipitate to remove salts. Resuspend in water.

7. Digest with Sac II for 2 hours. (Keep digest volume to 2 ml or less). It is possible that part of the plasmid could be partially digested. If the vector is cut with an enzyme that is internal to the two Sfi I sites, it will keep the partially digested fragments from joining in a ligation reaction.

8. Load entire digest onto a column (see 9). The volume of the sample load should not be more than 2 ml. If it is it will be necessary to ethanol precipitate.

9. The column contains Sephacryl S-1000 and is stored with 20% ethanol to prevent bacterial contamination. Prior to loading the sample the column must be equilibrated with cold running buffer for at least 24 hours. If the column has been sitting more than a couple of months it may be necessary to empty the column, equilibrate the resin 3–4 washes in cold running buffer, and then re-pour the column. After the column is poured it should be equilibrated overnight so that the resin is completely packed.

10. Collect fractions of about 0.5 ml. Typically the DNA comes off between fractions 25 and 50. Load a 5 μl aliquot from a range of fractions to determine which fractions contain the backbone fragment. The small insert fragment will start to come off the column before all of the backbone is eluted, so it will be necessary to be conservative when fractions are pooled. For this reason typically 40–60% of the DNA is lost at this step.

11. Pool the fractions that contain the backbone.

12. Ethanol precipitate the samples. Resuspend in a volume that produces about 10–50 ng/μl.

13. Store at −70° C.

Column running buffer: (store at 4° C.)

5 mM EDTA 100 mM NaCl 50 mM Tris-HCL pH 8.0

10 μg/ml tRNA (R-8759, Sigma)

I. Oligonucleotide Mutagenesis

Prepare Ampicillin-sensitive single stranded DNA of the template to be mutated. Design a mutagenic primer that will randomly generate all possible amino acid codons.

Mutagenesis Reaction

TABLE 11

| Component | Final concentration |
| --- | --- |
| Single Stranded Template | 0.05 pmol |
| Mutagenic Oligonucleotide | 1.25 pmol |
| Ampicillin Repair Oligo (Promega q631a) | 0.25 pmol |
| 10X annealing buffer* | 1X |
| Water to 20 μl | |

*10X Annealing buffer:
−200 mM Tris-HCl, pH 7.5
−100 mM MgCl$_2$
−500 mM NaCl

Heat reaction at 60° C. for 15 minutes and then immediately place on ice.

Synthesis Reaction

TABLE 12

| Component | Amount |
| --- | --- |
| Water | 5 μl |
| 10X synthesis buffer* | 3 μl |
| T4 DNA Polymerase (Promega m421a) | 1 μl (10 Units) |
| T4 DNA Ligase (Promega 180a) | 1 μl (3 Units) |

*10X Synthesis buffer
100 mM Tris-HCl, pH 7.5
5 mM dNTPs
10 mM ATP
20 mM DTT

Incubate at 37° C. for 90 minutes.

Transform into Mut-S strain BMH 71-18 (Promega strain Q6321)

Place Synthesis reaction in a 17×100 mm tube.

Add BMH 71-18 competent cells that have been thawed on ice to synthesis reaction.

Incubate on ice for 30 min

Heat Shock cells at 42° C. for 90 seconds.

Add 4 ml of LB medium and grow cells at 37° C. for 1 hour. Add Ampicillin to a final concentration of 1.25 ug/ml and then grow overnight at 37° C.

Isolate DNA with Wizard Plus Purification system (Promega a7100)

Transform isolated DNA into JM109 electrocompetent cells and transform onto LB Ampicillin plates.

J. Screening Procedure

JM109 clones (from a transformation reaction) are plated onto nitrocellulose filters placed on LB amp plates at a screening density of about 500 colonies per plate.

As listed in the Random Mutagenesis procedure, approximately 10% of the clones to be selected will have to be as stable as the same sequenced or better than source. Or stated another way, about 50 colonies per plate will be suitable for selection. There are 704 wells available for a full eight plate robotic run, so at least 15 LB amp plates will be needed for a full robotic run.

After overnight growth at 37° C. the plates containing the transformants are removed from the incubator and placed at room temperature.

The nitrocellulose filter is lifted on one side and 500 $\mu$l of 10 mM IPTG is added to each of the plates. The filter is then placed back onto the plate to allow diffusion of the IPTG into the colonies containing the different mutant luciferase genes. The plates are then incubated for about 4 hours at room temperature.

One (1) ml of a solution contains 1 mM luciferin and 100 mM sodium citrate is pipetted onto a slide warmer that is set at 50° C. A nitrocellulose filter that contains mutant luciferase colonies and has been treated with IPTG is then placed on top of the luciferin solution. After several minutes, the brightest colonies are picked with tooth picks which are used to inoculate wells in a microtiter plate that contain M9-minimal media with 1% gelatin.

After enough colonies are picked to 8 microtiter plates, the plates are placed in an incubator at 350 rpm at 30° C. incubation and are grown overnight.

In the morning the overnight plates are loaded onto the robot and the cell dilution procedure is run. (This procedure dilutes the cultures 1:10 into induction medium). The new plates are grown for 3 hours at 350 rpm at 30° C.

After growth, the plates are loaded to the robot for the main assay procedure.

Minimal Media
 6 g/Liter $Na_2HPO_4$
 3 g/Liter $KH_2PO_4$
 0.5 g/Liter NaCl
 1 g/Liter $NH_4Cl$
 2 mM $MgSO_4$
 0.1 mM
 1 mM Thiamine-HCl
 0.2% glucose
 12 $\mu$g/ml tetracycline
 100 $\mu$g/ml ampicillin
 *Overnight media contains 1% gelatin
 *Induction media contains 1 mM IPTG and no gelatin.

S.O.C. Media
 10 mM NaCl
 2.5 mM KCl
 20 MM $MgCl_2$
 20 mM glucose
 2% bactotryptone
 0.5% yeast extract Summary of Exemplary Evolutionary Progression
 1. Start with LucPpe2[T249M]
 2. Mutate 3 amino acids at N- and C-termini
 3. Mutate 7 cysteines
 4. Perform two iterations of evolution→Luc49-7C6
 5. Mutagenesis of altered codons (9)
 6. Two iterations of evolution→Luc78-0B10
 7. Mutagenesis of consensus codons (28)
 8. Mutagenesis of codon usage (24)→Luc90-1B5

One Iteration of Recursive Process
 1. 1 clone→3 libraries using error-prone PCR
  3×Visual screen (about 10,000 clones each)
  3×Quantitative screen (704) clones each)
 2. 3×18 clones→library using sPCR
  Visual screen (about 10,000 clones)
  Quantitative screen (704 clones)
 3. 18+18→library using sPCR
  Visual screen (about 10,000 clones)
  Quantitative screen (704 clones)
 4. Output: 18 clones

EXAMPLES 5

Mutagenesis Strategy from Clone Luc90-1B5 to Luc133-1B2 and Luc146-1H2

Upon storage, luciferin degrades and the degradation products inhibit luciferase. The production of inhibitors causes an apparent instability in the reagent containing both luciferase and luciferin. There are two ways to reduce this problem: 1) Store the luciferin and luciferase at pH 5.5–6.0 to reduce the rate of luciferin degradation, and/or 2) Evolve an enzyme that is resistant to the luciferin degradation products.

LucPpe2 mutants that were evolved after clone Luc90-1B5 were evolved to be more stable at low pH and have resistance to luciferin degradation products. These mutant enzymes are useful, for example, in an ATP detection kit. One embodiment of such a kit comprises a mixture of luciferin and luciferase. A luminescent reaction occurs when a sample comprising ATP is added to the mixture.

Three populations of random mutants were produced using clone Luc90-1B5 as a template. These three populations were screened on the robot as experiments 114, 115, and 117. Robotic screens for experiments 114, 115, 116, 117, 118, 119, and 122 were completed as described previously except that buffer C was prepared with citrate buffer pH 4.5 instead of HEPES buffer pH 7.8, and the assay reagent was prepared with HEPES pH 7.1 with 10 $\mu$M ATP instead of Tricine pH 8.0 and 175 $\mu$M ATP. These screening conditions were biased to select clones that have increased retention of luminescence activity over time at pH 4.5 at 48° C. and increased luminescence activity when assayed at pH 7.1 with 10 $\mu$M ATP. Seventeen clones from experiment 114, seven clones from experiment 115, and ten clones from experiment 116 were shuffled together using sPCR and selected mutants from this screen were run on the robot as experiment 117. Eighteen clones were selected from experiment 117.

The clone that was determined to have the most improved characteristics (increased retention of luminescence activity over time at pH 4.5 and 48° C. and increased luminescence activity when assayed at pH 7.1 with 10 $\mu$M ATP) was clone Luc117-3C1 and it was selected as a template for random mutagenesis. Two populations of random mutants were screened and then run on the robot as experiments 118 and 119. Seven clones from experiment 118 and five clones from experiment 119 were saved.

Clones from experiments 114, 115, 116, 117, 118, and 119 were selected based upon the following characteristics:

brighter luminescence than Luc90-1B5, and increased retention of luminescence activity over time at pH 4.5. These select clones were shuffled together and were run on the robot as experiment 122. Eleven clones from this experiment were saved.

Three populations of random mutants were prepared from clone Luc122-4D5 and run on the robot as experiments 125, 126, and 127. Thirteen clones from experiment 125, four clones form experiment 126, and three clones from experiment 127 were shuffled together and run on the robot as experiment 128. For experiments 125, 126, 127 and 128 the screen for $K_m$ was altered to select for clones that are more resistant to luciferin degradation products. The clones were also screened for retention of luminescence over time at pH 4.5.

Instead of screening for substrate utilization, a screen for resistance to inhibitor was conducted. In place of the 0.06× dilution of substrates, a 75:25 mix of D to L luciferin in 1×assay buffer was used and designated as "0.75×". In place of the 0.02×dilution of substrates, a 50:50 mix of D to L luciferin in 1×assay buffer and was designated as "0.5×". The 1×assay buffer in these experiments contained the following: 10 $\mu$M ATP, 50 M HEPES pH 7.8, 8 mM $MgSO_4$, and 0.1 mM EDTA. The 0.75×sample contained 75 $\mu$M D-luciferin and 25 $\mu$M L-luciferin. The 0.5×sample contained 50 $\mu$M D-luciferin and 50 $\mu$M L-luciferin. The 1×sample contained 250 $\mu$M D-luciferin. A $K_m$ regression was used as before and a $K_m$ value was calculated. Normalized values of greater than 1 indicate more resistance to inhibitor. Clones from these experiments that were shown to have greater resistance to L-luciferin were also more resistant to luciferin degradation products.

To more easily measure resistance to inhibitor on the robotic system, a new variable "Q" was designated. The "Q" variable replaces the $K_m$ variable used previously. The luminescence ratio is calculated the same as in the $K_m$ measurement, then the natural log(ln) of each luminescence ratio is calculated (Y-axis). The X-axis is an arbitrary time that is entered by the user. The first time point is zero and the samples are measured with 1×assay buffer that contains 250 $\mu$M D-luciferin. The next two time points have the same time value (i.e., 4 hours to simulate incubation of luciferin) and samples are measured with 1×assay buffer that contains a 50:50 mixture (as described above) of D-luciferin to L-luciferin. A linear regression correlating ln(lum ratio) to time is calculated. Q is calculated as the ln(0.5)/slope. Normalized values of "Q" greater than 1 indicate more resistance to inhibitor. Experiments 133 and higher were run using this program.

Figure 59:
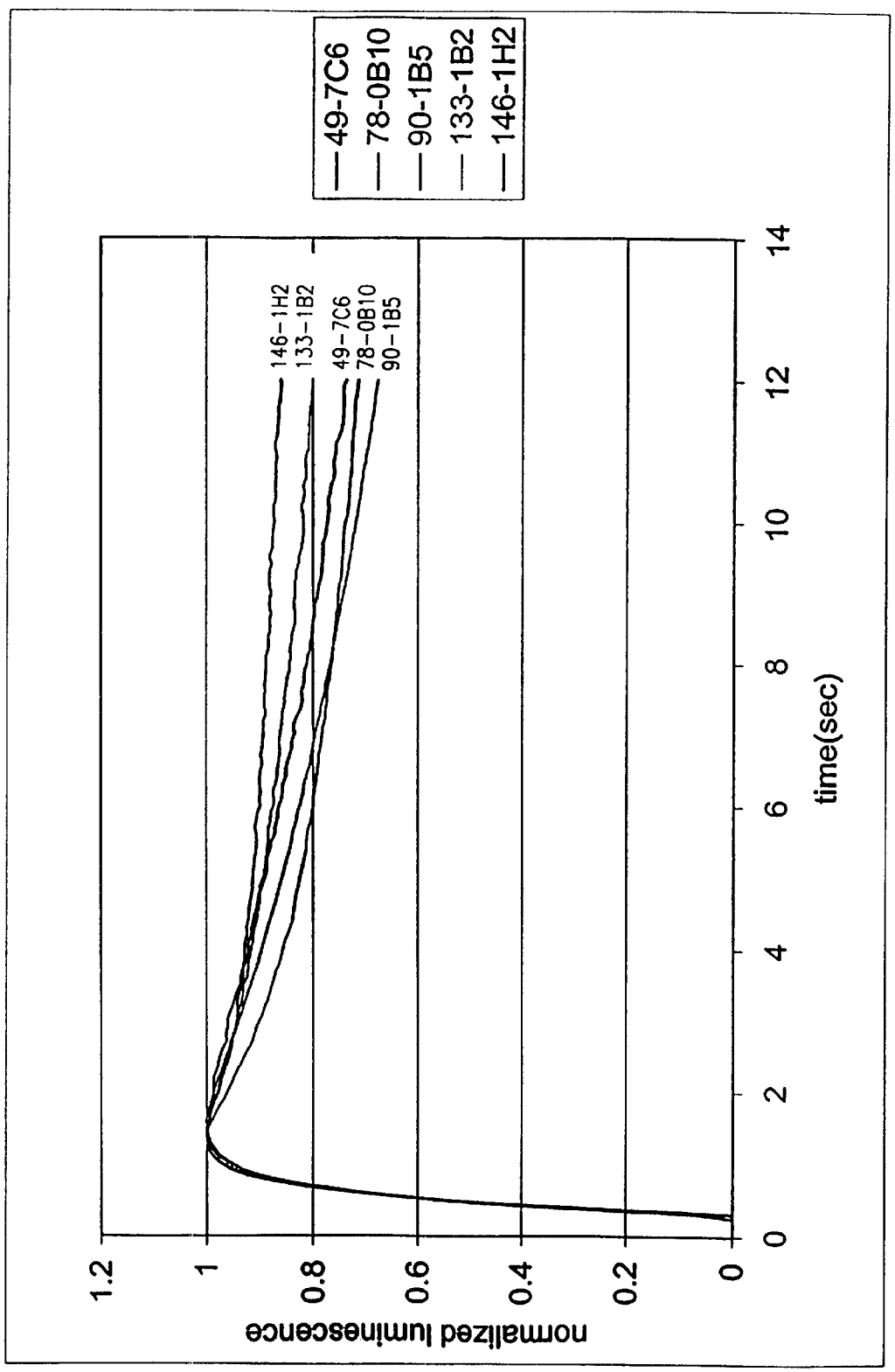
FIG. 59 is a graphical representation of the signal kinetics of clones Luc49-7C6; Luc78-0B10; Luc90-1B5; Luc133-1B2; and Luc146-1H2 at pH 7.8 at room temperature.
Figure 60:
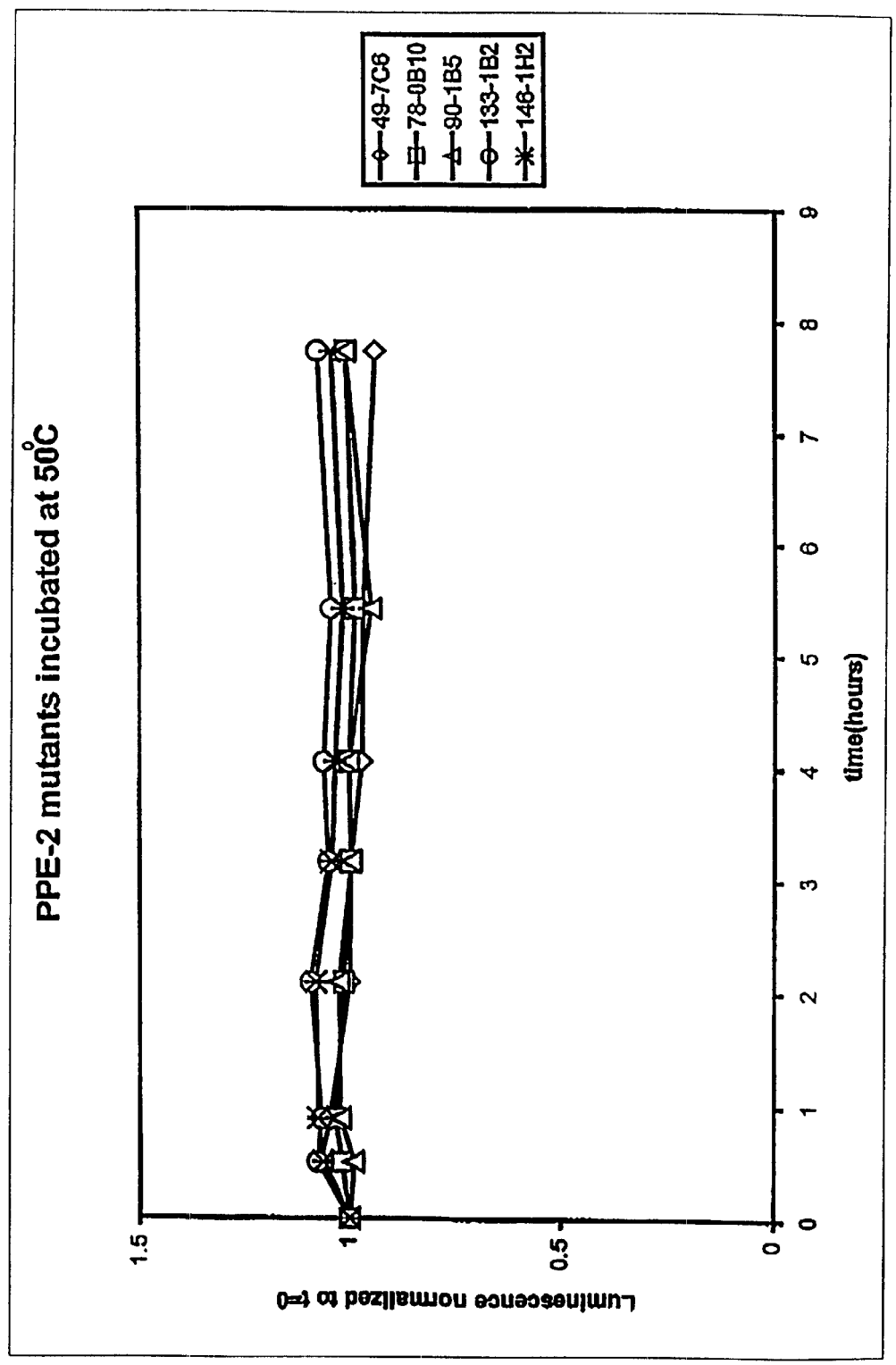
FIG. 60 is a graphical representation of the normalized luminescence at 50° C. pH 7.8 of Luc49-7C6; Luc78-0B10; Luc90-1B5; Luc133-1B2; and Luc146-1H2; from t=0 to about 8 hours.
Figure 61:
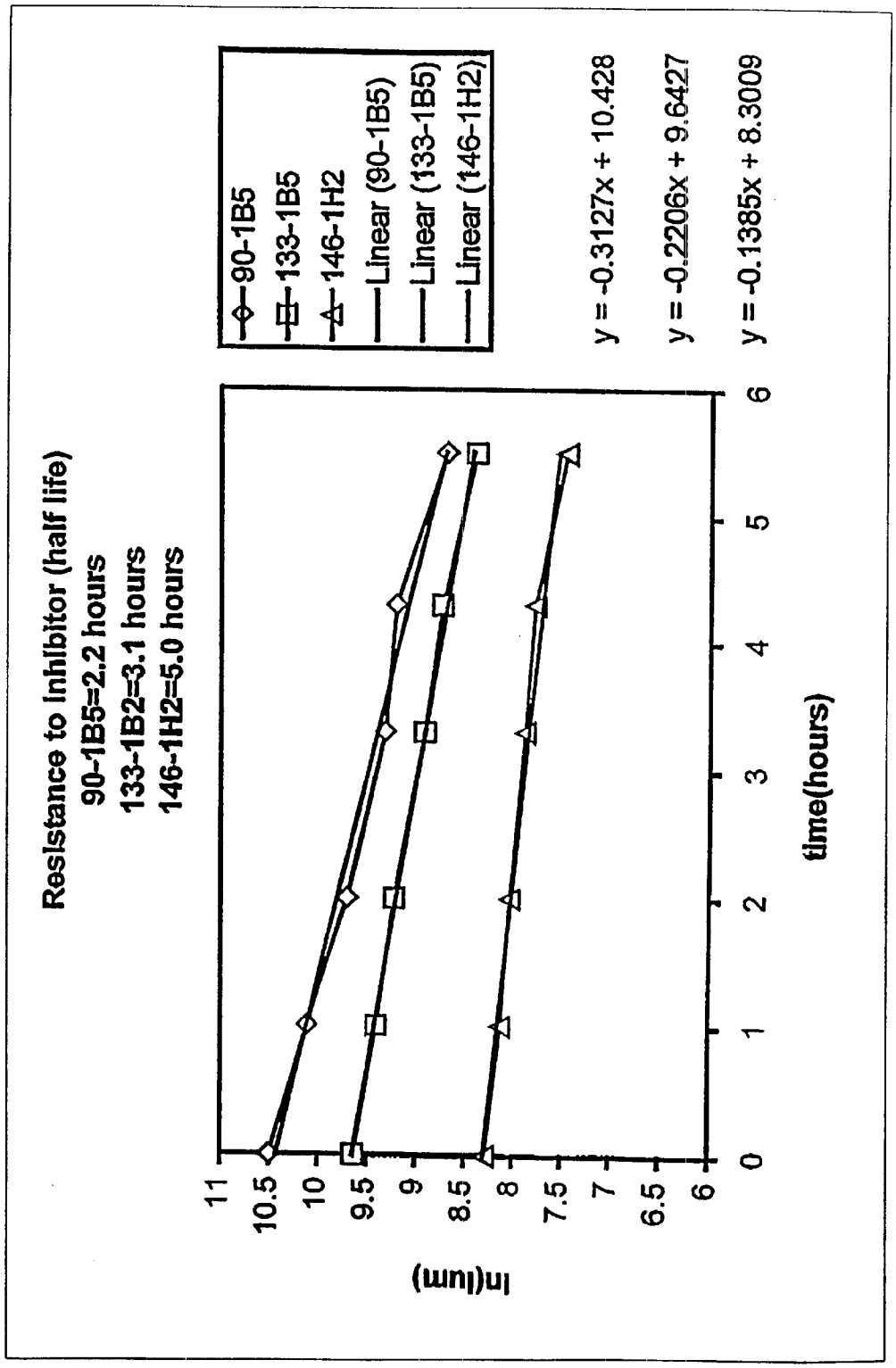
FIG. 61 is a graphical representation of the resistance of selected luciferases to a substrate inhibitor. The data is presented as the log of the luminescence versus time for Luc90-1B5; Luc133-1B5; and Luc146-1H2.
Figure 62:
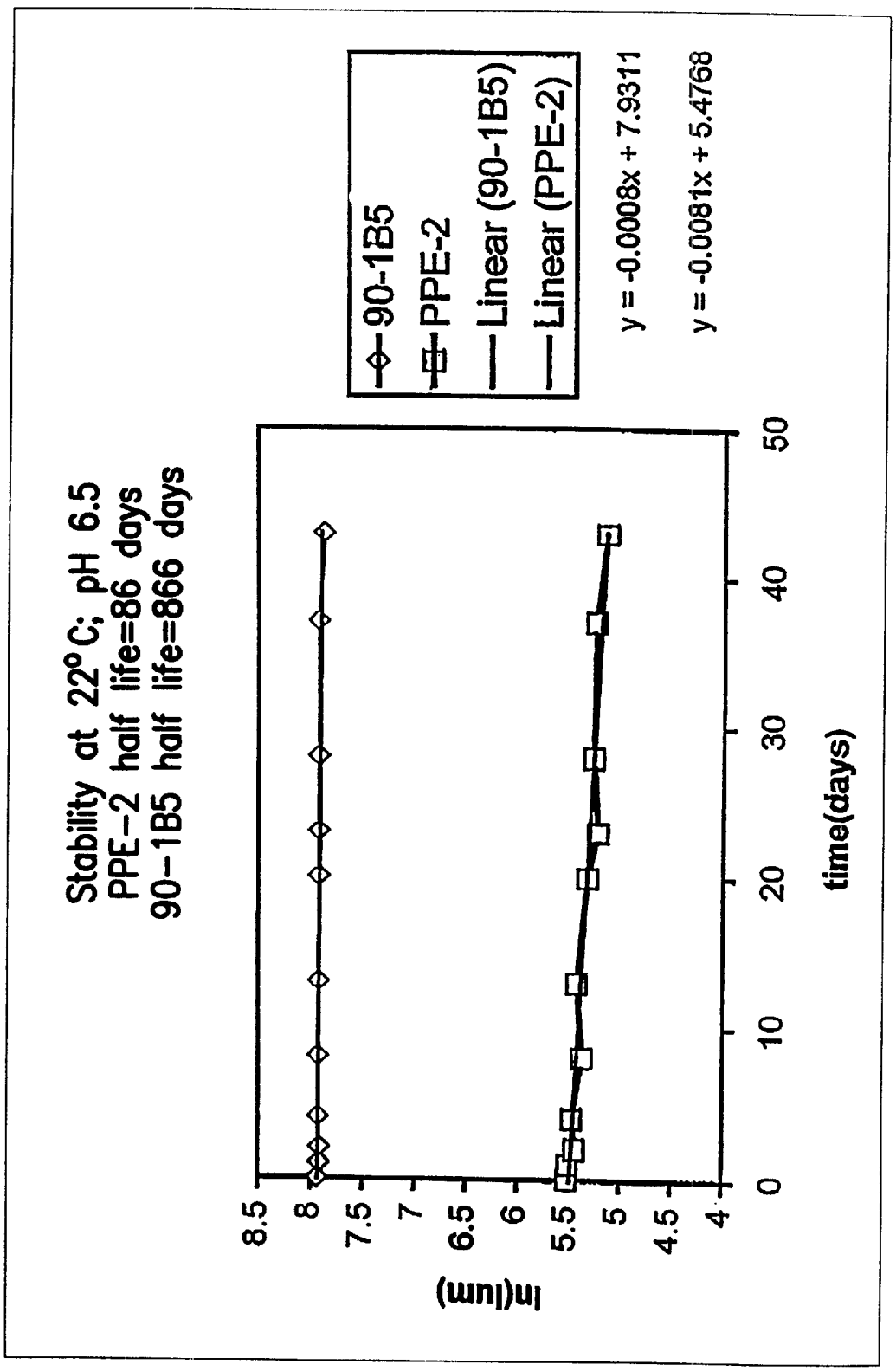
FIG. 62 is a graphical representation of the log of luminescence over time at 22° C., pH 6.5 for Luc90-1B5 and LucPpe2[T249M].

Sixteen clones from experiment 128 were shuffled with clones from experiment 122 and run on the robot as experiment 133. Two samples, Luc133-1B2 and Luc133-0D11, were selected as templates for random mutagenesis and run on the robot as experiments 145 and 146, respectively. The clone that showed an increased retention of luminescence over time at pH 4.5 and the most resistance to inhibitor was clone Luc146-1H2. Moreover, at pH 4.5 and 48° C., Luc133-1B2 and Luc146-1H2 had increased thermostability relative to Luc90-1B5, and increased resistance to inhibitor (FIGS. 54–61). A comparison of the luminescence signal for Luc49-7C6, Luc78-0B10, Luc90-1B5, Luc133-1B2, and Luc146-1H2 is shown in FIG. 59. A comparison of the thermostability at 50° C. for clones for Luc49-7C6, Luc78-0B10, Luc90-1B5, Luc133-1B2, and Luc146-1H2 is shown in FIG. 60. FIGS. 55–58 show the nucleotide sequence encoding and the inferred amino acid sequence of Luc133-1B2 and Luc146-1H2.

Materials and Methods
Assay to Detect Resistance to Luciferase Inhibitor

A 10 mM stock solution of luciferin is incubated at 50° C. in 50 mM HEPES, pH 7.8, to accelerate the production of luciferin breakdown products. At different time points an aliquot is removed and then placed at −20° C. After incubation is complete, assay reagent (100 $\mu$M Luciferin, 1 $\mu$M ATP, 50 mM HEPES, pH 7.8 and 8 mM $MgSO_4$) is prepared with luciferin from each of the different time points and a diluted lysate is then assayed with each assay reagent.

The lysate is prepared as follows. Overnight cultures of clones to be tested are prepared in LB supplemented with 100 $\mu$g/ml AMP. The cultures are diluted 1:10 in M-9 minimal media supplemented with 1 mM IPTG, 100 $\mu$g/ml AMP and grown for 3 hours at 30° C. Forty-five $\mu$l of cells is mixed with 20 $\mu$l of Buffer A and frozen. The mixture is thawed, 175 $\mu$l of Buffer B added, and the resulting mixture diluted 1:10 in Buffer C. A regression of luminescence versus time of luciferin incubation is then calculated, and from this graph half-life is extrapolated. A longer half-life means that the mutant being tested is more resistant to luciferin breakdown products.

EXAMPLE 6

Mutagenesis Strategy from LucPplYG to Clone Luc81-6G01

The luciferases from the luminous beetle, *Pyrophorus plagiophthalamus*, had been shown previously to generate different colors of luminescence (LucPpl). Analysis of these luciferases revealed that the different colors were caused by discreet amino acid substitutions to their protein sequences. This allowed the possibility to make a pair of genetic reporters capable of emitting a multiplexed luminescent signal, thus enabling quantitation of two biomolecular events simultaneously from within the same living system.

Amino acid substituted LucPpl were prepared which have the following properties:

Physical Stability of the Luciferases

Although the luminescence activity of LucPpl within colonies of *E. coli* appeared to be thermostable to above 60° C., in lysates these luciferases had relatively low stability. They were particularly unstable in the presence of Triton X-100 detergent. When lysates are prepared containing the commonly used firefly luciferase, the enzyme retains greater than 90% activity over 5 hours at room temperature. In contrast, the activity of the LucPpl luciferases would decrease several fold over the same period.

The thermostabilities of the LucPpl luciferases are also near the physiological temperature of mammalian cells. The green-emitting luciferase (LucPplGR) and red-emitting luciferase (LucPplRD) have different thermostabilities which may cause differences in the behaviors as genetic reporters within cells. The influence of temperature should be greatest near the point of denaturation for the enzymes, where small changes in temperature will have the greatest effect on protein structure. In contrast, temperature will have much less affect on protein structure when it is much below the denaturation point. Thus, the differential effect on two enzymes having slightly different denaturation temperatures will be less at relatively lower temperatures. It might therefore be preferable to have the denaturation temperature of the reporter enzyme significantly above the growth temperature of mammalian cells.

Spectral Overlap Between the Luciferases

Although a method was developed to quantify each luciferase in a mixture by using colored filters, the ability to discriminate between the luciferases is limited by their spectral overlap. This overlap reduces the ability to accurately measure both luciferases if their luminescence intensities differ by more than 10 fold. If the intensities differ by more than 50 fold, the luminescence signal of the dimmer luciferase is obscured by the other. Thus, it would be preferable to further separate the luminescence spectra of the two luciferases.

Many different mutations were identified which shifted the luminescence spectrum towards the red. But the limit for red luminescence appears to be about 620 nm. Further effort at shifting the spectrum of the red-emitting luciferase into still longer wavelengths might have some benefit. It was found that green-shifting mutations were rare, however, an extensive analysis was not conducted. Measurements from native luciferases show some examples of luminescence below 530 nm, about 15 nm less than the green-emitting prototype enzyme.

Differential Physical and Enzymological Characteristics

Ideally the two luciferase reporters would be identical in all characteristics except for the color of luminescence. However, as noted above, the physical stability of the luciferases was not identical. It was also found that mutations resulting in red-shifted luminescence also caused an increase in the $K_M$ for luciferin. Although some of these differences may be unavoidable, it is not clear whether the properties are fundamentally associated. For instance, luciferases from different beetle species sometimes have significantly differing $K_M$ even though their luminescence spectra are similar. It may be that much of the differences associated with development of the red-emitting luciferase are due to concomitant perturbations to the integrity of the enzyme structure, as the thermostability of a prototype of the red-emitting luciferase was increased without significantly altering the luminescence spectrum.

Stable Luminescence Signals

When firefly luciferase was first described as a genetic reporter, the luminescent signal was a relatively brief flash initiated upon injection of the reaction substrates. Subsequent development of the luminescent chemistry made the assay more convenient by enabling a stable signal for several minutes. Presently, such stabilized assays are standard for general laboratory applications. However, to allow high throughput screening in pharmaceutical research, the luminescence signal was further stabilized to extend for over an hour. This was necessary to allow sufficient time to assay several thousand samples in a batch. Although the luminescent signal of the new multiplexed luciferases was stable for minutes, they did not provide the extended signal stability needed for high throughput screening. It would be preferable if the signal stability could be further increased while optimizing other properties.

Methods to Optimize Luciferase Performance

To prepare luciferases having certain performance, a method for in vitro evolution of enzyme function, as described above, was employed. Briefly described, the method is a recursive process of generating random mutations and screening for desirable properties. It was originally developed primarily to increase the thermostability of luciferases, although other enzymological characteristics are also subject to optimization by the screening criteria. A slightly different strategy was used to achieve the properties described above since two related luciferases needed to be optimized concomitantly.

Initially, a single prototype enzyme is subjected to in vitro evolution to optimize physical stability and the luminescence signal. In the process, the mutant libraries are also screened for any new mutations causing changes in color. Particular emphasis is placed on isolating green shifted mutants. After initial optimization of a common prototype, a green- and red-emitting form of the enzymes is created, and these are further optimized separately to harmonize their physical and chemical properties. Particular attention is given to matching their physical stabilities and their substrate binding constants, especially for luciferin.

The choice for the initial prototype for optimization was the wild-type yellow-green-emitting luciferase isolated from the luminous beetles (LucPplYG). Of the luciferases originally cloned from *P. plagiophthalamus*, this one produced the brightest luminescence when expressed in *E. coli*. Furthermore, there was concern that the lack of green-shifting mutation resulted because the prior mutagenesis studies were done using a luciferase that already had the greenest luminescence. It was possible that if additional green-shifting mutations existed, they might be more evident when screened in a red-shifted background. The mutagenesis was performed as follows:

Remove Peroxisomal Targeting Sequence

The translocation signal at the C-terminus of the luciferases was removed. This was done using oligonucleotide-directed mutagenesis to convert the normal -KSKL to -XXX* (where X represents any amino acid, and * represents a termination codon). Several colonies yielding bright luminescence were selected and used as templates for the next stage of mutagenesis.

Removal of Sensitive Cysteines

The luciferases from *P. plagiophthalamus* have 13 cysteines, which are potentially sensitive to oxidation. This is in contrast to the commonly used firefly luciferase, which has only 4 cysteines. To remove any cysteines that may limit enzyme stability, oligonucleotide-directed mutagenesis was used to randomize the cysteine codons. Three sets of oligonucleotides were used: non-conserved cysteines in regions of low sequence homology (positions 69, 114, 160, 194, 335, and 460), non-conserved cysteines in regions of higher sequence homology (positions 127, 213, 310, and 311), and highly conserved cysteines (positions 60, 80, and 388). The best clones from each of these screens were isolated, and a new mutant library made by sPCR and screened again. At the screening temperature of 29° C., the activity of the wild-type yellow-green-emitting luciferase decreased about 500-fold over 10 hours. The activity of the most stable mutant (Luc20-4C10) was more stable, decreasing only about 2 fold.

First Cycle of Random Mutagenesis

Using the procedure developed previously, three mutant libraries were generated using error-prone PCR and screened. The best mutants from these were recombined into a new library by sPCR and screened again. Finally, the best clones of this screen were recombined with the best clones from the previous oligonucleotide-directed mutagenesis by sPCR, and screened again. At 41° C., the activity of the best mutant from this process (Luc30-4B02) decreased 63 fold over 10 hours, whereas the activity of the parent mutant (Luc20-4C10) decreased greater than 100,000 fold.

Sequence Analysis

Six of the best mutants from the last screen were isolated and sequenced. This revealed that the amino acids at 16 positions had been changed among the six clones. Thirteen positions had been changed in the preferred mutant, Luc30-4B02. Four of the changes were at the C-terminus in all the isolated mutants, where oligonucleotide mutagenesis had changed the wild-type sequence of -KSKL to -AGG*. Only two of the cysteines had been changed by the previous oligonucleotide mutagenesis; one highly conserved cysteine at position 60 was changed to valine and one moderately conserved cysteine at position 127 was changed to threonine. The remaining amino acid changes were all due to point mutations in the DNA, consistent with error-prone PCR. Interestingly, three of these changed the amino acid into that found in the wild-type green-emitting luciferase (two in mutant Luc30-4B02). Four of the remaining changes brought the mutant sequences closer to the consensus amino acid among other cloned beetle luciferases (two in mutant Luc30-4B02) (FIG. 19B). An additional 4 codons were changed without affecting the amino acid sequence.

Site-directed Mutagenesis

To further explore the potential of the mutations identified in the sequenced mutants, additional mutagenesis experiments were performed using oligonucleotides. Eight of the codons mutated by the error-prone PCR were randomized or partially randomized using oligonucleotide-directed mutagenesis. Four of the remaining cysteine codons were randomized; two highly conserved cysteines (positions 80 and 388) and two cysteines in a region of sequence homology (positions 310 and 311). One leucine was mutated to a leucine/proline; proline is the consensus amino acid among other beetle luciferases.

The mutagenesis was performed with four sets of oligonucleotides (Table 13), and the best clones from each set were selected. These were recombined by sPCR together with the selected clones from the previous random mutagenesis and screened again. The activity of the best clone from this process (Luc47-7A11) decreased 2.3 fold at 42° C.; the activity of the parent clone (Luc30-4B02) decreased greater than 2000 fold.

TABLE 13

| Experiment | Mutations |
|---|---|
| Set A | $C_{80} \rightarrow X + K_{84} \rightarrow X + I_{91} \rightarrow$(F, L, I, M, V, S, P, T, A) |
| Set B | $I_{288} \rightarrow$(F, L, I, M, V, S, P, T, A)   $C_{310} \rightarrow X + C_{311} \rightarrow X$ |
| Set C | $G_{351} \rightarrow$(I, M, V, T, A, N, K, D, E, S, R, G) + $L_{350} \rightarrow$(L, P) + $S_{356} \rightarrow P + L_{359} \rightarrow$(F, L, I, M, V, S, P, T, A) |
| Set D | $C_{388} \rightarrow X + V_{389} \rightarrow$(NYN)   $K_{457} \rightarrow X$ |

Second Cycle of Random Mutagenesis

The random mutagenesis process using error-prone PCR was applied again to the best clone from the oligonucleotide-directed mutagenesis (Luc47-7A11). Three libraries were again created and screened, and selected mutants were recombined by sPCR and screened again. Following recombination, the activity of the best mutant (Luc53-0G01) decreased 1.2 fold at 43° C. The parent clone (Luc47-7A11) decreased 150 fold. After recombining the best of these new mutants with the best mutants from the previous oligonucleotide-directed mutagenesis, the activity of the new best mutant (Luc55-2E09) decreased 31 fold at 47° C., compared to 80 fold for the parent (Luc53-0G01).

Third Cycle of Random Mutagenesis

The random mutagenesis process was repeated using the best clone from the previous cycle of mutagenesis (Luc53-0G01). After recombining the selected mutants with the mutants from the second cycle of mutagenesis, the activity of the best clone (Luc81-6G01) decreased 100-fold at 47° C., compared with 750 fold for the parent (Luc53-0G01). The discrepancy in measured activity of Luc53-0G01 in this cycle of mutagenesis compared to the previous cycle may be due to changes in the assay procedure and recalibration of the incubator temperature. It should be noted that the recorded thermostabilities from each stage of mutagenesis are calculated from robotic data using abbreviated assay procedures. The data are intended to indicate the relative stabilities of enzyme mutants when assayed in the same screen, rather than providing an accurate quantitation of thermostability.

Luminescence

Before making a final selection of the best clone from which to create the green- and red-emitting luciferases, further analysis was done on the best clones from the final screen. Three clones in particular were strong candidates as the final choice: Luc81-0B11, Luc81-5F01, and Luc81-6G01. The luminescence properties of these three mutant enzymes were compared among one another. They were also compared to the wild-type yellow-green-emitting luciferase to gauge the effect of the in vitro evolution process.

From colonies of E. Coli expressing the luciferases, Luc81-5F01 and Luc81-6G01 produced luminescence most rapidly at room temperature upon addition of luciferin. The luminescence was more rapid and brighter than colonies expressing the wild-type green- and yellow-green-emitting luciferases. The luminescence from all the selected colonies appeared green-shifted compared to the yellow-green parent clone. When the colonies are heated to 65° C., the yellow-green clone looses most luminescence and the green clone becomes dimmer. Some of the mutant clones loose their luminescence at 65° C., but the three preferred clones remain bright above 70° C. No spectral changes upon heating the colonies were evident until above 70° C., where those clones still retaining activity began to red-shift slightly (sometime, the initial phases of enzyme denaturation are accompanied by a red shift in the luminescence). The luminescence characteristics of the three preferred mutants are quite similar.

Figure 63:
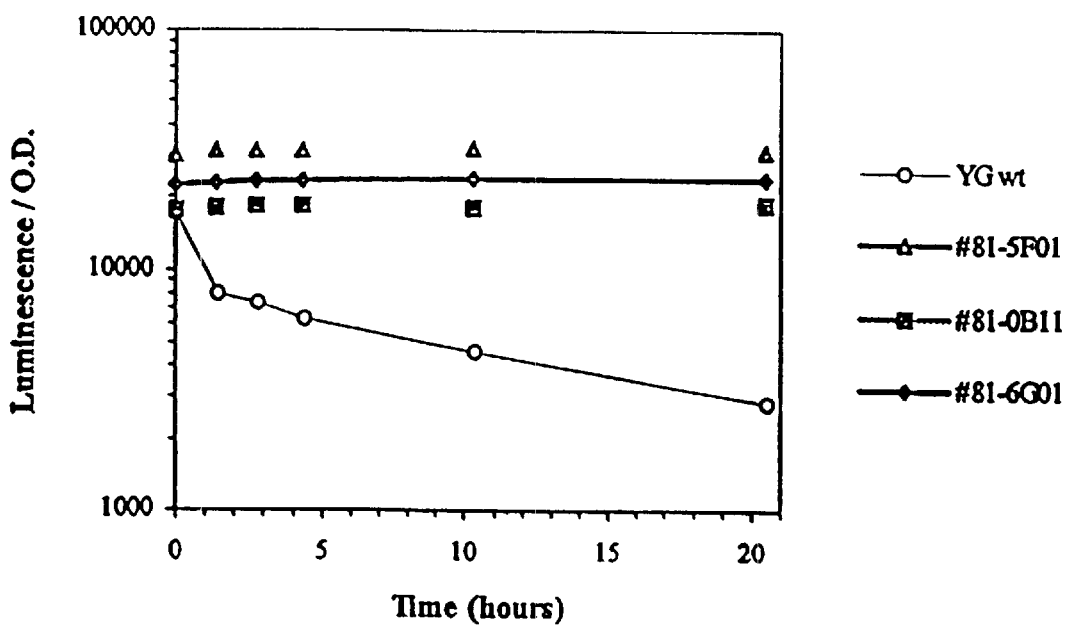
FIG. 63 is a graphical representation of thermostability of selected mutant luciferases and LucPplYG at room temperature in aqueous solution containing 1% Triton X-100 for up to 20 hours.

The thermostability of the mutant luciferases in cell lysates was compared at room temperature (FIG. 63). Dilute lysates were buffered at pH 7.5 and contained 1% Triton X-100; typical conditions for lysates of mammalian cells. The luminescence activity of all three mutant enzyme showed no decrease over 20 hours, whereas the activity of the wild-type yellow-green-emitting luciferase decreased substantially.

For luminescence assays requiring only a few second, the wild-type yellow-green-emitting luciferase produces a very stable signal (the initial rise in the signal evident in the first 2 seconds is due to the response time of the luminometer, not the kinetics of the luminescence reaction). However, the signal intensity was reduced about 30% by the presence of 1% Triton X-100 in the lysate (diluted 1:5 with the addition of assay reagent). In contrast, the luminescence intensity of the mutant luciferases was unaffected by the presence of Triton X-100. Under these conditions, the most stable signal was produced by Luc81-6G01, although the signal intensity was somewhat brighter for Luc81-5F01. However, the data are not corrected for the efficiency of enzyme expression in E. coli. Thus, differences in luminescence intensity may not correlate to changes in enzyme specific activity, nor is the expression efficiency in E. coli necessarily relevant to expression in mammalian cells.

Figure 64:
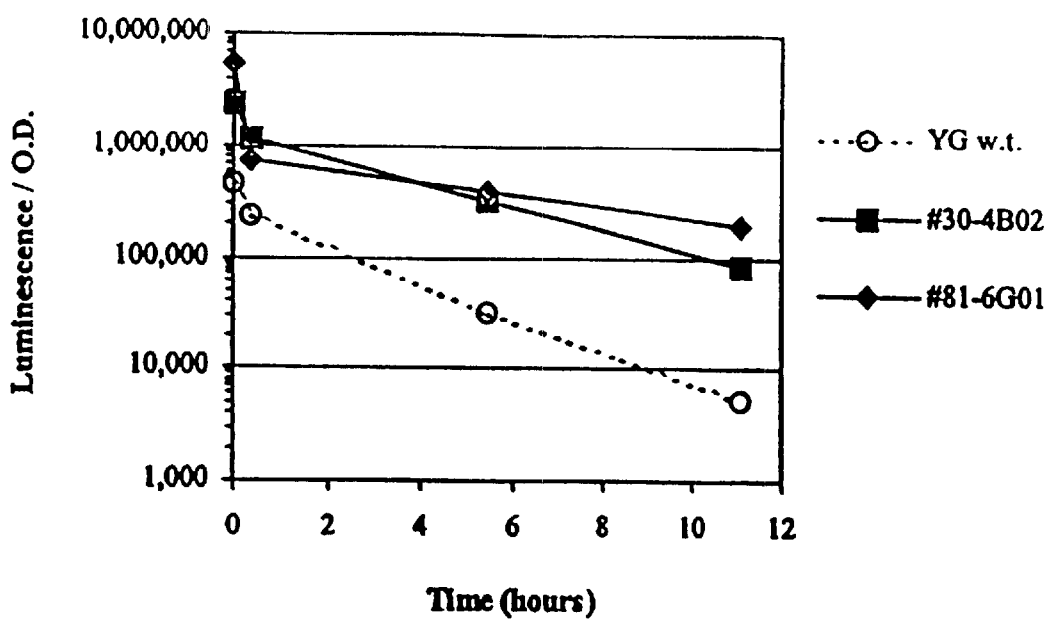
FIG. 64 is a graphical representation of the sustained luminescence activity (expressed as luminescence/O.D.) over time for certain luciferases.

For batches of assays requiring more than an hour to process, the signal stability of the yellow-green-emitting luciferase is inadequate under the conditions tested. The luminescence intensity decreases several fold per hour (FIG. 64). Attempts to correct this by the in vitro evolution yielded mixed results. The signal stability of all three mutant enzymes was generally much improved over the parent yellow-green enzyme for three hours after substrate addition. However, this was accompanied by a greater initial decrease in luminescence during the first half-hour. This initial decrease would be more acceptable if it had occurred more rapidly, so that batch processing of samples would not be delayed by 30 minutes in waiting for the signal to stabilize. It may be possible to improve this kinetic behavior by adjusting the assay conditions.

Figure 46:
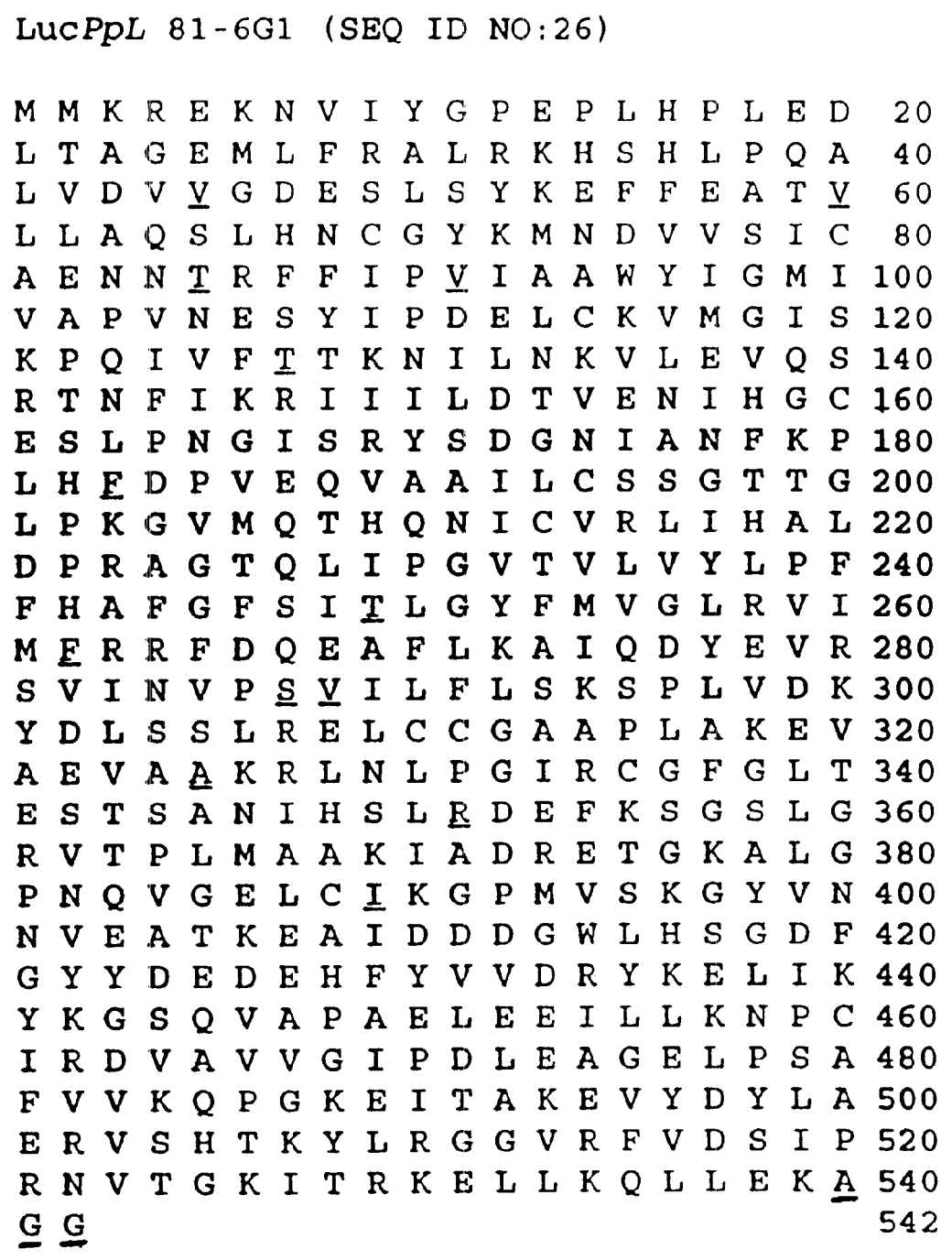

From these results, the mutant Luc81-6G01 was chosen as the best clone from which to subsequently create the green- and red-emitting luciferases. The sequence of Luc81-6G01 (FIGS. 46–47) and Luc81-0B11 was determined and compared with the sequences of Luc30-4B02 from earlier in the in vitro evolution process, and the wild-type yellow-green-emitting luciferase used as the initial parent clone (FIG. 19B). Relative to Luc30-4B02, the Luc81-6G01 mutant acquired new mutations in 9 codons, of which 8 caused changes in the amino acid sequence. Four of these 8 amino acid changes were probably acquired through recombination with clones generated prior to isolation of Luc30-4B02. Two are identical to mutations found in the other clones sequenced along with Luc30-4B02, and two are reversions to the wild-type parent sequence. The remaining four are novel in the sequence of Luc81-6G01. Two of the novel mutations change the amino acid to the consensus amino acid among other cloned luciferases.

Interestingly, in either the sequences of Luc81-6G01 or Luc81-0B11, there is no evidence that the prior oligonucleotide-directed mutagenesis had any beneficial effect. No novel nucleotide sequences appear at any of the targeted codons. The improved enzyme performance following the oligonucleotide-directed mutagenesis apparently was due to recombination of previously acquired mutations. All of the novel amino acid changes in Luc81-6G01 and Luc81-0B11 are at sites not targeted by the oligonucleotides and are due to single-base modifications of the codons, consistent with error-prone PCR. Even though the novel mutations in Luc81-6G01 were not found in the earlier sequence data, it is not certain when they were generated in the process. Most likely they were produced in the second and third cycles of random mutagenesis; however, they may have been present among other selected mutants prior to Luc30-4B02. Relative to the initial yellow-green-emitting luciferase, the Luc81-6G01 mutant has acquired 17 amino acid changes and 3 codon mutations not affecting the amino acid sequence.

The observation that the onset of luminescence within colonies of E. coli is faster for the new mutants, and that the luminescence is brighter at higher temperatures, is probably not due to differences in protein expression. Immunoblot analysis of cell expressing the different luciferases showed no significant differences in the amount of polypeptide present. As noted above, the greater light intensity at higher temperatures is due to the increased thermostability of the mutant luciferases. The apparent $K_M$'s for ATP and luciferin have also changed during the course of the in vitro evolution (Table 14). To estimate the $K_M$ values, the mutant luciferases were partially purified from lysates of E. coli by differential precipitation using ammonium sulfate (40–65% saturation fraction). The results show that the $K_M$'s for both ATP and luciferase are more than 10-fold lower.

When luciferin is added to an E. coli colony expressing luciferase, the intracellular concentration of luciferin slowly increases as it diffuses across the cell membrane. Thus, the intracellular concentration of luciferin reaches saturation sooner for those luciferases having the lowest $K_M$'s. Hence, the mutant luciferases appear brighter sooner than the wild-type parent clone. This also explains why the luminescence of the red-emitting prototype clone appears in E. coli colonies much more slowly than the green-emitting luciferase. Analysis of $K_M$ shows that the mutations causing the red luminescence also substantially increase the $K_M$ for luciferin.

TABLE 14

| Luciferase | $K_M$ for ATP ($\mu$M) | $K_M$ for luciferin ($\mu$M) |
|---|---|---|
| YG w.t. | 140 | 21 |
| Luc30-4B02 | 12 | 7.8 |
| Luc81-6G01 | 8.0 | 1.9 |

From the analysis of luminescence signal in vitro, the luminescence from the mutant luciferases might be expected to fade more quickly than the wild-type luciferase during the first 30 minutes. Following this, the luminescence should be most stable in the mutants. However, this has not been noticed in the colonies of E. coli, and it may be that the kinetics of luminescence are different within cells compared to diluted enzyme in buffer.

REFERENCES

Bowie, J. U., Reindhaar-Olsen, J. F., Lim, W. A., and Sauer, R. T., Science, (1990) 247:1306–1310.

Fromant, M., Blanquet, S., Plateau, P., Analytical-Biochemistry (1995) 224:347–53.

Hanahan, D. (1985) in DNA Cloning, v. 1, ed. Glover, D. W. (IRL Press, Oxford) pp. 109–135.

Hastings, J. W., Kricka, L. J., Stanley, P. E., (eds.) Bioluminescence and Chemiluminescence, Molecular reporting with Photons. Chichester: John Wiley & Sons (1996) 248–52.

Kajiyama, N., Nakano, E., Biosci. Biotech. (1994) 58(6):1170–1171.

Kajiyama, N., Nakano, E., Biochemistry (1993) 32:13795–13799.

Leach, et al., Biochimica, et Biophysica Acta, (1997) 1339 (1):39–52.

Saiki, R. K., Gefand, D. H., Stoffel, S., Scharf, S. J., Higuchi, R., Mullis, K. B., Erlich, H. A., Science (1988) 239:487–91.

Stemmer, W. P., DNA (1994) 91:10747–51.

Stemmer, W. P., Proc. Natl. Acad. Sci. U.S.A. (1994) 91:10747–51.

Stemmer, U.S. Pat. No. 5,605,793.

White, P. J. et al. (eds.), Bioluminescence and Chemiluminescence, Fundamentals and Applied Aspects. Chichester: John Wiley & Sons (1994) 419–422.

Wood, K. V., Photochemistry and Photobiology (1995) 62:662–673.

Wood, K. V., DeLuca, M., Analytical Biochemistry (1987) 161:501–7.

Ye, L., Buck, L. M., Schaeffer, H. J., Leach, F. R., Biochimica et Biophysica Acta (1997) 1339:39–52.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A luciferase having an amino acid sequence comprising a sequence selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:44, SEQ ID NO:45, and a portion thereof which has the luminescent activity of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:44, SEQ ID NO:45.

2. A luciferase having an amino acid sequence comprising SEQ ID NO:14, SEQ ID NO:19, SEQ ID NO:24, SEQ ID NO:26, SEQ ID NO:44, or SEQ ID NO:45.

3. A thermostable beetle luciferase that retains at least 50% activity in aqueous solution for at least 2 hours at a temperature of about 50° C., which thermostable beetle luciferase comprises at least one amino acid substitution relative to a reference beetle luciferase, and which comprises SEQ ID NO:14, SEQ ID NO:19, SEQ ID NO:24, SEQ ID NO:26, SEQ ID NO:44, or SEQ ID NO:45.

4. A fusion protein comprising the luciferase of claim 3.

5. A solid substrate comprising the luciferase of claim 1, 2 or 3.

6. A fusion protein comprising the luciferase of claim 1 or 2.

7. A kit comprising: a container comprising the luciferase of claim 1, 2 or 3.

8. The kit of claim 7 wherein the container comprises an aqueous mixture comprising the luciferase.

9. The kit of claim 7 wherein the container comprises lyophilized luciferase.

10. The kit of claim 7 further comprising a container comprising luciferin.

11. The kit of claim 7 wherein the container further comprises luciferin.

12. The kit of claim 10 wherein the container comprising luciferin comprises lyophilized luciferin.

13. The kit of claim 11 wherein the luciferin comprises lyophilized luciferin.

14. The kit of claim 7 further comprising packaging material enclosing, separately packaged, the container and instruction means directing the user to correlate the luciferase activity in a sample with the level of ATP in the sample.

15. The kit of claim 7 further comprising packaging material enclosing, separately packaged, the container and instruction means directing the user to correlate the luciferase activity in a sample with the level or presence of an agent in the sample that alters the level of ATP in the sample.

16. The kit of claim 7 further comprising packaging material enclosing, separately packaged, the container and instruction means directing the user to correlate the luciferase activity in a sample with the level or presence of a molecule other than ATP.

* * * * *

UNITED STATES PATENT AND TRADEMARK OFFICE
CERTIFICATE OF CORRECTION

PATENT NO. : 6,602,677 B1
DATED : August 5, 2003
INVENTOR(S) : Mary P. Hall, Keith V. Wood and Monika G. Wood It is certified that error appears in the above-identified patent and that said Letters Patent is hereby corrected as shown below:

<u>Title page,</u>
Item [75], Inventors, insert -- ; Monika G. Wood, Mt. Horeb, WI (US) -- below "Mary P. Hall, Madison, WI (US)".

Signed and Sealed this

Thirteenth Day of April, 2004

JON W. DUDAS
*Acting Director of the United States Patent and Trademark Office*